(12) United States Patent
Blake et al.

(10) Patent No.: US 8,003,662 B2
(45) Date of Patent: Aug. 23, 2011

(54) HETEROBICYCLIC THIOPHENE COMPOUNDS AND METHODS OF USE

(75) Inventors: James F. Blake, Longmont, CO (US); Steven Boyd, Longmont, CO (US); Jason De Meese, Firestone, CO (US); John J. Gaudino, Longmont, CO (US); Allison L. Marlow, Louisville, CO (US); Jeongbeob Seo, Broomfield, CO (US); Allen A. Thomas, Louisville, CO (US); Hongqi Tian, Longmont, CO (US)

(73) Assignee: Array BioPharma, Inc., Boulder, CO (US)

( * ) Notice: Subject to any disclaimer, the term of this patent is extended or adjusted under 35 U.S.C. 154(b) by 576 days.

(21) Appl. No.: 11/699,830

(22) Filed: Jan. 30, 2007

(65) Prior Publication Data

US 2007/0197537 A1  Aug. 23, 2007

Related U.S. Application Data

(60) Provisional application No. 60/763,414, filed on Jan. 30, 2006.

(51) Int. Cl.
*A61K 31/4365* (2006.01)

(52) U.S. Cl. .................. 514/301; 546/114
(58) Field of Classification Search .......... 546/114
See application file for complete search history.

(56) References Cited

U.S. PATENT DOCUMENTS

| | | | |
|---|---|---|---|
| 6,492,383 B1 | 12/2002 | Munchhof et al. |
| 6,833,456 B2 | 12/2004 | Romines, III et al. |
| 6,869,962 B2 | 3/2005 | Collins et al. |
| 6,964,961 B2 | 11/2005 | Luzzio et al. |
| 6,987,116 B2 | 1/2006 | Boschelli et al. |
| 6,995,171 B2 | 2/2006 | Autry et al. |
| 2002/0004511 A1 | 1/2002 | Luzzio et al. |
| 2004/0138251 A1 | 7/2004 | Boschelli et al. |
| 2004/0242603 A1 | 12/2004 | Fujiwara et al. |
| 2005/0009845 A1 | 1/2005 | Caferro et al. |
| 2005/0070508 A1 | 3/2005 | Lou et al. |
| 2005/0090509 A1 | 4/2005 | Lou et al. |
| 2005/0239820 A1 | 10/2005 | Borzilleri et al. |
| 2005/0245530 A1 | 11/2005 | Borzilleri et al. |
| 2006/0074056 A1 | 4/2006 | Vaisburg et al. |
| 2006/0252777 A1 | 11/2006 | Kim et al. |
| 2006/0287343 A1 | 12/2006 | Saavedra et al. |
| 2007/0004675 A1 | 1/2007 | Saavedra et al. |
| 2007/0054928 A1 | 3/2007 | Bannen et al. |
| 2007/0060613 A1 | 3/2007 | Kim |
| 2009/0270391 A1 | 10/2009 | Kubo et al. |

FOREIGN PATENT DOCUMENTS

| | | |
|---|---|---|
| WO | WO 03/106462 | 12/2003 |
| WO | WO 2004/018430 | 3/2004 |
| WO | WO 2005/021553 | 3/2005 |
| WO | WO 2005/080377 | 9/2005 |
| WO | 2005/116028 A2 | 12/2005 |
| WO | 2005/121125 A1 | 12/2005 |
| WO | 2006/014325 A2 | 2/2006 |
| WO | WO 2006/010264 | 2/2006 |
| WO | 2006/108059 A1 | 10/2006 |
| WO | 2006/116713 A1 | 11/2006 |
| WO | WO 2007/125405 | 11/2007 |
| WO | WO 2008/054674 | 5/2008 |

OTHER PUBLICATIONS

Ragan, J.A. et al., "Cross-Coupling Methods for the Large-Scale Preparation of an Imidazole—Theinopyridine: Synthesis of [2-(3-Methyl-3h-Imidazol-4-YL)-Thieno[3,2-b]Pyridin-7-YL]-(2-Methyl-1H-Indol-5-YL)-Amine", Organic Process Research & Development, 2003, vol. 7, No. 5, pp. 676-683.

Boschelli, Diane H. et al., "Synthesis and SRC Kinase Inhibitory Activity of 2-Phenyl- and 2-Thienyl-7-Phenylaminothieno[3,2-b]Pyridine-6-Carbonitriles", J. Med. Chem., 2005, vol. 48, pp. 3891-3902.

Munchhof, Michael J., "Design and SAR of Thienopyrimidine and Thienopyridine Inhibitors of VEGFR-2 Kinase Activity", Bioorganic & Medicinal Chemistry Letters 14, 2004, pp. 21-24.

International Search Report and Written Opinion of the International Searching Authority, PCT/US2007/002352, Dec. 3, 2008.

Database Chemical Abstracts, Chemical Abstracts Service, SHIMIZU, "Preparation of quinoline derivatives as TGF β inhibitors", XP002495469, Database accession No. 2004:182845, pp. 1-2, 2004.

Database Chemical Abstracts, Chemical Abstracts Service, SHIMIZU, "Preparation of pyridines and related compounds as TGF β inhibitors", XP002495470, Database accession No. 2005:962244, pp. 1-3, 2005.

*Primary Examiner* — James O Wilson
*Assistant Examiner* — Brian McDowell
(74) *Attorney, Agent, or Firm* — Viksnins Harris & Padys PLLP

(57) ABSTRACT

Compounds of Formula I and pharmaceutically acceptable salts thereof, are useful for inhibiting receptor tyrosine kinases and for treating disorders mediated thereby. Methods of using compounds of Formula I and pharmaceutically acceptable salts thereof, for in vitro, in situ, and in vivo diagnosis, prevention or treatment of such disorders in mammalian cells, or associated pathological conditions are disclosed.

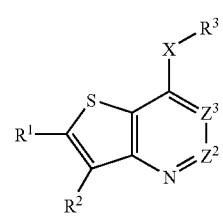

I

9 Claims, No Drawings

HETEROBICYCLIC THIOPHENE COMPOUNDS AND METHODS OF USE

PRIORITY OF INVENTION

This application claims priority to U.S. Provisional Application No. 60/763,414 that was filed on 30 Jan. 2006. The entire content of this provisional application is hereby incorporated herein by reference.

FIELD OF THE INVENTION

The invention relates to heterobicyclic thiophene compounds having protein tyrosine kinase activity. The heterobicyclic thiophene compounds may be useful in the treatment of hyperproliferative disorders, such as cancer, in mammals. The invention also relates to pharmaceutical compositions and formulations, methods of synthesis, and methods of use such as treating hyperproliferative disorders.

BACKGROUND OF THE INVENTION

Met tyrosine kinase is a high-affinity transmembrane receptor for the hepatocyte growth factor (HGF, Bottaro et al. (1991) Science 251:802-804). Met was cloned, named (Cooper et al. (1984) 311:29-33) and identified as an oncogene (Park et al. (1986) Cell 45:895-904). When deregulated by overexpression or mutations, Met receptor tyrosine kinase leads to tumor growth and invasion (Cristiani et al. (2005) Biochem. 44:14110-14119). Stimulation of Met by the ligand HGF, also known as Scatter Factor, initiates numerous physiological processes, including cell proliferation, scattering, morphogenic differentiation, angiogenesis, wound healing, tissue regeneration, and embryological development (Parr et al. (2004) Clin. Cancer Res. 10(1, Pt. 1) 202-211; Comoglio et al. (2002) J. Clin. Invest. 109:857-862; Maulik et al. (2002) Cytokine Growth Factor Reviews 13:41-59; Hecht et al. (2004) Cancer Res. 64(17):6109-6118). Receptor c-Met is rapidly internalized via clathrin-coated vesicles and traffics through an early endosomal compartment after hepatocyte growth factor stimulation. c-Met accumulates progressively in perinuclear compartments, which in part include the Golgi (Kermorgant et al. (2003) J. of Biol. Chem. 278(31):28921-28929).

The phenomena of: deregulation or dysregulation of Met and/or HGF; Met overexpression; and Met mutations are implicated in uncontrolled cell proliferation and survival, and play a key role in early-stage tumorigenesis, invasive growth of cancer cells, and metastasis (Danilkovitch-Miagkova et al. (2002) J. Clin. Invest. 109(7):863-867; Di Renzo et al. (1994) Int. J. Cancer 58:658-662; Matsumoto et al. (1994) J. Biol. Chem. 269:31807-31813; Tusolino et al. (1998) J. Cell Biol. 142:1145-1156; Jeffers et al. (1996) Mol. Cell. Biol. 16:1115-1125; Wong et al. (2004) Exper. Cell Res. 299(1): 248-256; Konda et al. (2004) Jour. of Urology 171(6), Pt. 1:2166-2170; Heideman et al. (2004) J. Gene Med. 6(3):317-327; Ma et al. (2003) Cancer Res. 63(19):6272-6281; Maulik et al. (2002) Clin. Cancer Res. 8:620-627), making Met an important target for anticancer drug development (Cohen, P. (2002) Nat. Rev. Drug Discovery 1:309-315). Overexpression of Met and HGF is associated with poor prognosis.

Recent data demonstrating the suppression of cancer cell proliferation, survival, and invasion upon inhibition of Met binding to HGF and Met receptor dimerization (Furge et al. (2001) Proc. Natl. Acad. Sci. USA 98:10722-10727; Michieli et al. (2004) Cancer Cell 6:61-73) confirm the relevance of Met in neoplasia and provide further proof of concept for the development of small-molecule compounds for antineoplastic therapy, e.g. against multiple myeloma (Hov et al. (2004) Clin. Cancer Res. 10(19):6686-6694). Inhibition of Met results in slowing tumor growth in tumor xenograft mouse models. Antibodies specific for c-Met have been expressed to block binding of HGF to c-Met (US 2005/0037431; US 2004/0166544).

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer). Protein kinases include two classes; protein tyrosine kinases (PTK) and serine-threonine kinases (STK).

One of the prime aspects of PTK activity is their involvement with growth factor receptors which are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, (1992) Neuron 9:303-391.

Growth factor receptors with PTK activity are known as receptor tyrosine kinases (RTK, Plowman et al. (1994) DN&P, 7(6):334-339), which comprise a large family of transmembrane receptors with diverse biological activity. At present, at least nineteen (19) distinct subfamilies of RTK have been identified. An example of these is the subfamily designated the "HER" RTK, which include EGFR (epithelial growth factor receptor), HER2, HER3 and HER4. These RTK consist of an extracellular glycosylated ligand binding domain, a transmembrane domain and an intracellular cytoplasmic catalytic domain that can phosphorylate tyrosine residues on proteins. Another RTK subfamily consists of insulin receptor (IR), insulin-like growth factor I receptor (IGF-1R) and insulin receptor related, receptor (IRR). IR and, IGF-1R interact with insulin, IGF-I and IGF-II to form a heterotetramer of two entirely extracellular glycosylated alpha subunits and two beta subunits which cross the cell membrane and which contain the tyrosine kinase domain. A third RTK subfamily is referred to as the platelet derived growth factor receptor (PDGFR) group, which includes PDGFR-alpha, PDGFR-beta, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences. Another group which, because of its similarity to the PDGFR subfamily, is sometimes subsumed into the later group is the fetus liver kinase (flk) receptor subfamily. This group is believed to be made up of kinase insert domain-receptor fetal liver kinase-1 (KDR/FLK-1), flk-1R, flk-4 and fms-like tyrosine kinase 1 (flt-1). Another member of the tyrosine kinase growth factor receptor family is the fibroblast growth factor ("FGF") receptor subgroup. This group consists of four receptors, FGFR1-4, and seven ligands, FGF1-7. While not yet well defined, it appears that these receptors consist of a glycosylated extracellular domain containing a variable number of immunoglobin-like loops and an intracellular domain in which the tyrosine kinase sequence is interrupted by regions of unrelated amino acid sequences. Still another member of the tyrosine kinase growth factor receptor family is the vascular endothelial growth factor (VEGF) receptor subgroup. VEGF is a dimeric glycoprotein similar to PDGF but has different biological functions and target cell specificity in vivo. In particular, VEGF is presently thought to play an essential role is vasculogenesis and angiogenesis.

Met is still another member of the tyrosine kinase growth factor receptor family, and often referred to as c-Met or human hepatocyte growth factor receptor tyrosine kinase (hHGFR). The expression of c-Met is thought to play a role in primary tumor growth and metastasis (Kim et al. Clin. Cancer Res. (2003) 9(14):5161-5170).

Modulation of the HGF/c-Met signaling pathway may be effected by regulating binding of HGF beta chain to cMet. In particular embodiments, the zymogen-like form of HGF beta mutant was shown to bind Met with 14-fold lower affinity than the wild-type serine protease-like form, suggesting optimal interactions result from conformational changes upon cleavage of the single-chain form (US 2005/0037431). Extensive mutagenesis of the HGF beta region corresponding to the active site and activation domain of serine proteases showed that 17 of the 38 purified two-chain HGF mutants resulted in impaired cell migration or Met phosphorylation but no loss in Met binding. However, reduced biological activities were well correlated with reduced Met binding of corresponding mutants of HGF beta itself in assays eliminating dominant alpha-chain binding contributions.

Protein-tyrosine kinases (PTK) are critical components of signaling pathways that control cellular proliferation and differentiation. PTK are subdivided into two large families, receptor tyrosine kinases (RTK) and non-receptor tyrosine kinases (NRTK). RTK span the plasma membrane and contain an extra-cellular domain, which binds ligand, and an intracellular portion, which possesses catalytic activity and regulatory sequences. Most RTK, like the hepatocyte growth factor receptor c-met, possess a single polypeptide chain and are monomeric in the absence of a ligand. Ligand binding to the extracellular portion of RTK, dimerizes monomeric receptors, resulting in autophosphorylation of specific tyrosine residues in the cytoplasmic portion (for review see: Blume-Jensen, P., and Hunter, T., Nature (2001) 411:355-365; Hubbard, S. R., et al., J. Biol. Chem. 273 (1998) 11987-11990; Zwick, E., et al., Trends Mol. Med. (2002) 8:17-23). In general, tyrosine autophosphorylation either stimulates the intrinsic catalytic kinase activity of the receptor or generates recruitment sites for downstream signaling proteins containing phosphotyrosine-recognition domains, such as the Src homology 2 (SH2) domain or the phosphotyrosine-binding (PTB) domain.

PTK have become primary targets for the development of novel therapeutics designed to block cancer cell proliferation, metastasis, and angiogenesis and promote apoptosis. The strategy that has progressed farthest in clinical development is the use of monoclonal antibodies to target growth factor receptor tyrosine kinases. The use of small molecule tyrosine kinase inhibitors however could have significant theoretical advantages over monoclonal antibodies. Small molecule inhibitors could have better tissue penetration, could have activity against intracellular targets and mutated targets and could be designed to have oral bioavailability. Several lead compounds have shown promising activity against such targets as the EGFR, the vascular endothelial cell growth factor receptor and bcr-abl. The hepatocyte growth factor receptor c-Met was first identified as an activated oncogene in an N-methyl-N'-nitrosoguanidinic treated human osteogenic sarcoma cell line (MUNG-HOS) by its ability to transform NIH 3T3 mouse fibroblasts. The receptor encoded by the c-Met protooncogene (located on chromosome 7) is a two-chain protein composed of 50 kDa (alpha) chain disulfide linked to a 145 kDa (beta) chain in an alpha-beta complex of 190 kDa. The alpha-chain is exposed at the cell surface while the beta chain spans the cell membrane and possesses an intracellular tyrosine kinase domain. The presence of this intracellular tyrosine kinase domain groups c-Met as a member of the receptor tyrosine kinase (RTK) family of cell surface molecules.

Much evidence supports the role of HGF as a regulator of carcinogenesis, cancer invasion and metastasis (for review see: Herynk, M. H., and Radinsky, R. (2000) In Vivo 14:587-596; Jiang et al. (1999) Crit. Rev. Oncol. Hematol. 29:209-248; Longati (2001) Curr. Drug Targets 2:41-55; Maulik et al., (2002) Cytokine Growth Factor Rev. 13:41-59; Parr, C., and Jiang, W. G., (2001) Histol. Histopathol. 16:251-268). HGF binds to and induces tyrosine phosphorylation of the mature c-met receptor beta-chain. Such events are thought to promote binding of intracellular signaling proteins containing src homology (SH) regions such as PLC-gamma, Ras-GAP, PI-3 kinase $pp^{60}$c-src and the GRB-2 Socs complex to the activated receptor. Each SH2-containing protein may activate a different subset of signaling phosphopeptides, thus eliciting different responses within the cell. c-Met mutations have been well-described in hereditary and sporadic human papillary renal carcinomas and have been reported in ovarian cancer, childhood hepatocellular carcinoma, metastatic head and neck squamous cell carcinomas, and gastric cancer. c-Met is also over-expressed in both non-small cell lung cancer and small cell lung cancer cells, in lung, breast, colon and prostate tumors (Herynk et al. (2003) Cancer Res. 63(11): 2990-2996; Maulik et al. (2002) Clin. Cancer Res. 8:620-627). Since c-Met appears to play an important role in oncogenesis of a variety of tumors, various inhibition strategies have been employed to therapeutically target this receptor tyrosine kinase. The usefulness of inhibiting the protein-tyrosine kinase c-Met for inhibiting tumor growth and invasion has been shown in many well documented preclinical experiments (Abounader et al. (1999) J. Natl. Cancer Inst. 91:1548-1556; Laterra et al. (1997) Lab. Invest. 76:565-577; Tomioka, D. (2001) Cancer Res. 61:7518-7524; Wang et al. (2001) J. Cell Biology 153:1023-1033).

cMet inhibitors have been reported (US 2004/0242603; US 2004/0110758; US 2005/0009845; WO 2003/000660; WO 98/007695; U.S. Pat. No. 5,792,783; U.S. Pat. No. 5,834,504; U.S. Pat. No. 5,880,141; US 2003/0125370; U.S. Pat. No. 6,599,902; WO 2005/030140; WO 2005/070891; US 2004/0198750; U.S. Pat. No. 6,790,852; WO 2003/087026; U.S. Pat. No. 6,790,852; WO 2003/097641; U.S. Pat. No. 6,297,238; WO 2005/005378; WO-2004/076412; WO 2005/004808; WO 2005/010005; US 2005/0009840; WO 2005/121125). PHA-665752 is a small molecule, ATP-competitive, active-site inhibitor of the catalytic activity of c-Met, as well as phenotypes such as cell growth, cell motility, invasion, and morphology of a variety of tumor cells (Ma et al. (2005) Clin. Cancer Res. 11:2312-2319; Christensen et al. (2003) Cancer Res. 63:7345-7355).

SUMMARY OF THE INVENTION

In one aspect, the invention relates to heterobicyclic thiophene compounds that are inhibitors of receptor tyrosine kinases (RTK), including c-Met. Certain hyperproliferative disorders are characterized by the overactivation of cMet kinase function, for example by mutations or overexpression of the protein. Accordingly, the compounds of the invention are useful in the treatment of hyperproliferative disorders such as cancer.

Another aspect of the invention provides heterobicyclic thiophene compounds of Formula I

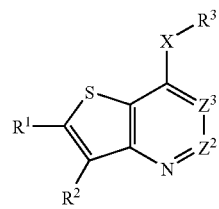

and stereoisomers, geometric isomers, tautomers, solvates, metabolites and pharmaceutically acceptable salts and prodrugs thereof, wherein $R^1$, $R^2$, $R^3$, X, $Z^2$ and $Z^3$ are as defined herein.

Another aspect of the present invention provides a compound of Formula I having the structure:

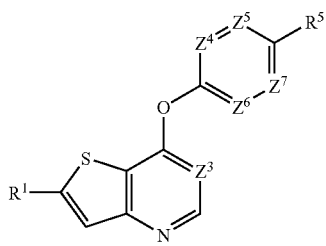

wherein $R^1$, $R^5$, $Z^3$, $Z^4$, $Z^5$, $Z^6$ and $Z^7$ are as defined herein.

Another aspect of the invention is a pharmaceutical composition comprising a heterobicyclic thiophene compound of Formula I and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating cardiovascular disease, agents for treating liver disease, anti-viral agents, agents for treating blood disorders, agents for treating diabetes, and agents for treating immunodeficiency disorders.

Another aspect of the invention provides methods of inhibiting or modulating receptor tyrosine kinase activity, comprising contacting the kinase with an effective inhibitory amount of a compound of Formula I.

Another aspect of the invention provides methods of inhibiting cMet kinase activity, comprising contacting a cMet kinase with an effective inhibitory amount of a compound of Formula I, or a stereoisomer, geometric isomer, tautomer, solvate, metabolite, or pharmaceutically acceptable salt or prodrug thereof.

Another aspect of the invention provides methods of preventing or treating a disease or disorder modulated by cMet kinases, comprising administering to a mammal in need of such treatment an effective amount of a compound of Formula I or a stereoisomer, geometric isomer, tautomer, solvate, metabolite, or pharmaceutically acceptable salt or prodrug thereof. Examples of such diseases, conditions and disorders include, but are not limited to, hyperproliferative disorders (such as cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of Formula I, or a stereoisomer, geometric isomer, tautomer, solvate, metabolite, or pharmaceutically acceptable salt or prodrug thereof, alone or in combination with one or more additional compounds having anti-hyperproliferative properties.

In a further aspect the present invention provides a method of using a compound of this invention to treat a disease or condition modulated by c-Met in a mammal.

An additional aspect of the invention is the use of a compound of this invention in the preparation of a medicament for the treatment or prevention of a disease or condition modulated by c-Met in a mammal.

Another aspect of the invention includes kits comprising a compound of Formula I, or a stereoisomer, geometric isomer, tautomer, solvate, metabolite, or pharmaceutically acceptable salt or prodrug thereof, a container, and optionally a package insert or label indicating a treatment.

Another aspect of the invention includes methods of preparing, methods of separating, and methods of purifying compounds of Formula I.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkyl" includes saturated linear or branched-chain monovalent hydrocarbon radicals of one to six carbon atoms (e.g., $C_1$-$C_6$ alkyl), wherein the alkyl radical may be optionally substituted independently with one or more substituents described below.

The term "$C_1$-$C_6$ fluoroalkyl" includes an alkyl group of 1-6 carbons substituted with a fluoro group. The fluoro group can be substituted at any place on the alkyl group. Examples include, but are not limited to, $CH_2F$, $CH_2CH_2F$, $CH_2CH_2CH_2F$, $CH_2CH_2CH_2CH_2F$, $CH_2CH_2CH_2CH_2CH_2F$, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—$C≡CH$), propynyl (propargyl, —$CH_2C≡CH$), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene, substituted benzenes, naphthalene, anthracene, biphenyl, indenyl, indanyl, 1,2-dihydronapthalene, 1,2,3,4-tetrahydronapthyl, and the like.

The terms "heterocycle," "hetercyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorous and sulfur, the remaining ring atoms being C, where one or more ring atoms is optionally substituted independently with one or more substituents described below. A heterocycle may be a monocycle having 3 to 7 ring members (2 to 6 carbon atoms and 1 to 3 heteroatoms selected from N, O, P, and S) or a bicycle having 6 to 10 ring members (4 to 9 carbon atoms and 1 to 3 heteroatoms selected from N, O, P, and S), for example: a bicyclo[4, 5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The heterocyclyl may be a carbon radical or heteroatom radical. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are unsubstituted or substituted in one or more substitutable positions with various groups.

The terms "heterocycle," "hetercyclyl" and "heterocyclic ring" include a saturated or a partially unsaturated (i.e., having one or more double and/or triple bonds within the ring) carbocyclic radical of 3 to 20 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The heterocyclyl may be a carbon radical or heteroatom radical. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are unsubstituted or substituted in one or more substitutable positions with various groups.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl may be C-attached or N-attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Substituted alkyl", "substituted alkenyl", "substituted alkynyl", "substituted aryl", "substituted heteroaryl", "substituted heterocyclyl" and "substituted cycloalkyl" mean alkyl, alkenyl, alkynyl, aryl, heteroaryl, heterocyclyl and cycloalkyl, respectively, in which one or more hydrogen atoms are each independently replaced with a substituent. Typical substituents include, but are not limited to, F, Cl, Br, I, CN, $CF_3$, OR, R, =O, =S, =NR, =N$^+$(O)(R), =N(OR), =N$^+$(O)(OR), =N—NRR', —C(=O)R, —C(=O)OR, —C(=O)NRR', —NRR', —N$^+$RR'R", —N(R)C(=O)R', —N(R)C(=O)OR', —N(R)C(=O)NR'R", —SR, —OC(=O)R, —OC(=O)OR, —OC(=O)NRR', —OS(O)$_2$(OR), —OP(=O)(OR)$_2$, —OP(OR)$_2$, —P(=O)(OR)$_2$, —P(=O)(OR)NR'R", —S(O)R, —S(O)$_2$R, —S(O)$_2$NR, —S(O)(OR), —S(O)$_2$(OR), —SC(=O)R, —SC(=O)OR, =O and —SC(=O)NRR'; wherein each R, R' and R" is independently selected from H, $C_1$-$C_{12}$ alkyl, $C_2$-$C_8$ alkenyl, $C_2$-$C_8$ alkynyl, $C_6$-$C_{20}$ aryl and $C_2$-$C_{20}$ heterocyclyl. Substituents may also be combinations of alkyl, alkenyl, alkynyl, carbocycle, aryl, and heteroaryl radicals, such as cyclopropylmethyl, cyclohexylethyl, benzyl, and N-ethylmorpholino, and substituted forms thereof.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The terms "treating", "treat", or "treatment" embrace both preventative, i.e., prophylactic, and palliative treatment.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1 1 (*Angew Chem. Intl. Ed. Engl.* (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN®V (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhône -Poulenc Rorer, Antony, France); chloranbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that is less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the cMet inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt," as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The compounds of Formulas I also include other salts of such compounds which are not necessarily pharmaceutically acceptable salts, and which may be useful as intermediates for preparing and/or purifying compounds of Formulas I and/or for separating enantiomers of compounds of Formulas I.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy -protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p -toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

The term "mammal" includes, but is not limited to, humans, dogs, cats, horses, cows, pigs, and sheep, and poultry.

c-Met Inhibitor Compounds

The present invention provides heterobicyclic thiophene compounds, and pharmaceutical formulations thereof, that are potentially useful in the treatment of diseases, conditions and/or disorders modulated by c-Met. More specifically, the present invention provides compounds of Formula I

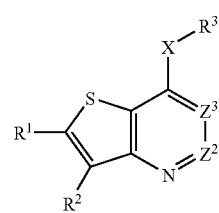

and stereoisomers, geometric isomers, tautomers, solvates, metabolites and pharmaceutically acceptable salts and prodrugs thereof, wherein:

X is O, S or $NR^{10}$;

$Z^2$ and $Z^3$ are independently selected from $CR^4$ and N, wherein only one of $Z^2$ and $Z^3$ is N;

$R^1$ is H, $C_1$-$C_{12}$ alkyl, $C_2$-$C_8$ alkenyl, $C_2$-$C_8$ alkynyl, —C(=O)$NR^{10}R^{11}$, —$(CR^{14}R^{15})_r NR^{10}R^{11}$, —$NR^{10}C(=Y)R^{11}$, —$NR^{10}C(=Y)OR^{11}$, —$NR^{12}C(=Y)NR^{11}R^{11}$, or $NR^{12}SO_2NR^{10}R^{11}$, or $R^1$ is a monocyclic or bicyclic $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from F, Cl, Br, I, CN, $CF_3$, oxo, $OR^{10}$, $SR^{10}$, —C(=Y)$R^{10}$, —C(=Y)$OR^{10}$, —C(=Y)$NR^{10}R^{11}$, —$(CR^{14}R^{15})_n$—$NR^{10}R^{11}$, —$NR^{10}C(=Y)R^{13}$, —$NR^{10}C(=Y)OR^{10}$, —$NR^{12}C(=Y)NR^{10}R^{11}$, —$NR^{12}SO_2R^{10}$, —OC(=Y)$R^{10}$, —OC(=Y)$OR^{10}$, —OC(=Y)$NR^{10}R^{11}$, —OS(O)$_2$($OR^{10}$), —OP(=Y)($OR^{10}$)($OR^{11}$), —OP($OR^{10}$)($OR^{11}$), —S(O)$R^{10}$, —S(O)$_2R^{10}$, —S(O)$_2NR^{10}R^{11}$, —S(O)($OR^{10}$), —S(O)$_2$($OR^{10}$), —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, —$(CR^{14}R^{15})_n$—$NR^{12}C(=O)(CR^{14}R^{15})_m NR^{10}R^{11}$, and —C(=O)($CR^{14}R^{15})_n NR^{10}R^{11}$;

$R^2$ and $R^4$ are independently H, F, Cl, Br, I, $CF_3$, CN, —C(=Y)$R^{10}$, —C(=Y)$OR^{10}$, —C(=Y)$NR^{10}R^{11}$, —$NR^{10}R^{11}$, —$NR^{10}C(=Y)R^{11}$, —$NR^{10}C(=Y)OR^{11}$, —$NR^{12}C(=Y)NR^{10}R^{11}$, —$NR^{12}SO_2NR^{10}R^{11}$, —$OR^{10}$, —OC(=Y)$R^{10}$, —OC(=Y)$OR^{10}$, —OC(=Y)$NR^{10}R^{11}$, —C(=O)$NR^{12}(CR^{14}R^{15})_n NR^{10}R^{11}$, —OP(=Y)($OR^{10}$)($OR^{11}$), —OP($OR^{10}$)($OR^{11}$), —$SR^{10}$, —S(O)$R^{10}$, —S(O)$_2R^{10}$, —S(O)$_2NR^{10}R^{11}$, —SC(=Y)$R^{10}$, —SC(=Y)$OR^{10}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, $OR^{10}$, and $NR^{10}R^{11}$;

$R^3$ is a monocyclic or bicyclic $C_3$-$C_{12}$ carbocyclyl, $C_2$-$C_{20}$ heterocyclyl, $C_6$-$C_{20}$ aryl or $C_1$-$C_{20}$ heteroaryl, wherein said carbocyclyl, heterocyclyl, aryl and heteroaryl are optionally substituted with one or more groups independently selected from F, Cl, Br, I, CN, $CF_3$, $OR^{10}$, $SR^{10}$, —C(=Y)$R^{10}$, —C(=Y)$OR^{10}$, —C(=Y)$NR^{10}R^{11}$, —$NR^{10}R^{11}$, —$NR^{10}C$ (=Y)R$^{13}$, —NR$^{10}$C(=Y)OR$^{11}$, —NR$^{12}$C(=Y)NR$^{10}$R$^{11}$, —NR$^{12}$C(=O)C(=O)R$^{10}$R$^{11}$, —NR$^{12}$C(=O)C(=O) NR$^{10}$R$^{11}$, —NR$^{12}$C(=O)C(=O)OR$^a$, —NR$^{12}$SO$_2$R$^{10}$, —NR$^{12}$C(=Y$^1$)(CR$^{14}$R$^{15}$)$_n$C(=Y$^2$)NR$^{10}$R$^{11}$, —NR$^{12}$C(=Y$^1$)NR$^{10}$C(=Y$^2$)(CR$^{14}$R$^{15}$)$_n$R$^{11}$, —NR$^{12}$C(=Y$^1$)(CR$^{14}$R$^{15}$)$_n$C(=Y$^2$)(CR$^{14}$R$^{15}$)$_m$R$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from F, Cl, Br, I, OH, alkyl, oxo, NR$^{10}$R$^{11}$, —C(=Y)NR$^{10}$R$^{11}$ and (CR$^{14}$R$^{15}$)$_n$-aryl;

R$^{10}$, R$^{11}$ and R$^{12}$ are independently H, OR$^a$, $C_1$-$C_{12}$ alkyl, $C_2$-$C_8$ alkenyl, or $C_2$-$C_8$ alkynyl, or monocyclic or bicyclic $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, SO$_2$R$^c$, CN, OR$^a$, NR$^a$R$^b$, C(=O)NR$^a$R$^b$, CR$^a$C(=O)R$^b$, $C_1$-$C_{12}$ alkyl, $C_2$-$C_8$ alkenyl, $C_2$-$C_8$ alkynyl, $C_3$-$C_{20}$ carbocyclyl, $C_6$-$C_{20}$ aryl, and $C_1$-$C_{20}$ heteroaryl;

or R$^{10}$ and R$^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, OR$^a$, NR$^a$R$^b$, CF$_3$, F, Cl, Br, I, SO$_2$R$^a$, C(=O)R$^a$, NR$^{10}$C(=Y)R$^{11}$, C(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl;

R$^{13}$ is H, $C_1$-$C_{12}$ alkyl, $C_2$-$C_8$ alkenyl, $C_2$-$C_8$ alkynyl, (CR$^{14}$R$^{15}$)$_n$-cycloalkyl, (CR$^{14}$R$^{15}$)$_n$-heterocyclyl, (CR$^{14}$R$^{15}$)$_n$-aryl, (CR$^{14}$R$^{15}$)$_n$-heteroaryl, (CR$^{14}$R$^{15}$)$_n$—O—(CR$^{14}$R$^{15}$)$_m$-aryl, (CR$^{14}$R$^{15}$)$_n$—OR$^{10}$, (CR$^{14}$R$^{15}$)$_n$—NR$^{10}$R$^{11}$, (CR$^{14}$R$^{15}$), —NR$^{10}$C(=O)R$^{11}$, or (CR$^{14}$R$^{15}$)$_n$—NR$^{10}$(SO$_2$Me)-R$^{11}$, wherein said alkyl, alkenyl, alkynyl, cycloalkyl, heterocycloalkyl, and heteroaryl portions are optionally substituted with one or more groups independently selected from F, Cl, Br, I, oxo, SO$_2$R$^c$, CN, OR$^a$, C(=O)R$^a$, C(=O)OR$^a$, NR$^a$R$^b$, NR$^a$C(=O)R$^b$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, and $C_1$-$C_{20}$ heteroaryl;

R$^{14}$ and R$^{15}$ are independently H, $C_1$-$C_{12}$ alkyl, or (CR$^{14}$R$^{15}$)$_t$-aryl, or R$^{14}$ and R$^{15}$ together with the atoms to which they are attached form a saturated or partially unsaturated $C_3$-$C_{12}$ carbocyclic ring;

or R$^{10}$ and R$^{15}$ together with the atoms to which they are attached form a saturated or partially unsaturated $C_1$-$C_{20}$ heterocyclic ring optionally substituted with one or more groups independently selected from F, Cl, Br, I, OR$^a$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl, or $C_1$-$C_{20}$ heteroaryl, wherein said alkyl and aryl are optionally substituted with one or more groups independently selected from F, Cl, Br, and I, or R$^{14}$ is null and R$^{10}$ and R$^{15}$ together with the atoms to which they are attached form a $C_1$-$C_{20}$ heteroaryl ring having one or more heteroatoms;

R$^a$ and R$^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more alkyl or halogen groups;

R$^c$ is $C_1$-$C_{12}$ alkyl or $C_6$-$C_{20}$ aryl, wherein said alkyl and aryl are optionally substituted with one or more groups independently selected from F, Cl, Br, I, OR$^a$ and C(=O)NR$^a$R$^b$;

Y, Y$^1$ and Y$^2$ are independently O or S;

t is 1, 2, 3, 4, 5 or 6; and n and m are independently 0, 1, 2, 3, 4, 5 or 6.

Compounds of Formula I include compounds wherein:

R$^3$ is a monocyclic or bicyclic $C_3$-$C_{12}$ carbocyclyl, $C_2$-$C_{20}$ heterocyclyl, $C_6$-$C_{20}$ aryl or $C_1$-$C_{20}$ heteroaryl, wherein said carbocyclyl, heterocyclyl, aryl and heteroaryl are optionally substituted with one or more groups independently selected from F, Cl, Br,; I, CN, CF$_3$, OR$^{10}$, SR$^{10}$, —C(=Y)R$^{10}$, —C(=Y)OR$^{10}$, —C(=Y)NR$^{10}$R$^{11}$, —NR$^{10}$R$^{11}$, —NR$^{10}$C(=Y)R$^{13}$, —NR$^{10}$C(=Y)OR$^{11}$, —NR$^{12}$C(=Y)NR$^{10}$R$^{11}$, —NR$^{12}$C(=O)C(=O)R$^{10}$R$^{11}$, —NR$^{12}$C(=O)C(=O)OR$^a$, —NR$^{12}$SO$_2$R$^{10}$, —NR$^{12}$C(=Y$^1$)(CR$^{14}$R$^{15}$)$_n$C(=Y$^2$)NR$^{10}$R$^{11}$, —NR$^{12}$C(=Y$^1$)NR$^{10}$C(=Y$^2$)(CR$^{14}$R$^{15}$)$_n$R$^{11}$, —NR$^{12}$C(=Y$^1$)(CR$^{14}$R$^{15}$)$_n$C(=Y$^2$)(CR$^{14}$R$^{15}$)$_m$R$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from F, Cl, Br, I, OH, alkyl, NR$^{10}$R$^{11}$, and (CR$^{14}$R$^{15}$)$_n$-aryl;

R$^{10}$, R$^{11}$ and R$^{12}$ are independently H, $C_1$-$C_{12}$ alkyl, $C_2$-$C_8$ alkenyl, or $C_2$-$C_8$ alkynyl, or monocyclic or bicyclic $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, SO$_2$R$^c$, CN, OR$^a$, NR$^a$R$^b$, C(=O)NR$^a$R$^b$, CR$^a$C(=O)R$^b$, $C_1$-$C_{12}$ alkyl, $C_2$-$C_8$ alkenyl, $C_2$-$C_8$ alkynyl, $C_6$-$C_{20}$ aryl, and $C_1$-$C_{20}$ heteroaryl;

R$^a$ and R$^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more alkyl groups.

Compounds of Formula I further include compounds of Formula Ib:

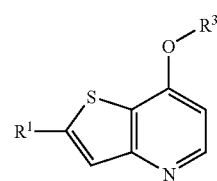

Ib and pharmaceutically acceptable salts thereof, wherein:

R$^1$ is H, $C_1$-$C_{12}$ alkyl, $C_2$-$C_8$ alkynyl, —C(=O)NR$^{10}$R$^{11}$, or R$^1$ is a monocyclic or bicyclic $C_3$-$C_{12}$ carbocyclyl, $C_2$-$C_{20}$ heterocyclyl, $C_6$-$C_{20}$ aryl or $C_1$-$C_{20}$ heteroaryl, wherein said alkyl, alkenyl, alkynyl, carbocyclyl, heterocyclyl, aryl and heteroaryl are optionally substituted with one or more groups independently selected from oxo, —C(=Y)R$^{10}$, —C(=Y)

OR$^{10}$, —C(=Y)NR$^{10}$R$^{11}$, —(CR$^{14}$R$^{15}$)$_n$—NR$^{10}$R$^{11}$, —NR$^{10}$C(=Y)R$^{13}$, C$_1$-C$_{12}$ alkyl, C$_2$-C$_{20}$ heterocyclyl, and C$_1$-C$_{20}$ heteroaryl; and R$^3$ is C$_6$-C$_{20}$ aryl or C$_1$-C$_{20}$ heteroaryl, wherein said aryl and heteroaryl are optionally substituted with one or more groups independently selected from F, Cl, —NR$^{10}$R$^{11}$, —NR$^{10}$C(=Y)R$^{13}$, —NR$^{10}$C(=Y)OR$^{11}$, —NR$^{12}$C(=Y)NR$^{10}$R$^{11}$, —NR$^{12}$C(=O)C(=O)NR$^{10}$R$^{11}$, —NR$^{12}$C(=O)C(=O)OR$^a$, —NR$^{12}$SO$_2$R$^{10}$, NR$^{12}$C(=Y$^1$)(CR$^{14}$R$^{15}$)$_n$C(=Y$^2$)NR$^{10}$R$^{11}$, —NR$^{12}$C(=Y$^1$)NR$^{10}$C(=Y$^2$)(CR$^{14}$R$^{15}$)$_n$R$^{11}$, —NR$^{12}$C(=Y$^1$)(CR$^{14}$R$^{15}$)$_n$C(=Y$^2$)(CR$^{14}$R$^{15}$)$_m$R$^{10}$, C$_1$-C$_{12}$ alkyl, C$_2$-C$_{20}$ heterocyclyl, and C$_1$-C$_{20}$ heteroaryl, wherein said alkyl, heterocyclyl, and heteroaryl are optionally substituted with one or more groups independently selected from F, Cl, Br, I, OH, C$_1$-C$_{12}$ alkyl, oxo, NR$^{10}$R$^{11}$, —C(=Y)NR$^{10}$R$^{11}$, and (CR$^{14}$R$^{15}$)$_n$-aryl.

Exemplary embodiments of Formula Ib include R$^3$ having the structure:

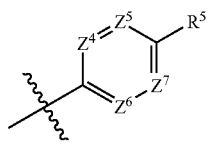

wherein:

the wavy line indicates the point of attachment to O;

Z$^4$, Z$^5$, Z$^6$, and Z$^7$ are independently CR$^4$ or N and 0, 1, or 2 of Z$^4$, Z$^5$, Z$^6$, and Z$^7$ is N, wherein when Z$^4$ and Z$^5$ or Z$^6$ and Z$^7$ are CR$^4$, then Z$^4$ and Z$^5$ or Z$^6$ and Z$^7$ optionally form a saturated, partially unsaturated or fully unsaturated carbocyclic or heterocyclic ring; and R$^5$ is F, Cl, —NR$^{10}$R$^{11}$, —NR$^{10}$C(=Y)R$^{13}$, —NR$^{10}$C(=Y)OR$^{11}$, —NR$^{12}$C(=Y)NR$^{10}$R$^{11}$, —NR$^{12}$C(=O)C(=O)NR$^{10}$R$^{11}$, —NR$^{12}$C(=O)C(=O)OR$^a$, —NR$^{12}$SO$_2$R$^{10}$, —NR$^{12}$C(=Y$^1$)(CR$^{14}$R$^{15}$)$_n$C(=Y$^2$)NR$^{10}$R$^{11}$, —NR$^{12}$C(=Y$^1$)NR$^{10}$C(=Y$^2$)(CR$^{14}$R$^{15}$)$_n$R$^{11}$, —NR$^{12}$C(=Y$^1$)(CR$^{14}$R$^{15}$)$_n$C(=Y$^2$)(CR$^{14}$R$^{15}$)$_m$R$^{10}$, C$_1$-C$_{12}$ alkyl, C$_2$-C$_{20}$ heterocyclyl, and C$_1$-C$_{20}$ heteroaryl, wherein said alkyl, heterocyclyl, and heteroaryl are optionally substituted with one or more groups independently selected from F, Cl, Br, I, OH, C$_1$-C$_{12}$ alkyl, oxo, NR$^{10}$R$^{11}$, —C(=Y)NR$^{10}$R$^{11}$, and (CR$^{14}$R$^{15}$)$_n$-aryl.

Compounds of the invention include Formula Ib when Z$^4$, Z$^5$, Z$^6$, and Z$^7$ are each CR$^4$; and R$^1$ is H, alkyl, or —C(=O)NR$^{10}$R$^{11}$; then R$^5$ is not F, Cl, —NR$^{10}$R$^{11}$, —NR$^{10}$C(=O)R$^{13}$, C$_1$-C$_{12}$ alkyl, or a C$_1$-C$_{20}$ heteroaryl other than a heteroaryl selected from the structures

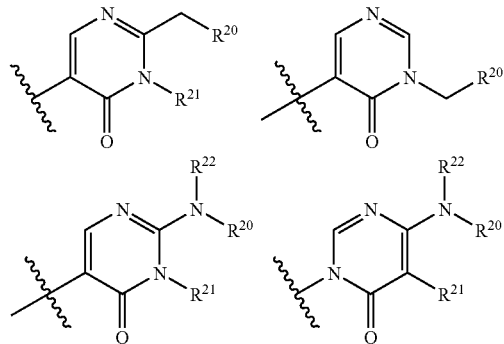

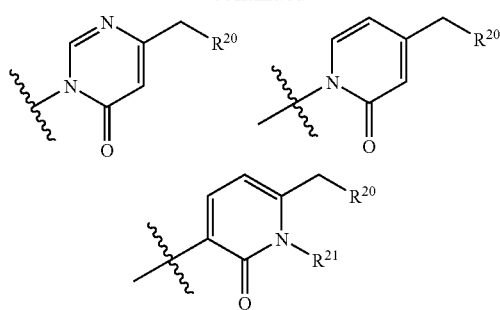

wherein R$^{20}$ is alkyl, cycloalkyl, aryl, or heteroaryl and R$^{21}$ and R$^{22}$ are independently selected from H or alkyl, wherein said alkyl, cycloalkyl, aryl, heteroaryl are optionally substituted with one or more groups independently selected from F, Cl, Br, I and alkyl.

In certain embodiments, the compounds of Formula I and Ib do not include the following compounds:

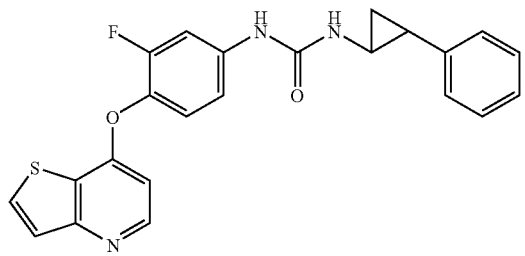

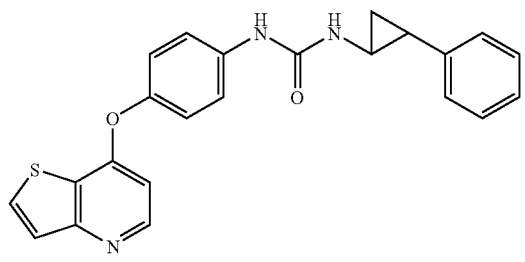

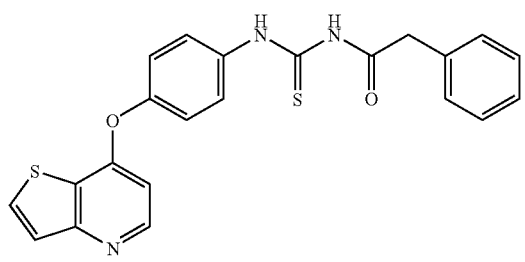

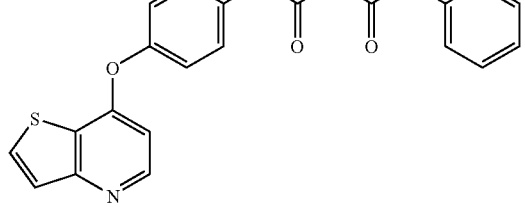

-continued

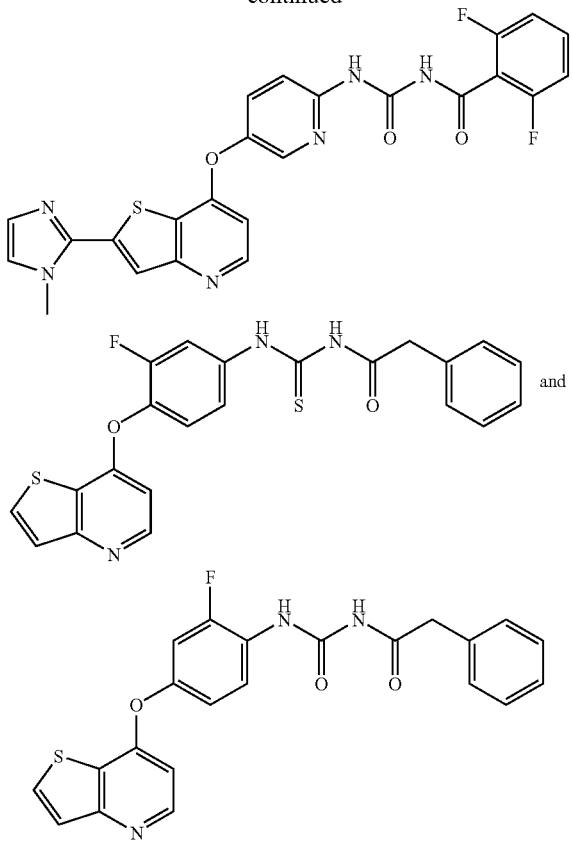

Compounds of the invention include compounds having the structure:

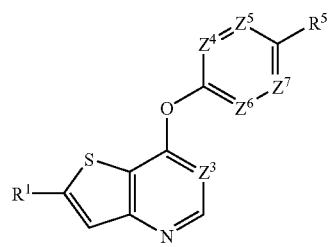

wherein when $Z^3$ is N or CH; $Z^4$, $Z^5$, $Z^6$, and $Z^7$ are each $CR^4$; and $R^1$ is H, alkyl, —C(=O)$NR^{10}R^{11}$ or —$(CR^{14}R^{15})_t$ $NR^{10}R^{11}$; then $R^5$ is not F, Cl, Br, I, CN, $CF_3$, $OR^{10}$, —C(=O)$R^{10}$, —C(=O)$OR^{10}$, —C(=O)$NR^{10}R^{11}$, —$NR^{10}R^{11}$, —$NR^{10}$C(=O)$R^{13}$—OC(=O)$R^{10}$, —OC(=O)$OR^{10}$, —S(O)$R^{10}$, —S(O)$_2R^{10}$, —S(O)$_2NR^{10}R^{11}$, —S(O)($OR^{10}$), $C_1$-$C_{12}$ alkyl, or a $C_1$-$C_{20}$ heteroaryl other than a heteroaryl selected from the structures Compounds of the invention include compounds having the structure:

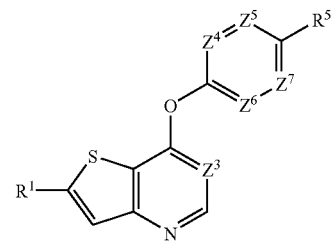

wherein $R^1$ and $Z^3$ are defined above, $Z^4$, $Z^5$, $Z^6$ and $Z^7$ are each independently N or $CR^4$, and $R^5$ is F, Cl, Br, I, CN, $CF_3$, $OR^{10}$, $SR^{10}$, —C(=Y)$R^{10}$, —C(=Y)$OR^{10}$, —C(=Y)$NR^{10}R^{11}$, —$NR^{10}R^{11}$, —$NR^{10}$C(=Y)$R^{13}$, —$NR^{10}$C(=Y)$OR^{11}$, —$NR^{12}$C(=Y)$NR^{10}R^{11}$, —$NR^{12}$C(=O)C(=O)$R^{10}R^{11}$, —$NR^{12}$C(=O)C(=O)$NR^{10}R^{11}$, —$NR^{12}$C(=O)C(=O)$OR^a$, —$NR^{12}SO_2R^{10}$, —$NR^{12}$C(=$Y^1$)$(CR^{14}R^{15})_n$C(=$Y^2$)$NR^{10}R^{11}$, —$NR^{12}$C(=$Y^1$)$NR^{10}$C(=$Y^2$)$(CR^{14}R^{15})_n$ $R^{11}$, —$NR^{12}$C(=$Y^1$)$(CR^{14}R^{15})_n$C(=$Y^2$)$(CR^{14}R^{15})_mR^{10}$, —OC(=Y)$R^{10}$, —OC(=Y)$OR^{10}$, —OC(=Y)$NR^{10}R^{11}$, —OS(O)$_2(OR^{10})$, —OP(=Y)$(OR^{10})(OR^{11})$, —OP($OR^{10}$)($OR^{11}$), —S(O)$R^{10}$, —S(O)$_2R^{10}$, —S(O)$_2NR^{10}R^{11}$, —S(O)($OR^{10}$), —S(O)$_2(OR^{10})$, —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from F, Cl, Br, I, OH, alkyl, oxo, $NR^{10}R^{11}$, —C(=Y)$NR^{10}R^{11}$ and $(CR^{14}R^{15})_n$-aryl.

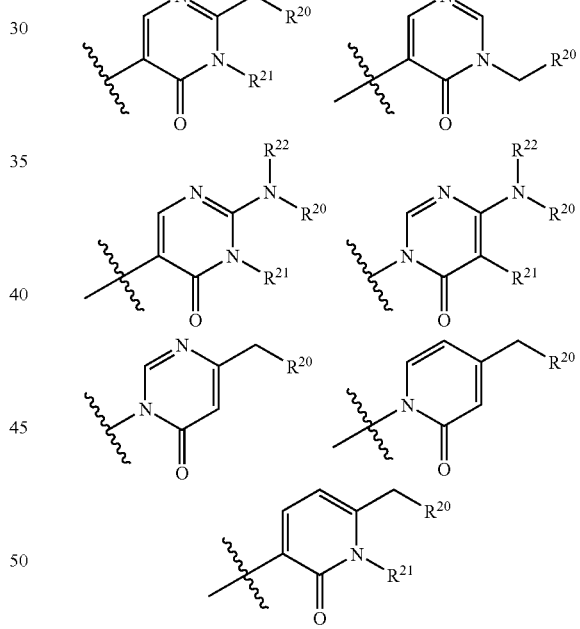

wherein $R^{20}$ is alkyl, cycloalkyl, aryl, heteroaryl and $R^{21}$ and $R^{22}$ are independently selected from H or alkyl, wherein said alkyl, cycloalkyl, aryl, heteroaryl are optionally substituted with one or more groups independently selected from F, Cl, Br, I and alkyl.

In certain embodiments, X is O.

In certain embodiments, X is S.

In certain embodiments, X is $NR^{10}$. In certain embodiments, $R^{10}$ is $C_1$-$C_6$ alkyl. In certain embodiments, X is NH.

In certain embodiments, $Z^2$ is CH, CCl or CF.

In certain embodiments, $Z^3$ is CH, CCl or CF.

Formula I compounds include embodiments wherein:

(i) $Z^2$ and $Z^3$ are $CR^4$, wherein each $R^4$ is independent of the other

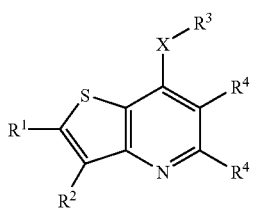

(ii) $Z^3$ is N and $Z^2$ is $CR^4$

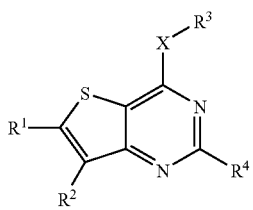

(iii) $Z^2$ is N and $Z^3$ is $CR^4$

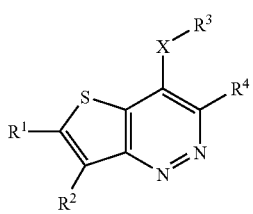

Exemplary embodiments of Formula I compounds include, but are not limited to, compounds wherein $R^1$ is optionally substituted alkynyl. In certain embodiments $R^1$ is —C≡C(CR$^{14}$R$^{15}$)$_n$—NR$^{10}$R$^{11}$, or —C≡C(CR$^{14}$R$^{15}$)$_n$NR$^{12}$C(=O)(CR$^{14}$R$^{15}$)$_m$NR$^{10}$R$^{11}$, wherein $R^{10}$, $R^{11}$, $R^{14}$, $R^{15}$, m and n are as defined herein. For example, in certain embodiments $R^1$ includes the following structures:

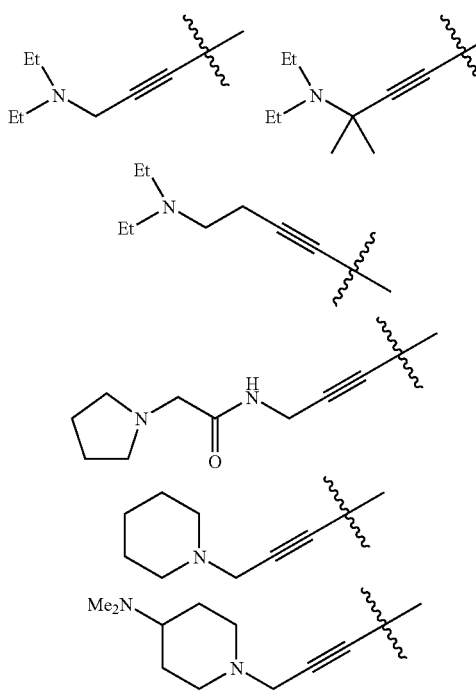

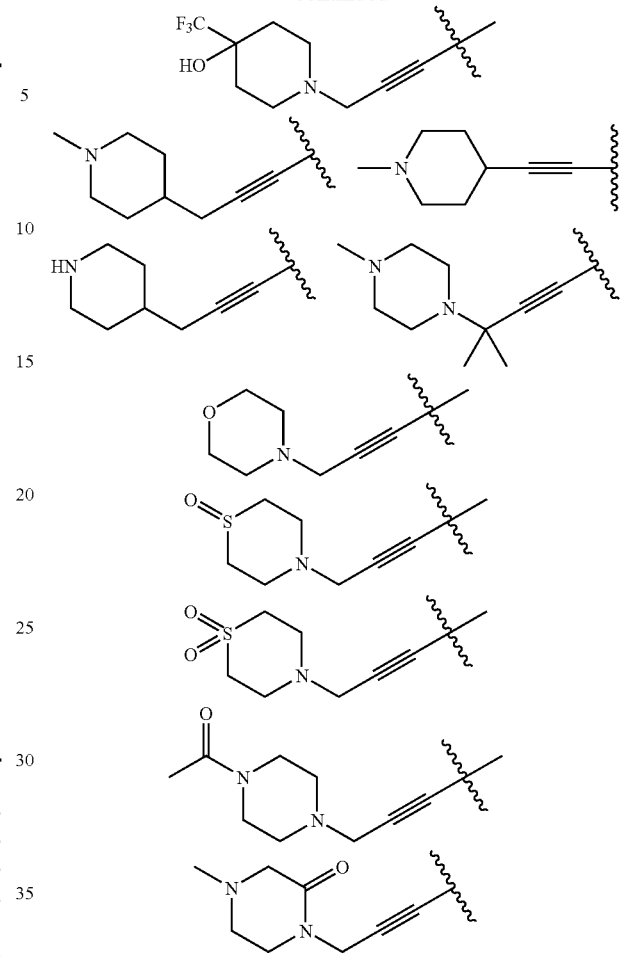

wherein the wavy line indicates the point of attachment to the 2-carbon of the thiophene ring.

In certain embodiments, $R^1$ is an optionally substituted alkynyl.

In certain embodiments, $R^1$ is an alkynyl substituted by an optionally substituted $C_5$-$C_8$ heterocyclyl.

In certain embodiments, $R^1$ is —C≡C(CR$^{14}$R$^{15}$)$_n$—NR$^{10}$R$^{11}$, or —C≡C(CR$^{14}$R$^{15}$)$_n$NR$^{12}$C(=O)(CR$^{14}$R$^{15}$)$_m$NR$^{10}$R$^{11}$.

In certain embodiments, n is 0 or 1.

In certain embodiments, m is 0 or 1.

In certain embodiments, $R^{10}$ is H or $C_1$-$C_6$ alkyl.

In certain embodiments, $R^{11}$ is H or $C_1$-$C_6$ alkyl.

In certain embodiments, $R^{10}$ and $R^{11}$ together with the atoms to which they are attached form a saturated or partially unsaturated 5 to 8 member heterocyclic ring, optionally having a second ring heteroatom selected from N, O, SO or SO$_2$, and optionally substituted with one or more groups independently selected from F, Cl, OR$^a$, $C_1$-$C_6$ alkyl, wherein said alkyl is optionally substituted with one or more groups independently selected from F or Cl.

In certain embodiments, $R^{12}$ is H or $C_1$-$C_6$ alkyl.

In certain embodiments, $R^{14}$ and $R^{15}$ are independently H or CH$_3$.

Additional embodiments also include compounds wherein $R^1$ is an optionally substituted alkynyl, for example:

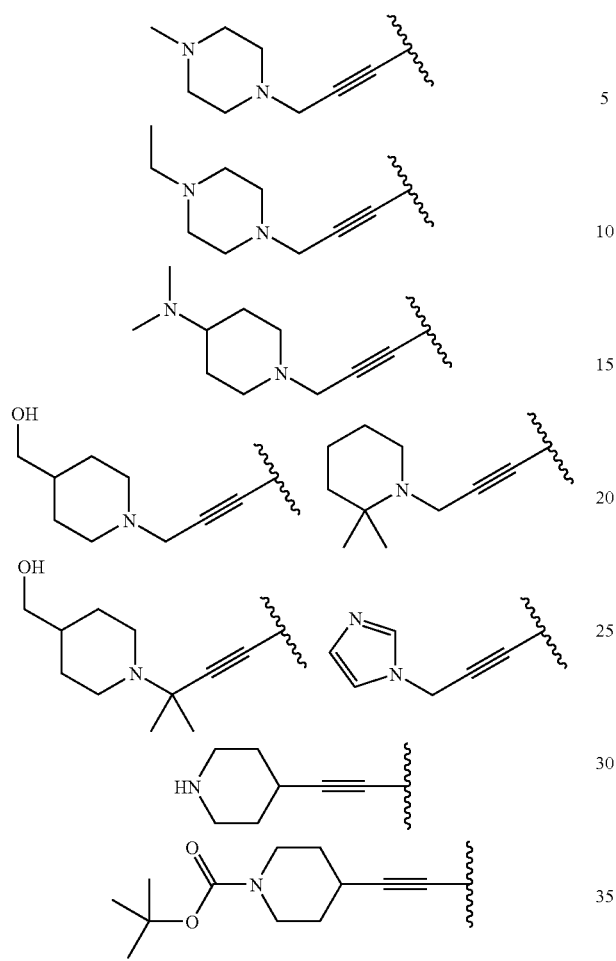
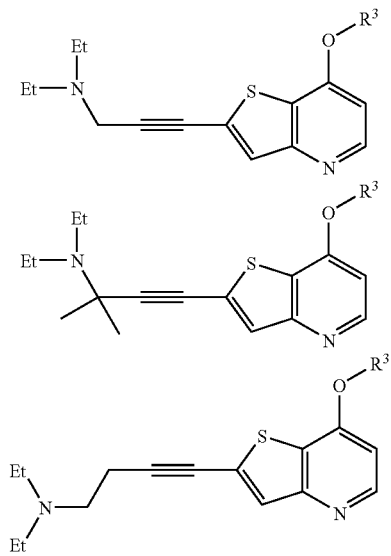
wherein the wavy line indicates the point of attachment to the 2-carbon of the thiophene ring.
Exemplary embodiments of Formula I compounds having such $R^1$ groups include the structures:
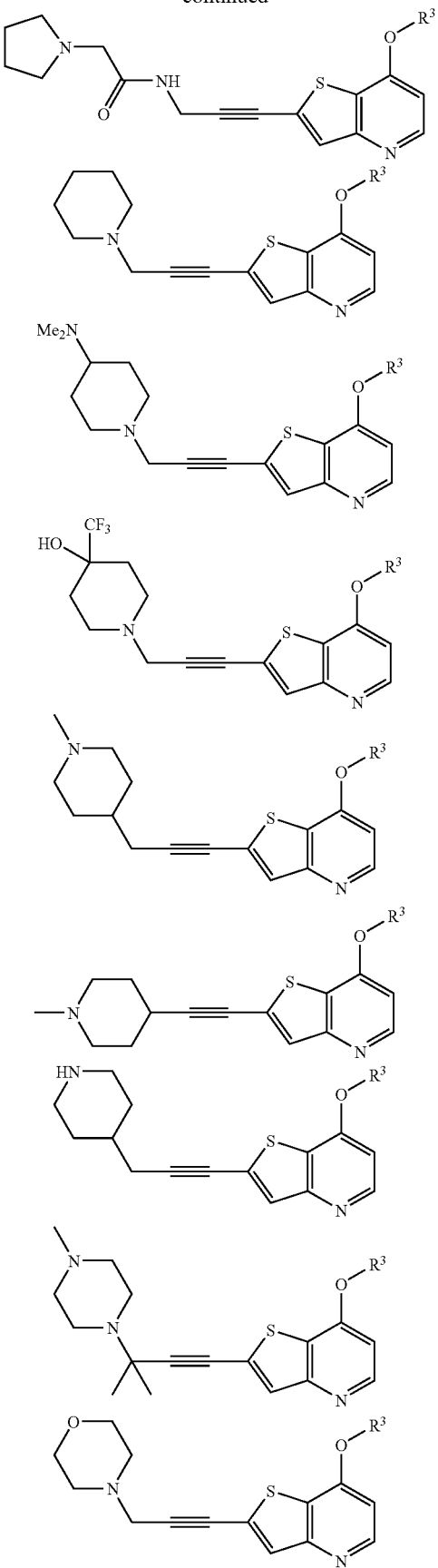

-continued

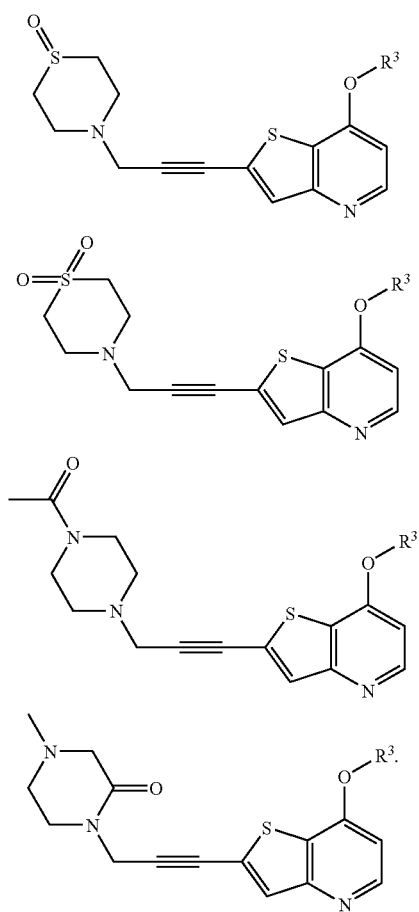

Exemplary embodiments of Formula I compounds also include compounds wherein $R^1$ is an optionally substituted aryl or heteroaryl. For example, in certain embodiments $R^1$ includes the structures:

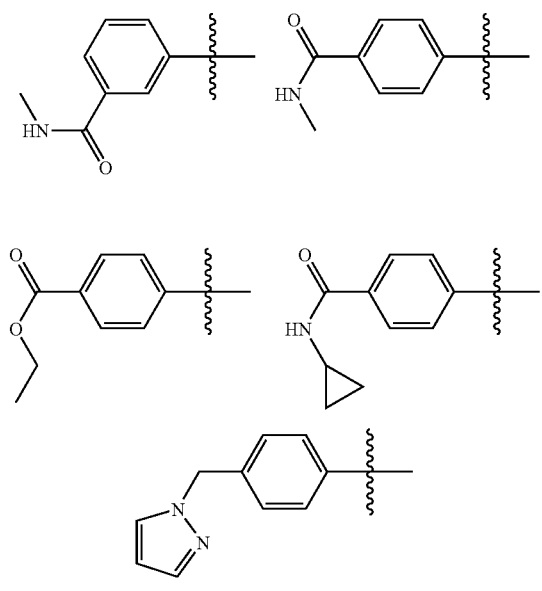

-continued

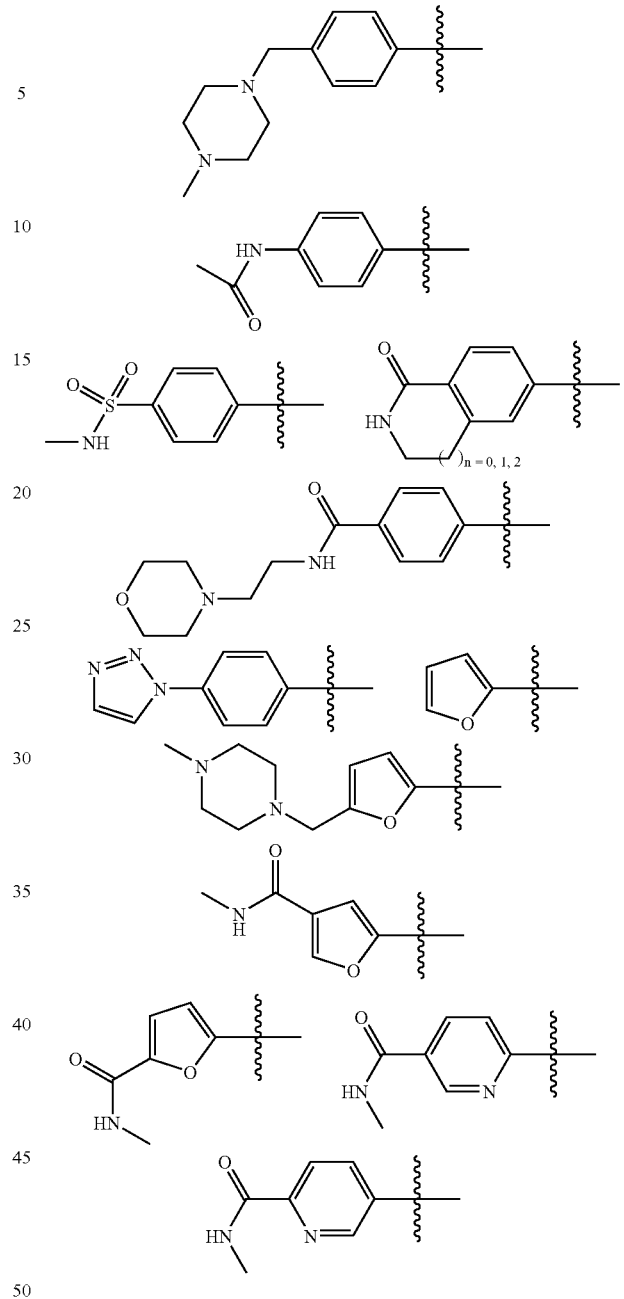

and substituted forms thereof, wherein the wavy line indicates the point of attachment to the 2-carbon of the thiophene ring. Exemplary embodiments of Formula I compounds having such $R^1$ groups include the structures:

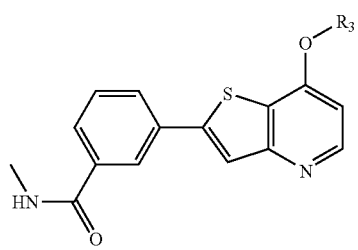

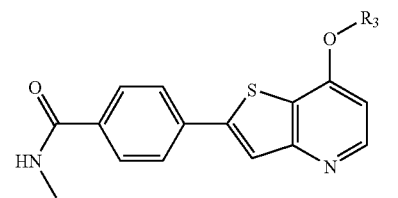
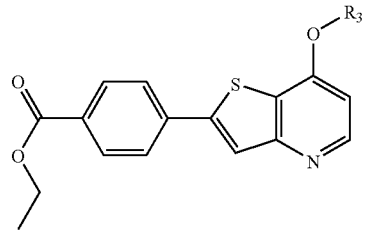
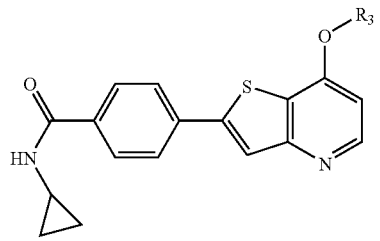
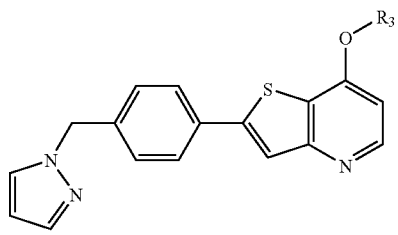
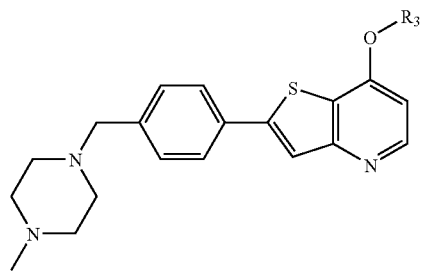
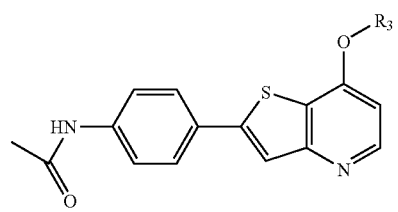
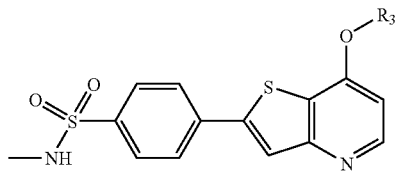
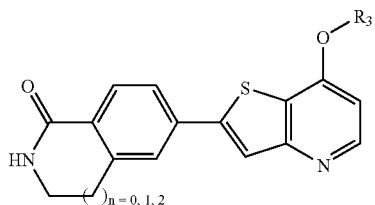
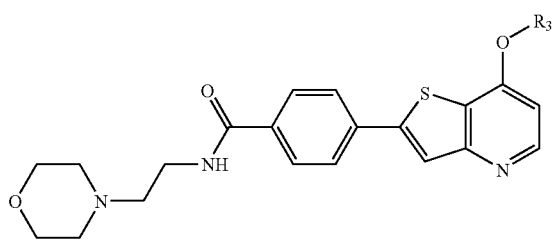
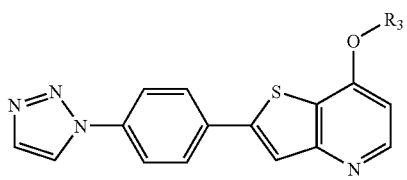
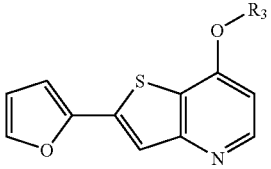
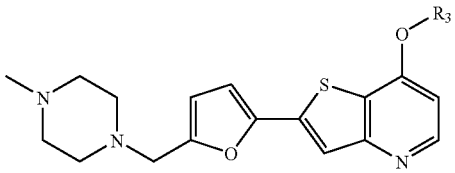
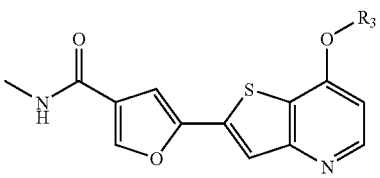
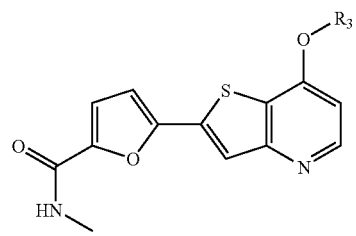
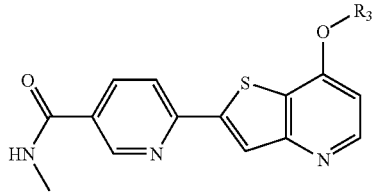

-continued

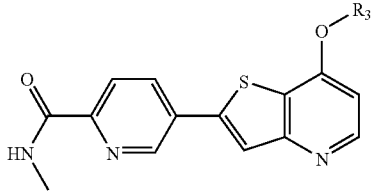

In certain embodiments, $R^1$ is phenyl optionally substituted with halogen (e.g., F or Cl), $C_1$-$C_6$ alkyl, $SO_2NH(C_1$-$C_6$ alkyl), heteroaryl or $CH_2$-heteroaryl (wherein said heteroaryl is a 5 or 6 membered ring having 2 or 3 ring nitrogen atoms and optionally substituted with $C_1$-$C_6$ alkyl), $CH_2$-hetCyc (wherein hetCyc is a 5 or 6 membered ring having 1 to 2 ring heteroatoms independently selected from N and O and optionally substituted with $C_1$-$C_6$ alkyl), $NR^hC(=O)R^i$, $C(=O)R^h$, $C(=O)NR^hR^i$, or $NR^hR^i$, wherein $R^h$ and $R^i$ are independently H, OH, $O(C_1$-$C_6$ alkyl), $C_1$-$C_6$ alkyl, $C_3$-$C_6$ carbocyclyl, or a 5 to 8 member heterocyclyl, wherein said $O(C_1$-$C_6$ alkyl), alkyl, carbocyclyl or heterocyclyl is optionally substituted with one or more groups selected from OH, $OCH_3$, $C_1$-$C_6$ alkyl and a 5 or 6 member heterocyclyl.

In certain embodiments, $R^1$ is a phenyl group fused to a 6, 7, or 8 membered azacyclic ring (such as a piperidinyl ring) optionally substituted with oxo.

In certain embodiments, $R^1$ is a 5 or 6 membered heteroaryl having one or two ring heteroatoms selected from N and O and optionally substituted with $C_1$-$C_6$ alkyl, $C(=O)NR^hR^i$ (wherein $R^h$ and $R^i$ are independently H, $C_1$-$C_6$ alkyl or $C_3$-$C_6$ carbocyclyl), hetCyc or $CH_2$-hetCyc, wherein hetCyc is a 5 or 6 membered azacycle (such as a piperazinyl group) optionally substituted with $C_1$-$C_6$ alkyl.

Additional embodiments also include compounds wherein $R^1$ is an optionally substituted aryl or heteroaryl, for example:

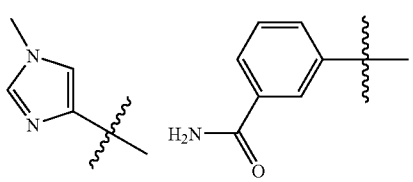

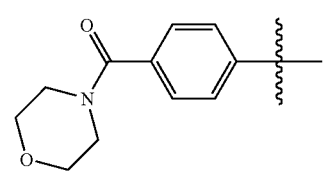

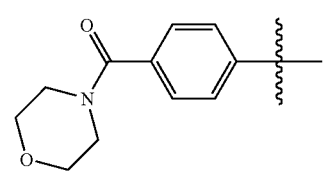

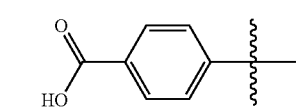

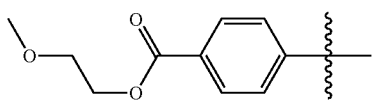

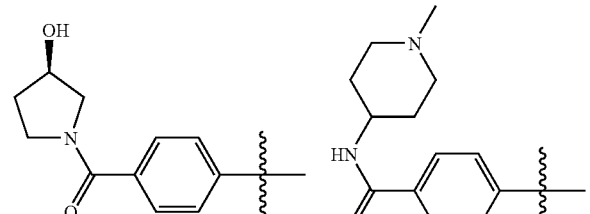

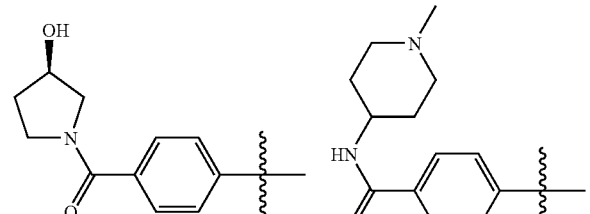

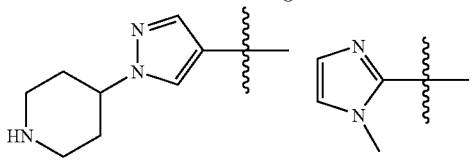

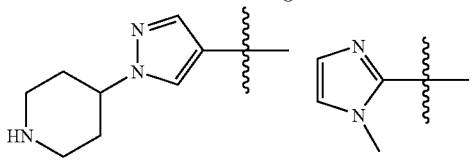

wherein the wavy line indicates the point of attachment to the 2-carbon of the thiophene ring.

Exemplary embodiments of Formula I compounds also include compounds wherein $R^1$ is $-C(=O)NR^{10}R^{11}$ or $-(CR^{14}R^{15})_tNR^{10}R^{11}$. For example, in certain embodiments $R^1$ is selected from the structures:

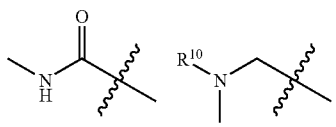

and substituted forms thereof, wherein the wavy line indicates the point of attachment to the 2-carbon of the thiophene ring.

In certain embodiments, $R^{14}$ and $R^{15}$ are H.

In certain embodiments, $R^{10}$ is H or $C_1$-$C_6$ alkyl.

In certain embodiments, $R^{11}$ is $C_1$-$C_6$ alkyl or ($C_1$-$C_6$ alkyl) $OR^h$ wherein $R^h$ is H or $C_1$-$C_6$ alkyl.

In certain embodiments, $R^{10}$ and $R^{11}$ together with the nitrogen atom to which they are attached form a 6 membered ring optionally having a second ring heteroatom selected from N and O optionally substituted with $C_1$-$C_6$ alkyl.

Additional embodiments also include compounds wherein $R^1$ is $-C(=O)NR^{10}R^{11}$, for example:

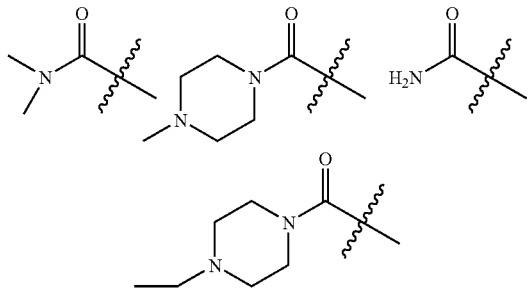

wherein the wavy line indicates the point of attachment to the 2-carbon of the thiophene ring.

Exemplary embodiments of Formula I compounds also include compounds wherein $R^1$ is an optionally substituted carbocyclyl or heterocyclyl. For example, in certain embodiments $R^1$ is selected from the structures:

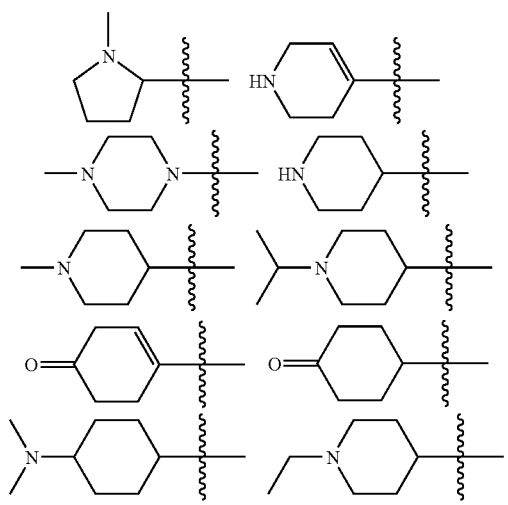

wherein the wavy line indicates the point of attachment to the 2-carbon of the thiophene ring.

In certain embodiments, R1 is 5 or 6 member carbocyclyl or heterocyclyl (having one or two hetero atoms) and optionally substituted by oxo or $C_1$-$C_6$ alkyl.

In certain embodiments of compounds of Formula I, $R^2$ and $R^4$ are independently F or Cl. Exemplary embodiments of compounds of Formula I having such $R^2$ and $R^4$ groups include, but are not limited to,

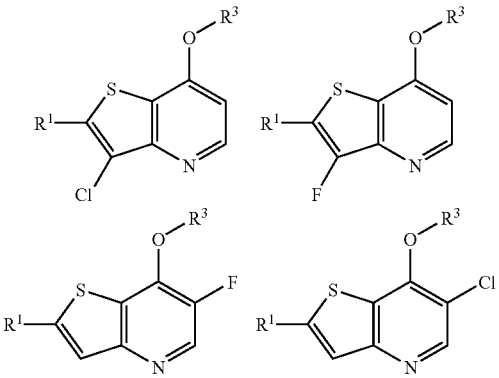

wherein $R^1$ and $R^3$ are as defined herein.

Exemplary embodiments of Formula I compounds include compounds wherein $R^3$ has the structure:

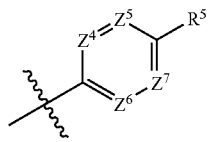

wherein:

the wavy line indicates the point of attachment to X;

$Z^4$, $Z^5$, $Z^6$, and $Z^7$ are independently $CR^4$ or N and 0, 1, or 2 of $Z^4$, $Z^5$, $Z^6$, and $Z^7$ is N, wherein when $Z^4$ and $Z^5$ or $Z^6$ and $Z^7$ are $CR^4$, then $Z^4$ and $Z^5$ or $Z^6$ and $Z^7$ optionally form a saturated, partially unsaturated or fully unsaturated carbocyclic or heterocyclic ring; and $R^5$ is F, Cl, Br, I, CN, $CF_3$, $OR^{10}$, $SR^{10}$, $-C(=Y)R^{10}$, $-C(=Y)OR^{10}$, $-C(=Y)NR^{10}R^{11}$, $-NR^{10}R^{11}$, $-NR^{10}C(=Y)R^{13}$, $-NR^{10}C(=Y)OR^{11}$, $-NR^{12}C(=Y)NR^{10}R^{11}$, $-NR^{12}C(=O)C(=O)R^{10}R^{11}$, $-NR^{12}C(=O)C(=O)NR^{10}R^{11}$, $-NR^{12}C(=O)C(=O)OR^a$, $-NR^{12}SO_2R^{10}$, $-NR^{12}C(=Y^1)(CR^{14}R^{15})_nC(=Y^2)NR^{10}R^{11}$, $-NR^{12}C(=Y^1)NR^{10}C(=Y^2)(CR^{14}R^{15})_nR^{11}$, $NR^{12}C(=Y^1)(CR^{14}R^{15})_nC(=Y^2)(CR^{14}R^{15})_mR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ cycloalkyl, $C_2$-$C_{20}$ heterocyclyl, $C_6$-$C_{20}$ aryl and $C_1$-$C_{20}$ heteroaryl, wherein said alkyl, alkenyl, alkynyl, cycloalkyl, heterocyclyl, aryl and heteroaryl are optionally substituted with one or more groups independently selected from alkyl, $NR^{10}R^{11}$, and $(CR^{14}R^{15})_n$-aryl.

$R^5$ includes F, Cl, Br, I, CN, $CF_3$, $OR^{10}$, $SR^{10}$, $-C(=Y)R^{10}$, $-C(=Y)OR^{10}$, $-C(=Y)NR^{10}R^{11}$, $-NR^{10}R^{11}$, $-NR^{10}C(=Y)R^{13}$, $-NR^{10}C(=Y)OR^{11}$, $-NR^{12}C(=Y)NR^{10}R^{11}$, $-NR^{12}C(=O)C(=O)R^{10}R^{11}$, $-NR^{12}C(=O)C(=O)OR^a$, $-NR^{12}SO_2R^{10}$, $-NR^{12}C(=Y^1)(CR^{14}R^{15})_nC(=Y^2)NR^{11}$, $-NR^{12}C(=Y^1)NR^{10}C(=Y^2)(CR^{14}R^{15})_nR^{11}$, $-NR^{12}C(=Y^1)(CR^{14}R^{15})_nC(=Y^2)(CR^{14}R^{15})_mR^{10}$, $-OC(=Y)R^{10}$, $-OC(=Y)OR^{10}$, $-OC(=Y)NR^{10}R^{11}$, $-OS$ (O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ cycloalkyl, C$_2$-C$_{20}$ heterocyclyl, C$_6$-C$_{20}$ aryl and C$_1$-C$_{20}$ heteroaryl, wherein said alkyl, alkenyl, alkynyl, cycloalkyl, heterocyclyl, aryl and heteroaryl are optionally substituted with one or more groups independently selected from alkyl, NR$^{10}$R$^{11}$, and (CR$^{14}$R$^{15}$)$_n$-aryl.

In certain embodiments of R$^3$ as defined above, R$^4$ is CH or N.

For example, in certain embodiments of Formula I compounds R$^3$ is selected from the structures:

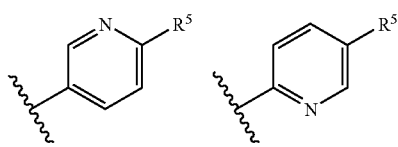

lp;lp

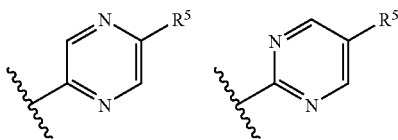

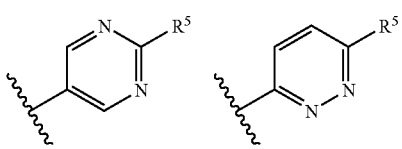

and substituted forms thereof, wherein the wavy line indicates the point of attachment to X, and R$^5$ is as defined herein. For example, in certain embodiments R$^3$ is selected from the structures:

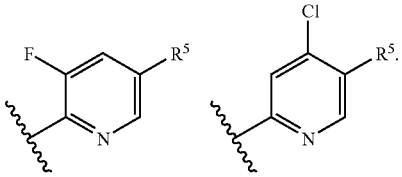

Additional embodiments of R$^3$ include the structures:

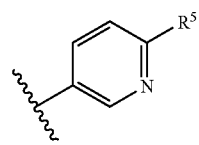

and substituted forms thereof, wherein the wavy line indicates the point of attachment to X, and R$^5$ is as defined herein. For example, in certain embodiments R$^3$ is selected from the structures:

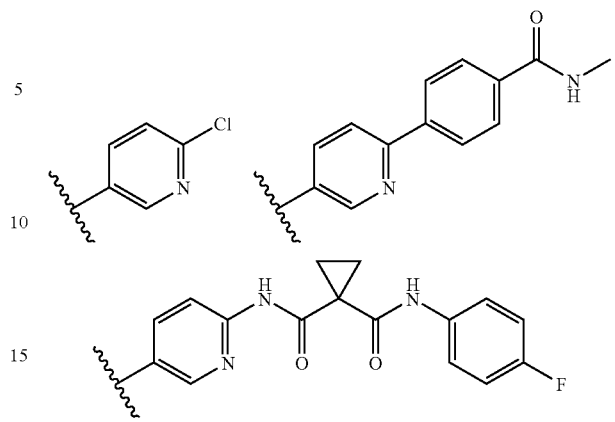

Further exemplary embodiments of Formula I compounds include compounds wherein R$^3$ has the structure:

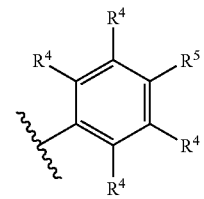

wherein the wavy line indicates the point of attachment to X, and R$^4$ and R$^5$ are as defined herein, and each R$^4$ is independent of the other. For example, in certain embodiments R$^3$ is selected from the structures:

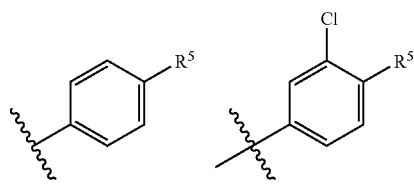
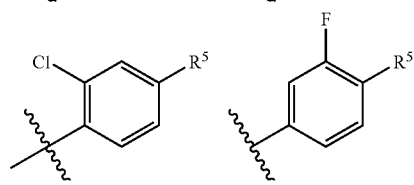
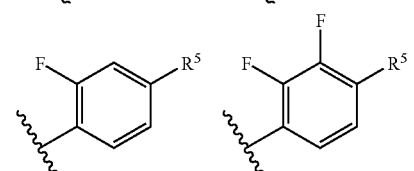
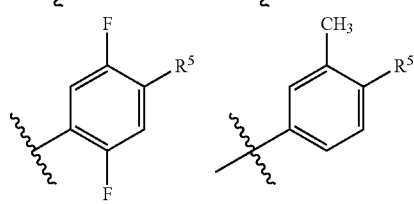

-continued

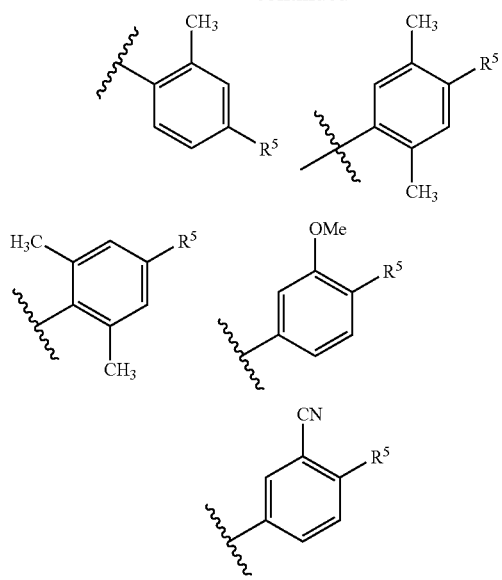

wherein the wavy line indicates the point of attachment to X, and $R^5$ is as defined herein.

In certain embodiments, each $R^4$ is independently selected from H, F, Cl, $C_1$-$C_6$ alkyl, O—($C_1$-$C_6$ alkyl), and CN.

Additional embodiments also include compounds wherein $R^3$ has the structure:

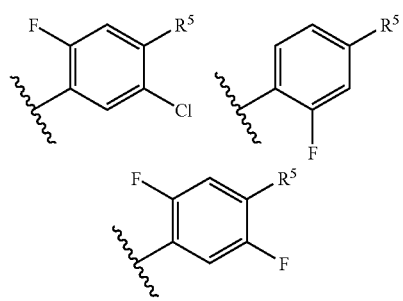

wherein the wavy line indicates the point of attachment to X, and $R^5$ is as defined herein.

Further exemplary embodiments of Formula I compounds include compounds wherein $R^3$ is

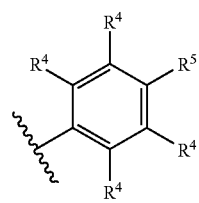

wherein $R^4$ and $R^5$ are as defined herein and wherein two of said $R^4$ groups together with the atoms to which they are attached form a saturated, partially unsaturated or fully unsaturated carbocyclic or heterocyclic ring. For example, in certain embodiments $R^3$ is selected from the structures:

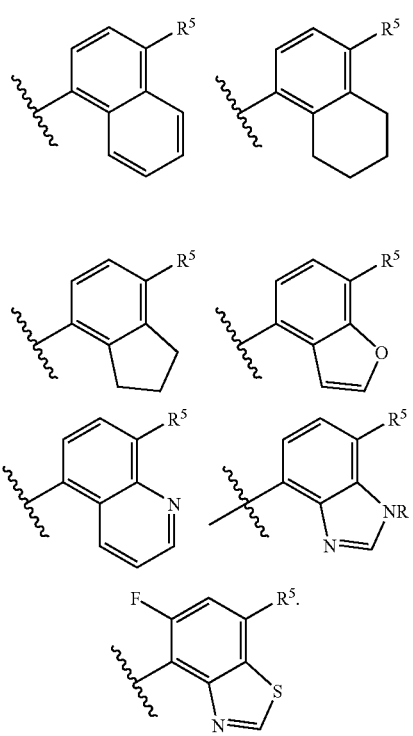

In certain embodiments of compounds of Formula I, $R^5$ has the structure:

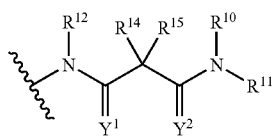

wherein $R^{10}$, $R^{11}$, $R^{12}$, $R^{14}$, $R^{15}$, $Y^1$ and $Y^2$ are as defined herein. For example, in certain embodiments $R^5$ is

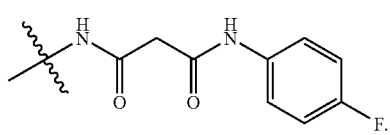

In certain embodiments, $Y^1$ is O.
In certain embodiments, $Y^2$ is O.
In certain embodiments, $R^{12}$ is H or $C_1$-$C_6$ alkyl.
In certain embodiments, $R^{14}$ is H.
In certain embodiments, $R^{15}$ is H.
In certain embodiments, $R^{10}$ is H.
In certain embodiments, $R^{11}$ is an aryl group optionally substituted with a halogen group. In a further embodiment, $R^{11}$ is a phenyl group optionally substituted with fluorine.

In other embodiments, $R^{14}$ and $R^{15}$ together with the atom to which they are attached form an optionally substituted carbocyclic ring. For example, in certain embodiments $R^5$ is:

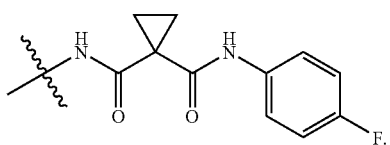

In other embodiments, $R^{15}$ and $R^{10}$ form an optionally substituted heterocyclic ring. For example, in certain embodiments $R^5$ is selected from the structures:

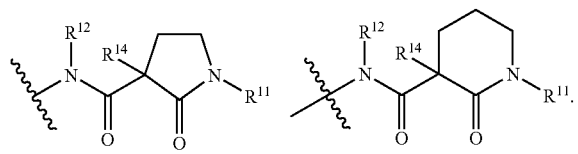

For example, in certain embodiments $R^5$ is selected from the structures:

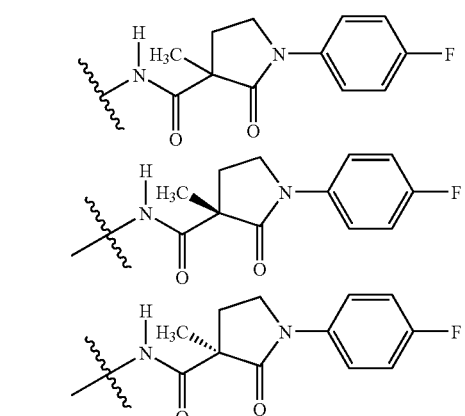

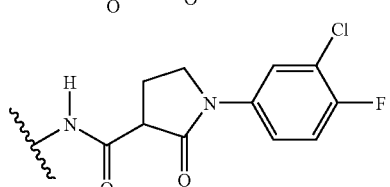

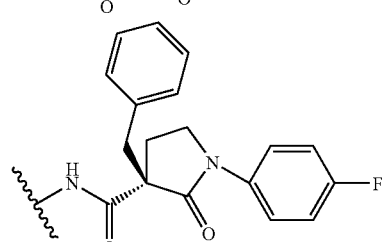

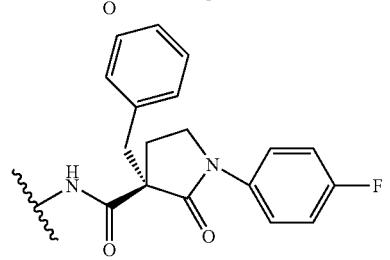

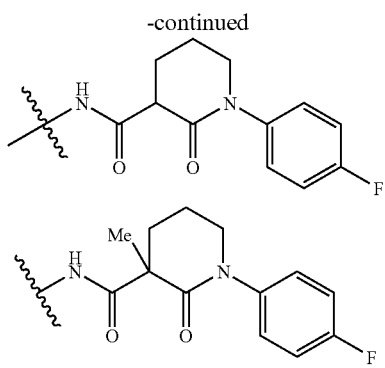

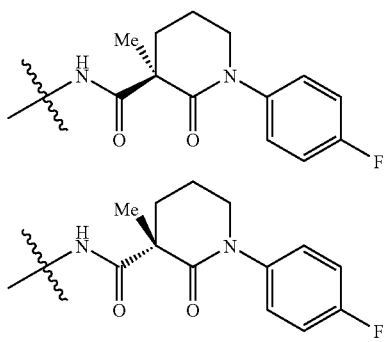

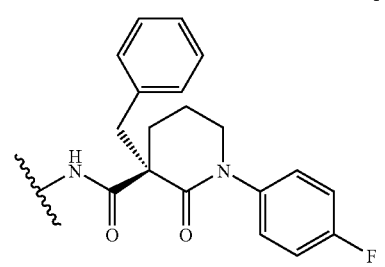

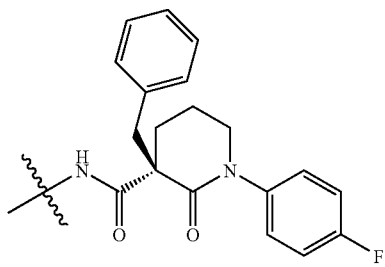

In certain embodiments, $R^{10}$ and $R^{15}$ together with the atoms to which they are attached form an oxo-substituted 5, 6, or 7 membered azacyclic ring.

In certain embodiments, $R^{12}$ is H.

In certain embodiments, $R^{14}$ is H, methyl, $CH_2(C_6H_5)$ or benzyl.

In certain embodiments, $R^{11}$ is H, $C_1$-$C_6$ alkyl, or phenyl optionally substituted with one or two groups independently selected from F and Cl.

In further exemplary embodiments, $R^{15}$ and $R^{10}$ together with the atoms to which they are attached form an oxo-substituted bicyclic azacyclic ring, for example an oxo-substituted 6 membered bicyclic azacyclic ring such as an azabicyclo[3.1.0]hexane group. An exemplary embodiment of $R^5$ includes the structure:

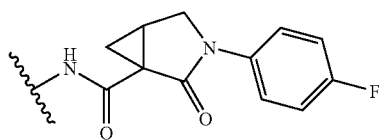

In certain embodiments, $R^{10}$ and $R^{15}$ together with the atoms to which they are attached form an oxo-substituted 6 membered heteroaryl ring having one or two ring nitrogen atoms.

In other embodiments, $R^{14}$ is null and $R^{10}$ and $R^{15}$ together with the atoms to which they are attached form an optionally substituted heteroaryl ring having a ring nitrogen atom and optionally having one or more additional heteroatoms selected from N, O and S. For example, in certain embodiments $R^5$ is selected from the structures:

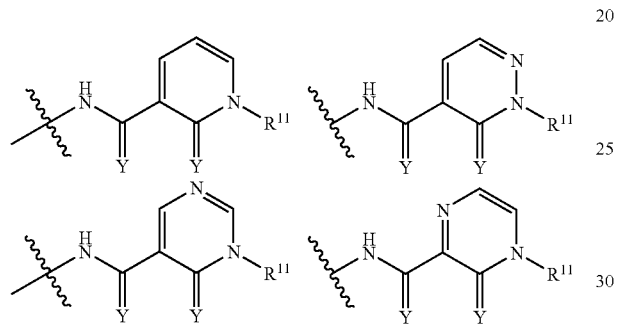

and substituted forms thereof. For example, in certain embodiments $R^5$ is selected from the structures:

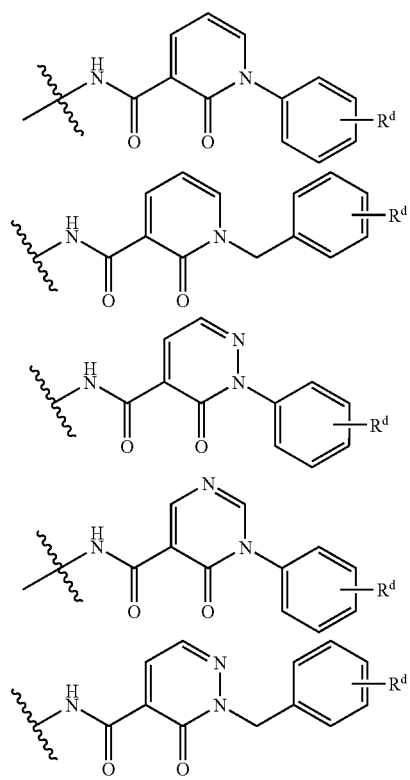

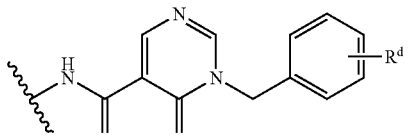
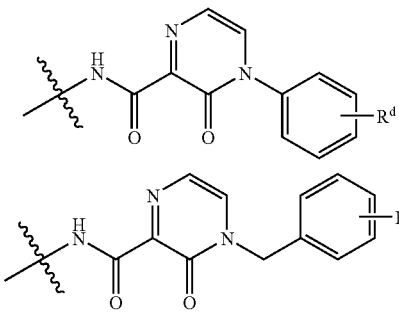
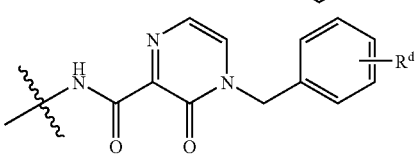
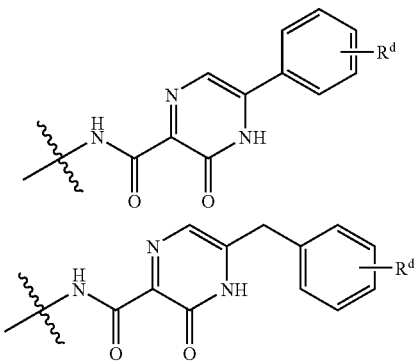

wherein the phenyl groups are optionally substituted with one or more $R^d$ groups independently selected from F, Cl, Br, I, $SO_2R^c$, CN, $OR^a$, $NR^aR^b$, $C(=O)NR^aR^b$, $CR^aC(=O)R^b$, $C_1$-$C_{12}$ alkyl, $C_2$-$C_8$ alkenyl, $C_2$-$C_8$ alkynyl, $C_6$-$C_{20}$ aryl, and $C_1$-$C_{20}$ heteroaryl. Exemplary embodiments of $R^5$ include the structures:

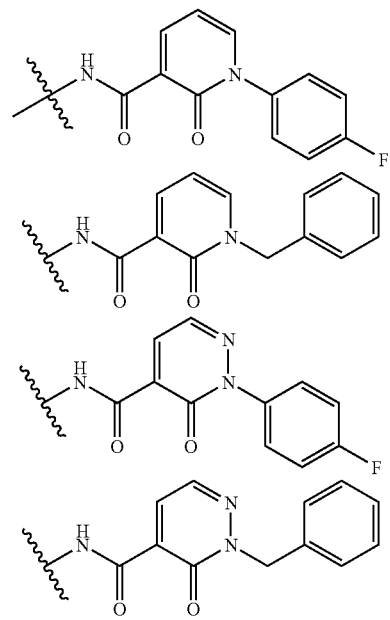

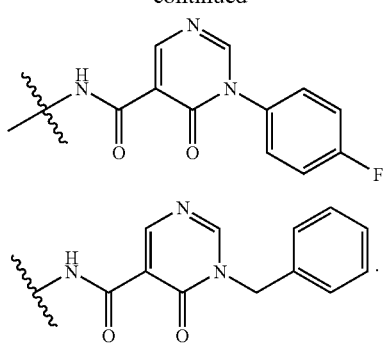

Additional embodiments of $R^5$ include the structures:

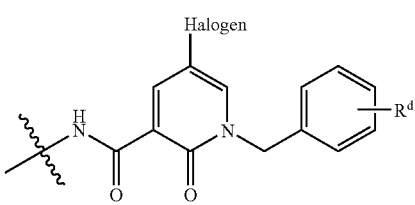

Additional exemplary embodiments of $R^5$ include the structures:

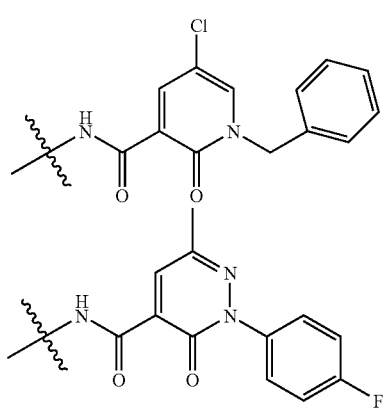

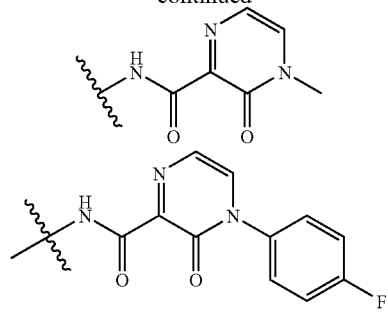

In certain embodiments, $Y^1$ is O.

In certain embodiments, $Y^2$ is O.

In certain embodiments, $R^{11}$ is phenyl optionally substituted with F.

In certain embodiments, $R^{11}$ is benzyl.

In certain embodiments, $R^{11}$ is $C_1$-$C_6$ alkyl.

In certain embodiments, the phenyl and cyclohexyl groups are optionally substituted with one $R^d$ group. In certain embodiments, $R^d$ is F.

In other embodiment, $R^{11}$ is alkyl.

In certain embodiments of compounds of Formula I, $R^5$ has the structure:

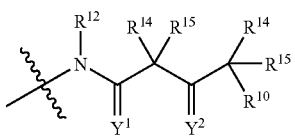

wherein $R^{10}$, $R^{12}$, $R^{14}$, $R^{15}$, $Y^1$ and $Y^2$ are as defined herein. In certain embodiments, $R^{14}$ and $R^{15}$ form an optionally substituted carbocyclic ring. For example, in certain embodiments $R^5$ is selected from the structures:

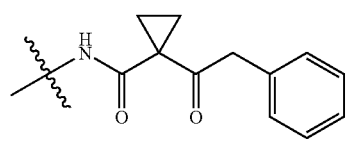

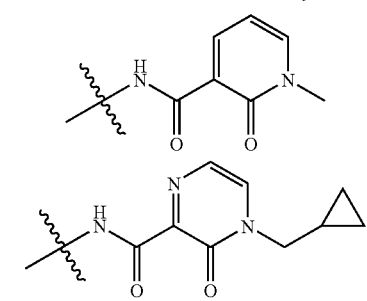

In certain embodiments, $Y^1$ is O.

In certain embodiments, $Y^2$ is O.

In certain embodiments, $R^{12}$ is H or $C_1$-$C_6$ alkyl.

In certain embodiments, $R^{10}$ is H, $C_1$-$C_6$ alkyl or $C_5$-$C_8$ aryl, wherein said alkyl and aryl are optionally substituted by halogen or alkyl.

In certain embodiments, $R^{14}$ is H, $C_1$-$C_6$ alkyl, or $C_3$-$C_6$ carbocyclyl.

In certain embodiments, $R^{15}$ is H, $C_1$-$C_6$ alkyl, or $C_3$-$C_6$ carbocyclyl.

In certain embodiments of compounds of Formula I, $R^5$ has the structure:

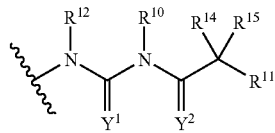

wherein $Y^1$, $Y^2$, $R^{10}$, $R^{11}$, $R^{12}$, $R^{14}$ and $R^{15}$ are as defined herein. In certain embodiments, $R^{11}$ is optionally substituted aryl. For example, in certain embodiments $R^5$ is:

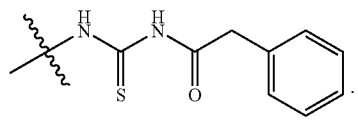

In certain embodiments, $Y^1$ is O.
In certain embodiments, $Y^2$ is O.
In certain embodiments, $R^{12}$ is H or $C_1$-$C_6$ alkyl.
In certain embodiments, $R^{10}$ is H or $C_1$-$C_6$ alkyl.
In certain embodiments, $R^{14}$ is H.
In certain embodiments, $R^{15}$ is H.
In certain embodiments, $R^{11}$ is phenyl optionally substituted with halogen, for example a fluoro group.

In certain embodiments of compounds of Formula I, $R^5$ has the structure:

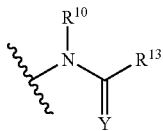

wherein Y, $R^{10}$ and $R^{13}$ are as defined herein. In certain embodiments, $R^{13}$ is alkyl, $(CR^{14}R^{15})_n$—O—$(CR^{14}R^{15})_m$-aryl, $(CR^{14}R^{15})_n$-aryl, $(CR^{14}R^{15})_n$-heteroaryl, $(CR^{14}R^{15})_n$-heterocyclyl, $(CR^{14}R^{15})_n$—$NR^{10}(SO_2Me)R^{11}$, or $(CR^{14}R^{15})_n$—$NR^{10}C(=O)R^{11}$, wherein said alkyl, aryl, heteroaryl and heterocyclyl portions are optionally substituted.

In certain embodiments of compounds of Formula I, $R^5$ has the structure:

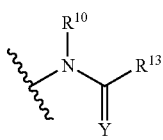

wherein Y, $R^{10}$ and $R^{13}$ are as defined herein. In certain embodiments, $R^{13}$ is alkyl, $(CR^{14}R^{15})_n$—O—$(CR^{14}R^{15})_m$-aryl, $(CR^{14}R^{15})$-aryl, $(CR^{14}R^{15})$-heteroaryl, $(CR^{14}R^{15})$-heterocyclyl, $(CR^{14}R^{15})$—$N(SO_2R^a)(CR^{14}R^{15})R^{11}$, or $(CR^{14}R^{15})NR^{10}C(=O)$-aryl, wherein said alkyl, aryl, heteroaryl and heterocyclyl portions are optionally substituted.

In certain embodiments, Y is O.
In certain embodiments, $R^{10}$ is H.
In particular embodiments, $R^{13}$ is $CR^{14}R^{15}O(CH_2)_m$-phenyl, wherein phenyl is optionally substituted with halogen (for example Cl), $R^{14}$ and $R^{15}$ are independently H or methyl and m is 0 or 1.

In particular embodiments, $R^{13}$ is $OR^a$, wherein $R^a$ is $C_1$-$C_6$ alkyl or phenyl.

In particular embodiments, $R^{13}$ is ($C_1$-$C_3$ alkyl)-phenyl.

In particular embodiments, $R^{13}$ is ($C_1$-$C_2$ alkyl)-hetAr wherein hetAr is a 6-9 membered heteroaryl monocyclic or bicyclic ring having one or two ring nitrogen atoms. A particular example of $R^{13}$ is ($C_1$-$C_2$ alkyl)-pyridyl.

In particular embodiments, $R^{13}$ is a 5-6 membered heteroaryl ring having 1 to 2 ring atoms independently selected from N, O and S and optionally substituted with one or two groups independently selected from NH-phenyl, morpholinyl, phenyl, and $C_1$-$C_6$ alkyl.

In particular embodiments, $R^{13}$ is phenyl optionally substituted with one or two groups independently selected from CN, F, phenyl, O-phenyl, $N(C_1$-$C_6$ alkyl)$_2$, and NHC(=O)($C_1$-$C_6$ alkyl).

In particular embodiments, $R^{13}$ is $CH_2$—$N(C_1$-$C_4$ alkyl)$SO_2R^a$ or $CH_2$—$N(CH_2Ph)SO_2R^a$. In particular embodiments, $R^a$ is $C_1$-$C_6$ alkyl, phenyl or a 5 membered heteroaryl ring having one or two ring heteroatoms independently selected from N and O and optionally substituted with $C_1$-$C_6$ alkyl.

In certain embodiments, $R^{13}$ is $(CH_2)_n$-hetCyc wherein n is 0 or 1 and hetCyc is a saturated or partially saturated 6 membered heterocyclic ring having a ring nitrogen atom and optionally substituted with oxo, C(=O)($C_1$-$C_6$ alkyl), $SO_2$($C_1$-$C_6$ alkyl), $SO_2$-phenyl or C(O)O($C_1$-$C_6$ alkyl).

In particular embodiments, $R^{13}$ is $C_1$-$C_6$ alkyl optionally substituted with ($C_3$-$C_6$)cycloalkyl or O—($C_1$-$C_6$ alkyl).

In particular embodiments, $R^{13}$ is $CH_2N(C_1$-$C_6$ alkyl)C(=O)phenyl.

For example, in certain embodiments $R^5$ is selected from the structures:

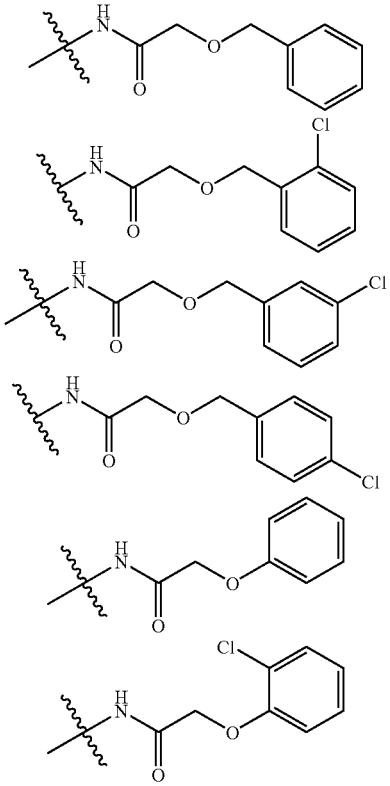

47
-continued
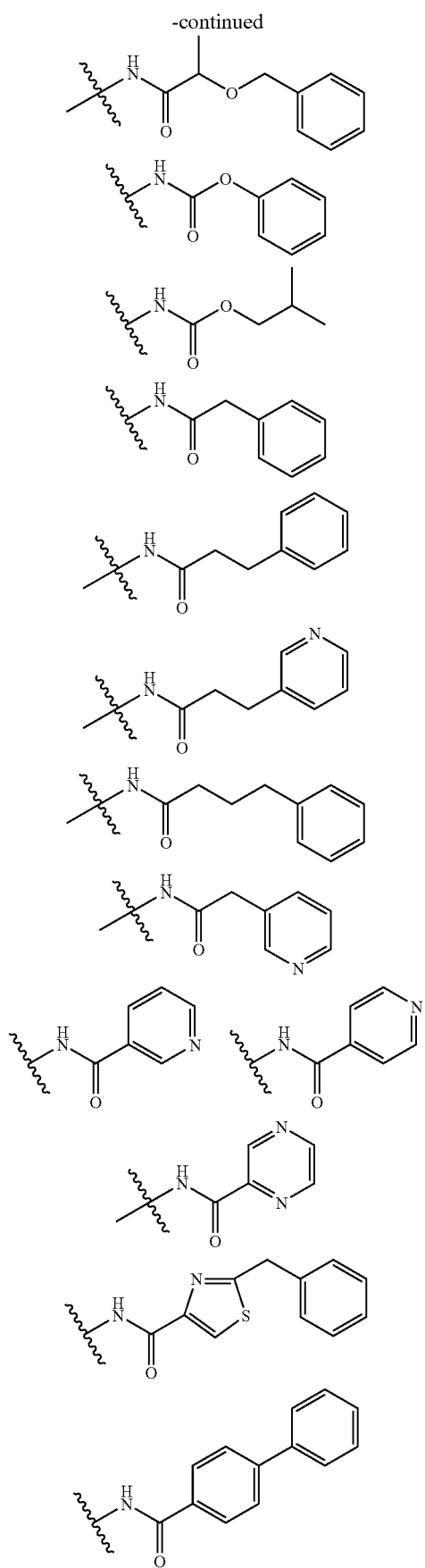
48
-continued
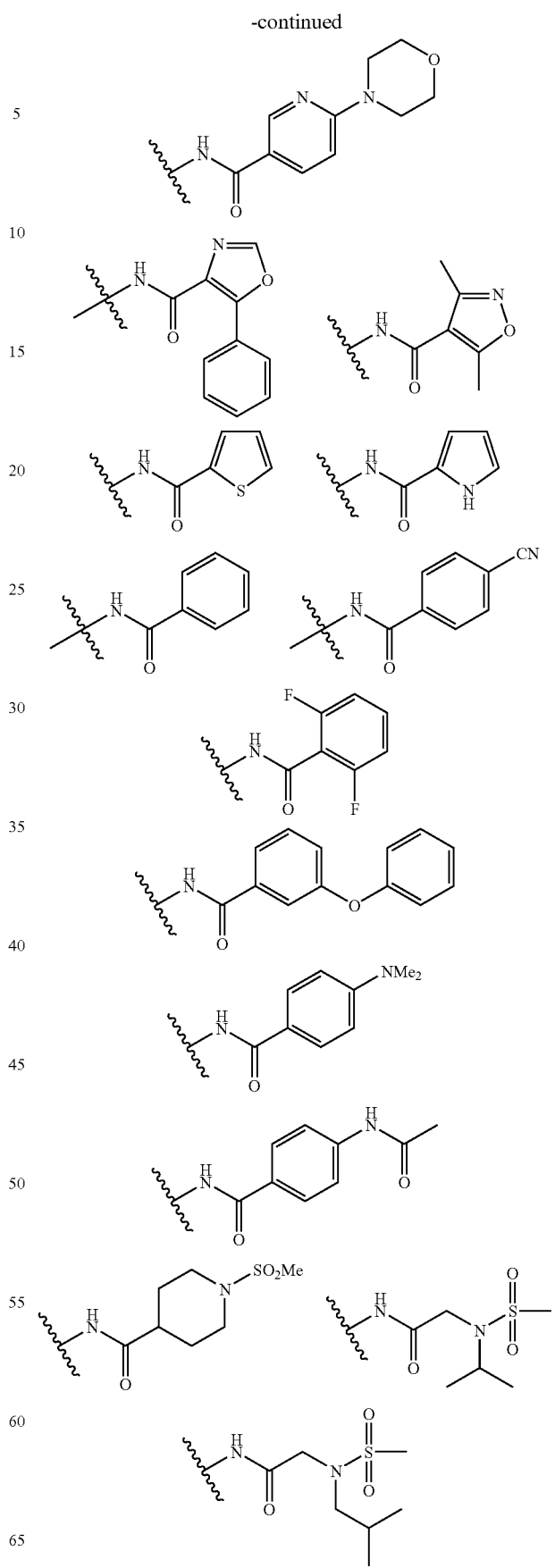

-continued

Additional embodiments of $R^5$ include the structures:

In certain embodiments of compounds of Formula I, $R^5$ has the structure

In certain embodiments, $R^{11}$ is optionally substituted aryl or heteroaryl. For example, in certain embodiments $R^5$ is selected from the structures:

Additional embodiments also include compounds wherein $R^5$ is selected from the structures:

In certain embodiments, $R^{10}$ is H or methyl.

In certain embodiments, $R^{11}$ is a 5-10 membered monocyclic or bicyclic heteroaryl having a ring nitrogen atom and optionally having a second heteroatom selected from N and O, wherein said heteroaryl is optionally substituted with $C_1$-$C_6$ alkyl.

In certain embodiments, $R^{12}$ is H.

In certain embodiments of compounds of Formula I, $R^5$ is $NR^{12}SO_2R^{10}$, wherein $R^{10}$ and $R^{12}$ are as defined herein. In certain embodiments, $R^{10}$ is an optionally substituted aryl. For example, in certain embodiments $R^5$ is selected from the structures:

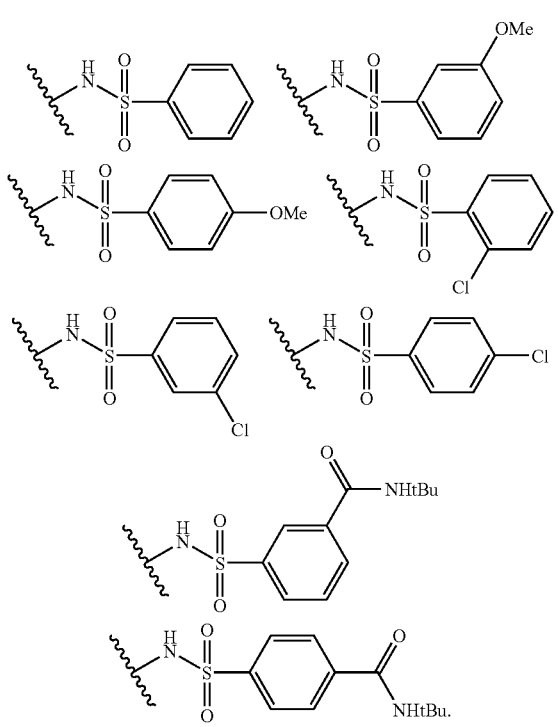

In certain embodiments, $R^{10}$ is phenyl optionally substituted with halogen, O—($C_1$-$C_6$ alkyl), or C(=O)NH($C_1$-$C_6$ alkyl).

In certain embodiments, $R^{12}$ is H.

In certain embodiments of compounds of Formula I, $R^5$ is $NR^{12}C(=O)C(=O)NR^{10}R^{11}$, wherein $R^{10}$, $R^{11}$ and $R^{12}$ are as defined herein. For example, in certain embodiments $R^5$ is selected from the structures:

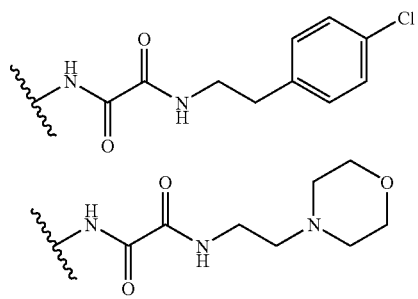

-continued

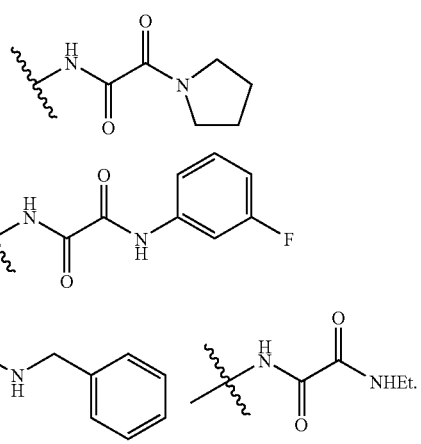

In certain embodiments, $R^{10}$ is H, $C_1$-$C_6$ alkyl, $(CH_2)_{0-2}$-phenyl optionally substituted with halogen, or a 5 or 6 membered heterocyclic ring having a ring nitrogen atom and optionally having a second heteroatom selected from N and O.

In certain embodiments, $R^{11}$ is H.

In certain embodiments, $R^{12}$ is H.

In certain embodiments of compounds of Formula I, $R^5$ is $NR^{12}C(=O)C(=O)OR^a$, wherein $R^{12}$ and $R^a$ are as defined herein. For example, in certain embodiments $R^5$ is

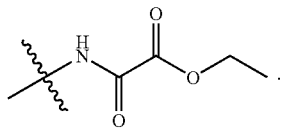

In certain embodiments, $R^{12}$ is H.

In certain embodiments, $R^a$ is $C_1$-$C_6$ alkyl.

In certain embodiments of compounds of Formula I, $R^5$ is an optionally substituted heteroaryl. For example, in certain embodiments, $R^5$ is selected from the structures:

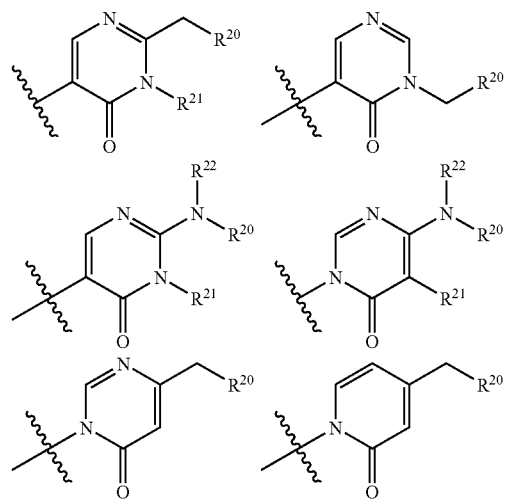

-continued

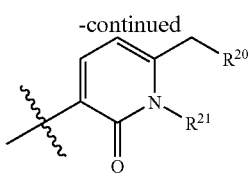

wherein $R^{20}$ is alkyl, cycloalkyl, aryl, or heteroaryl and $R^{21}$ and $R^{22}$ are independently selected from H or alkyl, wherein said alkyl, cycloalkyl, aryl, heteroaryl are optionally substituted with one or more groups independently selected from F, Cl, Br, I and alkyl. Exemplary embodiments of $R^5$ include the structures:

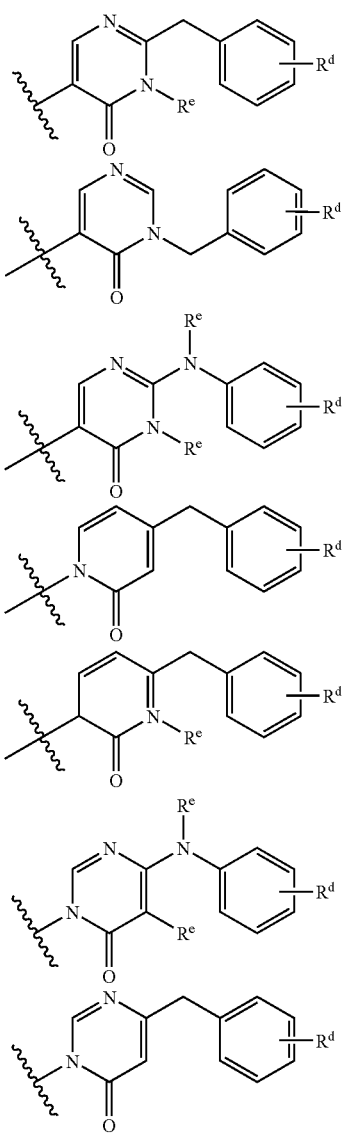

wherein $R^d$ is as defined herein and $R^e$ is H or an optionally substituted $C_1$-$C_4$ alkyl.

In certain embodiments, the phenyl group is substituted with one $R^d$ group.

In certain embodiments, $R^d$ is F, Cl, Br, I, SO2$R^c$, CN, O$R^a$, N$R^a R^b$, C(=O)N$R^a R^b$, C$R^a$C(=O)$R^b$, $C_1$-$C_{12}$ alkyl, $C_2$-$C_8$ alkenyl, $C_6$-$C_{20}$ aryl, and $C_1$-$C_{20}$ heteroaryl.

In certain embodiments, $R^e$ is independently H or $C_1$-$C_4$ alkyl.

In additional embodiments, $R^5$ is an optionally substituted heteroaryl is selected from the structures:

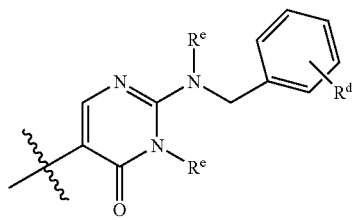

wherein $R^d$ is as defined herein and $R^e$ is H or an optionally substituted $C_1$-$C_4$ alkyl.

Further embodiments of $R^5$ include the structures:

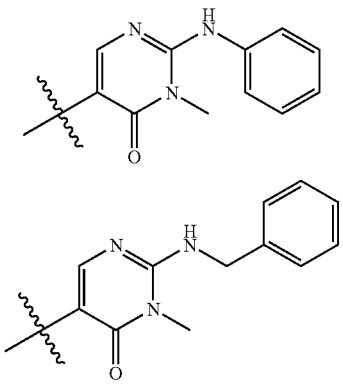

In certain embodiments of compounds of Formula I, $R^5$ is an optionally substituted heteroaryl. For example, in certain embodiments, $R^5$ is selected from the structure:

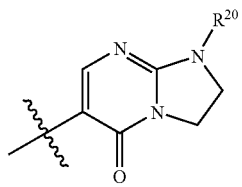

wherein $R^{20}$ is as defined herein. Exemplary embodiments of $R^5$ include the structures:

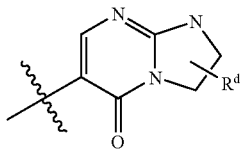

wherein $R^5$ is optionally substituted with one or more $R^d$.

Further embodiments of $R^5$ include the structure:

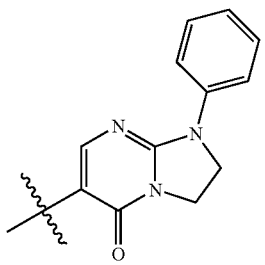

In certain embodiments of compounds of Formula I, $R^5$ is $-NR^{10}R^{11}$, wherein $R^{10}$ and $R^{11}$ are as defined herein. In certain embodiments, $R^{10}$ is H. In certain embodiments, $R^{11}$ is hetAr, wherein hetAr is a substituted or unsubstituted 5-6 membered heteroaryl group having at least one ring nitrogen atom and optionally having a second ring heteroatom selected from N and O. Examples of hetAr include pyridyl, isoxazolyl, and pyridazinyl groups. In certain embodiments, hetAr is substituted with one or two groups independently selected from $C_1$-$C_6$ alkyl and $C(=O)NR^aR^b$. In certain embodiments, $R^a$ is H. In certain embodiments, $R^b$ is phenyl optionally substituted with a halogen group. In certain embodiment, $R^b$ is $C_1$-$C_6$ alkyl, such as, but not limited to, methyl, ethyl or isopropyl. In certain embodiments, $R^b$ is a 6 membered heteroaryl having at least one nitrogen atom, for example pyridyl.

Exemplary embodiment of $R^5$ includes the structures:

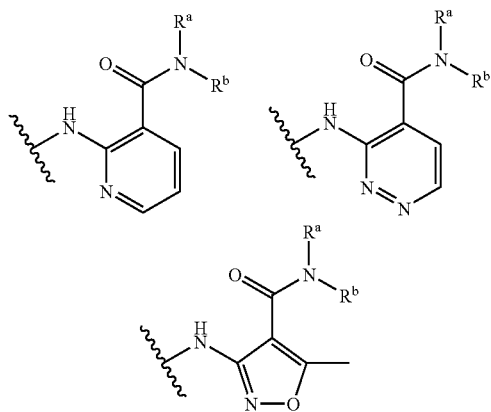

A particular embodiment of $R^5$ is the structure:

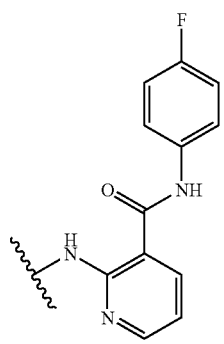

Another embodiment of the present invention provides a compound of Formula 1 as defined above and named in Examples 1-179.

The heterobicyclic thiophene compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a heterobicyclic thiophene compound of the present invention incorporates a double bond or a fused ring, the cis- and trans-forms, as well as mixtures thereof, are embraced within the scope of the invention. Both the single positional isomers and mixture of positional isomers, e.g., resulting from the N-oxidation of the pyrimidine and pyrazine rings, are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Synthesis of cMET Inhibitor Compounds

Heterobicyclic thiophene compounds of Formula I of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using procedures well-known to prepare 7-amino substituted thieno[3,2-b]pyridine compounds (Boschelli et al (2005) Bioorganic & Medicinal Chemistry Letters 15(21):4681-4684; Boschelli et al (2005) J. Med. Chem. 48(11):3891-3902; Boschelli et al (2004) J. Med. Chem. 47(27):6666-6668; US 2004/0242883; US 2004/0138251; WO 2004/048386; Munchhof et al (2004) Bioorganic & Medicinal Chemistry Letters 14(1):21-24; U.S. Pat. No. 6,833,456; Ragan et al (2003) Organic Process Research & Development 7(5):676-683; U.S. Pat. No. 6,492,383; US 2002/0004511; U.S. Pat. No. 6,964,961); 7-oxy substituted thieno[3,2-b]pyridine compounds (WO 2005/121125; WO 2005/080377; US 2005/0090509; US 2005/0070508; Boschelli et al (2004) J. Med. Chem. 47(27):6666-6668; U.S. Pat. No. 6,869,962; U.S. Pat. No. 6,833,456; US 2004/0171590); 7-thio substituted thieno[3,2-b]pyridine compounds (U.S. Pat. No. 6,232,320; WO 2000/075145; WO 99/62908); and other heterocycles, which are described in: Comprehensive Heterocyclic Chemistry, Editors Katrizky and Rees, Pergamon Press, 1984; Klemm et al. (1970) J. Hetero. Chem. 7(2):373-379; Klemm et al. (1974) J. Hetero. Chem. 11(3): 355-361; Klemm et al. (1976) J. Hetero. Chem. 13:273-275; Klemm et al. (1985) J. Hetero. Chem. 22(5): 1395-1396; Bisagni et al. (1974) Bull. Soc. Chim. Fr. (3-4, Pt. 2):515-518; Frehel et al. (1984) Heterocycles 22(5):1235-1247; WO 93/13664; WO 2004/012671; WO 2005/061476; U.S. Application Publication Nos. 2003/0045540, US 2003/0105089, and 2004/0024210; and U.S. Pat. Nos. 5,252,581, 6,232,320, and 6,579,882.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-14 show general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

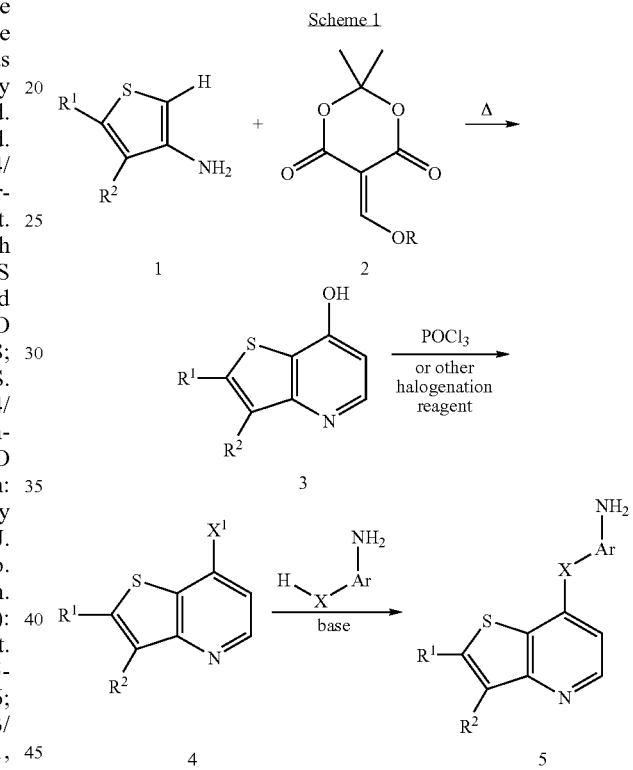

Scheme 1 shows a general scheme for the synthesis of intermediate compound 5, which is useful for the synthesis of compounds of Formula I. Syntheses of thieno[3,2-b]pyridines have been previously reported in WO 99/24440; WO 03/000194A2; WO 03/074529A2; and by Ragan, J. A. *Org. Proc. Res.* 2003, 7, 676; and Klemm, L. H., et al. *J. Hetero. Chem.* 1984, 21, 785. As shown in Scheme 1, reaction of a substituted 3-aminothiophene 1 ($R^1$ and $R^2$ are independently H, alkyl, alkenyl, alkynyl, aryl, halogen; see U.S. Pat. No. 6,492,383; Munchhof, M. J., et. al. *Tet. Lett.* 2004, 14(1), 21-24; Cioffi, C. L., et. al. *Synlett* 2004, 5, 841-845) with a vinyl ether of Meldrum's acid 2 (R=alkyl, such as methyl or ethyl) upon heating provides a Meldrum's acid enamine of the 3-aminothiophene (not shown). Such an enamine can be cyclized upon heating to provide phenol 3, wherein $R^1$ and $R^2$ are independently H, halogen, alkoxy, alkyl, alkenyl, alkynyl, aryl, heteroaryl, etc. Conversion of the phenol 3 to an aryl halide 4 ($X^1$=halogen or other leaving group such as triflate, etc.) can be achieved upon reaction with an appropriate electrophilic reagent (e.g. $POCl_3$, oxalyl chloride, $NCS/PPh_3$, POBr$_3$, NBS/PPh$_3$, CF$_3$SO$_2$Cl/2,6-lutidine, etc.). Nucleophilic substitution of aryl halide 4 with a compound of the formula HX—Ar—NH$_2$, wherein X is O, N or S, and Ar is an optionally substituted aryl or heteroaryl ring, can be conducted using an appropriate base (e.g. Cs$_2$CO$_3$, NaH, KOt-Bu, DMAP, or the like) to give intermediate 5.

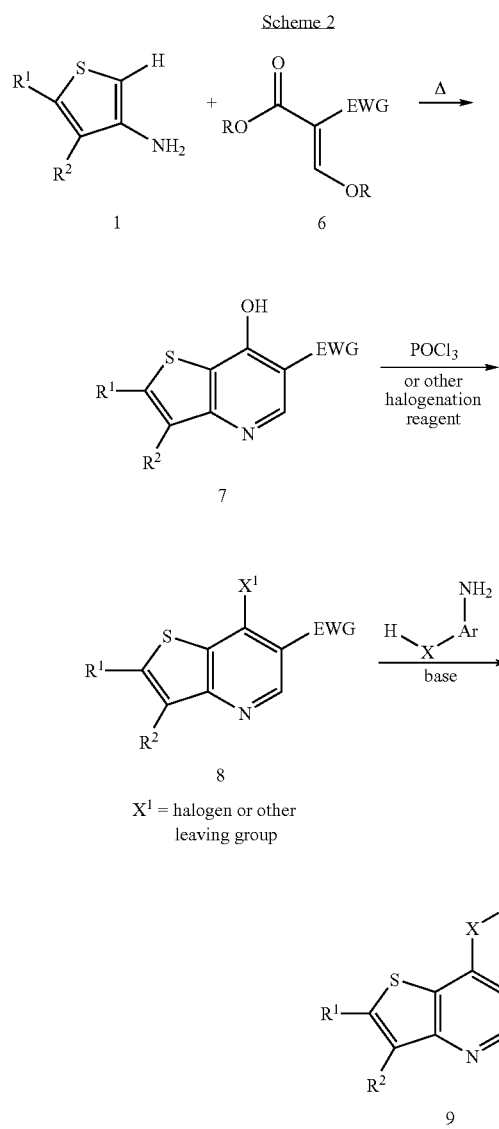

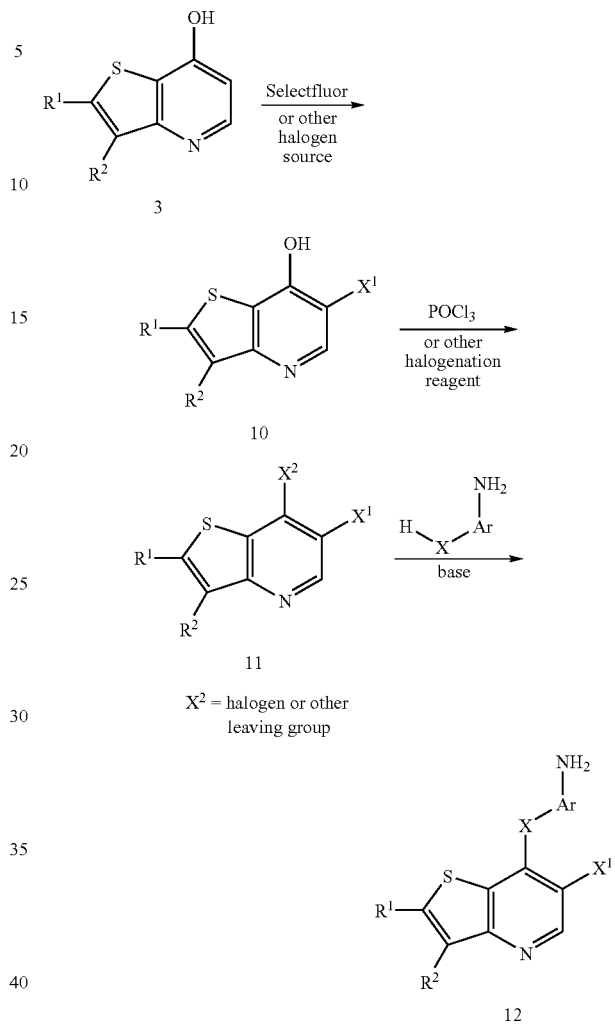

Scheme 2 shows a general scheme for the synthesis of intermediate 9 containing an electron withdrawing group (EWG), which is useful for the synthesis of compounds of Formula I. According to Scheme 2,6-substituted thienopyridine 9 may be obtained by reaction of a 3-aminothiophene 1 with a vinyl ether of a malonate isostere 6 (e.g. diethyl malonate, ethyl 2-cyanoacetate, ethyl 3-oxobutanoate, and the like) containing appropriate electron-withdrawing group EWG, wherein EWG is, e.g., carboxyl, carbonyl, cyano, sulfonyl, and the like, to provide compound 7. Similar methodology has been described in WO 99/30710. Compound 7 may be further elaborated in a similar manner as described for Scheme 1 to give intermediate 9, wherein X, Ar, R$^1$ and R$^2$ are as defined in Scheme 1.

Scheme 3 shows a general scheme for the synthesis of intermediate 12, which is useful for the synthesis of compounds of Formula I. As shown in Scheme 3, substitution at the 6-position of the thienopyridine core may be executed by halogenation of compound 3 with an appropriate halogenation reagent (e.g., Selectfluor, bromine, chlorine, and the like) to give compound 10 wherein X$^1$ is halogen. Compound 10 may be further elaborated in a similar manner as described for Scheme 1 to give intermediate 12 wherein X, Ar, R$^1$ and R$^2$ are as defined in Scheme 1.

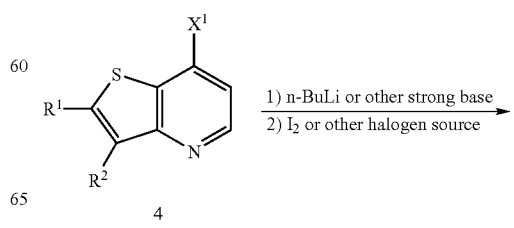

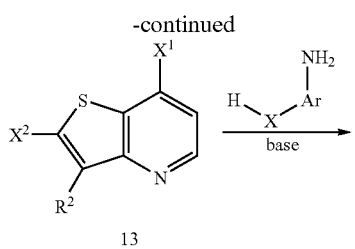

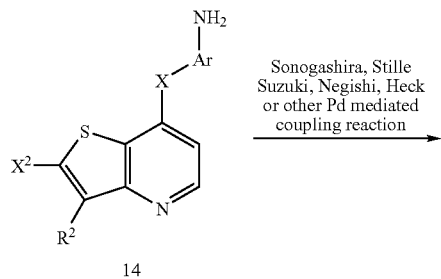

Scheme 4 shows a general scheme for the synthesis of intermediate 14, which is useful for the synthesis of compounds of Formula I. As shown in Scheme 4 substitution at the 2-position of the thienopyridine core may be achieved by metalation of intermediate 4 ($X^1$=halogen; $R^1$=H; and $R^2$=alkyl, alkenyl, alkynyl, aryl, heteroaryl, halogen, or alkoxy) using a strong base such as n-BuLi or the like, followed by quenching with an appropriate halogen source (e.g. $I_2$, $Br_2$, tetrachloroethane, or the like) to give 13. Intermediate 13 may be further elaborated in a similar manner as described for Scheme 1 to give intermediate 14, wherein X, Ar and $R^2$ are as defined in Scheme 1.

pounds of Formula I. Intermediate 14 ($X^2$=bromo or iodo) may be further elaborated at the 2-position by transition metal-mediated coupling reactions (e.g. Sonogashira, Stille, Suzuki, Negishi, Heck, or similar coupling reactions known to those skilled in the art) to give intermediates 15, wherein $R^1$ is aryl, heteroaryl, alkyl, alkenyl, alkynyl, or other functionalities that may be incorporated via related transition-metal mediated coupling with intermediate 14, and X, Ar and $R^2$ are as defined in Scheme 1.

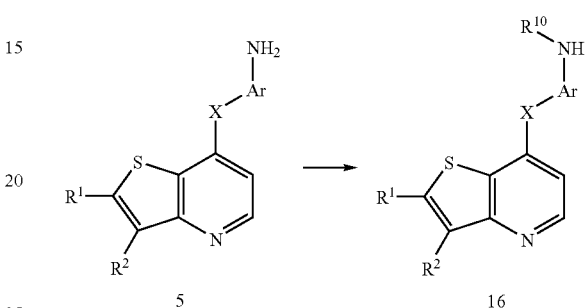

Scheme 6 shows a general scheme for the synthesis of amides and sulfonamides 16. Amides 16 can be prepared by reaction of amino-containing intermediate 5 (prepared as in Scheme 1) with an activated carboxyl- or sulfonyl-containing reagent (for example, acid chlorides, sulfonyl chlorides, polystyrene-2,3,5,6-tetrafluoro-4-(methylcarbamoyl)phenol (PS-TFP)-carboxylates, PS-TFP-sulfonates, carbamoyl chlorides, isocyanates, isothiocyanates, anhydrides, chloroformates, HOBt ester, carbodiimide-derived O-acylurea, or the like) in the presence of an appropriate base (e.g. TEA, DIEA, N-methylmorpholine, pyridine, DMAP, or the like), as needed. For example, amides 16 wherein $R^{10}$ is acyl, thiocarbonyl, carbamoyl, alkoxycarbonyl, or sulfonyl have been prepared by this method. Alternatively, intermediate 5 may be converted to a substituted amine 16 wherein $R^{10}$=alkyl by reductive alkylation methods. Intermediate 5 can also be coupled with an aryl or heteroaryl halide according to the procedures of Buchwald and Hartwig to provide a substituted amine 16 wherein $R^{10}$=aryl or heteroaryl.

Intermediate compounds 9, 12, 14 and 15 can similarly be converted to the corresponding substituted amines by any of the above methods described for intermediate 5.

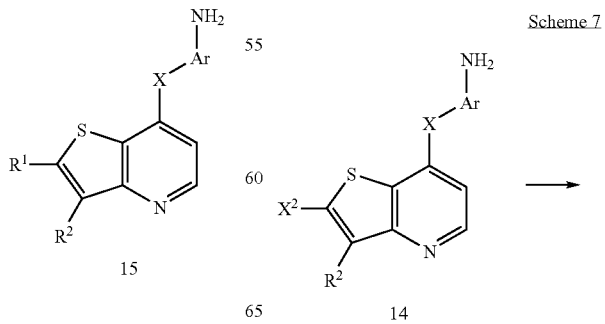

Scheme 5 shows a general scheme for the synthesis of intermediate 15, which is useful for the synthesis of com-

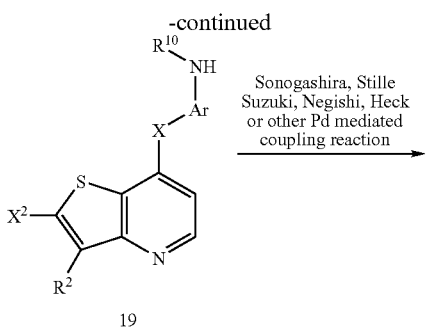

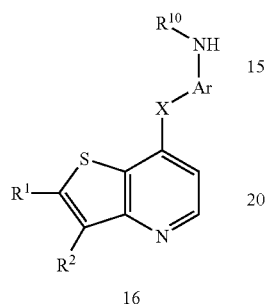

Scheme 7 shows an alternative method of preparing amides and sulfonamides 16 from intermediates 14 ($X^2$=bromo or iodo) in a two-step process. Elaboration of the amino group of intermediate 14 using similar activated carboxyl- or sulfonyl-containing reagents as described for Scheme 6 provides amide 19, wherein $R^{10}$ is as described in Scheme 6. Compound 19 can be elaborated by Pd-mediated coupling (or other transition metal-mediated coupling conditions known to those skilled in the art) using the protocol described for Scheme 5 to yield amides 16, wherein $R^1$=aryl, heteroaryl, alkyl, alkenyl, alkynyl, or other functionalities that may be incorporated via related transition-metal mediated coupling with intermediate 19, and X, Ar and $R^2$ are as defined in Scheme 1.

Scheme 8 shows a general method for the synthesis of oxalamides 18. Oxalamides 18 may be prepared from intermediate compound 5 (prepared as in Scheme 1) in a two-step process. Reaction of the amino group of compound 5 with an alkyl 2-chloro-2-oxoacetate (R=methyl, ethyl, or other alkyl group) in the presence of an appropriate base (e.g. TEA, DIEA, or the like) provides oxalate 17. Heating compound 17 with an amine having the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) gives oxalamides 18 wherein X, Ar, $R^1$ and $R^2$ are as defined in Scheme 1.

Intermediate compounds 9, 12, 14 and 15 can similarly be converted to the corresponding oxalamides by the above method described for intermediate 5.

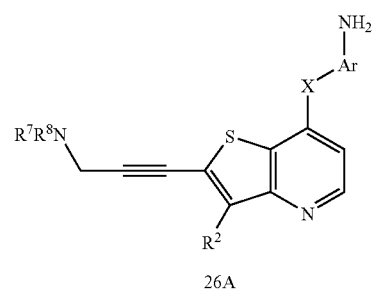

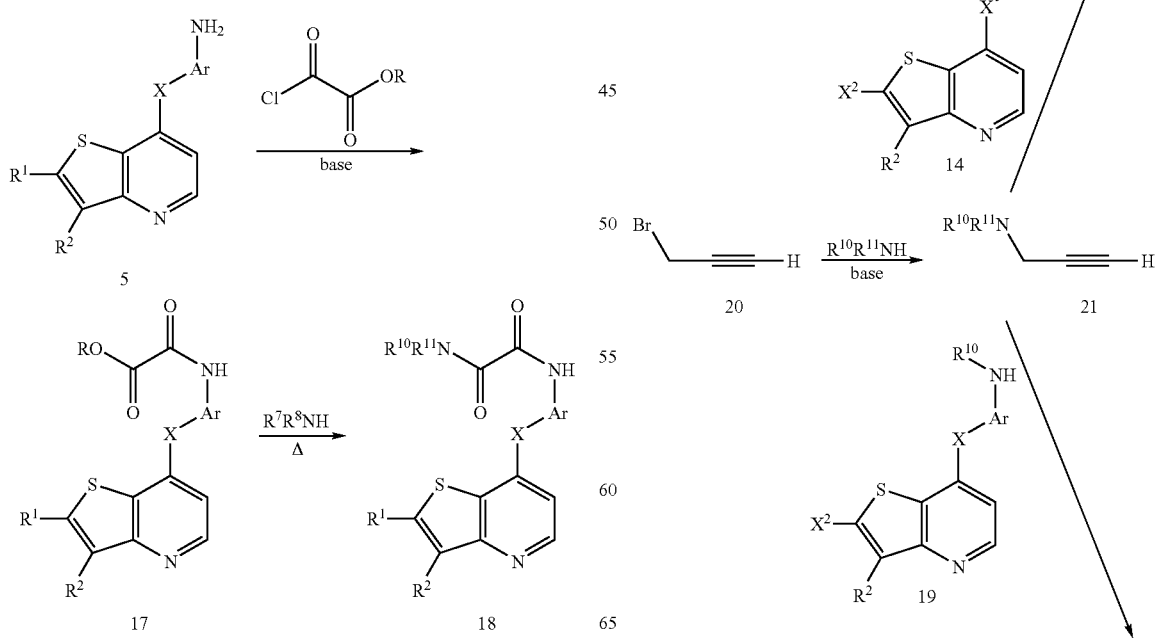

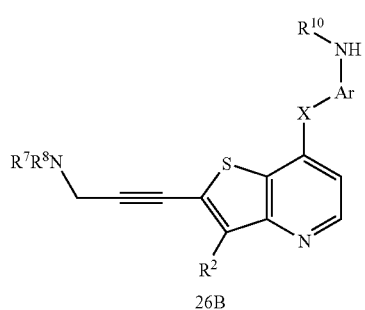

26B

Scheme 9 shows a general method for the synthesis of alkynes 21, which can be used to prepare alkynylated derivatives of compounds 14 and 19. Propargylic amines 21 may be prepared by reaction of propargyl bromide 20 with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* 1995, 2, 1039-1074; and Viehe, H. G., *Angew. Chem., Int. Ed. Eng.* 1967, 6(9), 767-778. Alkynes 21 may subsequently be reacted with intermediates 14 or 19 (via Sonogashira coupling), according to the descriptions provided for Schemes 5 and 7 to provide compounds 26A and 26B, respectively, wherein X, Ar, and $R^2$ are as defined in Scheme 1.

Scheme 10

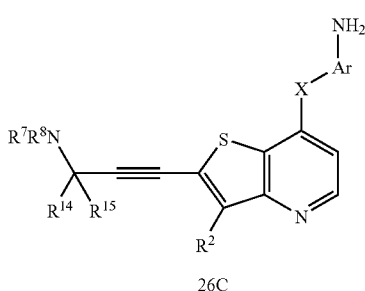

26C

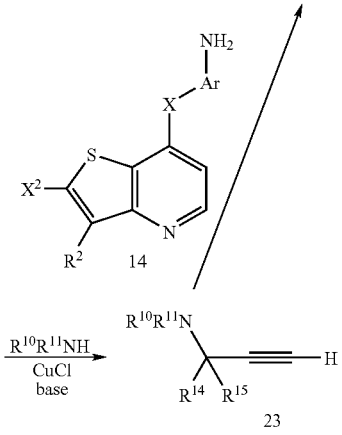

14

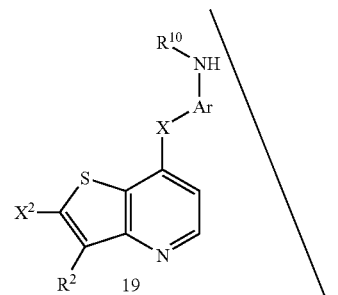

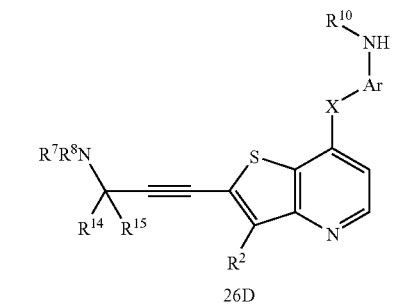

26D

Scheme 10 shows a general method for the synthesis of alkynes 23, which can be used to prepare alkynylated derivatives of compounds 14 and 19. Gem-dialkyl propargylic amines 23 may be prepared using methods described by Zaragoza, F., et al. *J. Med. Chem.* 2004, 47, 2833. According to Scheme 10, gem-dialkyl chloride 22 ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the alkyne 23. Alkyne 23 can be reacted with intermediates 14 or 19 (via Sonogashira coupling), according to the descriptions provided for Schemes 5 and 7 to provide compounds 26C and 26D, respectively, wherein X, Ar, and $R^2$ are as defined in Scheme 1.

Scheme 11

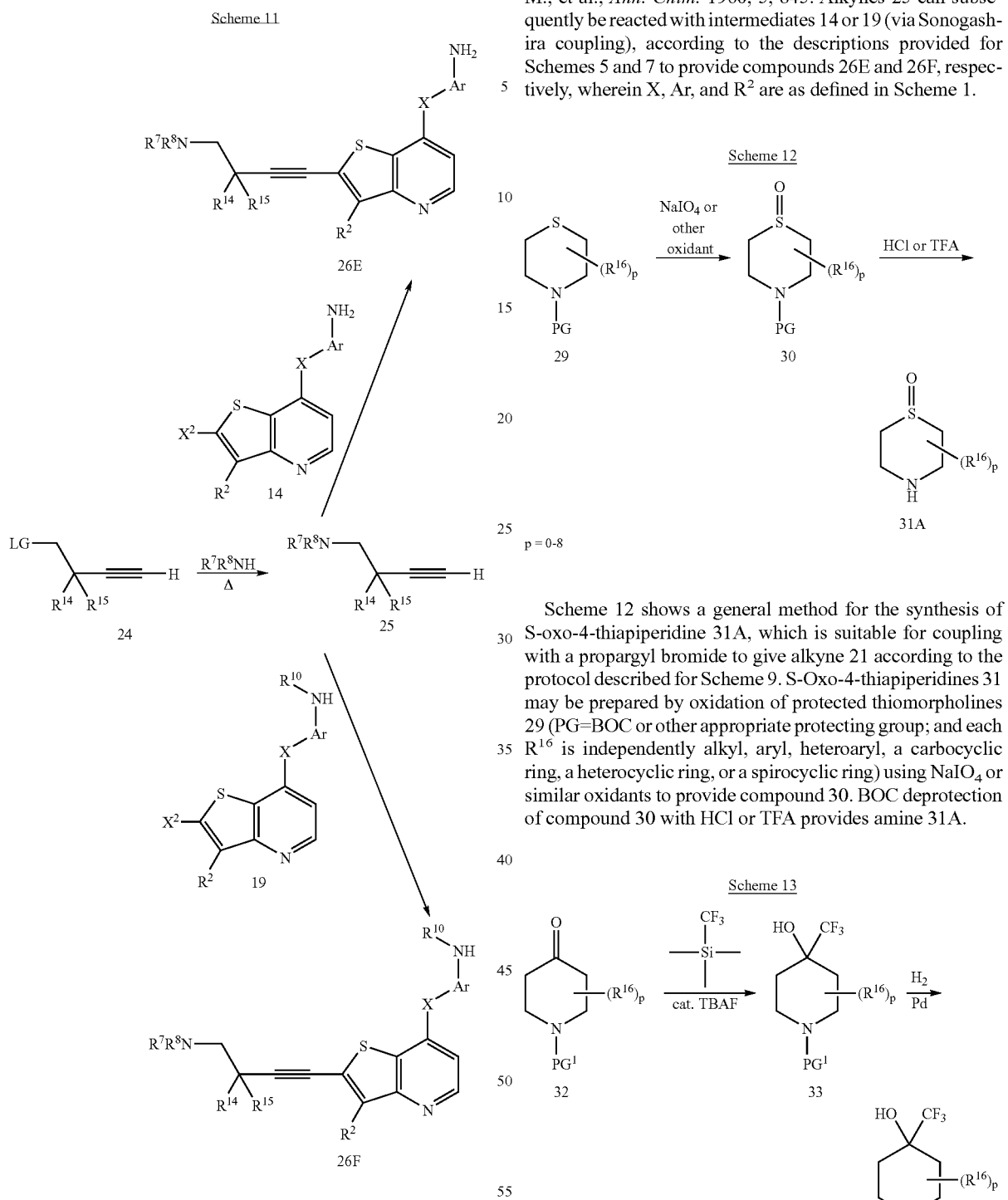

Scheme 11 shows a general scheme for the synthesis of alkynes 25, which can be used to prepare alkynylated derivatives of compounds 14 and 19. But-3-yn-1-amines 25 (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes 24 (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki, M., et al., *Ann. Chim.* 1960, 5, 845. Alkynes 25 can subsequently be reacted with intermediates 14 or 19 (via Sonogashira coupling), according to the descriptions provided for Schemes 5 and 7 to provide compounds 26E and 26F, respectively, wherein X, Ar, and $R^2$ are as defined in Scheme 1.

Scheme 12

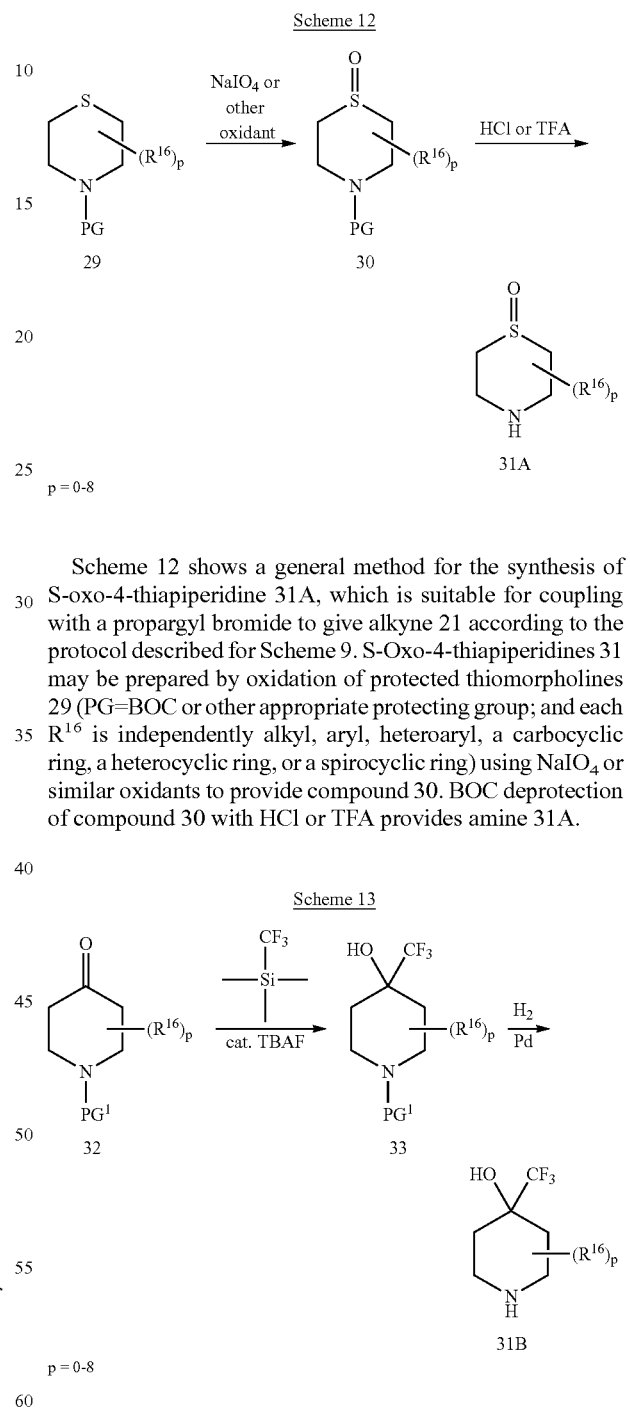

p = 0-8

Scheme 12 shows a general method for the synthesis of S-oxo-4-thiapiperidine 31A, which is suitable for coupling with a propargyl bromide to give alkyne 21 according to the protocol described for Scheme 9. S-Oxo-4-thiapiperidines 31 may be prepared by oxidation of protected thiomorpholines 29 (PG=BOC or other appropriate protecting group; and each $R^{16}$ is independently alkyl, aryl, heteroaryl, a carbocyclic ring, a heterocyclic ring, or a spirocyclic ring) using $NaIO_4$ or similar oxidants to provide compound 30. BOC deprotection of compound 30 with HCl or TFA provides amine 31A.

Scheme 13 p = 0-8

Scheme 13 shows a general method for the synthesis of 4-(trifluoromethyl)piperidin-4-ols 31B, which is suitable for coupling with a propargyl bromide to give alkyne 21 according to the protocol described for Scheme 9. 4-(Trifluoromethyl)piperidin-4-ols 31B may be prepared by a TBAF-catalyzed trifluoromethylation of protected piperidin-4-ones 32

(PG=CBZ or other appropriate protecting group; and each R[16] is independently alkyl, aryl, heteroaryl, a carbocyclic ring, a heterocyclic ring, or a spirocyclic ring) using trimethyl (trifluoromethyl)silane to provide compound 33. Deprotection of compound 33 via Pd-catalyzed hydrogenolysis provides amine 31B.

Scheme 14

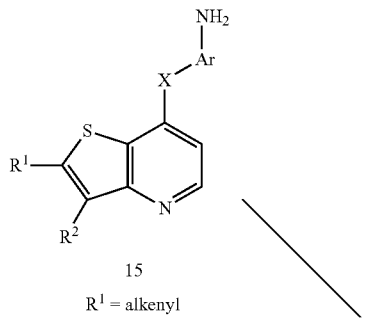

15
R[1] = alkenyl

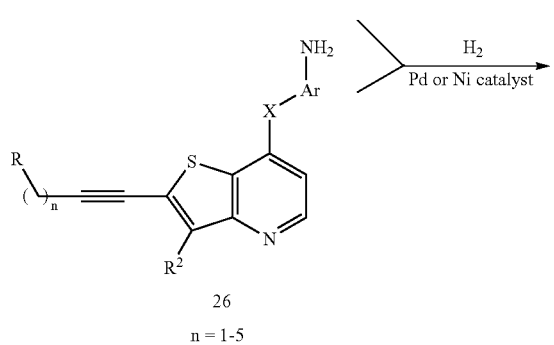

26
n = 1-5

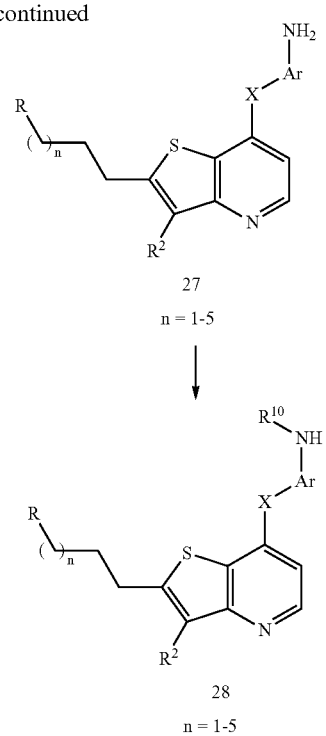

27
n = 1-5

28
n = 1-5

Scheme 14 shows several routes for the synthesis of 2-alkylthienopyridines 27 and the corresponding amides 28. Pd or Ni-catalyzed hydrogenation of the double or triple bond of intermediate 15 or 26, respectively, provides alkyl-substituted thienopyridine 27 (wherein R is H, alkyl, carbocycle, heterocycle, aryl, heteroaryl, or R[10]R[11]N). Intermediates 27 may subsequently be elaborated into amides 28 using methods described for Scheme 6.

Alternatively, substitution at the 2-position of the thienopyridine core with an alkyl group may be achieved by Negishi coupling of intermediate 14 or 19 with an appropriate alkyl zinc reagent $R_2Zn$ according to the descriptions provided for Schemes 5 and 7.

Use of intermediate 14 in the above reaction will give the intermediate 27 which can be elaborated into amides 28 using methods described for Scheme 6.

Scheme 15

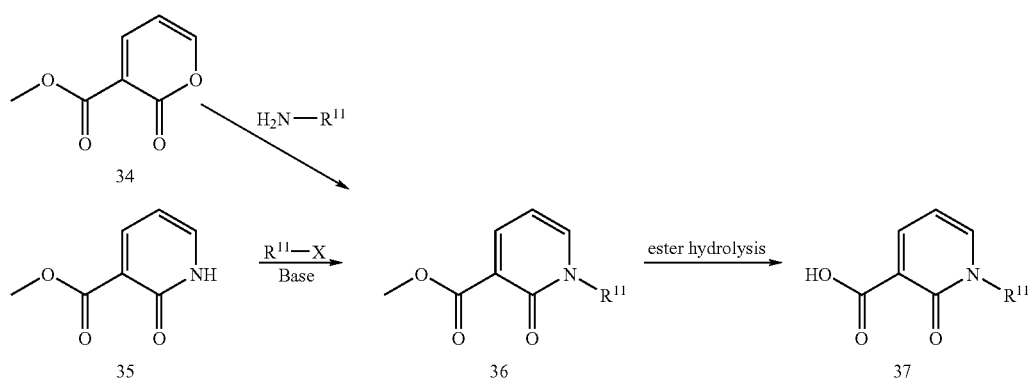

Scheme 15 shows routes for the preparation of acid intermediate 37. Acids of this type may be prepared from either reaction of the corresponding commercially available carboxypyrone ester 34 with an appropriate amine or from commercially available carboxy pyridone ester 35 via reaction with the appropriate activated electrophile followed by hydrolysis of the methyl ester 36 to the acid 37 in either case. These acids may then be coupled to appropriate aniline intermediates as in Schemes 6, 7 or 14.

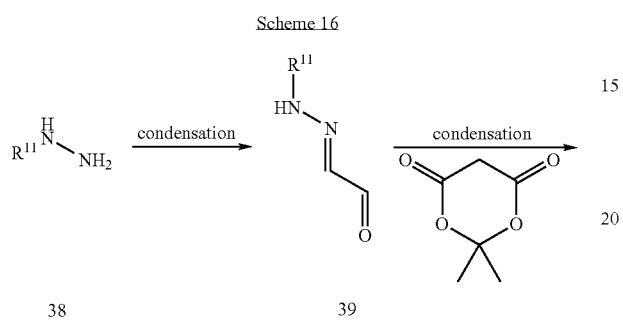

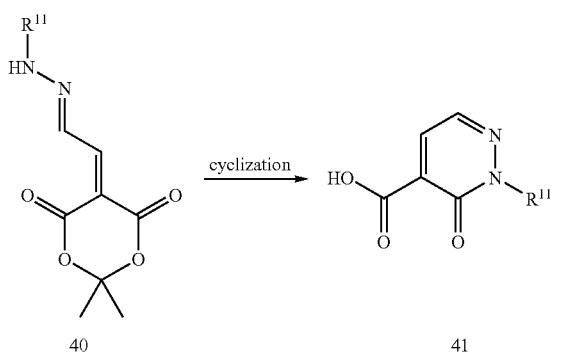

Scheme 16 shows a route for the preparation of acid intermediate 41 according to the general methods described by McNab H., et al. *J. Chem. Soc. Perkin Trans.* 1 1982, 1845. Substituted hydrazine 38 can be converted to hydrazono acetaldehyde 39 with standard dehydrating conditions such as in the presence of acetic acid at room temperature. The aldehyde/Meldrum's acid condensation product 40 is prepared in a suitable organic solvent such as toluene, benzene or dioxane at room temperature using piperidinium acetate as catalyst. Carboxylic acid pyridazinone 41 is prepared from hydrazono ethylidene 40 by cyclization under basic conditions (sodium methoxide in methanol) at 70° C.

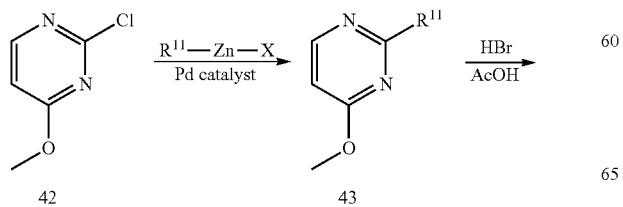

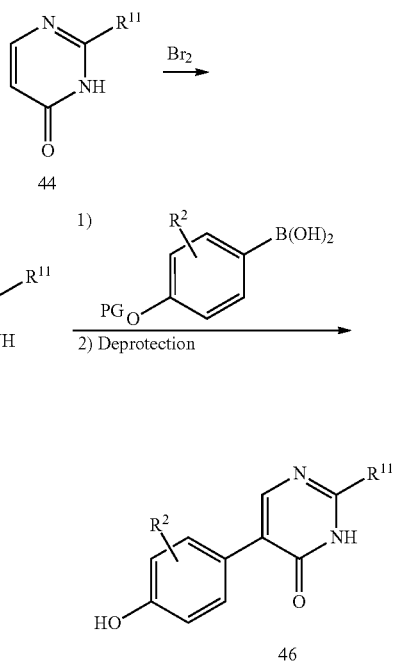

Scheme 17 shows a route for the preparation of phenol intermediate 46. Commercially available 2-chloro-4-methoxypyrimidine 42 is reacted with the appropriate zinc reagent and palladium catalyst to give 2-substituted 4-methoxypyrimidine 43. Deprotection of the methoxypyrimidine with HBr in acetic acid provides 2-substituted pyrimidinone 44. Bromination in the 5-position gives pyrimidinone intermediate 45. Suzuki coupling of 45 to an appropriate boronic acid gives a bicyclic intermediate, which after final deprotection of the phenol gives intermediate 46 which can be substituted for a phenoxy aniline derivative and reacted with appropriate core intermediates as in Schemes 1, 2, 3 and 4.

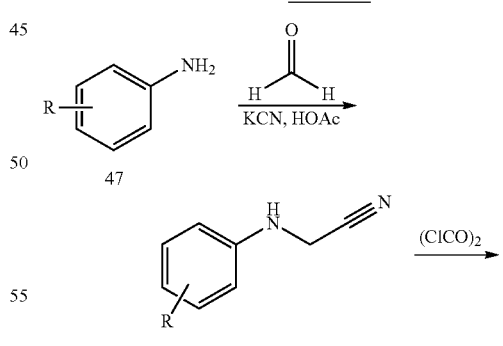

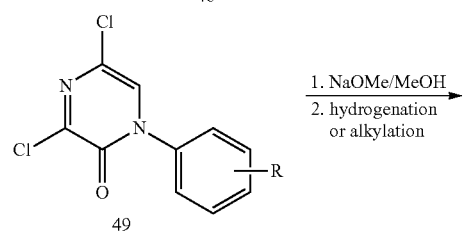

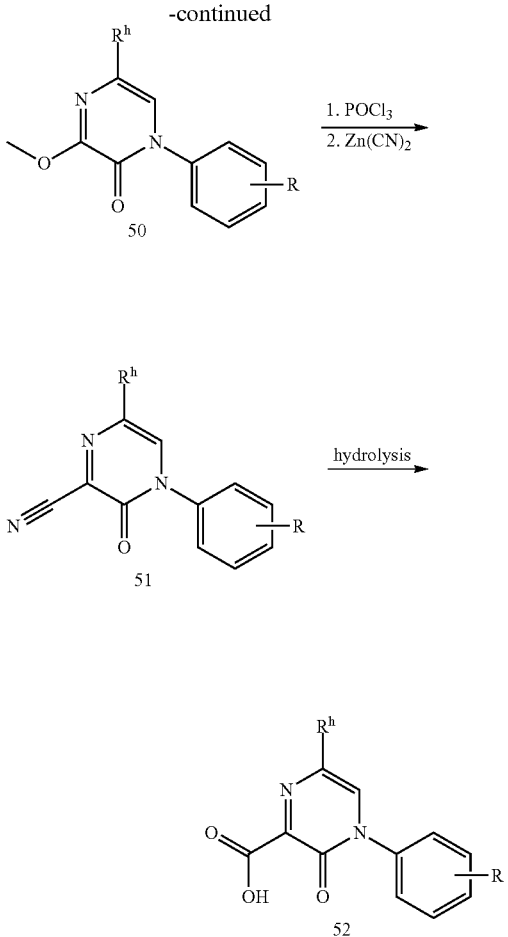

the key intermediate 51 which can be prepared according to the general methods described by M. Tutonda, et al., Tetrahedron, 1990, 46, 5715. Substituted aniline 47 can be converted to amino acetonitrile compound 48 using standard conditions such as KCN and formaldehyde in acetic acid at room temperature. The cycylization product 49 is prepared with oxalyl chloride in a suitable organic solvent such as dichlorobenzene at elevated temperature (100° C.). Pyrazinone 50 can be made in a two step sequence. In the first step, 3,5-dichloro pyrazinone 49 is treated with sodium methoxide in a suitable organic solvent such as MeOH or THF or MeOH/THF mixture at temperatures ranging from 0° C. to reflux. Preferably, sodium methoxide is added to a solution of dichloro pyrazinone 49 in MeOH at room temperature. This mixture is then refluxed for 6 hours to generate the desired methoxy pyrazinone. In the second step, palladium catalyzed hydrogenation of the 5-chloro pyrazinone provides 5-H pyrazinone 50. Another conversion of the 5-chloro pyrazinone intermediates to compound 50 (wherein $R^h$ is alkyl, cycloalkyl, heterocyclic, or heteroaryl) can be achieved using palladium mediated cross-coupling conditions. Nitrile 51 can be synthesized from methoxy pyrazinone 50 by chlorination followed by nitrilation. The chlorination can be accomplished with $POCl_3$, thionyl chloride, oxalyl chloride, or $PCl_5$. Preferably, this transformation is achieved with $POCl_3$ under DMF as solvent at elevated temperature (about 90° C.). Nitrilation can be achieved by standard conditions with $Zn(CN)_2$ using Pd mediated cross-coupling conditions in a suitable organic solvent such as N-methylpyrrolidone (NMP) at elevated temperature (120° C.). Carboxylic acid pyrazinone 52 can be made in a three step sequence in a one-pot reaction. In the first step, nitrile compound 51 is treated with concentrated $H_2SO_4$ neat at room temperature. The resulting amide is treated with MeOH. This mixture is then refluxed to generate a methyl ester pyrazinone intermediate. Then, desired carboxylic acid pyrazinone 52 can be prepared by basic hydrolysis under standard conditions using either NaOH or LiOH in standard mixture aqueous/organic solvent systems. The acid 52 can then be coupled to an appropriate aniline intermediate as in Schemes 6, 7 or 14.

Scheme 18 shows a route for the preparation of pyrazinone acid intermediate 52 (wherein $R^h$ is independently selected from H, alkyl, cycloalkyl, heterocyclic, or heteroaryl) from

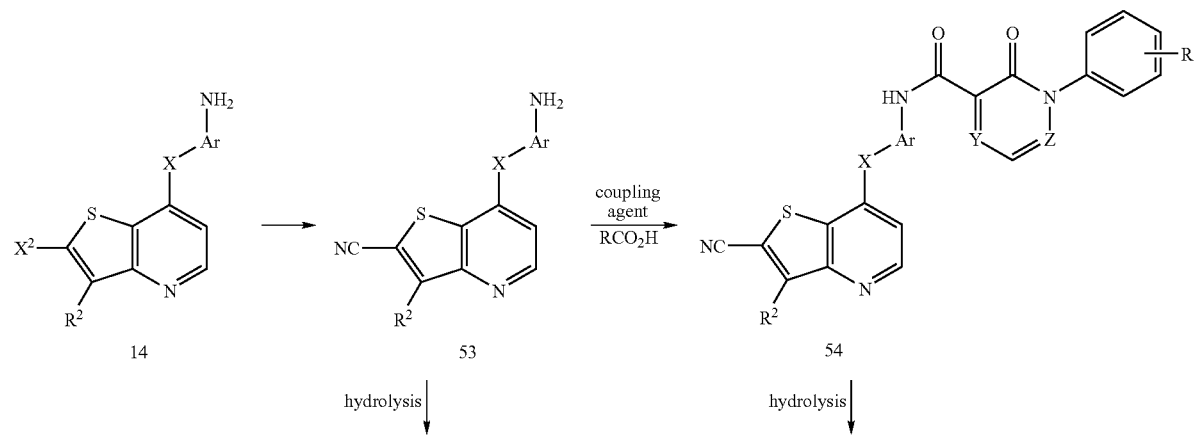

Scheme 19

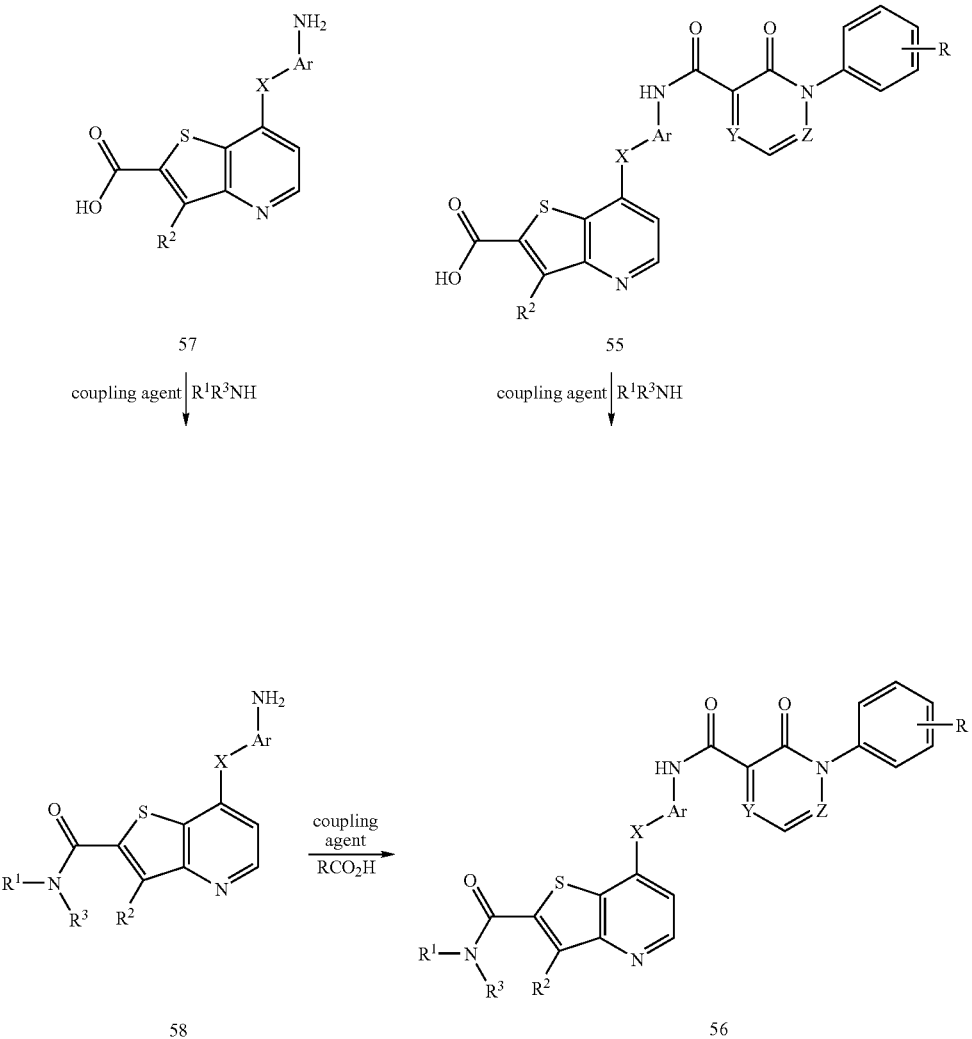

Scheme 19 shows a route for the preparation of thienopyridine 56 from aniline 14 (prepared as described in Scheme 4). Aniline 53 can be prepared by treating 14 with CuCN in a suitable organic solvent such as DMF at elevated temperature (160° C.). Amide 54 (wherein Y=CH and Z=N) can be prepared using standard coupling procedures, including but not limited to EDCI, HOBt, or PyBOP and the acid in suitable organic solvents such as DMF, THF or methylene chloride. Carboxylic acid 55 can be made in a three step sequence in a one-pot reaction. In the first step, nitrile compound 54 is treated with concentrated $H_2SO_4$ neat at room temperature. The resulting amide is treated with MeOH. This mixture is then refluxed for 3 hours to generate methyl ester pyrazinone intermediate. Then, desired carboxylic acid 55 can be prepared by basic hydrolysis under standard conditions using either NaOH or LiOH in standard mixture aqueous/organic solvent systems. The carboxylic acid 55 can be converted to amide 56 by the standard methods with the appropriate amine as described above for the synthesis of 54. 56 (wherein Y=N and Z=CH or Y=CH and Z=N) can also be prepared from 53 in a three step process. Carboxylic acid 57 can be prepared from nitrile 53 by hydrolysis as described above. The first amide 58 can be prepared using standard conditions with the appropriate amine then the second amide 56 can be made by standard coupling procedures with the carboxylic acid as described above.

Scheme 20

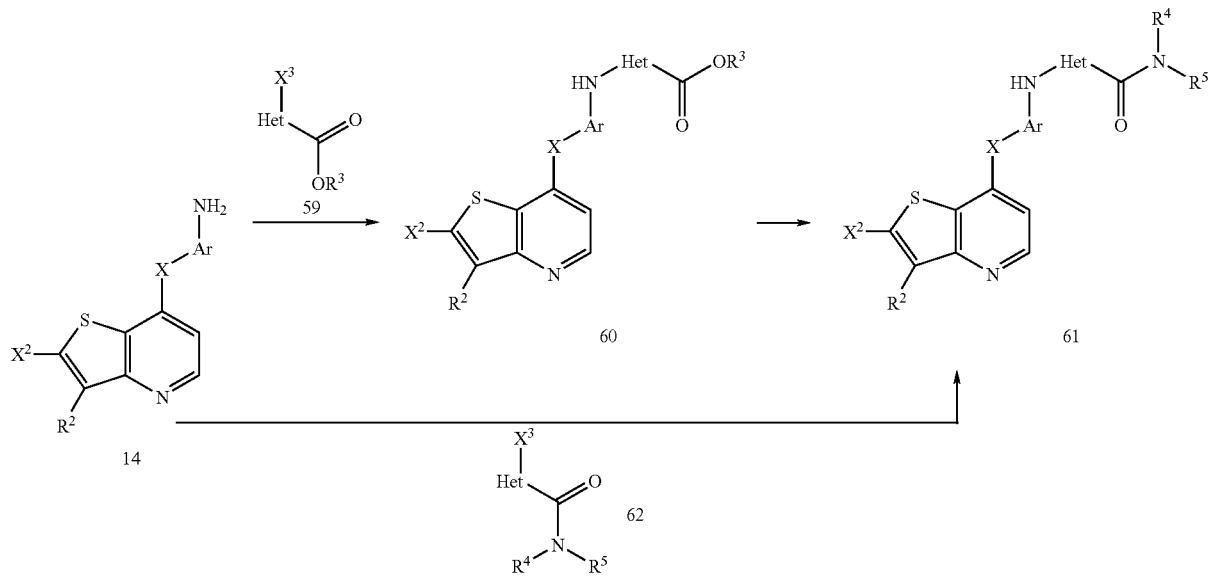

Scheme 20 shows a general scheme for the synthesis of intermediate 61 which is useful for the synthesis of compounds of Formula I. As shown in Scheme 20, elaboration of the thienopyridine 4-position phenoxy group into an amine linked heterocyclic amide may proceed via optional pathways. Intermediate 14 bearing an amino group may be reacted with a heterocyclic ester bearing leaving group $X^3$ (59) typically under transition metal catalyzed or thermal conditions to give intermediate 60. 60 may then be converted using standard ester hydrolysis conditions followed by standard amide bond forming conditions to give intermediate 61. Alternatively, 14 may be reacted with a heterocyclic amide bearing leaving group $X^3$ (62) typically under transition metal catalyzed or thermal conditions to give intermediate 61 directly. When $X^2$ is an appropriate substituent, intermediate 61 may be considered a final compound of Formula I. If $X^2$ is a handle for further elaboration, intermediate 61 may be subjected to further elaboration as in Schemes 7, 9, 10, 11 and 14 for example to give compounds of Formula I.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) *J. Chromatogr.*, 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl -β-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. $J.$ $Org.$ $Chem.$, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determining the activity of cMet kinase activity of a compound of Formula I is possible by a number of direct and indirect detection methods. One example of an assay used for the determination of cMet kinase activity is based on an enzyme linked immunosorbant assay (ELISA). The assay includes a compound of Formula I, cMet (His-tagged recombinant human Met (amino acids 974-end), expressed by baculovirus), and ATP in assay buffer, as described in Example 106.

In MKN45 cells, the activity of cMet inhibitors of Formula I was determined by the in vitro fluorescence assay as described in Example 107.

Exemplary compounds described herein were prepared, characterized, and assayed for their cMet binding activity and in vitro activity against tumor cells. The range of cMet binding activities was less than 1 nM to about 10 μM. Certain exemplary compounds of the invention had cMet binding activity $IC_{50}$ values less than 10 nM. Certain compounds of the invention had MKN45 cell-based activity $IC_{50}$ values less than 100 nM.

Administration of Compounds of Formula I

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Methods of Treatment with Compounds of Formula I

Compounds of the present invention are useful for treating diseases, conditions and/or disorders, for example, but not limited to, those characterized by over expression of receptor tyrosine kinases (RTK), e.g. cMet kinase. Accordingly, another aspect of this invention includes methods of treating or preventing diseases or conditions that can be treated or prevented by inhibiting receptor tyrosine kinases (RTK), including c-Met. In one embodiment, the method comprises administering to a mammal in need thereof a therapeutically effective amount of a compound of Formula I, or a stereoisomer, geometric isomer, tautomer, solvate, metabolite, or pharmaceutically acceptable salt or prodrug thereof.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone -related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula I and a pharmaceutically acceptable carrier, adjuvant, or vehicle, wherein said compound of Formula I is present in an amount to detectably inhibit cMet kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The inhibitory compound for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formulas I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Also provided are compositions comprising a compound of Formula I in an amount to detectably inhibit Met kinase activity and a pharmaceutically acceptable carrier, adjuvant, or vehicle.

Combination Therapy

The compounds of Formula I may be employed alone or in combination with other therapeutic agents for the treatment of a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such molecules are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In a particular embodiment, in anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. In certain embodiments, combination therapies according to the present invention comprise the administration of at least one compound of Formula I, or a stereoisomer, geometric isomer, tautomer, solvate, metabolite, or pharmaceutically acceptable salt or prodrug thereof, and at least one other pharmaceutically active chemotherapeutic agent. The compound(s) of Formula I and the other pharmaceutically active chemotherapeutic agent(s) may be administered together in a unitary pharmaceutical composition or separately and, when administered separately this may occur simultaneously or sequentially in any order. Such sequential administration may be close in time or remote in time. The amounts of the compound(s) of Formula I and the other pharmaceutically active chemotherapeutic agent(s) and the relative timings of administration will be selected in order to achieve the desired combined therapeutic effect.

Also provided are compositions comprising a compound of Formula I in combination with an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

Metabolites of Compounds of Formula I

Also falling within the scope of this invention are the in vivo metabolic products of heterobicyclic thiophene compounds of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Prodrugs of Compounds of Formula I

In addition to compounds of Formula I, the invention also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula I can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, $\alpha$-amino$(C_1-C_4)$alkanoyl, arylacyl and $\alpha$-aminoacyl, or $\alpha$-aminoacyl-$\alpha$-aminoacyl, where each $\alpha$-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural x-aminoacyl or natural α-aminoacyl-natural α-aminoacyl, —C(OH)C(O)OY wherein Y is H, (C$_1$-C$_6$)alkyl or benzyl, —C(OY$_0$)Y$_1$ wherein Y$_0$ is (C$_1$-C$_4$) alkyl and Y$_1$ is (C$_1$-C$_6$)alkyl, carboxy(C$_1$-C$_6$) alkyl, amino(C$_1$-C$_4$)alkyl or mono-N- or di-N,N—(C$_1$-C$_6$) alkylaminoalkyl, or —C(Y$_2$)Y$_3$ wherein Y$_2$ is H or methyl and Y$_3$ is mono-N- or di-N,N—(C$_1$-C$_6$)alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a heterobicyclic thiophene compound of Formula I, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, an article of manufacture may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the article of manufacture may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other cMet inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Representative Examples are shown merely to illustrate representative chemistry, which can be used to prepare compounds of the present invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained as $CDCl_3$, $d_6$-DMSO, $CH_3OD$ or $d_6$-acetone solutions (reported in ppm), using chloroform as the reference standard (7.25 ppm). When peak multiplicities are reported, the following abbreviations are used: s (singlet), d (doublet), t (triplet), m (multiplet), q (quartet), br (broadened), dd (doublet of doublets), dt (doublet of triplets). Coupling constants, when given, are reported in Hertz (Hz).

Example 1

Preparation of N-(3-fluoro-4-(thieno[3,2-b]pyridin-7-yloxy)phenylcarbamothioyl)-2-phenylacetamide

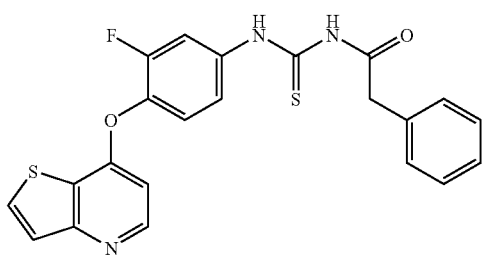

Step A: Preparation of 7-chlorothieno[3,2-b]pyridine: To a stirred solution of $POCl_3$ (28.6 mL, 313 mmol) in 1,2-dichloroethane (200 mL) was added commercially available thieno[3,2-b]pyridin-7-ol (94.7 g, 626 mmol) as a powder in one portion. The reaction was stirred for 2 hours at reflux under $N_2$. The mixture was concentrated, using toluene (3×100 mL) to azeotrope. The dark residue was resuspended in $CH_2Cl_2$ (1 L), and a saturated aqueous solution of $NaHCO_3$ (500 mL) was carefully added. The mixture was stirred for 30 minutes until bubbling had ceased. The biphase was separated, and the aqueous was re-extracted with $CH_2Cl_2$ (500 mL). The combined organic phases were dried ($Na_2SO_4$), filtered, and concentrated, to obtain a brown oil, which crystallized upon standing (38.4 g, 71%). 7-Chlorothieno[3,2-b]pyridine has also been prepared using oxalyl chloride (WO 99/24440). $^1$H NMR (400 MHz, $CDCl_3$) δ 8.61 (d, J=5 Hz, 1H), 7.80 (d, J=6 Hz, 1H), 7.60 (d, J=6 Hz, 1H), 7.29 (d, J=5 Hz, 1H).

Step B: Preparation of 3-fluoro-4-(thieno[3,2-b]pyridin-7-yloxy)aniline: To a stirred suspension of NaH (0.432 g, 18.0 mmol) in DMSO (30 mL) was carefully added 4-amino-2-fluorophenol (1.91 g, 15.0 mmol) in portions. The reaction was stirred under $N_2$ for 15 minutes. 7-Chlorothieno[3,2-b]pyridine (2.54 g, 15.0 mmol) was added as a solid. The reaction was heated to 100° C. for 2 hours. The reaction was allowed to cool to room temperature, and water (40 mL) was carefully added. The suspension was filtered. The brown solid was washed with water (2×10 mL), and dried by toluene azeotrope (5×20 mL) by rotary evaporation at 50° C. The solid was recrystallized from hot toluene (10 mL) to obtain a brown, crystalline solid (2.64 g, 68%). $^1$H NMR (400 MHz, $CDCl_3$) δ 8.49 (d, J=6 Hz, 1H), 7.73 (d, J=6 Hz, 1H), 7.56 (d, J=6 Hz, 1H), 7.04 (t, J=9 Hz, 1H), 6.51 (m, 3H), 3.83 (br s, 2H). LRMS (APCI pos) m/e 261 (M+1).

Step C: Preparation of N-(3-fluoro-4-(thieno[3,2-b]pyridin-7-yloxy)phenylcarbamothioyl)-2-phenylacetamide: To a stirred solution of 3-fluoro-4-(thieno[3,2-b]pyridin-7-yloxy)aniline (0.105 g, 0.403 mmol) in THF (1 mL) was added 2-phenylethanoyl isothiocyanate (0.257 g, 1.45 mmol; prepared according to the procedure described by J. Org. Chem. 1964, 29, 1115-1119). The reaction was stirred for 4 hours at room temperature. The reaction mixture was partially purified by Biotage Flash 40 silica gel chromatography, eluting with a gradient of 10-50% EtOAc in hexanes. The product was further purified by preparative TLC (10% MeOH in $CH_2Cl_2$). Yield: 18 mg (9%). $^1$H NMR (400 MHz, $CDCl_3$) δ 12.55 (s, 1H), 9.00 (s, 1H), 8.53 (d, J=5 Hz, 1H), 7.94 (m, 1H), 7.75 (d, J=5 Hz, 1H), 7.58 (d, J=5 Hz, 1H), 7.08-7.50 (m, 7H), 6.54 (d, J=5 Hz, 1H), 3.75 (s, 2H). LRMS (APCI neg) m/e 436 (M−1).

Example 2

Preparation of ethyl 2-(3-fluoro-4-(thieno[3,2-b]pyridin-7-yloxy)phenylamino)-2-oxoacetate

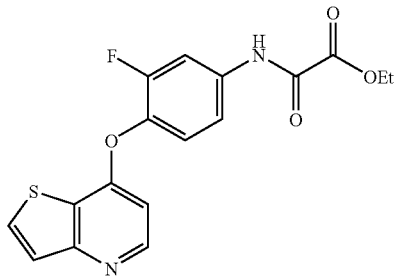

To a stirred solution of 3-fluoro-4-(thieno[3,2-b]pyridin-7-yloxy)aniline (prepared in Example 1, Step B; 0.78 g, 3.0 mmol), triethylamine (0.84 mL, 6.0 mmol), and $CH_2Cl_2$ (5 mL) was added a solution of ethyl 2-chloro-2-oxoacetate (0.45 g, 3.3 mmol) in $CH_2Cl_2$ (1 mL) dropwise at room temperature. Stirring was continued for 15 minutes. The mixture was washed with water (3×5 mL), dried ($Na_2SO_4$), filtered, and concentrated. The resulting crude was purified by Biotage Flash 40 silica gel chromatography, eluting with 30% EtOAc/hexanes, then 1:1 EtOAc/hexanes. The product was obtained as a white powder (656 mg, 61%). $^1$H NMR (400 MHz, $CDCl_3$) δ 9.10 (s, 1H), 8.53 (d, J=6 Hz, 1H), 7.85 (d, J=12 Hz, 1H), 7.76 (d, J=6 Hz, 1H), 7.58 (d, J=6 Hz, 1H), 7.39 (d, J=9 Hz, 1H), 7.30 (d, J=9 Hz, 1H), 6.52 (d, J=6 Hz, 1H), 4.44 (q, J=7 Hz, 2H), 1.44 (t, J=7 Hz, 3H). LRMS (APCI pos) m/e 361 (M+1). HPLC: 99% purity (220 nm).

Example 3

Preparation of N1-(3-fluoro-4-(thieno[3,2-b]pyridin-7-yloxy)phenyl)-N2-(2-morpholinoethyl)oxalamide

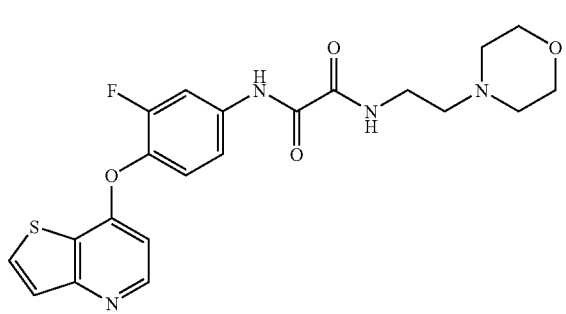

Ethyl 2-(3-fluoro-4-(thieno[3,2-b]pyridin-7-yloxy)phenylamino)-2-oxoacetate (prepared in Example 2; 36 mg, 0.10 mmol) and 2-morpholinoethanamine (65 mg, 0.50 mmol) were heated to 60° C. for 18 hours. The mixture was diluted with diethyl ether (1 mL) and filtered. The white solid was washed with diethyl ether (3×2 mL). The solid was dried under high vacuum. The product was obtained as a white powder (17 mg, 38%). $^1$H NMR (400 MHz, CDCl$_3$) δ 9.50 (s, 1H), 8.52 (d, J=6 Hz, 1H), 7.99 (m, 1H), 7.87 (m, 1H), 7.76 (d, J=6 Hz, 1H), 7.58 (d, J=6 Hz, 1H), 7.41 (m, 1H), 7.29 (m, 1H), 6.52 (d, J=6 Hz, 1H), 3.74 (m, 4H), 3.49 (m, 2H), 2.59 (m, 2H), 2.50 (m, 4H). LRMS (ESI pos) m/e 445 (M+1). HPLC: 100% purity (220 nm).

Example 4

Preparation of N-(3-fluoro-4-(thieno[3,2-b]pyridin-7-yloxy)phenyl)-2-oxo-2-(pyrrolidin-1-yl)acetamide

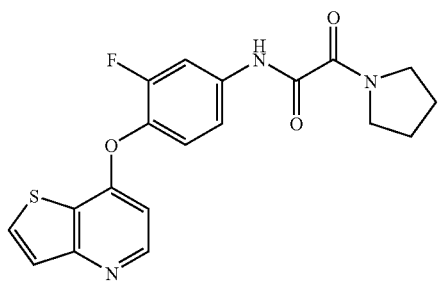

Prepared from ethyl 2-(3-fluoro-4-(thieno[3,2-b]pyridin-7-yloxy)phenylamino)-2-oxoacetate (Example 2; 36 mg, 0.10 mmol) and pyrrolidine (36 mg, 0.50 mmol) according to the procedure for Example 3. The product was purified on a pre-packed Isoelute silica gel column (10 g silica), eluting with a gradient of 20% EtOAc/hexanes, 1:1 EtOAc/hexanes, 2:1 EtOAc/hexanes, and then neat EtOAc. The product was obtained as a white powder (33 mg, 86%). $^1$H NMR (400 MHz, CDCl$_3$) δ 9.74 (s, 1H), 8.52 (d, J=5 Hz, 1H), 7.87 (m, 1H), 7.75 (d, J=6 Hz, 1H), 7.58 (d, J=6 Hz, 1H), 7.37 (m, 1H), 7.26 (m, 1H), 6.52 (d, J=5 Hz, 1H), 4.09 (t, J=7 Hz, 2H), 3.63 (t, J=7 Hz, 2H), 2.02 (m, 2H), 1.91 (m, 2H). LRMS (ESI pos) m/e 386 (M+1). HPLC: 100% purity (220 nm).

Example 5

Preparation of N1-(3-fluoro-4-(thieno[3,2-b]pyridin-7-yloxy)phenyl)-N2-(3-fluorophenyl)oxalamide

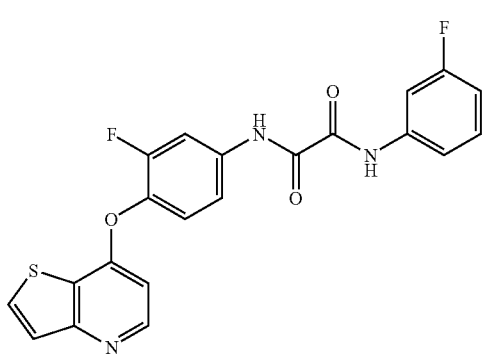

Prepared from ethyl 2-(3-fluoro-4-(thieno[3,2-b]pyridin-7-yloxy)phenylamino)-2-oxoacetate (Example 2; 36 mg, 0.10 mmol) and 3-fluoroaniline (139 mg, 1.25 mmol) according to the procedure for Example 3, except the reaction was heated to 100° C. for 18 hours. The product was purified by preparative TLC (1:1 EtOAc/hexanes). The product was obtained as a white powder (7 mg, 6%). $^1$H NMR (400 MHz, CDCl$_3$+MeOD-d3) δ 8.48 (d, J=6 Hz, 1H), 7.92 (m, 1H), 7.83 (d, J=6 Hz, 1H), 7.67 (m, 1H), 7.57 (d, J=6 Hz, 1H), 7.51 (m, 1H), 7.35 (m, 3H), 6.94 (m, 1H), 6.57 (d, J=6 Hz, 1H). LRMS (ESI pos) m/e 426 (M+1). HPLC: 97% purity (220 nm).

Example 6

Preparation of N-(4-(2-(3-(diethylamino)prop-1-ynyl)thieno[3,2-b]pyridin-7-yloxy)-3-fluorophenylcarbamothioyl)-2-phenylacetamide

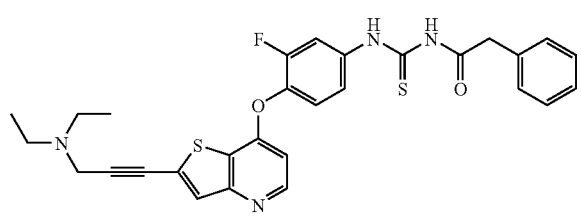

Step A: Preparation of 3-fluoro-4-(2-iodothieno[3,2-b]pyridin-7-yloxy)aniline: A vigorously stirred mixture of 7-chloro-2-iodothieno[3,2-b]pyridine (5.00 g, 14.4 mmol; obtained from 7-chlorothieno[3,2-b]pyridine, Example 1, Step A, according to the procedure described by Ragan, J. A. Org. Proc. Res. 2003, 7, 676), 4-amino-2-fluorophenol (2.01 g, 15.8 mmol), Cs$_2$CO$_3$ (4.69 g, 14.4 mmol), and DMF (60 mL) was heated to 135° C. for 3 hours under N$_2$. The reaction was cooled to room temperature, diluted with EtOAc (200 mL), and washed with brine (3×200 mL). The organic phase was concentrated, and the crude was purified by a Biotage 40M silica gel chromatography system eluting with 2:1 EtOAc/hexanes. The product was further purified by recrystallization from a hot mixture of 1:1 CH$_3$CN/water (70 mL). The filtrate yielded two additional crops of product which matched the purity of the first crop. The combined crops yielded 2.35 g (40%). $^1$H NMR (400 MHz, CDCl$_3$) δ 8.41 (d, J=6 Hz, 1H), 7.75 (s, 1H), 7.02 (t, J=9 Hz, 1H), 6.54 (m, 1H), 6.47 (m, 2H), 3.84 (br s, 2H). LRMS (ESI pos) m/e 387 (M+1).

Step B: Preparation of 4-(2-(3-(diethylamino)prop-1-ynyl)thieno[3,2-b]pyridin-7-yloxy)-3-fluoroaniline: A stirred mixture of 3-fluoro-4-(2-iodothieno[3,2-b]pyridin-7-yloxy) benzenamine (965 mg, 2.50 mmol), N,N-diethylprop-2-yn-1-amine (417 mg, 3.75 mmol), copper(I) iodide (24 mg, 0.125 mmol), triethylamine (8.7 mL, 63 mmol), and THF (20 mL) was sparged with N$_2$ for 5 minutes, then tetrakis(triphenyl-phosphine)palladium(0) (144 mg, 0.125 mmol) was added. The sealed reaction was heated to 40° C. for 18 hours. The mixture was concentrated, and then purified by Biotage Flash 40M silica gel chromatography system, eluting with EtOAc followed by 5% MeOH in EtOAc. The product was obtained as a waxy solid (783 mg, 80%). $^1$H NMR (400 MHz, CDCl$_3$) δ 8.48 (d, J=6 Hz, 1H), 7.59 (s, 1H), 7.03 (t, J=9 Hz, 1H), 6.53 (m, 3H), 3.86 (br s, 2H), 3.78 (s, 2H), 2.73 (q, J=7 Hz, 4H), 1.19 (t, J=7 Hz, 6H). LRMS (ESI pos) m/e 370 (M+1).

Step C: Preparation of N-(4-(2-(3-(diethylamino)prop-1-ynyl)thieno[3,2-b]pyridin-7-yloxy)-3-fluorophenylcarbamothioyl)-2-phenylacetamide: To a stirred solution of 4-(2-(3-(diethylamino)prop-1-ynyl)thieno[3,2-b]pyridin-7-yloxy)-3-fluorobenzenamine (369 mg, 1.00 mmol) in 1:1 toluene/ethanol (5 mL) was added a solution of 4N HCl (0.375 mL, 1.50 mmol) in dioxane. Then 2-phenylethanoyl isothiocyanate (886 mg, 5.00 mmol; prepared according to J. Org. Chem. 1964, 29, 1115-1119) was added as a solution in toluene (1 mL) all at once. After stirring for 30 minutes at room temperature, the reaction mixture was concentrated. The residue was triturated with EtOAc (5 mL), and the resulting suspension was stirred for 1 hour to break up large chunks. The yellow suspension was filtered. The yellow solid was partitioned between EtOAc (15 mL) and a saturated aqueous solution of NaHCO$_3$ (20 mL). The phases were separated, and the aqueous phase was re-extracted with EtOAc (2×15 mL). The combined organic phases were washed with brine (20 mL), dried (Na$_2$SO$_4$), filtered, and concentrated. The crude was purified on a Biotage Horizon system using a reverse phase C18 column (M25 size). The following gradient was utilized [solvent A=water, solvent B=CH$_3$CN]: 15-30% B (100 mL), 30-70% B (300 mL), 70-95% B (100 mL), 95-100% B (100 mL), collecting in 96×9 mL tubes. Residual water/CH$_3$CN was azeotroped with absolute EtOH (3×20 mL). The product was obtained as a white powder (170 mg, 31%). $^1$H NMR (400 MHz, CDCl$_3$) δ 12.51 (br s, 1H), 8.59 (br s, 1H), 8.51 (d, J=6 Hz, 1H), 7.94 (m, 1H), 7.59 (s, 1H), 7.41 (m, 4H), 7.32 (m 2H), 7.26 (m, 1H, overlaps chloroform), 6.54 (d, J=6 Hz, 1H), 3.76 (s, 2H), 3.74 (s, 2H), 2.67 (q, J=7 Hz, 4H), 1.15 (t, J=7 Hz, 6H). LRMS (APCI neg) m/e 545 (M−1). HPLC: 100% purity (220 nm).

Example 7

Preparation of 1-(3-fluoro-4-(2-(3-(2-(pyrrolidin-1-yl)acetamido)prop-1-ynyl)thieno[3,2-b]pyridin-7-yloxy)phenyl)-3-(2-phenylacetyl)thiourea

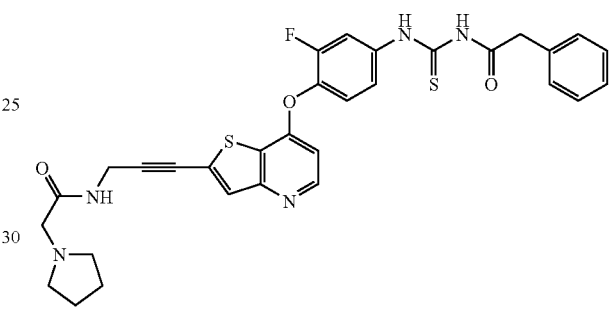

Step A: Preparation of N-(3-(7-(4-amino-2-fluorophenoxy)thieno[3,2-b]pyridin-2-yl)prop-2-ynyl)-2-(pyrrolidin-1-yl)acetamide: Prepared from 3-fluoro-4-(2-iodothieno[3,2-b]pyridin-7-yloxy)benzenamine (Example 6, Step A; 72 mg, 0.186 mmol) and N-(prop-2-ynyl)-2-(pyrrolidin-1-yl)acetamide (34 mg, 0.205 mmol; prepared according to the method described in WO 04/076412A) according to the procedure described for Example 6, Step B, except the reaction was executed at room temperature for 3 hours. The product was purified by preparative TLC (10% MeOH/CH$_2$Cl$_2$). The product was obtained as a waxy solid (69 mg, 65%). $^1$H NMR (400 MHz, CDCl$_3$) δ 8.48 (d, J=6 Hz, 1H), 7.60 (s, 1H), 7.52 (br s, 1H), 7.03 (t, J=9 Hz, 1H), 6.54 (m, 2H), 6.48 (m, 1H), 4.39 (d, J=6 Hz, 2H), 3.86 (br s, 2H), 3.28 (s, 2H), 2.69 (m, 4H), 1.85 (m, 4H). LRMS (ESI pos) m/e 425 (M+1).

Step B: Preparation of 1-(3-fluoro-4-(2-(3-(2-(pyrrolidin-1-yl)acetamido)prop-1-ynyl)thieno[3,2-b]pyridin-7-yloxy)phenyl)-3-(2-phenylacetyl)thiourea: Prepared from N-(3-(7-(4-amino-2-fluorophenoxy)thieno[3,2-b]pyridin-2-yl)prop-2-ynyl)-2-(pyrrolidin-1-yl)acetamide (69 mg, 0.163 mmol) using the procedure described for Example 6, Step C, except the crude was purified by preparative TLC (10% MeOH/CH$_2$Cl$_2$). The product was obtained as a waxy solid (2 mg, 1%). $^1$H NMR (400 MHz, CDCl$_3$) δ 12.51 (br s, 1H), 8.56 (br s, 1H), 8.51 (d, J=5 Hz, 1H), 7.95 (m, 1H), 7.62 (s, 1H), 7.59 (br s, 1H), 7.43 (m, 4H), 7.33 (m, 2H), 7.26 (m, 1H, overlaps with chloroform), 6.56 (d, J=5 Hz, 1H), 4.39 (d, J=6 Hz, 2H), 3.77 (s, 2H), 3.31 (br s, 2H), 2.72 (m, 4H), 1.87 (m, 4H). LRMS (APCI neg) m/e 600 (M−1).

Example 8

Preparation of N-(3-fluoro-4-(2-(3-(2-(pyrrolidin-1-yl)acetamido)prop-1-ynyl)-thieno[3,2-b]pyridin-7-yloxy)phenyl)-2-phenylacetamide

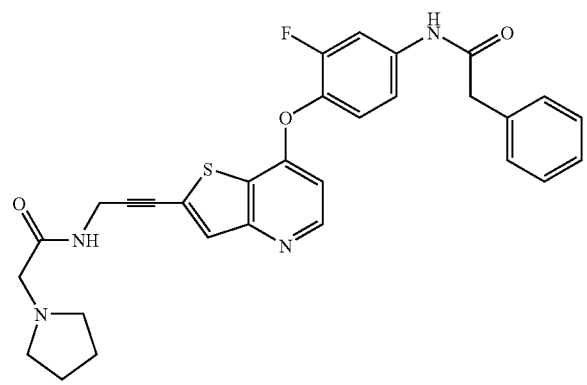

The title compound was obtained as a by-product from reaction of N-(3-(7-(4-amino-2-fluorophenoxy)thieno[3,2-b]pyridin-2-yl)prop-2-ynyl)-2-(pyrrolidin-1-yl)acetamide (Example 7, Step A; 69 mg, 0.163 mmol) with 2-phenylethanoyl isothiocyanate (32 mg, 0.179 mmol; prepared according to *J. Org. Chem.* 1964, 29, 1115-1119) using the procedure described for Example 6, Step C. The crude was purified by preparative TLC (10% MeOH/CH$_2$Cl$_2$). The product was obtained as a waxy solid (3 mg, 4%). $^1$H NMR (400 MHz, CDCl$_3$) δ 8.47 (d, J=6 Hz, 1H), 7.67 (m, 1H), 7.60 (s, 1H), 7.56 (m, 1H), 7.42 (m, 2H), 7.37 (m, 4H), 7.14 (m, 2H), 6.48 (d, J=6 Hz, 1H), 4.39 (d, J=6 Hz, 2H), 3.78 (s, 2H), 3.27 (s, 2H), 2.69 (m, 4H), 1.85 (m, 4H). LRMS (APCI neg) m/e 541 (M−1).

Example 9

Preparation of N-(4-(2-(3-(diethylamino)prop-1-ynyl)thieno[3,2-b]pyridin-7-yloxy)-3-fluorophenyl)-2-phenylacetamide

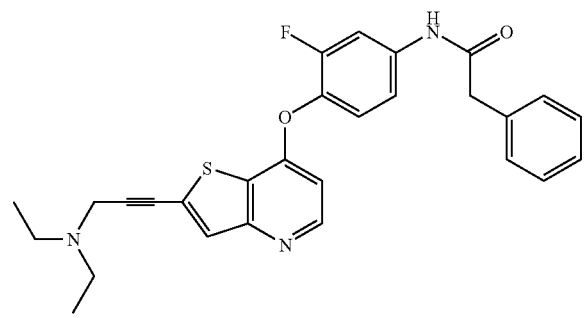

The title compound was obtained as a by-product from reaction of 4-(2-(3-(diethylamino)prop-1-ynyl)thieno[3,2-b]pyridin-7-yloxy)-3-fluoroaniline (Example 6, Step B; 54 mg, 0.146 mmol) with 2-phenylethanoyl isothiocyanate (29 mg, 0.161 mmol; prepared according to *J. Org. Chem.* 1964, 29, 1115-1119) using the procedure described for Example 6, Step C. The crude was purified by preparative TLC (10% MeOH/CH$_2$Cl$_2$). The product was obtained as a waxy solid (3 mg, 4%). $^1$H NMR (400 MHz, CDCl$_3$) δ 8.47 (d, J=5 Hz, 1H), 7.68 (m, 1H), 7.57 (s, 1H), 7.23-7.48 (m, 7H), 7.13 (m, 2H), 6.46 (d, J=5 Hz, 1H), 3.77 (s, 2H), 3.73 (s, 2H), 2.67 (m, 4H), 1.14 (m, 6H). LRMS (APCI neg) m/e 487 (M−1).

Example 10

Preparation of N1-(3-fluoro-4-(thieno[3,2-b]pyridin-7-yloxy)phenyl)-N3-(4-fluorophenyl)malonamide

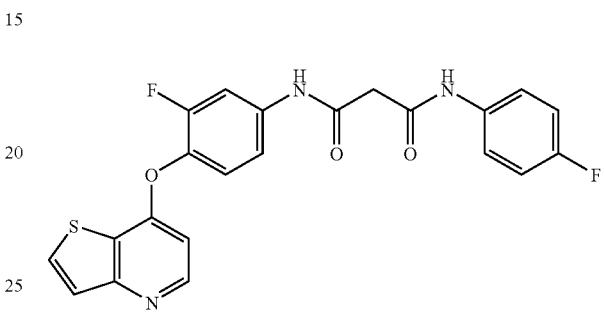

To a stirred mixture of 3-fluoro-4-(thieno[3,2-b]pyridin-7-yloxy)benzenamine (Example 1-B; 26 mg, 0.10 mmol), 3-(4-fluorophenylamino)-3-oxopropanoic acid (22 mg, 0.11 mmol; prepared from malonic acid and 4-fluoroaniline according to the methods described in WO 2005/030140 and by Shih and Rankin, *Synth. Comm.* 1996, 26(4), 833-836), and CH$_2$Cl$_2$ (1 mL) was added EDCI (38 mg, 0.20 mmol). The reaction was stirred at room temperature for 2 days. The mixture was diluted with EtOAc (10 mL) and washed with water (3×5 mL), brine (5 mL), dried (Na$_2$SO$_4$), filtered, and concentrated. The crude was purified on a pre-packed Isoelute silica gel column (10 g silica), eluting with a gradient of 20% EtOAc/hexanes, 1:1 EtOAc/hexanes, 2:1 EtOAc/hexanes, and then neat EtOAc. The product was obtained as a waxy solid (5 mg, 11%). $^1$H NMR (400 MHz, CDCl$_3$) δ 9.57 (s, 1H), 9.10 (s, 1H), 8.52 (m, 1H), 7.80 (m, 2H), 7.57 (m, 3H), 7.27 (m, 2H), 7.04 (m, 2H), 6.53 (d, J=4 Hz, 1H), 3.52 (s, 2H). LRMS (ESI pos) m/e 440 (M+1). HPLC: 97% purity (220 nm).

Example 11

Preparation of N-(3-fluoro-4-(thieno[3,2-b]pyridin-7-yloxy)phenyl)-N-(4-fluorophenyl)cyclopropane-1,1-dicarboxamide

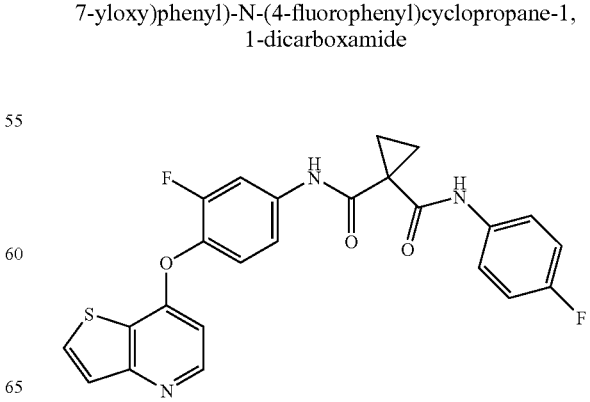

Prepared from 3-fluoro-4-(thieno[3,2-b]pyridin-7-yloxy) benzenamine (Example 1, Step B; 130 mg, 0.50 mmol) and 1-((4-fluorophenyl)carbamoyl) -cyclopropanecarboxylic acid (123 mg, 0.550 mmol; prepared from cyclopropane-1,1-dicarboxylic acid and 4-fluoroaniline using the methods described in WO 2005/030140 and by Shih and Rankin, *Synth. Comm.* 1996, 26(4), 833-836) according to the procedure described for Example 10. The crude was purified by preparative TLC (10% MeOH/CH$_2$Cl$_2$). The product was obtained as a waxy solid (60 mg, 25%). $^1$H NMR (400 MHz, CDCl$_3$) δ 10.06 (s, 1H), 8.51 (s, 1H), 8.29 (s, 1H), 7.75 (m, 2H), 7.56 (d, J=5 Hz, 1H), 7.45 (m, 2H), 7.26 (m, 2H), 7.06 (m, 2H), 6.51 (d, J=5 Hz, 1H), 1.80 (m, 2H), 1.62 (m, 2H). LRMS (ESI pos) m/e 466 (M+1). HPLC: 97% purity (220 nm).

Example 12

Preparation of N-(4-(2-(3-(diethylamino)prop-1-ynyl)thieno[3,2-b]pyridin-7-yloxy)-3-fluorophenyl)-N-(4-fluorophenyl)cyclopropane-1,1-dicarboxamide

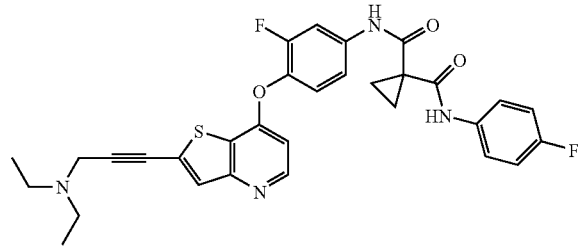

Step A: Preparation of N-(3-fluoro-4-(2-iodothieno[3,2-b]pyridin-7-yloxy)phenyl)-N-(4-fluorophenyl)cyclopropane-1,1-dicarboxamide: To a stirred mixture of 1-((4-fluorophenyl)carbamoyl)-cyclopropanecarboxylic acid (867 mg, 3.88 mmol; prepared from cyclopropane-1,1-dicarboxylic acid and 4-fluoroaniline using the methods described in WO 2005/030140 and by Shih and Rankin, *Synth. Comm.* 1996, 26(4), 833-836) and a catalytic amount of DMF (10 µL) in THF (10 mL) was added oxalyl dichloride (0.33 mL, 3.9 mmol) dropwise. After stirring at room temperature for 30 minutes, a solution of 3-fluoro-4-(2-iodothieno[3,2-b]pyridin-7-yloxy) benzenamine (Example 6, Step A; 600 mg, 1.55 mmol) in THF (2 mL) was added. After stirring for 1 hour at room temperature, the reaction was diluted into aqueous saturated NaHCO$_3$ (50 mL) and water (50 mL). The product was extracted with EtOAc, washed with brine, dried (Na$_2$SO$_4$), filtered and concentrated. The product was purified by Biotage 40S silica gel column eluting with 2:1 EtOAc/hexanes. The product was obtained as a fluff-y white solid (745 mg, 67%). $^1$H NMR (400 MHz, CDCl$_3$) δ 10.13 (s, 1H), 8.41 (d, J=6 Hz, 1H), 8.34 (s, 1H), 7.74 (m, 2H), 7.44 (m, 2H), 7.22 (m, 2H), 7.06 (m, 2H), 6.46 (d, J=6 Hz, 1H), 1.79 (m, 2H), 1.61 (m, 2H). LRMS (ESI pos) m/e 592 (M+1).

Step B: Preparation of N-(4-(2-(3-(diethylamino)prop-1-ynyl)thieno[3,2-b]pyridin-7-yloxy)-3-fluorophenyl)-N-(4-fluorophenyl)cyclopropane -1,1-dicarboxamide: Prepared from N-(3-fluoro-4-(2-iodothieno[3,2-b]pyridin-7-yloxy) phenyl) -N-(4-fluorophenyl)cyclopropane-1,1-dicarboxamide (500 mg, 0.845 mmol) and N, N-diethylprop-2-yn-1-amine (118 mg, 1.06 mmol) according to the procedure described for Example 6, Step B, except the reaction was heated at 50° C. for 1 hour. The crude was purified by two successive Biotage 40M silica gel columns eluting with 5% MeOH in EtOAc, and then on a second column with 5% MeOH (containing 7N NH$_3$) in CHCl$_3$. Yield: 115 mg (24%). $^1$H NMR (400 MHz, CDCl$_3$) δ 10.15 (s, 1H), 8.47 (m, 2H), 7.77 (m, 1H), 7.55 (s, 1H), 7.45 (m, 2H), 7.20 (m, 2H), 7.05 (m, 2H), 6.50 (d, J=5 Hz, 1H), 3.71 (s, 2H), 2.65 (m, 4H), 1.78 (m, 2H), 1.62 (m, 2H), 1.13 (m, 6H). LRMS (APCI pos) m/e 575 (M+1). HPLC: 99% purity (220 nm).

Example 13

Preparation of 1-(4-(2-(3-(diethylamino)-3-methylbut-1-ynyl)thieno[3,2-b]pyridin-7-yloxy)-3-fluorophenyl)-3-(2-phenylacetyl)thiourea

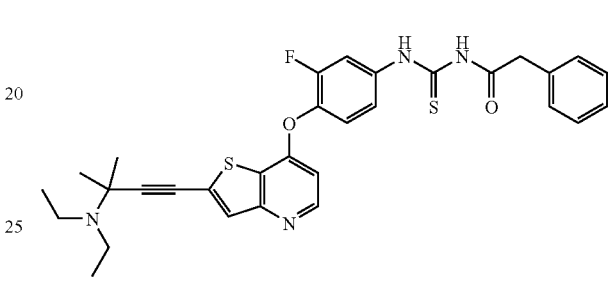

Step A: Preparation of N,N-diethyl-2-methylbut-3-yn-2-amine: Prepared using methodology described by Zaragoza, F., et al. *J. Med. Chem.* 2004, 47, 2833. To a stirred mixture of diethylamine (10.3 mL, 99.6 mmol), 3-chloro-3-methylbut-1-yne (10.2 g, 99.6 mmol), triethylamine (16.7 mL, 119 mmol), and THF (100 mL) at 0° C. was added copper(I) chloride (0.986 g, 9.96 mmol). The resulting suspension was allowed to warm to room temperature, and stirring continued for 4 hours. The reaction mixture was partitioned between diethyl ether (250 mL) and a saturated aqueous solution of NaHCO$_3$ (100 mL). The phases were separated, and the aqueous phase was re-extracted with diethyl ether (100 mL). The combined organic phases were dried (Na$_2$SO$_4$), filtered, and concentrated. The brown oil was distilled (105-110° C.) at atmospheric pressure under N$_2$. The product was obtained as an oil (1.85 g, 9%). $^1$H NMR (400 MHz, CDCl$_3$) δ 2.66 (q, J=7 Hz, 4H), 2.21 (s, 1H), 1.40 (s, 6H), 1.08 (t, J=7 Hz, 6H).

Step B: Preparation of 4-(2-(3-(diethylamino)-3-methylbut-1-ynyl)thieno[3,2-b]pyridin-7-yloxy)-3-fluorobenzenamine: Prepared from N,N-diethyl-2-methylbut-3-yn-2-amine (21 mg, 0.15 mmol) and 3-fluoro-4-(2-iodothieno[3,2-b]pyridin-7-yloxy)benzenamine (Example 6, Step A; 39 mg, 0.10 mmol) using the procedure described for Example 6, Step B, except the reaction was heated to 50° C. for 24 hours. The crude was purified by preparative TLC (10% MeOH/CH$_2$Cl$_2$). The product was obtained as a waxy solid (13 mg, 31%). $^1$H NMR (400 MHz, CDCl$_3$) δ 8.47 (m, 1H), 7.51 (s, 1H), 7.02 (m, 1H), 6.49 (m, 3H), 3.85 (s, 2H), 2.76 (m, 4H), 1.52 (s, 6H), 1.14 (m, 6H).

Step C: Preparation of 1-(4-(2-(3-(diethylamino)-3-methylbut-1-ynyl)thieno[3,2-b]pyridin-7-yloxy)-3-fluorophenyl)-3-(2-phenylacetyl)thiourea: Prepared from 4-(2-(3-(diethylamino)-3-methylbut-1-ynyl)thieno[3,2-b]pyridin-7-yloxy)-3-fluorobenzenamine (13 mg, 0.033 mmol) according to the procedure described for Example 6, Step C. The crude was purified by preparative TLC (10% MeOH/EtOAc). The product was obtained as a waxy solid (8 mg, 40%). $^1$H NMR (400 MHz, CDCl$_3$) δ 12.5 (s, 1H), 8.60 (s, 1H), 8.50 (d, J=6 Hz, 1H), 7.92 (m, 1H), 7.53 (s, 1H), 7.41 (m, 4H), 7.32 (m, 2H), 7.25 (m, 1H, overlaps with chloroform), 6.53 (d, J=6 Hz, 1H), 3.76 (s, 2H), 2.77 (m, 4H), 1.52 (s, 6H), 1.14 (m, 6H). LRMS (ESI neg) m/e 573 (M−1).

Example 14

Preparation of 1-(4-(2-(4-(diethylamino)but-1-ynyl)thieno[3,2-b]pyridin-7-yloxy)-3-fluorophenyl)-3-(2-phenylacetyl)thiourea

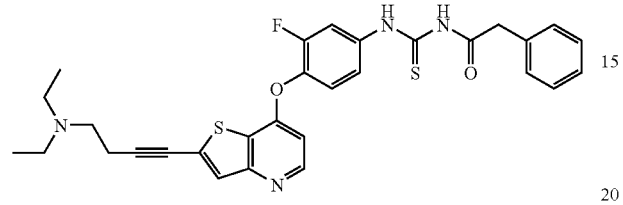

Step A: Preparation of N,N-diethylbut-3-yn-1-amine: Prepared using methodology described by Olomucki, M., et al. *Ann. Chim.* 1960, 5, 845. A stirred mixture of but-3-ynyl 4-methylbenzenesulfonate (21.2 g, 94.5 mmol), diethylamine (6.91 g, 94.5 mmol), and p-dioxane (100 mL) was heated to 80° C. under $N_2$ for 6 hours. After cooling to room temperature, the suspension was diluted with diethyl ether (100 mL) and filtered. The solids were washed with diethyl ether (50 mL). The filtrate was concentrated to a brown oil. The crude was co-distilled (55-65° C.) with p-dioxane under a mild vacuum (10-50 torr). The product was obtained as an oil (7.6 g, 27%), in a 42:58 mixture with p-dioxane based on $^1$H NMR. $^1$H NMR (400 MHz, CDCl$_3$) δ 2.70 (t, J=8 Hz, 2H), 2.55 (q, J=7 Hz, 4H), 2.32 (m, 2H), 1.97 (t, J=3 Hz, 1H), 1.04 (t, J=7 Hz, 6H).

Step B: Preparation of 4-(2-(4-(diethylamino)but-1-ynyl)thieno[3,2-b]pyridin-7-yloxy)-3-fluorobenzenamine: Prepared from N,N-diethylbut-3-yn-1-amine (30 mg, 1.04 mmol) and 3-fluoro-4-(2-iodothieno[3,2-b]pyridin-7-yloxy)benzenamine (Example 6, Step A; 200 mg, 0.518 mmol) according to the procedure described for Example 6, Step B, except the reaction was heated to 50° C. for 7 hours. The crude was purified by preparative TLC (10% MeOH/EtOAc). The product was obtained as a waxy solid (12 mg, 6%). $^1$H NMR (400 MHz, CDCl$_3$) δ 8.46 (d, J=6 Hz, 1H), 7.52 (s, 1H), 7.03 (m, 1H), 6.52 (m, 3H), 3.85 (s, 2H), 2.88 (m, 2H), 2.67 (m, 6H), 1.12 (m, 6H).

Step C: Preparation of 1-(4-(2-(4-(diethylamino)but-1-ynyl)thieno[3,2-b]pyridin-7-yloxy)-3-fluorophenyl)-3-(2-phenylacetyl)thiourea: Prepared from 4-(2-(4-(diethylamino)but-1-ynyl)thieno[3,2-b]pyridin-7-yloxy)-3-fluorobenzenamine (12 mg, 0.031 mmol) according to the procedure described in Example 6, Step C. After the reaction was completed, it was partitioned between EtOAc (10 mL) and a saturated aqueous solution of NaHCO$_3$ (10 mL). The phases were separated, and the aqueous phase was re-extracted with EtOAc (2×10 mL). The combined organic phases were washed with brine (10 mL), dried (Na$_2$SO$_4$), filtered, and concentrated. The resulting crude was purified by preparative TLC (10% MeOH/EtOAc). The prepped product was obtained as a waxy solid (5 mg, 28%). $^1$H NMR (400 MHz, CDCl$_3$) δ 12.51 (s, 1H), 8.58 (br s, 1H), 8.49 (d, J=5 Hz, 1H), 7.95 (m, 1H), 7.54 (s, 1H), 7.42 (m, 4H), 7.32 (m, 2H), 7.26 (m, 1H, overlaps chloroform), 6.53 (d, J=5 Hz, 1H), 3.75 (s, 2H), 2.87 (t, J=8 Hz, 2H), 2.66 (m, 6H), 1.10 (t, J=7 Hz, 6H). LRMS (APCI neg) m/e 559 (M−1). HPLC: 99% purity (220 nm).

Example 15

Preparation of 1-(3-fluoro-4-(2-propylthieno[3,2-b]pyridin-7-yloxy)phenyl)-3-(2-phenylacetyl)thiourea

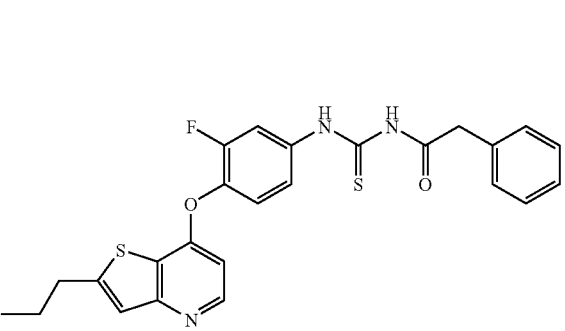

Step A: Preparation of 3-fluoro-4-(2-propylthieno[3,2-b]pyridin-7-yloxy)benzenamine: Obtained as a by-product during hydrogenation of the alkyne of 4-(2-(3-(diethylamino)prop-1-ynyl)thieno[3,2-b]pyridin-7-yloxy)-3-fluoroaniline (Example 6, Step B). A mixture of N-4-(2-(3-(diethylamino)prop-1-ynyl)thieno[3,2-b]pyridin-7-yloxy)-3-fluorobenzenamine (Example 6, Step B; 106 mg, 0.287 mmol), 4N HCl in dioxane (72 μL, 0.29 mmol), palladium on carbon (61 mg, 0.029 mmol; Degussa type, 10 wt % Pd. 50% water), and 1:1 CH$_2$Cl$_2$/EtOH (10 mL) was purged with $N_2$ (3×), and then shaken under H$_2$ (50 psi) for 18 hours at room temperature on a Parr shaker. The mixture was filtered, rinsing the Pd/C with MeOH. The resulting filtrate was concentrated, and the residue was partitioned between EtOAc (20 mL) and a saturated aqueous solution of NaHCO$_3$ (20 mL). The phases were separated, and the aqueous phase was re-extracted with EtOAc (2×10 mL). The combined organic phases were washed with brine (10 mL), dried (Na$_2$SO$_4$), filtered, and concentrated. The crude was purified by preparative TLC (25% MeOH in CH$_2$Cl$_2$). The product was obtained as a waxy solid (8 mg, 8%). $^1$H NMR (400 MHz, CDCl$_3$) δ 8.41 (m, 1H), 7.23 (s, 1H, overlaps with chloroform), 7.03 (m, 1H), 6.52 (m, 3H), 3.81 (br s, 2H), 2.93 (m, 2H), 1.80 (m, 2H), 1.03 (m, 3H).

Step B: Preparation of 1-(3-fluoro-4-(2-propylthieno[3,2-b]pyridin-7-yloxy)phenyl)-3-(2-phenylacetyl)thiourea: A mixture of 3-fluoro-4-(2-propylthieno[3,2-b]pyridin-7-yloxy)benzenamine (8 mg, 0.03 mmol) and 2-phenylethanoyl isothiocyanate (9 mg, 0.05 mmol; prepared according to *J. Org. Chem.* 1964, 29, 1115-1119) in 1:1 toluene/ethanol (0.5 mL) were stirred at room temperature for 2 hours. The reaction mixture was purified by preparative TLC (5% MeOH/EtOAc). The product was obtained as a waxy solid (8 mg, 58%). $^1$H NMR (400 MHz, CDCl$_3$) δ 12.49 (s, 1H), 8.57 (s, 1H), 8.45 (m, 1H), 7.94 (m, 1H), 7.44 (m, 4H), 7.32 (m, 2H), 7.25 (m, 2H, overlaps chloroform), 6.48 (m, 1H), 3.76 (s, 2H), 2.93 (m, 2H), 1.81 (m, 2H), 1.04 (m, 3H). LRMS (ESI neg) m/e 478 (M−1).

Example 16

Preparation of 1-(3-fluoro-4-(2-(3-(piperidin-1-yl)prop-1-ynyl)thieno[3,2-b]pyridin-7-yloxy)phenyl)-3-(2-phenylacetyl)thiourea

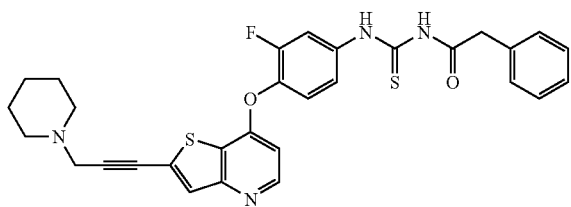

Step A: Preparation of 1-(prop-2-ynyl)piperidine: Prepared using methodology as described in US 2005/0026944. To a stirred mixture of piperidine (851 mg, 10.0 mmol), cesium carbonate (3.26 g, 10.0 mmol) and acetone (20 mL) was added 3-bromoprop-1-yne (1.49 g, 10.0 mmol; 80% in toluene) at room temperature. The white suspension was stirred for 18 hours at room temperature. The suspension was filtered, and the filtrate was concentrated. The resulting residue was triturated with diethyl ether (10 mL), filtered, and the filtrate concentrated to obtain the product as an oil (0.70 g, 56%). $^1$H NMR (400 MHz, CDCl$_3$) δ 3.27 (d, J=2 Hz, 2H), 2.50 (m, 4H), 2.22 (t, J=2 Hz, 1H), 1.62 (m, J=6 Hz, 4H), 1.43 (m, 2H).

Step B: Preparation of 3-fluoro-4-(2-(3-(piperidin-1-yl)prop-1-ynyl)thieno[3,2-b]pyridin-7-yloxy)benzenamine: Prepared from 1-(prop-2-ynyl)piperidine (24 mg, 0.19 mmol) and 3-fluoro-4-(2-iodothieno[3,2-b]pyridin-7-yloxy)benzenamine (Example 6, Step A; 50 mg, 0.13 mmol) according to the procedure described for Example 6, Step B, except the reaction was heated at 50° C. for 5 hours. The crude was purified by preparative TLC [5% MeOH (containing 7N NH$_3$) in CHCl$_3$]. The product was obtained as a waxy solid (41 mg, 71%). $^1$H NMR (400 MHz, CDCl$_3$) δ 8.47 (d, J=6 Hz, 1H), 7.58 (s, 1H), 7.03 (t, J=9 Hz, 1H), 6.52 (m, 3H), 3.85 (br s, 2H), 3.56 (s, 2H), 2.60 (m, 4H), 1.66 (m, 4H), 1.47 (m, 2H).

Step C: Preparation of 1-(3-fluoro-4-(2-(3-(piperidin-1-yl)prop-1-ynyl)thieno[3,2-b]pyridin-7-yloxy)phenyl)-3-(2-phenylacetyl)thiourea: Prepared from 3-fluoro-4-(2-(3-(piperidin-1-yl)prop-1-ynyl)thieno[3,2-b]pyridin-7-yloxy)benzenamine (41 mg, 0.11 mmol) according to the procedure described for Example 6, Step C, except 4:1 EtOH/toluene (5 mL) and DMF (3 drops) were used as solvent and stirring was continued for 2 hours at room temperature. Workup and purification were as described for Example 14, Step C. The product was obtained as a waxy solid (15 mg, 22%). $^1$H NMR (400 MHz, CDCl$_3$) δ 12.52 (s, 1H), 8.72 (s, 1H), 8.51 (d, J=6 Hz, 1H), 7.93 (m, 1H), 7.60 (s, 1H), 7.42 (m, 4H), 7.32 (m, 3H), 6.54 (d, J=6 Hz, 1H), 3.75 (s, 2H), 3.57 (s, 2H), 2.60 (m, 4H), 1.66 (m, 4H), 1.47 (m, 2H). LRMS (APCI neg) m/e 557 (M−1).

Example 17

Preparation of 1-(3-fluoro-4-(2-(3-(4-methylpiperazin-1-yl)prop-1-ynyl)thieno[3,2-b]pyridin-7-yloxy)phenyl)-3-(2-phenylacetyl)thiourea

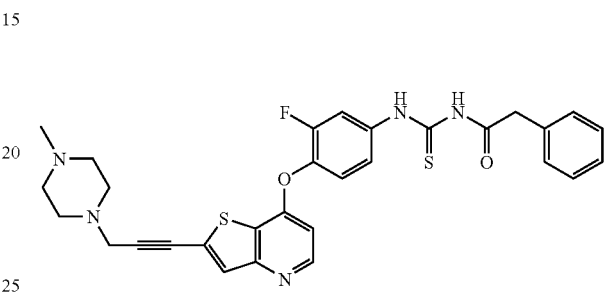

Step A: Preparation of 1-methyl-4-(prop-2-ynyl)piperazine: Prepared from 1-methylpiperazine (1.00 g, 10.00 mmol) using the procedure described for Example 16, Step A. The crude product was obtained as an oil (0.92 g, 50%; 75% purity by $^1$H NMR). $^1$H NMR (400 MHz, CDCl$_3$) δ 3.31 (m, 2H), 2.89 (m, 1H), 2.3-2.6 (m, 8H), 2.30 (m, 3H).

Step B: Preparation of 3-fluoro-4-(2-(3-(4-methylpiperazin-1-yl)prop-1-ynyl)thieno[3,2-b]pyridin-7-yloxy)benzenamine: Prepared from 1-methyl-4-(prop-2-ynyl)piperazine (26.8 mg, 0.194 mmol) and 3-fluoro-4-(2-iodothieno[3,2-b]pyridin-7-yloxy)benzenamine (Example 6, Step A; 50 mg, 0.13 mmol) according to the procedure described for Example 6, Step B, except the reaction was heated at 50° C. for 7 hours. The crude was purified by preparative TLC eluting with 5% MeOH (containing 7N NH$_3$) in CH$_2$Cl$_2$. The product was obtained as a waxy solid (40 mg, 75%). $^1$H NMR (400 MHz, CDCl$_3$) δ 8.47 (d, J=6 Hz, 1H), 7.58 (s, 1H), 7.03 (m, 1H), 6.53 (m, 3H), 3.86 (br s, 2H), 3.61 (s, 2H), 2.5-2.8 (m, 8H), 2.37 (s, 3H).

Step C: Preparation of 1-(3-fluoro-4-(2-(3-(4-methylpiperazin-1-yl)prop-1-ynyl)thieno[3,2-b]pyridin-7-yloxy)phenyl)-3-(2-phenylacetyl)thiourea: Prepared from 3-fluoro-4-(2-(3-(4-methylpiperazin-1-yl)prop-1-ynyl)thieno[3,2-b]pyridin-7-yloxy)benzenamine (40 mg, 0.10 mmol) according to the procedure described for Example 6, Step C, except DMF (6 mL) was used as co-solvent in addition to 1:1 toluene/ethanol (2 mL), and vigorous stirring was continued for 2 hours at room temperature. Workup and purification were as described for Example 14, Step C [(1-(4-(2-(4-(diethylamino)but-1-ynyl)thieno[3,2-b]pyridin-7-yloxy)-3-fluorophenyl)-3-(2-phenylacetyl)thiourea], using 20% MeOH in CH$_2$Cl$_2$ to develop the preparative TLC plate. The product was obtained as a beige powder (3 mg, 5%). $^1$H NMR (400 MHz, CDCl$_3$) δ 12.52 (s, 1H), 8.58 (s, 1H), 8.51 (d, J=5 Hz, 1H), 7.95 (m, 1H), 7.60 (s, 1H), 7.41 (m, 3H), 7.30 (m, 4H), 6.54 (d, J=5 Hz, 1H), 3.76 (s, 2H), 3.60 (s, 2H), 2.4-2.9 (m, 8H), 2.36 (s, 3H). LRMS (APCI neg) m/e 572 (M−1). HPLC: 100% purity (220 nm).

Example 18

Preparation of 1-(4-(2-(3-(4-ethylpiperazin-1-yl)prop-1-ynyl)thieno[3,2-b]pyridin-7-yloxy)-3-fluorophenyl)-3-(2-phenylacetyl)thiourea

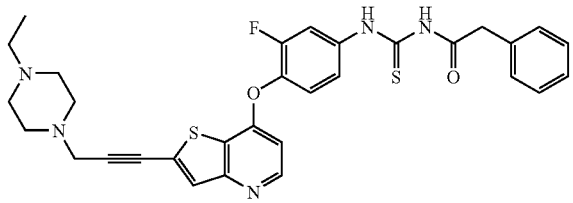

Step A: Preparation of 1-ethyl-4-(prop-2-ynyl)piperazine: Prepared from 1-ethylpiperazine (1.14 g, 10.0 mmol) using the procedure described for Example 16, Step A. The crude product was obtained as an oil (1.15 g, 73%). $^1$H NMR (400 MHz, CDCl$_3$) δ 3.30 (d, J=2 Hz, 2H), 2.42 (q, J=7 Hz, 2H), 2.4-2.8 (m, 8H), 2.24 (t, J=2 Hz, 1H), 1.09 (t, J=7 Hz, 3H).

Step B: Preparation of 4-(2-(3-(4-ethylpiperazin-1-yl)prop-1-ynyl)thieno[3,2-b]pyridin-7-yloxy)-3-fluorobenzenamine: Prepared from 1-ethyl-4-(prop -2-ynyl)piperazine (59 mg, 0.39 mmol) and 3-fluoro-4-(2-iodothieno[3,2-b]pyridin-7-yloxy)benzenamine (Example 6, Step A; 100 mg, 0.26 mmol) according to the procedure described for Example 6, Step B, except the reaction was heated at 50° C. for 7 hours. The crude was purified by preparative TLC [5% MeOH (containing 7N NH$_3$) in CH$_2$Cl$_2$]. The product was obtained as a waxy solid (48 mg, 40%). $^1$H NMR (400 MHz, CDCl$_3$) δ 8.47 (d, J=6 Hz, 1H), 7.58 (s, 1H), 7.03 (t, J=9 Hz, 1H), 6.53 (m, 2H), 6.47 (m, 1H), 3.86 (br s, 2H), 3.60 (s, 2H), 2.45-2.74 (m, 8H), 2.46 (q, J=7 Hz, 2H), 1.11 (t, J=7 Hz, 3H).

Step C: Preparation of 1-(4-(2-(3-(4-ethylpiperazin-1-yl)prop-1-ynyl)thieno[3,2-b]pyridin-7-yloxy)-3-fluorophenyl)-3-(2-phenylacetyl)thiourea: Prepared from 4-(2-(3-(4-ethylpiperazin-1-yl)prop-1-ynyl)thieno[3,2-b]pyridin-7-yloxy)-3-fluorobenzenamine (44 mg, 0.11 mmol) according to the procedure described for Example 6, Step C, except DMF (2 mL) was used as co-solvent in addition to 1:1 toluene/ethanol (2 mL), and stirring was continued for 2 hours at room temperature. Workup and purification were as described for Example 14, Step C, using 20% MeOH in CH$_2$Cl$_2$ to develop the preparative TLC plate. The product was obtained as a beige powder (5 mg, 8%). $^1$H NMR (400 MHz, CDCl$_3$) δ 12.51 (s, 1H), 8.62 (s, 1H), 8.51 (d, J=6 Hz, 1H), 7.96 (s, 1H), 7.60 (s, 1H), 7.44 (m, 4H), 7.30 (m, 3H, overlaps chloroform), 6.55 (d, J=6 Hz, 1H), 3.76 (s, 2H), 3.61 (s, 2H), 2.4-2.8 (m, 8H), 2.49 (m, 2H), 1.13 (m, 3H). LRMS (APCI neg) m/e 586 (M−1). HPLC: 100% purity (220 nm).

Example 19

Preparation of 1-(3-fluoro-4-(2-(3-morpholinoprop)-1-ynyl)thieno[3,2-b]pyridin-7-yloxy)phenyl)-3-(2-phenylacetyl)thiourea

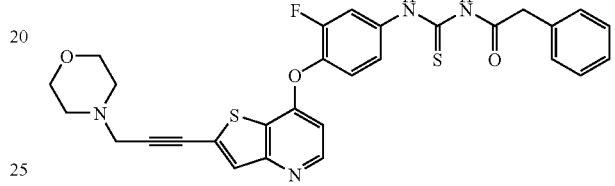

Step A: Preparation of 4-(prop-2-ynyl)morpholine: Prepared from morpholine (0.871 g, 10.00 mmol) using the procedure described for Example 16, Step A. The crude product was obtained as an oil (1.13 g, 84%). $^1$H NMR (400 MHz, CDCl$_3$) δ 3.74 (m, 4H), 3.29 (d, J=2 Hz, 2H), 2.57 (m, 4H), 2.27 (t, J=2 Hz, 1H).

Step B: Preparation of 3-fluoro-4-(2-(3-morpholinoprop-1-ynyl)thieno[3,2-b]pyridin-7-yloxy)benzenamine: Prepared from 4-(prop-2-ynyl)morpholine (24 mg, 0.19 mmol) and 3-fluoro-4-(2-iodothieno[3,2-b]pyridin-7-yloxy)benzenamine (Example 6, Step A; 50 mg, 0.13 mmol) according to the procedure described for Example 6, Step B, except the reaction was heated at 50° C. for 7 hours. The crude was purified by preparative TLC [5% MeOH (containing 7N NH$_3$) in CH$_2$Cl$_2$]. The product was obtained as a waxy solid (39 mg, 77%). $^1$H NMR (400 MHz, CDCl$_3$) δ 8.48 (d, J=5 Hz, 1H), 7.59 (s, 1H), 7.03 (m, 1H), 6.53 (m, 3H), 3.79 (m, 6H), 3.59 (s, 2H), 2.66 (m, 4H).

Step C: Preparation of 1-(3-fluoro-4-(2-(3-morpholinoprop-1-ynyl)thieno[3,2-b]pyridin-7-yloxy)phenyl)-3-(2-phenylacetyl)thiourea: Prepared from 3-fluoro-4-(2-(3-morpholinoprop-1-ynyl)thieno[3,2-b]pyridin-7-yloxy)benzenamine (39 mg, 0.10 mmol) according to the procedure described for Example 6, Step C, except in addition to 3:1 ethanol/toluene (4 mL), DMF (4 mL) was used as co-solvent and stirring was continued for 2 hours at room temperature. Workup and purification were as described for Example 14, Step C. The product was obtained as a white powder (15 mg, 26%). $^1$H NMR (400 MHz, CDCl$_3$) δ 12.5 (s, 1H), 8.51 (d, J=6 Hz, 1H), 8.50 (s, 1H), 7.94 (m, 1H), 7.61 (s, 1H), 7.43 (m, 4H), 7.29 (m, 3H, overlaps chloroform), 6.55 (d, J=6 Hz, 1H), 3.79 (m, 4H), 3.76 (s, 2H), 3.59 (s, 2H), 2.66 (m, 4H). LRMS (APCI neg) m/e 559 (M−1). HPLC: 98% purity (220 nm).

Example 20

Preparation of 1-(4-(2-(3-(4-(dimethylamino)piperidin-1-yl)prop-1-ynyl)thieno[3,2-b]pyridin-7-yloxy)-3-fluorophenyl)-3-(2-phenylacetyl)thiourea

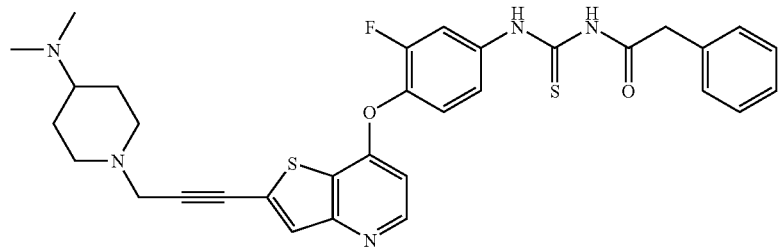

Step A: Preparation of N,N-dimethyl-1-(prop-2-ynyl)piperidin-4-amine: Prepared from N,N-dimethylpiperidin-4-amine (1.28 g, 10.0 mmol) using the procedure described for Example 16, Step A. The crude product was obtained as an oil (1.60 g, 65%; 67% purity by $^1$H NMR). $^1$H NMR (400 MHz, CDCl$_3$) δ 3.30 (d, J=3 Hz, 2H), 2.93 (m, 2H), 2.63 (m, 1H), 2.28 (s, 6H), 2.22 (m, 2H), 1.82 (m, 2H), 1.55 (m, 2H).

Step B: Preparation of 1-(3-(7-(4-amino-2-fluorophenoxy)thieno[3,2-b]pyridin-2-yl)prop-2-ynyl)-N,N-dimethylpiperidin-4-amine: Prepared from N,N-dimethyl-1-(prop-2-ynyl)piperidin-4-amine (32 mg, 0.19 mmol) and 3-fluoro-4-(2-iodothieno[3,2-b]pyridin-7-yloxy)benzenamine (Example 6, Step A; 50 mg, 0.13 mmol) according to the procedure described for Example 6, Step B, except the reaction was heated at 50° C. for 7 hours. The crude was partially purified by preparative TLC [5% MeOH (containing 7N NH$_3$) in CH$_2$Cl$_2$]. The product was obtained as a waxy solid (34 mg, 31%; 50% purity by $^1$H NMR), and carried forward without further purification. LRMS (APCI pos) m/e 425 (M+1).

Step C: Preparation of 1-(4-(2-(3-(4-(dimethylamino)piperidin-1-yl)prop-1-ynyl)thieno[3,2-b]pyridin-7-yloxy)-3-fluorophenyl)-3-(2-phenylacetyl)thiourea: Prepared from 1-(3-(7-(4-amino-2-fluorophenoxy)thieno[3,2-b]pyridin-2-yl)prop-2-ynyl)-N,N-dimethylpiperidin-4-amine (34 mg, 0.080 mmol) according to the procedure described for Example 6, Step C, except that in addition to 3:1 ethanol/toluene (4 mL), DMF (2 mL) was used as co-solvent and stirring was continued for 2 hours at room temperature. Workup and purification were as described in Example 14, Step C, except purification by two successive preparative TLC plates was required (eluting with 20% MeOH in CH$_2$Cl$_2$ for the first plate and then 30% MeOH/CH$_2$Cl$_2$ for the second plate). The product was obtained as a beige powder (2 mg, 4%). $^1$H NMR (400 MHz, CDCl$_3$) δ 12.5 (s, 1H), 8.51 (d, J=5 Hz, 1H), 7.91 (m, 1H), 7.59 (s, 1H), 7.42 (m, 4H), 7.33 (m, 2H), 7.26 (m, 2H, overlaps chloroform), 6.58 (d, J=5 Hz, 1H), 3.78 (s, 2H), 3.60 (s, 2H), 3.04 (m, 2H), 2.34 (m, 9H), 1.90 (m, 2H, overlaps water peak), 1.64 (m, 2H, overlaps water peak). LRMS (APCI neg) m/e 600 (M−1). HPLC: 92% purity (220 nm).

Example 21

Preparation of 1-(3-fluoro-4-(2-(3-(S,S-dioxo-4-thiapiperidin-1-yl)prop-1-ynyl)thieno[3,2-b]pyridin-7-yloxy)phenyl)-3-(2-phenylacetyl)thiourea

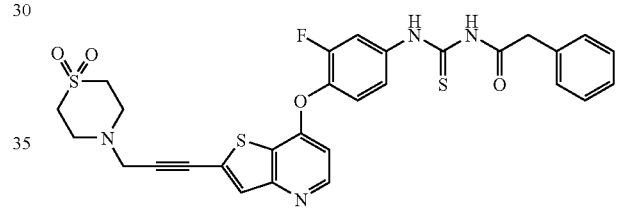

Step A: Preparation of 4-(2-(3-(S,S-dioxo-4-thiapiperidin-1-yl)prop-1-ynyl)thieno[3,2-b]pyridin-7-yloxy)-3-fluorobenzenamine: Prepared from 3-fluoro-4-(2-iodothieno[3,2-b]pyridin-7-yloxy)benzenamine (Example 6, Step A; 50 mg, 0.13 mmol) and commercially available N-propargyl-S,S-dioxo-4-thiapiperidine (34 mg, 0.19 mmol) according to the procedure described for Example 6, Step B, except the reaction was heated at 50° C. for 5 hours. The crude was purified by preparative TLC [5% MeOH (containing 7N NH$_3$) in CH$_2$Cl$_2$]. The product was obtained as a white powder (45 mg, 67%). $^1$H NMR (400 MHz, CDCl$_3$) δ 8.49 (d, J=6 Hz, 1H), 7.61 (s, 1H), 7.03 (t, J=9 Hz, 1H), 6.55 (m, 2H), 6.49 (m, 1H), 3.86 (br s, 2H), 3.72 (s, 2H), 3.17 (m, 8H).

Step B: Preparation of 1-(3-fluoro-4-(2-(3-(S,S-dioxo-4-thiapiperidin-1-yl)prop-1-ynyl)thieno[3,2-b]pyridin-7-yloxy)phenyl)-3-(2-phenylacetyl)thiourea: Prepared from 4-(2-(3-(S, S-dioxo-4-thiapiperidin-1-yl)prop-1-ynyl)thieno[3,2-b]pyridin-7-yloxy)-3-fluorobenzenamine (55 mg, 0.13 mmol) according to the procedure described for Example 6, Step C, except in addition to 4:1 ethanol/toluene (5 mL), DMF (0.1 mL) was used as co-solvent and stirring was continued for 2 hours at room temperature. Workup and purification were as described in Example 14, Step C. The product was obtained as a beige powder (14 mg, 16%). $^1$H NMR (400 MHz, CDCl$_3$) δ 12.51 (s, 1H), 8.56 (m, 2H), 7.95 (m, 1H), 7.64 (s, 1H), 7.44 (m, 4H), 7.31 (m, 3H), 6.58 (d, J=5 Hz, 1H), 3.76 (s, 2H), 3.73 (s, 2H), 3.17 (m, 8H). LRMS (APCI neg) m/e 607 (M–1).

Example 22

Preparation of 1-(3-fluoro-4-(2-(3-(S-oxo-4-thiapiperidin-1-yl)prop-1-ynyl)thieno[3,2-b]pyridin-7-yloxy)phenyl)-3-(2-phenylacetyl)thiourea

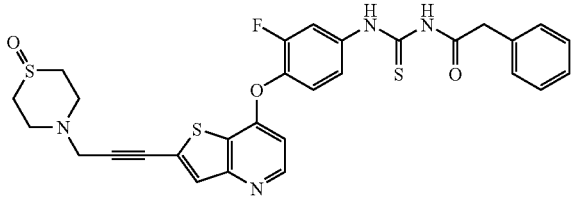

Step A: Preparation of tert-butyl thiomorpholine-4-carboxylate: A stirred solution of thiomorpholine (194 g, 1.87 mol) in $CH_2Cl_2$ (1 L) was cooled to 0° C. under $N_2$. A solution of tert-butyl tert-butyloxycarbonylcarbonate (389 g, 1.78 mol) in $CH_2Cl_2$ (800 mL) was added over a 4 hour period via addition funnel. The reaction was allowed to warm to room temperature, and stirring was continued for 18 hours. The reaction mixture was washed with a saturated aqueous solution of $NH_4Cl$ (2×500 mL), 1M aqueous HCl (500 mL), and brine (500 mL). The organic phase was dried ($MgSO_4$), filtered, and concentrated. The crude was stirred with diethyl ether (400 mL) for 18 hours and then filtered to obtain a white powder (243 g, 67%).

Step B: Preparation of N-tert-butoxycarbonyl-5-oxo-4-thiapiperidine: A mechanically-stirred mixture of tert-butyl thiomorpholine-4-carboxylate (243 g, 1.19 mol), MeOH (1.5 L), and $H_2O$ (1.5 L) was cooled to 0° C. Solid $NaIO_4$ (280 g, 1.3 mol) was added in portions over a 2 hour period. For convenience, the suspension was stirred for 3 days at room temperature. The solids were filtered, washing with MeOH (3×500 mL). The filtrate was concentrated. Residual water was saturated with solid NaCl, and the aqueous phase was extracted with EtOAc (4×200 mL). The combined organic phases were dried ($MgSO_4$), filtered, and concentrated to obtain the product (255 g, 97%).

Step C: Preparation of S-oxo-4-thiapiperidine hydrochloride: A mixture of N-tert -butoxycarbonyl-5-oxo-4-thiapiperidine (02 g, 0.918 mol) and 2N HCl in diethyl ether (1.3 L) was mechanically stirred at room temperature for 18 hours. The suspension was filtered. The solid was triturated with hot isopropanol (300 mL), cooled to room temperature, filtered, and washed with isopropanol (2×50 mL) and diethyl ether (2×50 mL). After drying under high vacuum the product was obtained as a beige powder (100 g, 70%). $^1H$ NMR (400 MHz, DMSO-d6) δ 9.64 (br s, 2H), 3.50 (m, 2H), 3.33 (m, 2H), 3.18 (m, 2H), 3.06 (m, 2H).

Step D: Preparation of N-propargyl S-oxo-4-thiapiperidine: Prepared from S-oxo-4-thiapiperidine hydrochloride (1.28 g, 10.0 mmol) using the procedure described for Example 16, Step A. The crude product was obtained as a waxy solid (242 mg, 51%). $^1H$ NMR (400 MHz, DMSO-d6) δ 3.33 (d, J=2 Hz, 2H), 3.21 (t, J=2 Hz, 1H), 2.98 (m, 2H), 2.86 (m, 2H), 2.78 (m, 2H), 2.64 (m, 4H).

Step E: Preparation of 1-(3-(7-(4-amino-2-fluorophenoxy) thieno[3,2-b]pyridin-2-yl)prop-2-ynyl)-S-oxo-4-thiapiperidine: Prepared from N-propargyl S-oxo-4-thiapiperidine (30.5 mg, 0.194 mmol) and 3-fluoro-4-(2-iodothieno[3,2-b]pyridin-7-yloxy)benzenamine (Example 6, Step A; 50 mg, 0.13 mmol) according to the procedure described for Example 6, Step B, except the reaction was heated at 50° C. for 7 hours. The crude was purified by preparative TLC [5% MeOH (containing 7N $NH_3$) in $CH_2Cl_2$]. The product was obtained as a waxy solid (45 mg, 74%). $^1H$ NMR (400 MHz, $CDCl_3$) δ 8.48 (d, J=6 Hz, 1H), 7.61 (s, 1H), 7.03 (m, 1H), 6.53 (m, 2H), 6.47 (m, 1H), 3.89 (br s, 2H), 3.64 (s, 2H), 3.25 (m, 2H), 2.92 (m, 6H).

Step F: Preparation of 1-(3-fluoro-4-(2-(3-(S-oxo-4-thiapiperidin-1-yl)prop-1-ynyl)thieno[3,2-b]pyridin-7-yloxy) phenyl)-3-(2-phenylacetyl)thiourea: Prepared from 1-(3-(7-(4-amino-2-fluorophenoxy)thieno[3,2-b]pyridin-2-yl)prop-2-ynyl)-S-oxo-4-thiapiperidine (45 mg, 0.11 mmol) according to the procedure described for Example 6, Step C, except in addition to 1:1 ethanol/toluene (2 mL), DMF (2 mL) was used as co-solvent and stirring was continued for 2 hours at room temperature. Workup and purification were as described in Example 14, Step C, except 20% MeOH in EtOAc was used to develop the preparative TLC plate. The product was obtained as a beige powder (10 mg, 15%). $^1H$ NMR (400 MHz, $CDCl_3$) δ 12.56 (s, 1H), 9.04 (s, 1H), 8.52 (m, 1H), 7.95 (m, 1H), 7.63 (s, 1H), 7.35 (m, 7H), 6.57 (m, 1H), 3.77 (s, 2H), 3.66 (s, 2H), 3.29 (m, 2H), 2.97 (m, 6H). LRMS (APCI neg) m/e 591 (M–1). HPLC: 99% purity (220 nm).

Example 23

Preparation of 1-(3-fluoro-4-(2-(3-(4-hydroxy-4-(trifluoromethyl)piperidin-1-yl)prop-1-ynyl)thieno[3,2-b]pyridin-7-yloxy)phenyl)-3-(2-phenylacetyl)thiourea

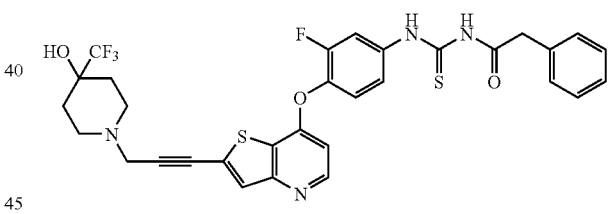

Step A: Preparation of benzyl 4-hydroxy-4-(trifluoromethyl)piperidine-1-carboxylate: To a stirred solution of benzyl 4-oxopiperidine-1-carboxylate (308 g, 1.32 mol) in THF (1 L) cooled in an ice bath was added trimethyl(trifluoromethyl)silane (229 g, 1.61 mol) via an addition funnel over a period of 15 minutes. A 1.0 M solution of TBAF in THF (13.2 mL, 13.2 mmol) was slowly added dropwise to the mixture. After being stirred for 16 hours at ambient temperature, the mixture was charged with additional trimethyl(trifluoromethyl)silane (25.0 g, 176 mmol) and stirred for 2 hours. The mixture was concentrated to a volume of 500 mL, diluted with MeOH (3 L), cooled in an ice bath, and carefully quenched with concentrated aqueous HCl (250 mL). The mixture was removed from the ice bath, stirred for 1 hour, and concentrated in vacuo. The resulting aqueous suspension was extracted with $CH_2Cl_2$ (1 L, then 2×500 mL). The combined $CH_2Cl_2$ extracts were dried ($MgSO_4$), filtered, and concentrated. The crude material was crystallized from toluene to give 357 g (89%) of product as a white solid.

Step B: Preparation of 4-(trifluoromethyl)piperidin-4-ol: To a stirred solution of benzyl 4-hydroxy-4-(trifluoromethyl)

piperidine-1-carboxylate (347 g, 1.15 mole) in EtOH (1.2 L) was added Pd—C (Degussa type, 10 wt. % Pd, 50% H$_2$O, 26.0 g, 12.2 mmol) and cyclohexene (850 mL, 8.39 mol). The mixture was heated to a gentle reflux for 1 hour resulting in a slight exotherm and the vigorous evolution of gas. Upon cooling to ambient temperature, the mixture was filtered through Celite®, and the filtrate was concentrated. The resulting residue was dissolved in CH$_2$Cl$_2$ (500 mL), dried (Na$_2$SO$_4$), filtered, and concentrated to give an orange solid. The crude material was crystallized from MTBE to give 160 g (83%) of product as an off-white solid. $^1$H NMR (400 MHz, DMSO-d6) δ 5.71 (br s, 1H), 2.74 (m, 4H), 2.42 (br s, 1H, overlaps DMSO), 1.53 (m, 4H).

Step C: Preparation of 1-(prop-2-ynyl)-4-(trifluoromethyl)piperidin-4-ol: Prepared from 4-(trifluoromethyl)piperidin-4-ol (169 mg, 1.00 mmol) using the procedure described for Example 16, Step A. The crude product was obtained as a waxy solid (140 mg, 66%). $^1$H NMR (400 MHz, CDCl$_3$) δ 3.33 (d, J=3 Hz, 2H), 2.81 (m, 2H), 2.54 (m, 2H), 2.27 (t, J=3 Hz, 1H), 1.99 (m, 2H), 1.93 (br s, 1H), 1.76 (m, 2H).

Step D: Preparation of 1-(3-(7-(4-amino-2-fluorophenoxy)thieno[3,2-b]pyridin-2-yl)prop-2-ynyl)-4-(trifluoromethyl)piperidin-4-ol: Prepared from 1-(prop-2-ynyl)-4-(trifluoromethyl)piperidin-4-ol (40 mg, 0.19 mmol) and 3-fluoro-4-(2-iodothieno[3,2-b]pyridin-7-yloxy)benzenamine (Example 6, Step A; 50 mg, 0.13 mmol) according to the procedure described for Example 6, Step B, except the reaction was heated at 50° C. for 7 hours. The crude was partially purified by preparative TLC [5% MeOH (containing 7N NH$_3$) in CH$_2$Cl$_2$]. The product was obtained as a waxy solid (24 mg) and carried forward without further purification, Step E: Preparation of 1-(3-fluoro-4-(2-(3-(4-hydroxy-4-(trifluoromethyl)piperidin-1-yl)prop-1-ynyl)thieno[3,2-b]pyridin-7-yloxy)phenyl)-3-(2-phenylacetyl)thiourea: Prepared from 1-(3-(7-(4-amino-2-fluorophenoxy)thieno[3,2-b]pyridin-2-yl)prop-2-ynyl)-4-(trifluoromethyl)piperidin-4-ol (24 mg, 0.052 mmol) according to the procedure described for Example 6, Step C, except stirring was continued for 2 hours at room temperature. Workup and purification were as described in Example 14, Step C, except 5% MeOH in EtOAc was used to develop the preparative TLC plate. The product was obtained as a beige powder (1 mg, 3%). $^1$H NMR (400 MHz, CDCl$_3$) δ 12.5 (s, 1H), 8.51 (m, 2H), 7.94 (m, 1H), 7.61 (s, 1H), 7.45 (m, 4H), 7.31 (m, 2H), 7.26 (m, 1H, overlaps chloroform), 6.57 (d, J=6 Hz, 1H), 3.76 (s, 2H), 3.64 (s, 2H), 2.90 (m, 2H), 2.66 (m, 2H), 2.05 (m, 3H), 1.82 (m, 2H, overlaps water peak). LRMS (APCI neg) m/e 641 (M−1). HPLC: 100% purity (220 nm).

Examples 24-71 described the preparation of compounds having the structure:

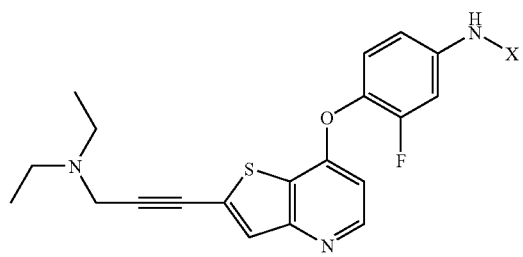

These compounds were prepared from the reaction of 4-(2-(3-(diethylamino)-prop-1-ynyl)thieno[3,2-b]pyridin-7-yloxy)-3-fluorobenzenamine ((Example 6, Step B) with polystyrene-2,3,5,6-tetrafluoro-4-(methylcarbamoyl)phenol (PS-TFP) resin loaded with different carboxylic and sulfonic acids (Table 1). PS-TFP resin was loaded with carboxylic and sulfonic acid inputs from Table 1 using conditions described by Salvino, J. W. et al. *J. Comb. Chem.* 2000, 2, 691-697.

Example 24

Preparation of N-(4-(2-(3-(diethylamino)prop-1-ynyl)thieno[3,2-b]pyridin-7-yloxy)-3-fluorophenyl)acetamide

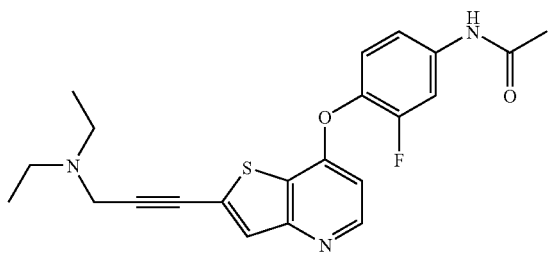

Step A: Preparation of polystyrene-2,3,5,6-tetrafluoro-4-(methylcarbamoyl)phenyl acetate: This is a representative procedure for the preparation of the PS-TFP resins listed in Table 1. In this example, the resin has the structure:

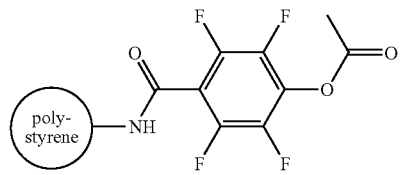

To 200 mg of PS-TFP resin (1.0 mmol/g, 0.20 mmol) was added 0.5 mL of a 0.60 M solution of acetic acid in dry DMF (0.30 mmol) and 1.5 mL of a 0.08 M DMAP solution in CH$_2$Cl$_2$ (0.12 mmol). The mixture was shaken/agitated for 10 minutes. This was followed by the addition of 0.5 mL of 1.76 M DIC in CH$_2$Cl$_2$ (0.88 mmol) and the solution was mixed for 3 hours at room temperature. The mixture was filtered, and the resin was washed with DMF (3×3 mL), THF (3×3 mL), DMF (3×3 mL), and CH$_2$Cl$_2$ (3×3 mL) and dried to afford purified resin-bound TFP active ester.

Step B: Preparation of N-(4-(2-(3-(diethylamino)prop-1-ynyl)thieno[3,2-b]pyridin-7-yloxy)-3-fluorophenyl)acetamide: This is a representative example for the synthesis of the title compounds in Examples 24-71.

A 20 mL scintillation vial was charged with polystyrene-2,3,5,6-tetrafluoro-4-(methylcarbamoyl)phenyl acetate (0.179 g, 0.238 mmol). 4-(2-(3-(Diethylamino)-prop-1-ynyl)thieno[3,2-b]pyridin-7-yloxy)-3-fluorobenzenamine (Example 6, Step B 0.022 g, 0.0595 mmol) in DMA (2 mL) was added to the resin, and the mixture was heated at 100° C. with shaking for 96 hours. The reaction was cooled to room temperature and filtered using a vacuum master and Jones tubes. The filtrate was collected in 13 mm test tubes. The resin was washed with DMA (2 mL) making the total volume 4 mL. The crude material was dried using a GeneVac DD-4 set at 50° C. for the chamber and vial holder. Vacuum was set to aqua speed and reached a pressure of 7 mm Hg. The crude oil was purified by reverse phase chromatography (see purification method A, below). The final product was a TFA salt and a yellow oil (6.9 mg, 16%). Final Purity: 97%, LRMS (APCI pos) m/e 412.1 (M+1).

Purification Method A (Used for Examples 24-71):
Columns:
  Preparative: YMC Basic 250×20 mm S-10 um S/N #209461
  Analytical UV: YMC ODS-AQ 50×4.6 mm S-3 um S/N #040507227
  Analytical MS: (Instrument-Southpark) Zorbax Extend-C18 50×4.6 mm S-3.5 um S/N #USIA001491

Solvents:
  Pump A: $H_2O$ with 0.10% TFA
  Pump B: Acetonitrile with 0.05% TFA
Detectors:
  Preparative: UV @ 254 nm
  Analytical: UV @ 220 and 254 nm; Finnigan LCQ Duo
  Sample dissolved in 2 mL 50/50$H_2O$/acetonitrile+2.2 mL acetonitrile with 0.05% TFA.
  Mobile Phase Gradient: 25-95% B, total run time 25 minutes, injection volume 4200 μL.
  Table 1: PS-TFP activated agents (carboxylic and sulfonic acids) used to prepare compounds in Examples 24-71 (in no particular order).

TABLE 1

| Structure | Formula | Mol Weight of Acid Fragment | Name of Acid Loaded to Resin |
|---|---|---|---|
| 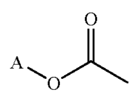 | $C_2H_3O_2A$ | 59.0 | Acetic Acid |
| 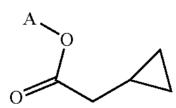 | $C_5H_7O_2A$ | 99.1 | Cyclopropyl acetic acid |
| 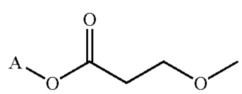 | $C_4H_7O_3A$ | 103.1 | 3-Methoxypropionic acid |
| 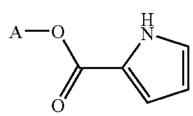 | $C_5H_4NO_2A$ | 110.1 | Pyrrole-2-carboxylic acid |
| 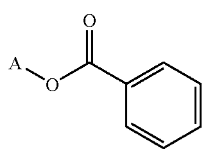 | $C_7H_5O_2A$ | 121.1 | Benzoic acid |
| | $C_6H_4NO_2A$ | 122.1 | Picolinic acid |
| | $C_6H_4NO_2A$ | 122.1 | Nicotinic acid |
| | $C_6H_4NO_2A$ | 122.1 | Isonicotinic acid |
| 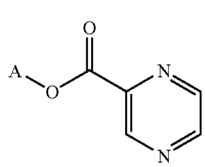 | $C_5H_3N_2O_2A$ | 123.1 | Pyrazine-2-carboxylic acid |

TABLE 1-continued

| Structure | Formula | Mol Weight of Acid Fragment | Name of Acid Loaded to Resin |
|---|---|---|---|
| 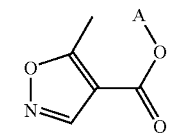 | $C_5H_4NO_3A$ | 126.1 | 5-Methylisoxazole-4-carboxylic acid |
| 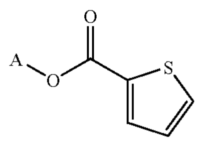 | $C_5H_3O_2SA$ | 127.1 | Thiophene-2-carboxylic acid |
| 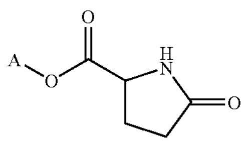 | $C_5H_6NO_3A$ | 128.1 | DL-Pyroglutamic acid |
| 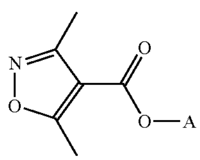 | $C_6H_6NO_3A$ | 140.1 | 3,5-Dimethylisoxazole-4-carboxylic acid |
| 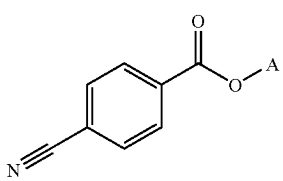 | $C_8H_4NO_2A$ | 146.1 | 4-Cyanobenzoic acid |
| 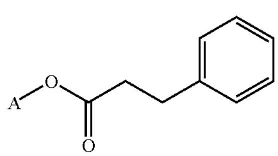 | $C_9H_9O_2A$ | 149.2 | Hydrocinnamic acid |
| 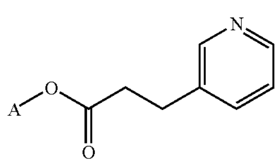 | $C_8H_8NO_2A$ | 150.2 | 3-Pyridine propionic acid |
| 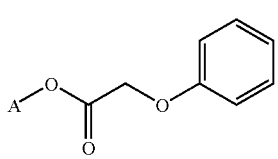 | $C_8H_7O_3A$ | 151.1 | Phenoxyacetic acid |
| 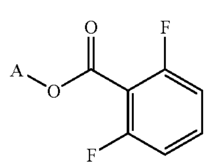 | $C_7H_3F_2O_2A$ | 157.1 | 2,6-Difluorobenzoic acid |

TABLE 1-continued

| Structure | Formula | Mol Weight of Acid Fragment | Name of Acid Loaded to Resin |
|---|---|---|---|
| 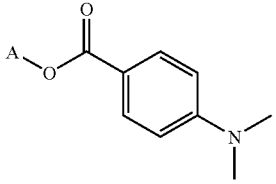 | C₉H₁₀NO₂A | 164.2 | 4-(Dimethylamino)benzoic acid |
| 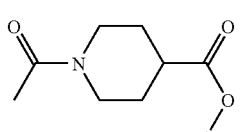 | C₈H₁₂NO₃A | 170.2 | 1-Acetylpiperidine-4-carboxylic acid |
| 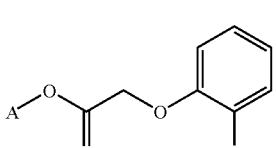 | C₈H₆ClO₃A | 185.6 | 2-Chlorophenoxyacetic acid |
| 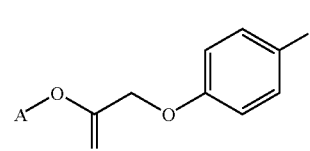 | C₈H₆ClO₃A | 185.6 | 4-Chlorophenoxyacetic acid |
| 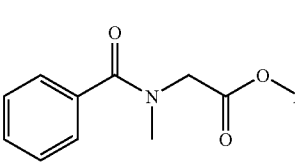 | C₁₀H₁₀NO₃A | 192.2 | N-Methylhippuric acid |
| 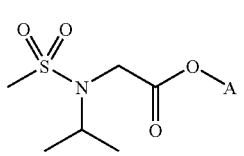 | C₆H₁₂NO₄SA | 194.2 | (Isopropyl-methanesulfonyl-amino)-acetic acid |
| 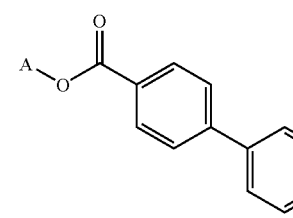 | C₁₃H₉O₂A | 197.2 | 4-Biphenyl carboxylic acid |
| 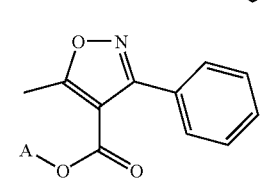 | C₁₁H₈NO₃A | 202.2 | 5-Methyl-3-phenyl isoxazole-4-carboxylic acid |
| 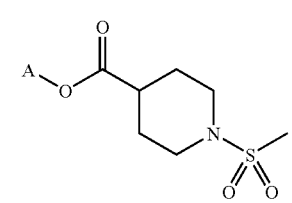 | C₇H₁₂NO₄SA | 206.2 | 1-Methane sulfonyl piperidine-4-carboxylic acid |

TABLE 1-continued

| Structure | Formula | Mol Weight of Acid Fragment | Name of Acid Loaded to Resin |
|---|---|---|---|
| 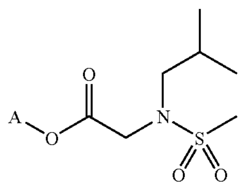 | $C_7H_{14}NO_4SA$ | 208.3 | (Isobutyl-methane sulfonylamino)acetic acid |
|  | $C_{13}H_9O_3A$ | 213.2 | 4-Phenoxybenzoic acid |
|  | $C_{13}H_9O_3A$ | 213.2 | 3-Phenoxybenzoic acid |
| 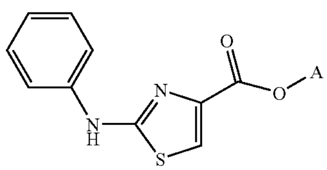 | $C_{10}H_7N_2O_2SA$ | 219.2 | 2-Phenylaminothiazole-4-carboxylic acid |
| 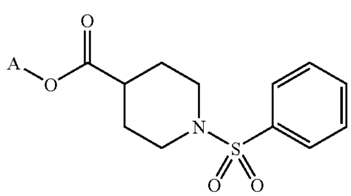 | $C_{12}H_{14}NO_4SA$ | 268.3 | 1-Benzenesulfonyl piperidine-4-carboxylic acid |
| 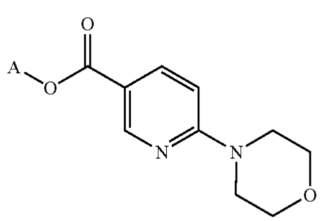 | $C_{10}H_{11}N_2O_3A$ | 207.2 | 6-Morpholin-4-yl nicotinic acid |
| 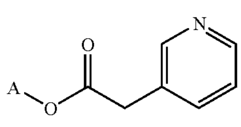 | $C_7H_6NO_2A$ | 136.1 | 3-Pyridyl acetic acid HCl |
| 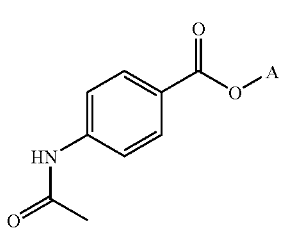 | $C_9H_8NO_3A$ | 178.2 | 4-Acetamidobenzoic acid |

TABLE 1-continued

| Structure | Formula | Mol Weight of Acid Fragment | Name of Acid Loaded to Resin |
|---|---|---|---|
| (6-oxo-1,6-dihydropyridine-3-carboxylate, A-O-C(=O)-pyridinone) | $C_6H_4NO_3A$ | 138.1 | 6-Oxo-1,6-dihydro-pyridine-3-carboxylic acid; 6-Hydroxynicotinic acid (tautomer) |
| (4-chlorophenylsulfonate) | $C_6H_4SO_3Cl$ | 191.6 | 4-chlorophenylsulfonic acid |
| (4-methoxyphenylsulfonate) | $C_7H_7O_4SA$ | 187.2 | 4-methoxyphenylsulfonic acid |
| (3-(tert-butylcarbamoyl)benzenesulfonate) | $C_{11}H_{14}O_4SNA$ | 256.3 | 3-(tert-butylcarbamoyl)benzenesulfonic acid |
| (4-(tert-butylcarbamoyl)benzenesulfonate) | $C_{11}H_{14}O_4SNA$ | 256.3 | 4-(tert-butylcarbamoyl)benzenesulfonic acid |
| (phenyl carbonate) | $C_7H_5O_3A$ | 137.1 | phenyl hydrogen carbonate |
| (benzenesulfonate) | $C_6H_5SO_3A$ | 157.2 | benzenesulfonic acid |
| (3-chlorobenzenesulfonate) | $C_6H_4SO_3ClA$ | 191.6 | 3-chlorobenzenesulfonic acid |
| (2-chlorobenzenesulfonate) | $C_6H_4SO_3ClA$ | 191.6 | 2-chlorobenzenesulfonic acid |

TABLE 1-continued

| Structure | Formula | Mol Weight of Acid Fragment | Name of Acid Loaded to Resin |
|---|---|---|---|
| 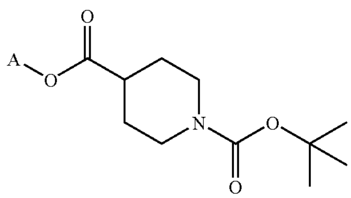 | $C_{11}H_{18}NO_4A$ | 228.3 | 1-(tert-butoxycarbonyl)piperidine-4-carboxylic acid |
| 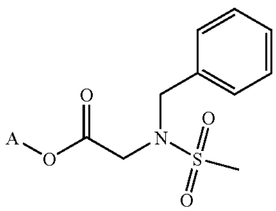 | $C_{10}H_{12}SNO_4A$ | 242.3 | 2-(N-benzylmethan-6-ylsulfonamido)acetic acid |
| 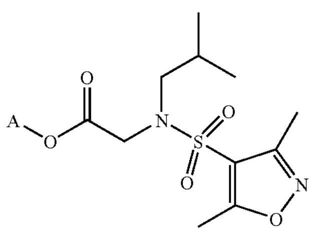 | $C_{11}H_{17}SN_2O_3A$ | 289.3 | 2-(N-isobutyl-3,5-dimethylisoxazole-4-sulfonamido)acetic acid |

Table 2 summarizes the compounds of Examples 24-71, prepared according to the representative Example 24, Steps A and B.

TABLE 2

| Example Number | Structure | Name | M.W. | Purity |
|---|---|---|---|---|
| 24 | 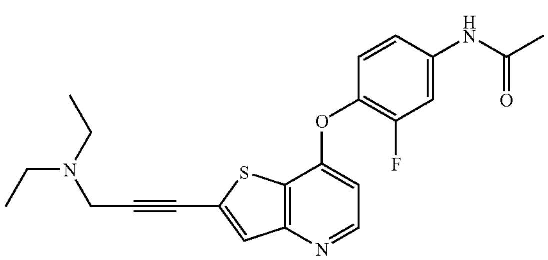 | N-(4-(2-(3-(diethylamino)prop-1-ynyl)thieno[3,2-b]pyridin-7-yloxy)-3-fluorophenyl)acetamide | 411 | 97 |
| 25 | 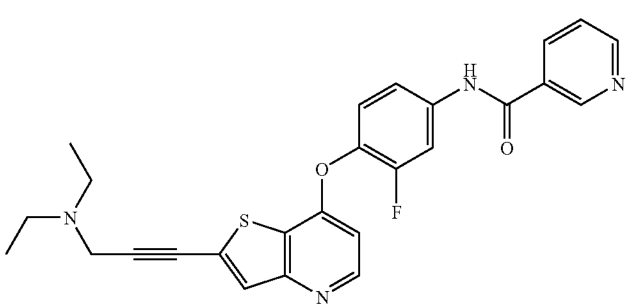 | N-(4-(2-(3-(diethylamino)prop-1-ynyl)thieno[3,2-b]pyridin-7-yloxy)-3-fluorophenyl)nicotinamide | 476 | 89 |

TABLE 2-continued

| Example Number | Structure | Name | M.W. | Purity |
|---|---|---|---|---|
| 26 | 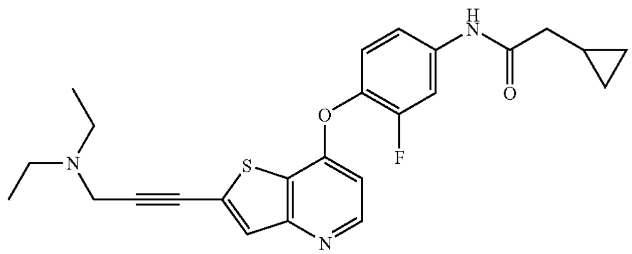 | 2-cyclopropyl-N-(4-(2-(3-(diethylamino)prop-1-ynyl)thieno[3,2-b]pyridin-7-yloxy)-3-fluorophenyl)acetamide | 453 | 100 |
| 27 | 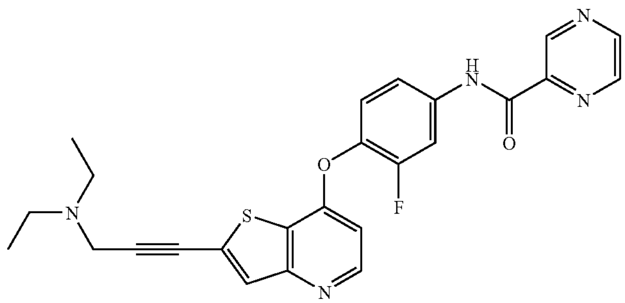 | N-(4-(2-(3-(diethylamino)prop-1-ynyl)thieno[3,2-b]pyridin-7-yloxy)-3-fluorophenyl)pyrazine-2-carboxamide | 476 | 99 |
| 28 | 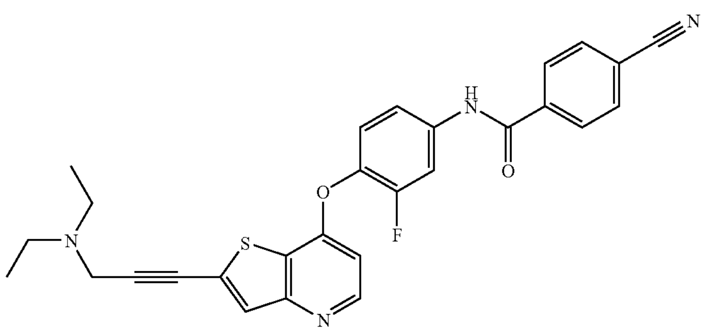 | 4-cyano-N-(4-(2-(3-(diethylamino)prop-1-ynyl)thieno[3,2-b]pyridin-7-yloxy)-3-fluorophenyl)benzamide | 500 | 99 |
| 29 | 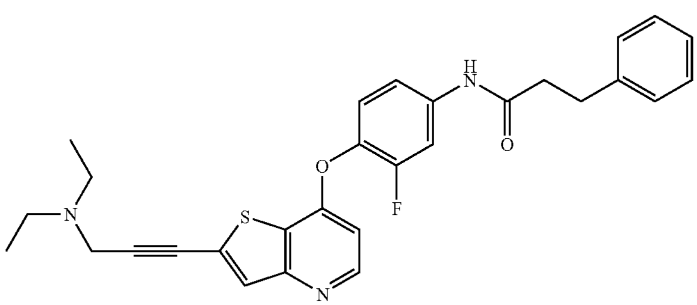 | N-(4-(2-(3-(diethylamino)prop-1-ynyl)thieno[3,2-b]pyridin-7-yloxy)-3-fluorophenyl)-3-phenylpropanamide | 503 | 99 |
| 30 | 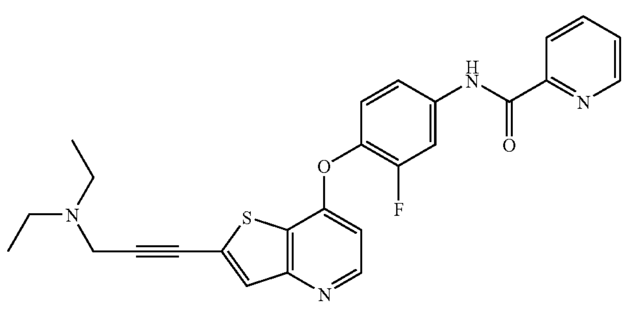 | N-(4-(2-(3-(diethylamino)prop-1-ynyl)thieno[3,2-b]pyridin-7-yloxy)-3-fluorophenyl)picolinamide | 476 | 97 |

| Example Number | Structure | Name | M.W. | Purity |
|---|---|---|---|---|
| 31 | 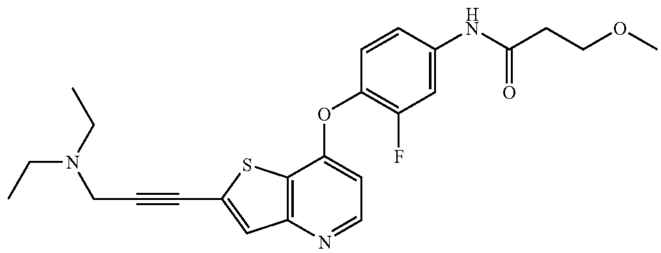 | N-(4-(2-(3-(diethylamino)prop-1-ynyl)thieno[3,2-b]pyridin-7-yloxy)-3-fluorophenyl)-3-methoxypropanamide | 457 | 100 |
| 32 | 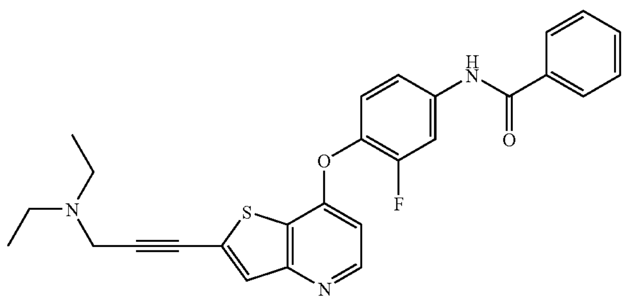 | N-(4-(2-(3-(diethylamino)prop-1-ynyl)thieno[3,2-b]pyridin-7-yloxy)-3-fluorophenyl)benzamide | 475 | 100 |
| 33 | 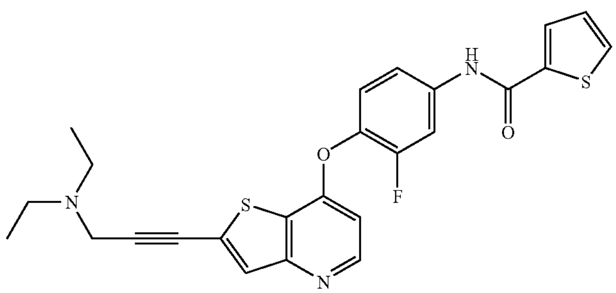 | N-(4-(2-(3-(diethylamino)prop-1-ynyl)thieno[3,2-b]pyridin-7-yloxy)-3-fluorophenyl)thiophene-2-carboxamide | 481 | 100 |
| 34 | 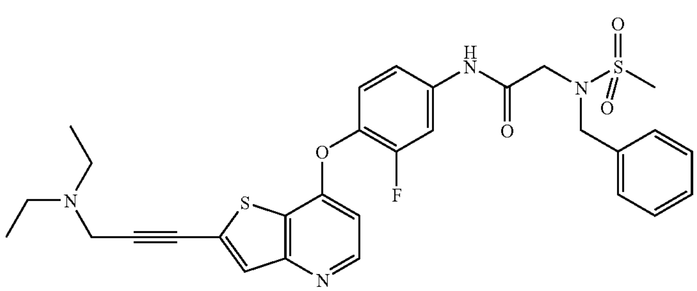 | 2-(N-benzylmethan-3-ylsulfonamido)-N-(4-(2-(3-(diethylamino)prop-1-ynyl)thieno[3,2-b]pyridin-7-yloxy)-3-fluorophenyl)acetamide | 596 | 99 |
| 35 | 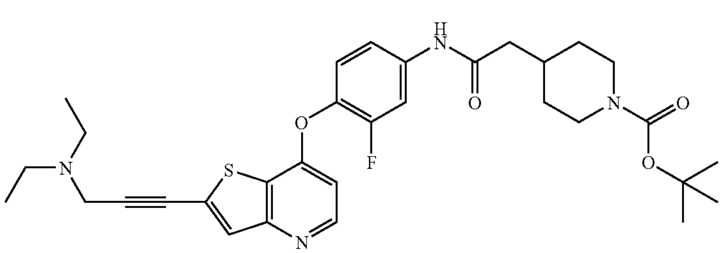 | tert-butyl 4-(2-(4-(2-(3-(diethylamino)prop-1-ynyl)thieno[3,2-b]pyridin-7-yloxy)-3-fluorophenylamino)-2-oxoethyl)piperidine-1-carboxylate | 596 | 100 |

TABLE 2-continued

| Example Number | Structure | Name | M.W. | Purity |
|---|---|---|---|---|
| 36 | 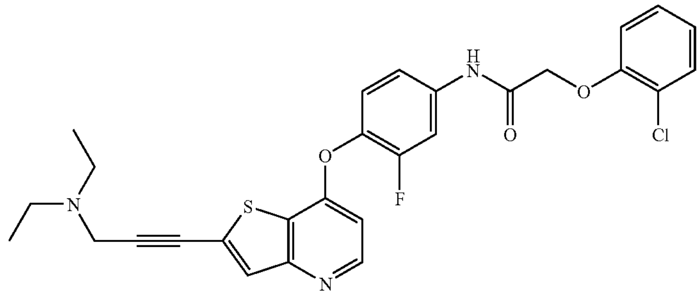 | 2-(2-chlorophenoxy)-N-(4-(2-(3-(diethylamino)prop-1-ynyl)thieno[3,2-b]pyridin-7-yloxy)-3-fluorophenyl)acetamide | 539 | 98 |
| 37 | 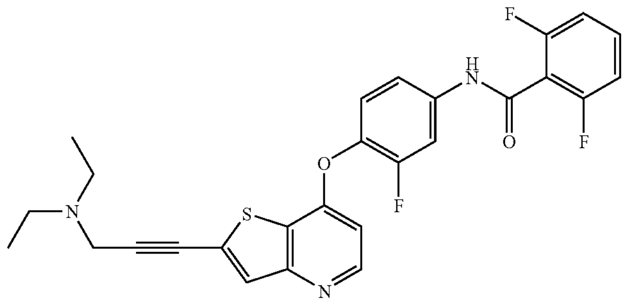 | N-(4-(2-(3-(diethylamino)prop-1-ynyl)thieno[3,2-b]pyridin-7-yloxy)-3-fluorophenyl)-2,6-difluorobenzamide | 511 | 95 |
| 38 | 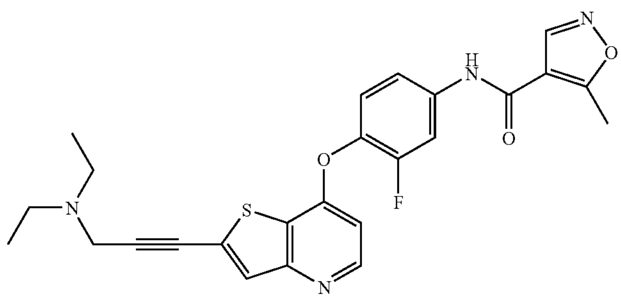 | N-(4-(2-(3-(diethylamino)prop-1-ynyl)thieno[3,2-b]pyridin-7-yloxy)-3-fluorophenyl)-5-methylisoxazole-4-carboxamide | 480 | 86 |
| 39 | 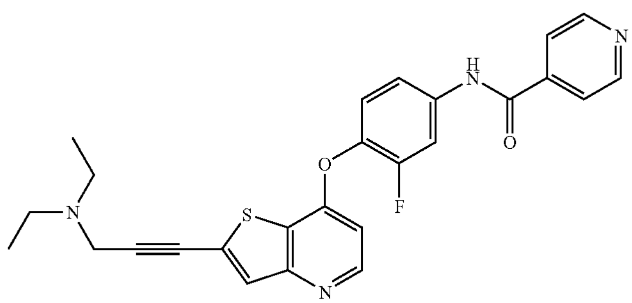 | N-(4-(2-(3-(diethylamino)prop-1-ynyl)thieno[3,2-b]pyridin-7-yloxy)-3-fluorophenyl)isonicotinamide | 475 | 85 |
| 40 | 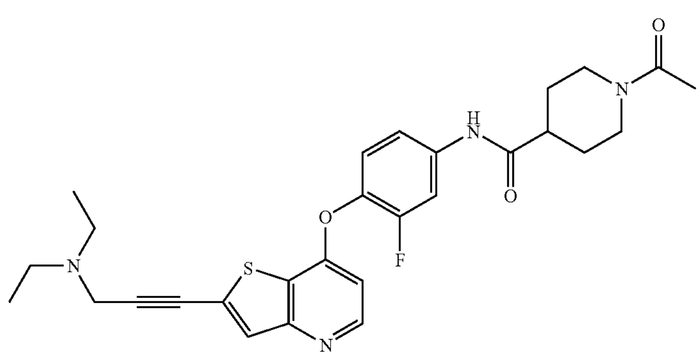 | 1-acetyl-N-(4-(2-(3-(diethylamino)prop-1-ynyl)thieno[3,2-b]pyridin-7-yloxy)-3-fluorophenyl)piperidine-4-carboxamide | 524 | 97 |

| Example Number | Structure | Name | M.W. | Purity |
|---|---|---|---|---|
| 41 | 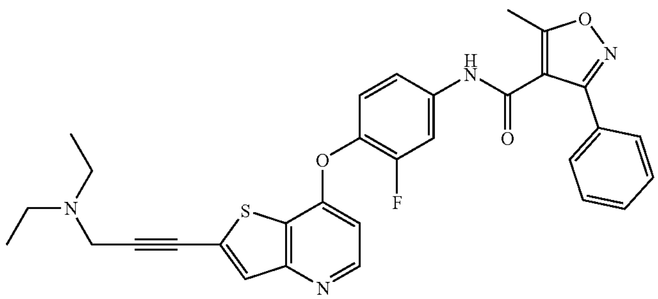 | N-(4-(2-(3-(diethylamino)prop-1-ynyl)thieno[3,2-b]pyridin-7-yloxy)-3-fluorophenyl)-5-methyl-3-phenylisoxazole-4-carboxamide | 556 | 95 |
| 42 | 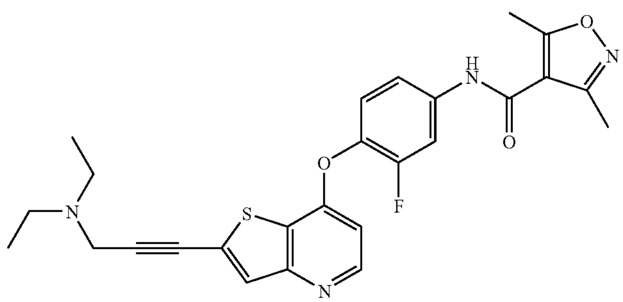 | N-(4-(2-(3-(diethylamino)prop-1-ynyl)thieno[3,2-b]pyridin-7-yloxy)-3-fluorophenyl)-3,5-dimethylisoxazole-4-carboxamide | 494 | 85 |
| 43 | 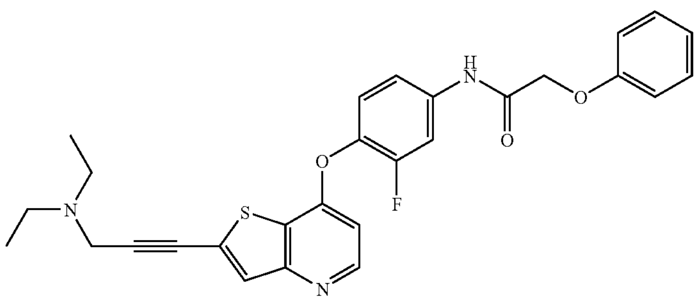 | N-(4-(2-(3-(diethylamino)prop-1-ynyl)thieno[3,2-b]pyridin-7-yloxy)-3-fluorophenyl)-2-phenoxyacetamide | 505 | 85 |
| 44 | 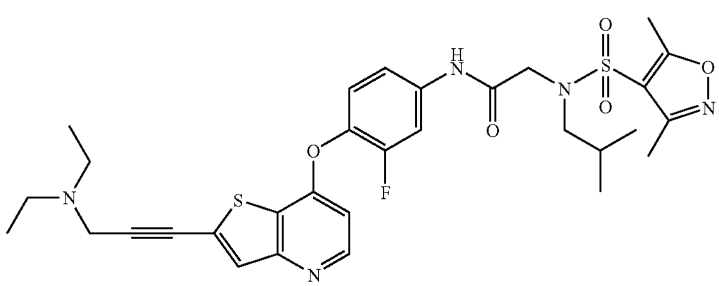 | N-(4-(2-(3-(diethylamino)prop-1-ynyl)thieno[3,2-b]pyridin-7-yloxy)-3-fluorophenyl)-2-(N-isobutyl-3,5-dimethylisoxazole-4-sulfonamido)acetamide | 643 | 96 |
| 45 | 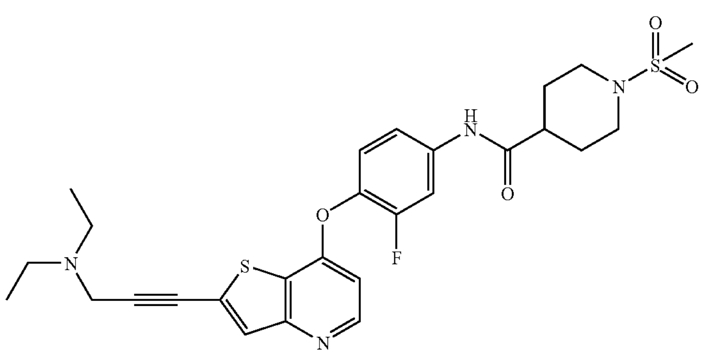 | N-(4-(2-(3-(diethylamino)prop-1-ynyl)thieno[3,2-b]pyridin-7-yloxy)-3-fluorophenyl)-1-(methylsulfonyl)piperidine-4-carboxamide | 560 | 100 |

TABLE 2-continued

| Example Number | Structure | Name | M.W. | Purity |
|---|---|---|---|---|
| 46 | 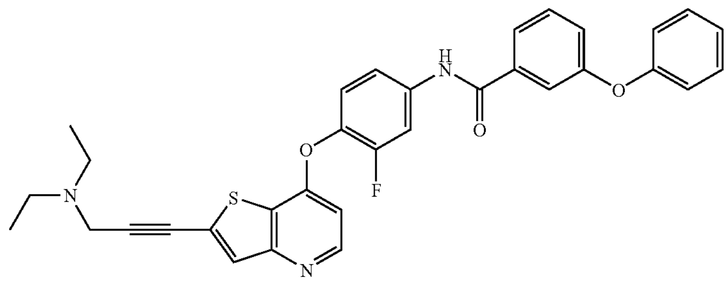 | N-(4-(2-(3-(diethylamino)prop-1-ynyl)thieno[3,2-b]pyridin-7-yloxy)-3-fluorophenyl)-3-phenoxybenzamide | 567 | 98 |
| 47 | 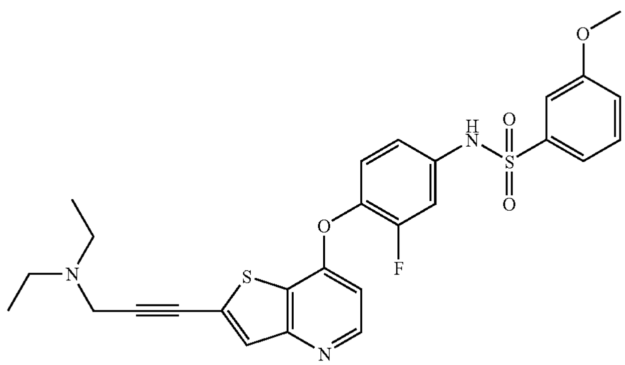 | N-(4-(2-(3-(diethylamino)prop-1-ynyl)thieno[3,2-b]pyridin-7-yloxy)-3-fluorophenyl)-3-methoxybenzenesulfonamide | 541 | 96 |
| 48 | 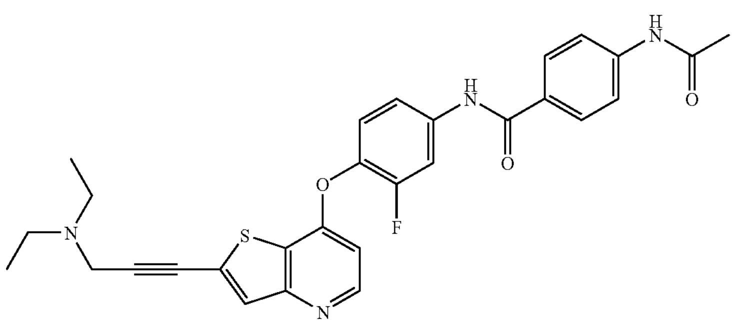 | 4-acetamido-N-(4-(2-(3-(diethylamino)prop-1-ynyl)thieno[3,2-b]pyridin-7-yloxy)-3-fluorophenyl)benzamide | 532 | 97 |
| 49 | 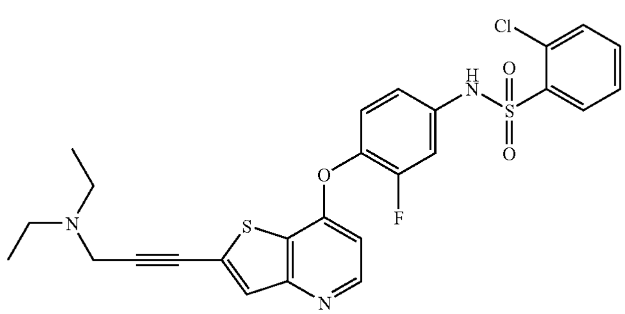 | 2-chloro-N-(4-(2-(3-(diethylamino)prop-1-ynyl)thieno[3,2-b]pyridin-7-yloxy)-3-fluorophenyl)benzenesulfonamide | 511 | 94 |
| 50 | 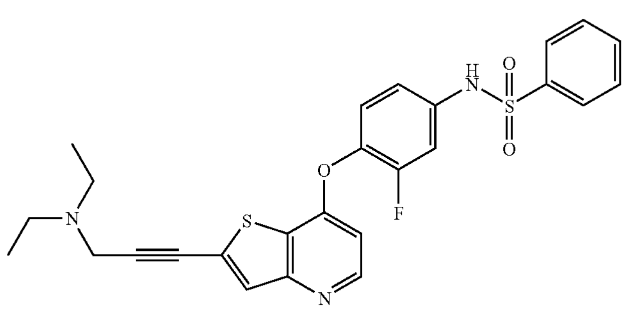 | N-(4-(2-(3-(diethylamino)prop-1-ynyl)thieno[3,2-b]pyridin-7-yloxy)-3-fluorophenyl)benzenesulfonamide | 511 | 99 |

TABLE 2-continued

| Example Number | Structure | Name | M.W. | Purity |
|---|---|---|---|---|
| 51 | 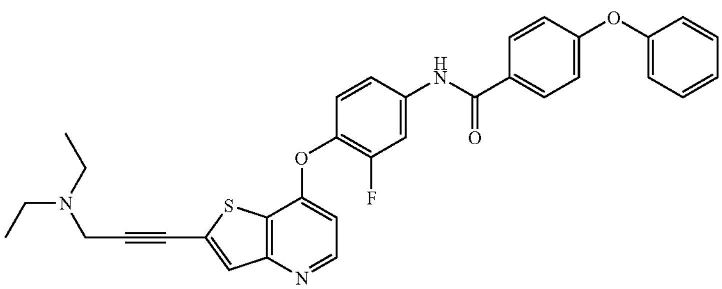 | N-(4-(2-(3-(diethylamino)prop-1-ynyl)thieno[3,2-b]pyridin-7-yloxy)-3-fluorophenyl)-4-phenoxybenzamide | 567 | 98 |
| 52 | 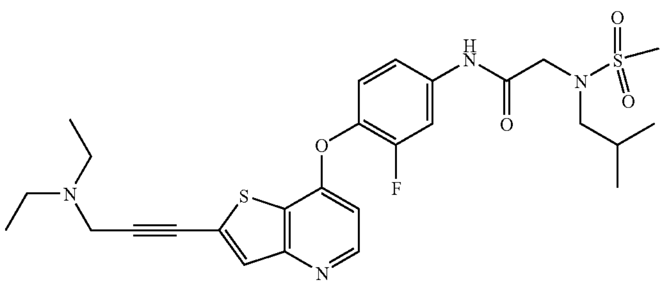 | N-(4-(2-(3-(diethylamino)prop-1-ynyl)thieno[3,2-b]pyridin-7-yloxy)-3-fluorophenyl)-2-(N-isobutylmethan-8-ylsulfonamido)acetamide | 562 | 100 |
| 53 | 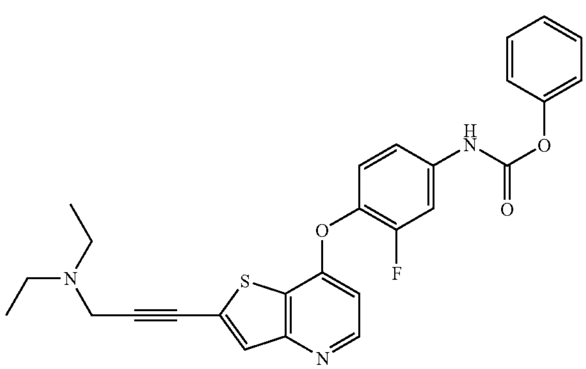 | phenyl 4-(2-(3-(diethylamino)prop-1-ynyl)thieno[3,2-b]pyridin-7-yloxy)-3-fluorophenylcarbamate | 491 | 96 |
| 54 | 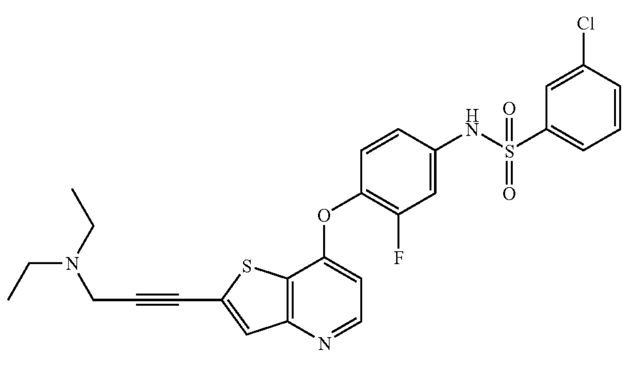 | 3-chloro-N-(4-(2-(3-(diethylamino)prop-1-ynyl)thieno[3,2-b]pyridin-7-yloxy)-3-fluorophenyl)benzenesulfonamide | 545 | 85 |

TABLE 2-continued

| Example Number | Structure | Name | M.W. | Purity |
|---|---|---|---|---|
| 55 | 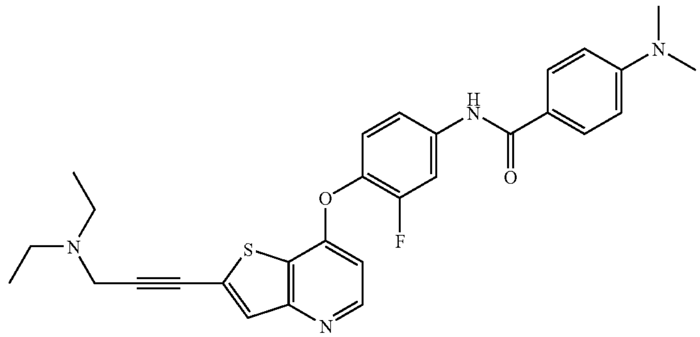 | N-(4-(2-(3-(diethylamino)prop-1-ynyl)thieno[3,2-b]pyridin-7-yloxy)-3-fluorophenyl)-4-(dimethylamino)benzamide | 518 | 93 |
| 56 | 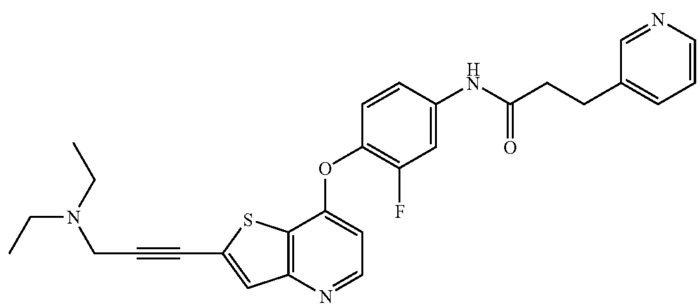 | N-(4-(2-(3-(diethylamino)prop-1-ynyl)thieno[3,2-b]pyridin-7-yloxy)-3-fluorophenyl)-3-(pyridin-3-yl)propanamide | 504 | 94 |
| 57 | 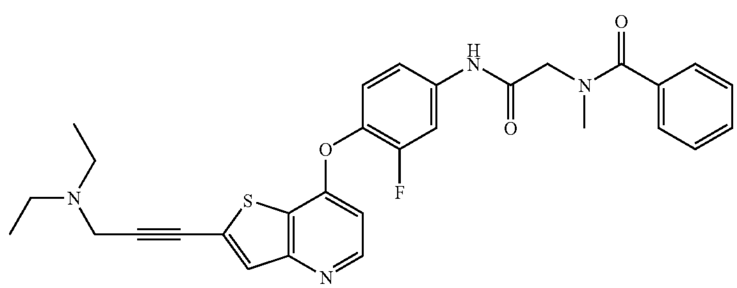 | N-(2-(4-(2-(3-(diethylamino)prop-1-ynyl)thieno[3,2-b]pyridin-7-yloxy)-3-fluorophenylamino)-2-oxoethyl)-N-methylbenzamide | 546 | 88 |
| 58 | 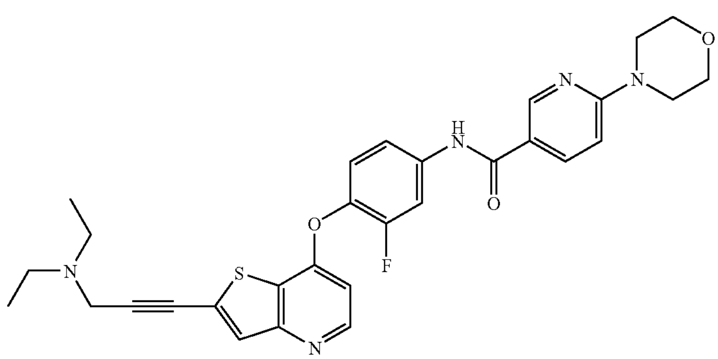 | N-(4-(2-(3-(diethylamino)prop-1-ynyl)thieno[3,2-b]pyridin-7-yloxy)-3-fluorophenyl)-6-morpholinonicotinamide | 561 | 87 |

TABLE 2-continued

| Example Number | Structure | Name | M.W. | Purity |
|---|---|---|---|---|
| 59 | 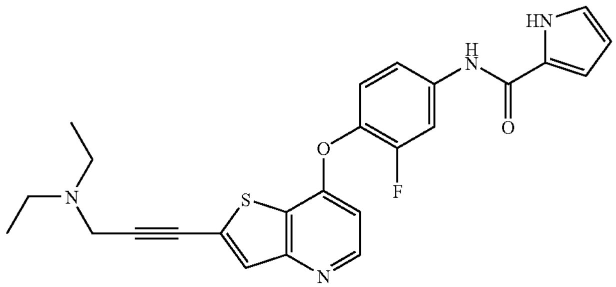 | N-(4-(2-(3-(diethylamino)prop-1-ynyl)thieno[3,2-b]pyridin-7-yloxy)-3-fluorophenyl)-1H-pyrrole-2-carboxamide | 464 | 95 |
| 60 | 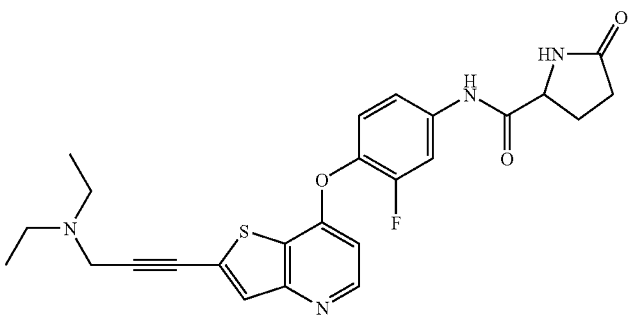 | N-(4-(2-(3-(diethylamino)prop-1-ynyl)thieno[3,2-b]pyridin-7-yloxy)-3-fluorophenyl)-5-oxopyrrolidine-2-carboxamide | 482 | 85 |
| 61 | 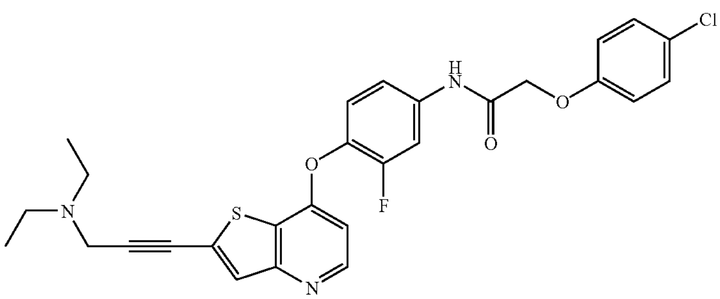 | 2-(4-chlorophenoxy)-N-(4-(2-(3-(diethylamino)prop-1-ynyl)thieno[3,2-b]pyridin-7-yloxy)-3-fluorophenyl)acetamide | 539 | 96 |
| 62 | 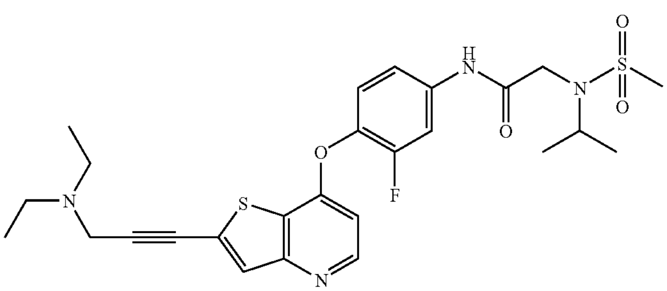 | N-(4-(2-(3-(diethylamino)prop-1-ynyl)thieno[3,2-b]pyridin-7-yloxy)-3-fluorophenyl)-2-(N-isopropylmethan-3-ylsulfonamido)acetamide | 548 | 88 |
| 63 | 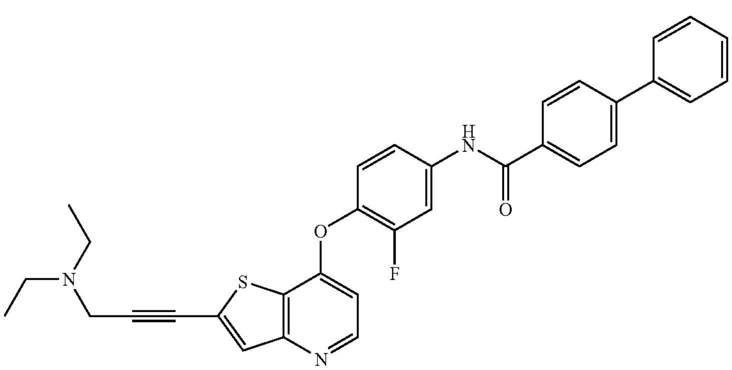 | N-(4-(2-(3-(diethylamino)prop-1-ynyl)thieno[3,2-b]pyridin-7-yloxy)-3-fluorophenyl)-4-phenylbenzamide | 551 | 98 |

TABLE 2-continued

| Example Number | Structure | Name | M.W. | Purity |
|---|---|---|---|---|
| 64 | 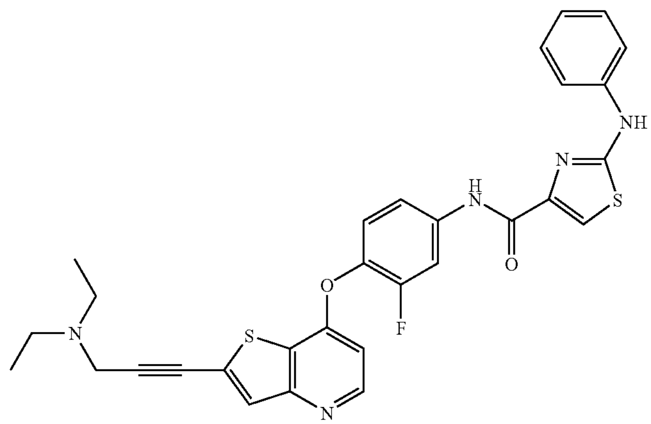 | N-(4-(2-(3-(diethylamino)prop-1-ynyl)thieno[3,2-b]pyridin-7-yloxy)-3-fluorophenyl)-2-(phenylamino)thiazole-4-carboxamide | 573 | 86 |
| 65 | 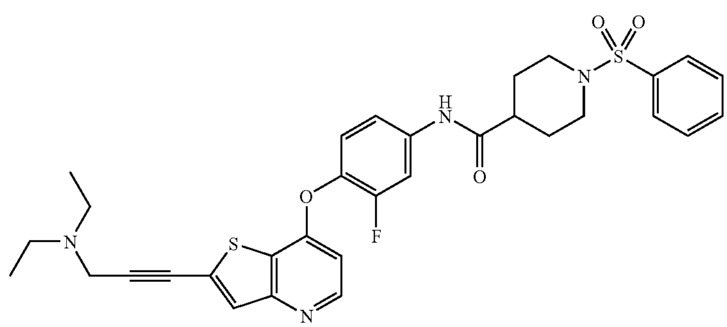 | N-(4-(2-(3-(diethylamino)prop-1-ynyl)thieno[3,2-b]pyridin-7-yloxy)-3-fluorophenyl)-1-(phenylsulfonyl)piperidine-4-carboxamide | 622 | 96 |
| 66 | 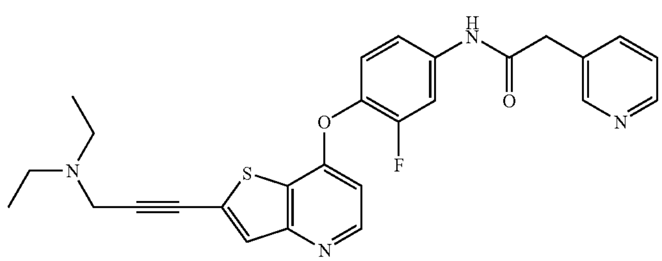 | N-(4-(2-(3-(diethylamino)prop-1-ynyl)thieno[3,2-b]pyridin-7-yloxy)-3-fluorophenyl)-2-(pyridin-3-yl)acetamide | 490 | 83 |
| 67 | 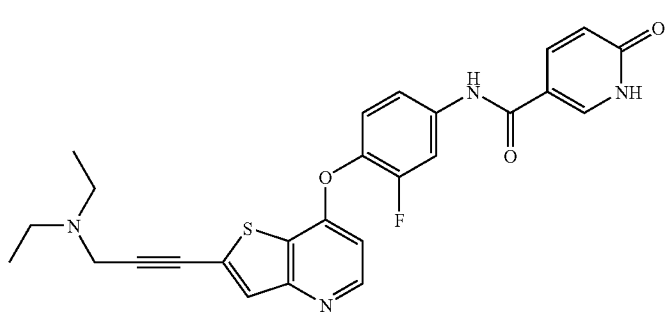 | N-(4-(2-(3-(diethylamino)prop-1-ynyl)thieno[3,2-b]pyridin-7-yloxy)-3-fluorophenyl)-6-oxo-1,6-dihydropyridine-3-carboxamide | 492 | 91 |

TABLE 2-continued

| Example Number | Structure | Name | M.W. | Purity |
|---|---|---|---|---|
| 68 | 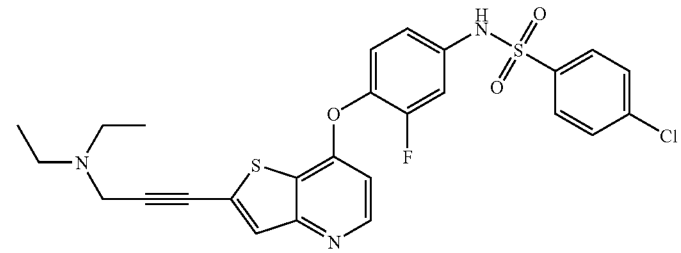 | 4-chloro-N-(4-(2-(3-(diethylamino)prop-1-ynyl)thieno[3,2-b]pyridin-7-yloxy)-3-fluorophenyl)benzenesulfonamide | 545 | 99 |
| 69 | 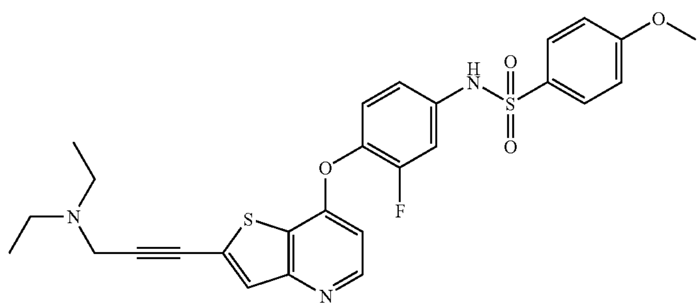 | N-(4-(2-(3-(diethylamino)prop-1-ynyl)thieno[3,2-b]pyridin-7-yloxy)-3-fluorophenyl)-4-methoxybenzenesulfonamide | 541 | 91 |
| 70 | 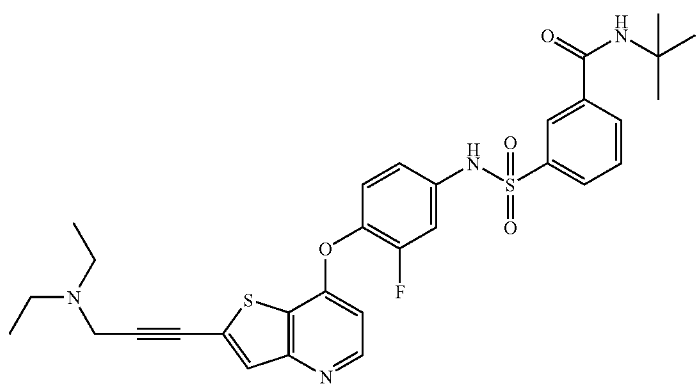 | 3-acetyltbutylamide-N-(4-(2-(3-(diethylamino)prop-1-ynyl)thieno[3,2-b]pyridin-7-yloxy)-3-fluorophenyl)benzenesulfonamide | 610 | 93 |
| 71 | 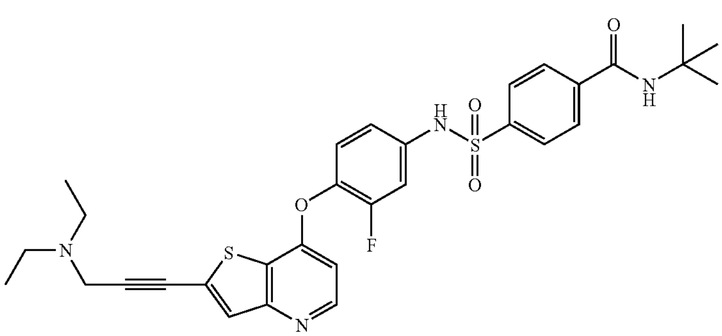 | 4-acetyltbutylamide-N-(4-(2-(3-(diethylamino)prop-1-ynyl)thieno[3,2-b]pyridin-7-yloxy)-3-fluorophenyl)benzenesulfonamide | 610 | 97 |

Example 72

Preparation of N-(4-(2-(3-(diethylamino)prop-1-ynyl)thieno[3,2-b]pyridin-7-yloxy)phenyl)-N-(4-fluorophenyl)cyclopropane-1,1-dicarboxamide

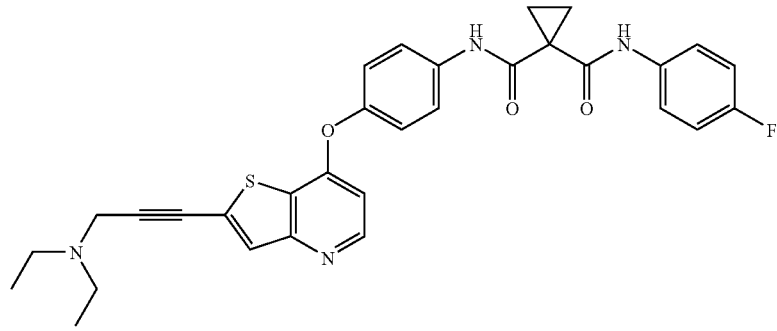

Step A: Preparation of 4-(2-iodothieno[3,2-b]pyridin-7-yloxy)benzenamine: Prepared in the same manner as Example 6, Step A, except 4-aminophenol was substituted for 2-fluoro-4-aminophenol. The oil was triturated with 1:1 ACN/Water to provide a light orange solid (350 mg, 31%). LRMS (ESI pos) m/e 369 (M+1).

Step B: Preparation of N-(4-fluorophenyl)-N-(4-(2-iodothieno[3,2-b]pyridin-7-yloxy)phenyl)cyclopropane-1,1-dicarboxamide: A 100 mL, single-neck, round-bottomed flask was charged with 1-((4-fluorophenyl)carbamoyl)cyclopropanecarboxylic acid (0.2773 g, 1.243 mmol; prepared from cyclopropane-1,1-dicarboxylic acid and 4-fluoroaniline using the methods described in WO 2005/030140 and by Shih and Rankin, *Synth. Comm.* 1996, 26(4), 833-836), and THF (10 mL). Catalytic DMF (10 microliters) was added to the reaction mixture. While stirring oxalyl dichloride (0.1067 mL, 1.243 mmol) was added dropwise, and the reaction mixture was stirred for 30 minutes. 4-(2-Iodothieno[3,2-b]pyridin-7-yloxy)benzenamine (example 72, Step A 0.500 g, 0.8284 mmol) in THF (2 mL) was added, and the reaction mixture was stirred for 1 hour, water (50 mL) and saturated NaHCO$_3$ (50 mL) were added. The reaction mixture was extracted with EtOAc, and the organic layer was washed with brine, dried over sodium sulfate, filtered, and concentrated. The residue was purified on a Biotage 40S column (2:1 EtOAc/Hexane). The product was a beige solid (155 mg, 29%). $^1$H NMR (CDCl$_3$, 400 MHz) δ 9.37 (s, 1H), 8.59 (s, 1H), 8.41 (d, J=6 Hz, 1H), 7.76 (s, 1H), 7.62 (d, J=9 Hz, 2H), 7.46 (m, 2H), 7.15 (d, J=9 Hz, 2H), 7.06 (t, J=9 Hz, 2H), 6.51 (d, J=6 Hz, 1H), 1.71 (m, 4H). LRMS (ESI pos) m/e 574 (M+1).

Step C: Preparation of N-(4-(2-(3-(diethylamino)prop-1-ynyl)thieno[3,2-b]pyridin-7-yloxy)phenyl)-N-(4-fluorophenyl)cyclopropane-1,1-dicarboxamide: Prepared from N-(4-fluorophenyl)-N-(4-(2-iodothieno[3,2-b]pyridin-7-yloxy) phenyl)cyclopropane-1,1-dicarboxamide (155 mg, 0.24 mmol) and N,N-diethylprop-2-yn-1-amine (24 mg, 0.21 mmol) according to the procedure for Example 6, Step B. The crude product was purified on a Horizon reverse phase using Biotage 12M C18 column. The crude was loaded to the samplet with EtOAc and dried under vacuum. Product eluted at 55-75% acetonitrile and was obtained as a white powder (32 mg, 24%). $^1$H NMR (CDCl$_3$, 400 MHz) δ 9.58 (s, 1H), 8.94 (s, 1H), 8.46 (d, J=5 Hz, 1H), 7.61 (d, J=8.6 Hz, 2H), 7.54 (s, 1H), 7.47 (m, 2H), 7.14 (d, J=9.0 Hz, 2H), 7.03 (t, J=8.6 Hz, 2H), 6.55 (d, J=5 Hz, 1H), 3.70 (s, 2H), 2.65 (q, J=7, 14 Hz, 4H), 1.71 (m, 4H), 1.13 (t, J=7.4 Hz, 6H) (350 mg, 31%). LRMS (ESI pos) m/e 557 (M+1).

Example 73

Preparation of isobutyl 4-(2-(3-(diethylamino)prop-1-ynyl)thieno[3,2-b]pyridin-7-yloxy)phenylcarbamate A 25 mL, single-neck, round-bottomed flask was charged with 1-((4-fluorophenyl)carbamoyl)cyclopropanecarboxylic acid (42 mg, 0.1694 mmol) and THF (2 mL) under nitrogen and cooled to −78° C. on a dry ice bath. N-methylmorpholine (0.037 mL, 0.34 mmol), and isobutyl chloroformate (0.019 ml, 0.15 mmol) were added. After 15 minutes 4-(2-(3-(diethylamino)prop-1-ynyl)thieno[3,2-b]pyridin -7-yloxy)benzenamine (40 mg, 0.11 mmol) in THF (1 mL) was added, and the reaction was allowed to warm to room temperature overnight. The reaction mixture was concentrated and the residue was purified on a Biotage 15M column (95:5 EtOAc/MeOH). The product was a white waxy solid (0.8 mg, 2%). $^1$H NMR (CDCl$_3$, 400 MHz) δ 8.47 (d, J=5.5 Hz, 1H), 7.57 (s, 1H), 7.49 (m, 2H), 7.14 (m, 2H), 6.68 (br s, 1H), 6.54 (d, J=5.5 Hz, 1H), 3.98 (d, J=6.6 Hz, 2H), 3.72 (s, 2H), 2.65 (q, J=7, 14 Hz, 4H), 2.00 (m, 1H), 1.14 (t, J=7.0 Hz, 6H), 0.99 (d, J=7.0 Hz, 6H). LRMS (ESI pos) m/e 452 (M+1).

Example 74

Preparation of 1-(4-(2-(3-(diethylamino)prop-1-ynyl) thieno[3,2-b]pyridin-7-yloxy)phenyl)-3-(2-phenylacetyl)thiourea

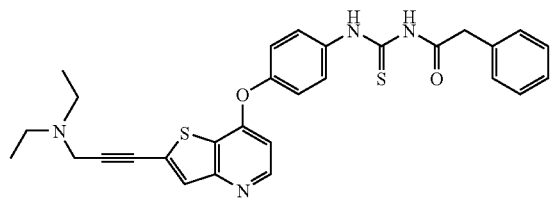

Step A: Preparation of 4-(2-(3-(diethylamino)prop-1-ynyl) thieno[3,2-b]pyridin-7-yloxy)benzenamine: Prepared from 4-(2-iodothieno[3,2-b]pyridin-7-yloxy)benzenamine (Example 72, Step A; 130 mg, 0.353 mmol), and N,N-diethylprop-2-yn-1-amine (58.9 mg, 0.530 mmol), according to the procedure for Example 6, Step B. The product was purified by Biotage 40S column (EtOAc). Product was an orange oil which crystallized upon standing (40 mg, 31%). $^1$H NMR (CDCl$_3$, 400 MHz) δ 8.46 (d, J=5.5 Hz, 1H), 7.57 (s, 1H), 6.96 (d, J=9 Hz, 2H), 6.72 (d, J=9 Hz, 2H), 6.52 (d, J=5 Hz, 1H), 3.77 (s, 2H), 3.71 (s, 2H), 2.64 (q, J=7, 14 Hz, 4H), 1.13 (t, J=7 Hz, 6H). LRMS (ESI pos) m/e 352 (M+1).

Step B: Preparation of 1-(4-(2-(3-(diethylamino)prop-1-ynyl)thieno[3,2-b]pyridin-7-yloxy)phenyl)-3-(2-phenylacetyl)thiourea: Prepared from 4-(2-(3-(diethylamino)prop-1-ynyl)thieno[3,2-b]pyridin-7-yloxy)benzenamine (20 mg, 0.06 mmol) according to the procedure for Example 6, Step C. The product was purified by preparative TLC eluting with EtOAc. The product was obtained as an orange oil (0.5 mg, 2%). $^1$H NMR (CDCl$_3$, 400 MHz) δ 12.35 (bs, 1H), 8.50 (d, J=5.5 Hz, 1H), 8.45 (br s, 1H), 7.74 (d, J=9.0 Hz, 2H), 7.58 (s, 1H), 7.43 (m, 4H), 7.33 (m, 3H), 7.19 (d, J=9.0 Hz, 2H), 6.61 (d, J=5.5 Hz, 1H), 3.75 (s, 2H), 3.63 (m, 4H), 1.15 (t, J=7.4 Hz, 6H). LRMS (APCI pos) m/e 529 (M+1).

Example 75

Preparation of N-(4-(2-(3-(diethylamino)prop-1-ynyl)thieno[3,2-b]pyridin-7-yloxy)phenyl)-2-phenylacetamide

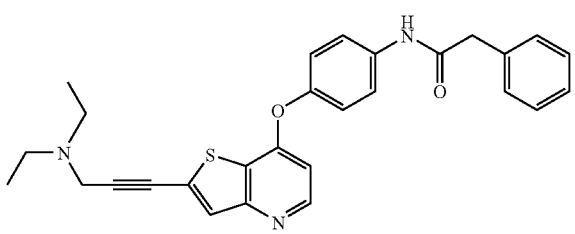

The title compound was a by-product from 4-(2-(3-(diethylamino)prop-1-ynyl)thieno[3,2-b]pyridin-7-yloxy)benzenamine (Example 74, Step A; 20 mg, 0.06 mmol) using the procedure described for Example 6, Step C. The product was purified by preparative TLC eluting with EtOAc. The product was obtained as a clear oil (0.6 mg, 2%). $^1$H NMR (CDCl$_3$, 400 MHz) δ 8.47 (d, J=5.5 Hz, 1H), 7.60 (s, 1H), 7.51 (d, J=8.6 Hz, 2H), 7.43 (m, 5H), 7.11 (m, 4H), 6.53 (d, J=5.5 Hz, 1H), 3.78 (m, 8H), 1.21 (t, J=7.2 Hz, 3H). LRMS (APCI pos) m/e 470 (M+1).

Example 76

Preparation of 1-(3-fluoro-4-(2-phenylthieno[3,2-b] pyridin-7-yloxy)phenyl)-3-(2-phenylacetyl)thiourea

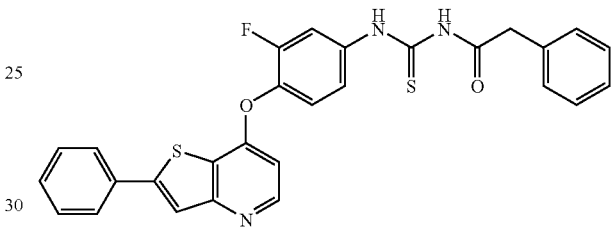

Step A: Preparation of 3-fluoro-4-(2-phenylthieno[3,2-b]pyridin-7-yloxy)benzenamine: A vigorously stirred mixture of cesium carbonate (190 mg, 0.583 mmol), 3-fluoro-4-(2-iodothieno[3,2-b]pyridin-7-yloxy)benzenamine (Example 6, Step A; 150 mg, 0.388 mmol), phenylboronic acid (59.2 mg, 0.486 mmol), toluene (4 mL) and EtOH (1 mL) was degassed under nitrogen for 10 minutes, and then Pd(PPh$_3$)$_4$ (22.4 mg, 0.0194 mmol) was added. The reaction mixture was heated at 80° C. for 18 hours, then cooled to room temperature and diluted with water (20 mL). The reaction mixture was extracted with EtOAc, and the organic layer was dried organic over sodium sulfate, filtered and concentrated. The residue was purified on a Biotage 40S (2:1 EtOAc/Hexane). The product was a light orange solid (75 mg, 53%). $^1$H NMR (CDCl$_3$, 400 MHz) δ 8.46 (d, J=5.5 Hz, 1H), 7.75 (m, 3H), 7.46 (t, J=7.2 Hz, 2H), 7.40 (m, 1H), 7.06 (t, J=8.8 Hz, 1H), 6.54 (m, 1H), 6.50 (m, 2H), 3.84 (br s, 2H). LRMS (ESI pos) m/e 337 (M+1).

Step B: Preparation of 1-(3-fluoro-4-(2-phenylthieno[3,2-b]pyridin-7-yloxy)phenyl)-3-(2-phenylacetyl)thiourea: Prepared from 3-fluoro-4-(2-phenylthieno[3,2-b]pyridin-7-yloxy)benzenamine (35 mg, 0.10 mmol) according to the procedure for Example 6, Step C. Purified by preparative TLC eluting with EtOAc. Isolated the product as an orange oil that solidified upon standing (1.0 mg, 1.7%). $^1$H NMR (CDCl$_3$, 400 MHz) δ 12.49 (br s, 1H), 8.49 (m, 2H), 7.96 (m, 1H), 7.77 (m, 3H), 7.45 (m, 7H), 7.31 (m, 3H), 6.54 (m, 1H), 3.76 (s, 2H). LRMS (APCI pos) m/e 514 (M+1).

Example 77

Preparation of N-(3-fluoro-4-(2-phenylthieno[3,2-b]pyridin-7-yloxy)phenyl)-N-(4-fluorophenyl)cyclopropane-1,1-dicarboxamide

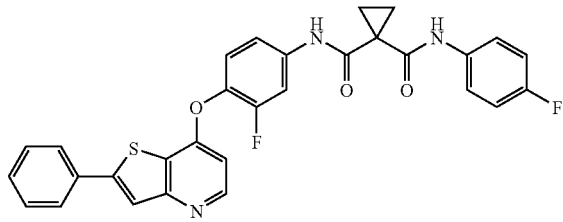

Prepared from 1-((4-fluorophenyl)carbamoyl)cyclopropanecarboxylic acid (34.84 mg, 0.1561 mmol; prepared from cyclopropane-1,1-dicarboxylic acid and 4-fluoroaniline using the methods described in WO 2005/030140 and by Shih and Rankin, *Synth. Comm.* 1996, 26(4), 833-836), and 3-fluoro-4-(2-phenylthieno[3,2-b]pyridin-7-yloxy)benzenamine (Example 76, Step A; 35 mg, 0.1040 mmol) according to the procedure for Example 73. The product was purified by preparative TLC eluting with EtOAc/MeOH (9:1). Isolated the product as a light yellow oil, which solidified upon standing (4.3 mg, 8%). $^1$H NMR (CDCl$_3$, 400 MHz) δ 10.03 (s, 1H), 8.47 (d, J=5.5 Hz, 1H), 8.27 (s, 1H), 7.77 (m, 3H), 7.46 (m, 5H), 7.24 (m, 2H), 7.06 (d, J=9.0 Hz, 2H), 6.49 (m, 2H) 1.80, (m, 2H), 1.62 (m, 2H). LRMS (APCI pos) m/e 542 (M+1).

Example 78

Preparation of N-(4-(2-(3-(diethylamino)prop-1-ynyl)thieno[3,2-b]pyridin-7-yloxy)-2-methylphenyl)-N-(4-fluorophenyl)cyclopropane-1,1-dicarboxamide

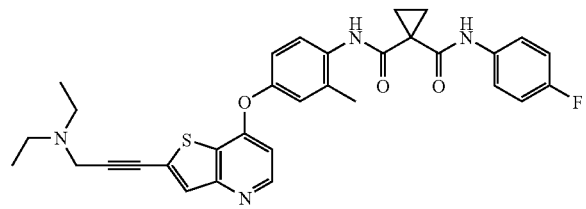

Step A: Preparation of 4-(2-iodothieno[3,2-b]pyridin-7-yloxy)-2-methylbenzenamine: Prepared in the same manner as Example 6, Step A, except 4-amino-3-methylphenol was substituted for 2-fluoro-4-aminophenol. The crude was purified by Biotage 40S (EtOAc). The resulting oil was triturated with hot hexanes to obtain product as a brown solid (270 mg, 17%). $^1$H NMR (CDCl$_3$, 400 MHz) δ 8.38 (d, J=5.5 Hz, 1H), 7.74 (s, 1H), 6.71 (d, J=8.6 Hz, 1H), 6.60 (m, 1H), 6.56 (m, 1H), 6.49 (d, J=5.5 Hz, 1H), 3.66 (br s, 2H), 2.13 (s, 3H). LRMS (ESI pos) m/e 383 (M+1).

Step B: Preparation of 4-(2-(3-(diethylamino)prop-1-ynyl)thieno[3,2-b]pyridin-7-yloxy)-2-methylbenzenamine: Prepared from 4-(2-iodothieno[3,2-b]pyridin-7-yloxy)-2-methylbenzenamine (0.250 g, 0.556 mmol), and N,N-diethylprop-2-yn-1-amine (0.0680 g, 0.612 mmol), according to the procedure for Example 6, Step B. The crude was purified by Biotage 40S (EtOAc). The product was an orange oil (116 mg, 39%). LRMS (ESI pos) m/e 366 (M+1).

Step C: Preparation of N-(4-(2-(3-(diethylamino)prop-1-ynyl)thieno[3,2-b]pyridin-7-yloxy)-2-methylphenyl)-N-(4-fluorophenyl)cyclopropane-1,1-dicarboxamide: Prepared from 4-(2-(3-(diethylamino)prop-1-ynyl)thieno[3,2-b]pyridin-7-yloxy)-2-methylbenzenamine (0.070 g, 0.1322 mmol), and 1-((4-fluorophenyl)carbamoyl)cyclopropanecarboxylic acid (0.04424 g, 0.1982 mmol; prepared from cyclopropane-1,1-dicarboxylic acid and 4-fluoroaniline using the methods described in WO 2005/030140 and by Shih and Rankin, *Synth. Comm.* 1996, 26(4), 833-836) according to the procedure for Example 73. The crude was purified by preparative TLC eluting with EtOAc/MeOH (9:1). The product was a light yellow oil (3.9 mg, 5%). $^1$H NMR (CDCl$_3$, 400 MHz) δ 9.19 (s, 1H), 8.88 (s, 1H), 8.47 (d, J=5.5 Hz, 1H), 7.87 (d, J=9.8 Hz, 1H), 7.57 (s, 1H), 7.48 (m, 2H), 7.04 (m, 4H), 6.58 (d, J=5.5 Hz, 1H), 3.73 (s, 2H), 2.68 (q, J=7, 14 Hz, 4H), 2.34 (s, 3H) 1.73 (m, 4H), 1.15 (t, J=7.2 Hz, 6H). LRMS (APCI pos) m/e 571 (M+1).

Example 79

Preparation of N-(4-(2-(3-(diethylamino)prop-1-ynyl)thieno[3,2-b]pyridin-7-yloxy)-3,5-dimethylphenyl)-N-(4-fluorophenyl)cyclopropane-1,1-dicarboxamide

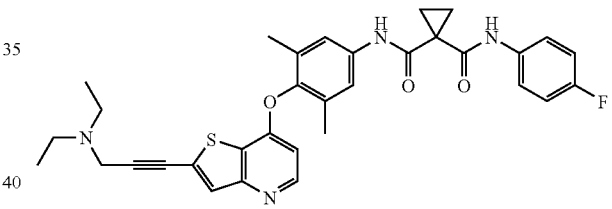

Step A: Preparation of 4-(2-iodothieno[3,2-b]pyridin-7-yloxy)-3,5-dimethylbenzenamine: Prepared in the same manner as Example 6, Step A, except 4-amino-2,6-dimethylphenol was substituted for 2-fluoro-4-aminophenol. The crude was purified by Biotage 40S (EtOAc). The resulting oil was triturated with hot hexanes to obtain product as a brown solid (200 mg, 11%). LRMS (ESI pos) m/e 397 (M+1).

Step B: Preparation of 4-(2-(3-(diethylamino)prop-1-ynyl)thieno[3,2-b]pyridin-7-yloxy)-3,5-dimethylbenzenamine: Prepared from 4-(2-iodothieno[3,2-b]pyridin-7-yloxy)-2-methylbenzenamine (0.200 g, 0.363 mmol), and N,N-diethylprop-2-yn-1-amine (0.040 g, 0.363 mmol), according to the procedure for Example 6, Step B. The crude was purified by Biotage 40S (EtOAc). The product was a brown oil (110 mg, 33%). LRMS (ESI pos) m/e 380 (M+1).

Step C: Preparation of N-(4-(2-(3-(diethylamino)prop-1-ynyl)thieno[3,2-b]pyridin-7-yloxy)-3,5-dimethylphenyl)-N-(4-fluorophenyl)cyclopropane-1,1-dicarboxamide: Prepared from 4-(2-(3-(diethylamino)prop-1-ynyl)thieno[3,2-b]pyridin-7-yloxy)-2-methylbenzenamine (0.070 g, 0.1322 mmol), and 1-((4-fluorophenyl)carbamoyl)cyclopropanecarboxylic acid (44 mg, 0.20 mmol; prepared from cyclopropane-1,1-dicarboxylic acid and 4-fluoroaniline using the methods described in WO 2005/030140 and by Shih and Rankin, *Synth. Comm.* 1996, 26(4), 833-836) according to the procedure for Example 73. The crude was purified by preparative TLC eluting with EtOAc/MeOH (9:1). The product was a light yellow oil (1.0 mg, 1%). $^1$H NMR (CDCl$_3$, 400 MHz) δ 8.96 (s, 1H), 8.90 (s, 1H), 8.44 (d, J=5.5 Hz, 1H), 7.78 (s, 1H), 7.57 (s, 1H), 7.49 (m, 2H), 7.05 (t, J=8.8 Hz, 2H), 6.96 (s, 1H), 6.41 (d, J=5.5 Hz, 1H), 3.72 (s, 2H), 2.66 (q, J=7, 14 Hz, 4H), 2.29 (s, 3H), 2.14 (s, 3H), 1.73 (m, 4H), 1.14 (t, J=7.2 Hz, 6H). LRMS (APCI pos) m/e 585 (M+1).

Example 80

Preparation of N-(4-(2-(3-(diethylamino)prop-1-ynyl)thieno[3,2-b]pyridin-7-yloxy)-3-methylphenyl)-N-(4-fluorophenyl)cyclopropane-1,1-dicarboxamide

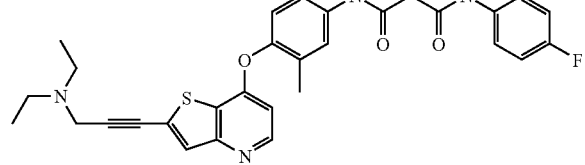

Step A: Preparation of 4-(2-iodothieno[3,2-b]pyridin-7-yloxy)-3-methylbenzenamine: Prepared in the same manner as Example 6, Step A, except 4-amino -2-methylphenol was substituted for 2-fluoro-4-aminophenol. The crude was purified by Biotage 40S (EtOAc). The resulting oil was triturated with hot hexanes with the product dissolving in the hexanes. After filtration and concentration the product was a brown solid (60 mg, 4%). $^1$H NMR (CDCl$_3$, 400 MHz) δ 8.37 (d, J=5.5 Hz, 1H), 7.74 (s, 1H), 6.89 (d, J=8.6 Hz, 1H), 6.61 (m, 1H), 6.57 (m, 1H), 6.40 (d, J=5.5 Hz, 1H), 3.69 (br s, 2H), 2.06 (s, 3H). LRMS (ESI pos) m/e 383 (M+1).

Step B: Preparation of 4-(2-(3-(diethylamino)prop-1-ynyl)thieno[3,2-b]pyridin-7-yloxy)-3-methylbenzenamine: Prepared from 4-(2-iodothieno[3,2-b]pyridin-7-yloxy)-2-methylbenzenamine (60 mg, 0.13 mmol), and N,N-diethylprop-2-yn-1-amine (16 mg, 0.14 mmol), according to the procedure for Example 6, Step B. The crude was purified by Biotage 40S (EtOAc). The product was a brown oil (51 mg, 67%). LRMS (ESI pos) m/e 366 (M+1).

Step C: Preparation of N-(4-(2-(3-(diethylamino)prop-1-ynyl)thieno[3,2-b]pyridin-7-yloxy)-3-methylphenyl)-N-(4-fluorophenyl)cyclopropane-1,1-dicarboxamide: Prepared from 4-(2-(3-(diethylamino)prop-1-ynyl)thieno[3,2-b]pyridin-7-yloxy)-2-methylbenzenamine (50 mg, 0.14 mmol), and 1-((4-fluorophenyl)carbamoyl)cyclopropanecarboxylic acid (46 mg, 0.21 mmol; prepared from cyclopropane-1,1-dicarboxylic acid and 4-fluoroaniline using the methods described in WO 2005/030140 and by Shih and Rankin, Synth. Comm. 1996, 26(4), 833-836) according to the procedure for Example 74. The crude was purified by preparative TLC eluting with EtOAc/MeOH (9:1). The product was a light yellow oil (0.8 mg, 1%). $^1$H NMR (CDCl$_3$, 400 MHz) δ 9.21 (s, 1H), 8.70 (s, 1H), 8.45 (d, J=5.5 Hz, 1H), 7.57 (s, 1H), 7.48 (m, 4H), 7.06 (m, 3H), 6.41 (d, J=5.5 Hz, 1H), 3.71 (s, 2H), 2.65 (q, J=7, 14 Hz, 4H), 2.17 (s, 3H), 1.71 (m, 4H), 1.13 (t, J=7.0 Hz, 6H). LRMS (APCI pos) m/e 571 (M+1).

Example 81

Preparation of N-(3-chloro-4-(2-(3-(diethylamino)prop-1-ynyl)thieno[3,2-b]pyridin-7-yloxy)phenyl)-N-(4-fluorophenyl)cyclopropane-1,1-dicarboxamide Step A: Preparation of 3-chloro-4-(2-iodothieno[3,2-b]pyridin-7-yloxy)benzenamine: Prepared in the same manner as Example 6, Step A, except 4-amino -2-chlorophenol was substituted for 4-amino-2-fluorophenol. The crude was purified by Biotage 40S (EtOAc). The resulting oil was triturated with hot hexanes with the product dissolving in the hexanes. After filtration and concentration the product was a brown oil (900 mg, 15%). LRMS (ESI pos) m/e 403 (M+1).

Step B: Preparation of N-(3-chloro-4-(2-iodothieno[3,2-b]pyridin -7-yloxy)phenyl)-N-(4-fluorophenyl)cyclopropane-1,1-dicarboxamide: Prepared from 3-chloro-4-(2-iodothieno[3,2-b]pyridin-7-yloxy)benzenamine (0.300 g, 0.499 mmol) and 1-((4-fluorophenyl)carbamoyl)cyclopropanecarboxylic acid (0.167 g, 0.749 mmol; prepared from cyclopropane-1,1-dicarboxylic acid and 4-fluoroaniline using the methods described in WO 2005/030140 and by Shih and Rankin, Synth. Comm. 1996, 26(4), 833-836) according to the procedure for Example 72, Step B. The crude was purified by Biotage 40S (2:1EtOAc/Hexane). After concentration the product was a brown oil (160 mg, 26%). LRMS (ESI pos) m/e 608 (M+1).

Step C: Preparation of N-(3-chloro-4-(2-(3-(diethylamino)prop-1-ynyl)thieno[3,2-b]pyridin-7-yloxy)phenyl)-N-(4-fluorophenyl)cyclopropane-1,1-dicarboxamide: Prepared from N-(3-chloro-4-(2-iodothieno[3,2-b]pyridin-7-yloxy)phenyl) -N-(4-fluorophenyl)cyclopropane-1,1-dicarboxamide (0.160 g, 0.132 mmol), and N, N-diethylprop-2-yn-1-amine (0.0132 g, 0.118 mmol) according to the procedure for Example 6, Step B. The product was purified by Horizon reverse phase using Biotage 12M C18 column. The crude was loaded to the samplet with EtOAc and dried under vacuum. The product was eluted with 55-75% acetonitrile in water and was obtained as a white powder (20 mg, 26%). $^1$H NMR (CDCl$_3$, 400 MHz) δ 10.14 (s, 1H), 8.50 (s, 1H), 8.46 (d, J=5.5 Hz, 1H), 7.90 (s, 1H), 7.54 (s, 1H), 7.46 (m, 3H), 7.20 (d, J=8.6 Hz, 1H), 7.05 (t, J=8.8 Hz, 2H), 6.42 (d, J=5.5 Hz, 1H), 3.71 (s, 2H), 2.65 (q, J=7, 14 Hz, 4H), 1.77 (m, 4H), 1.13 (t, J=7.2 Hz, 6H). LRMS (ESI pos) m/e 591 (M+1).

Example 82

Preparation of 2-(benzyloxy)-N-(3-fluoro-4-(thieno[3,2-b]pyridin-7-yloxy)phenyl)acetamide

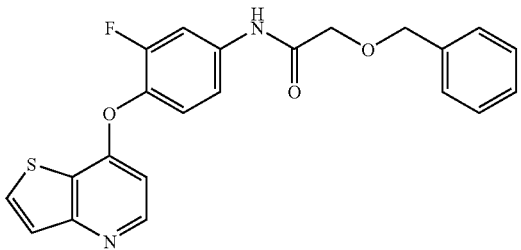

To a stirred solution of 3-fluoro-4-(thieno[3,2-b]pyridin-7-yloxy)aniline (Example 1-B; 67 mg, 0.258 mmol) in 1 mL CH$_2$Cl$_2$ at room temperature under nitrogen was added diisopropylethylamine (68 μL, 0.387 mmol) followed by 2-(benzyloxy)acetyl chloride (41 μL, 0.258 mmol). After 1 hour, the reaction was diluted to 30 mL with CH$_2$Cl$_2$ and washed 2×30 mL with 10% citric acid and 2×30 mL with saturated NaHCO$_3$. The organics were isolated, dried (MgSO$_4$), filtered and concentrated. The crude product was loaded onto a Biotage 12S column with 2/3 EtOAc/hexanes and eluted. The fractions containing the product were pooled and concentrated to a yellow oil (68 mg, 64%). $^1$H NMR (400 MHz, CDCl$_3$) δ 8.51 (d, 1H), 8.44 (br s, 1H), 7.74 (d, 1H), 7.57 (d, 1H), 7.39 (m, 5H), 7.24 (m, 3H), 6.50 (d, 1H), 4.68 (s, 2H), 4.13 (s, 2H). LRMS (ESI pos) m/e 409.0 (M+1).

Example 83

Preparation of N-(3-fluoro-4-(thieno[3,2-b]pyridin-7-yloxy)phenyl)-4-phenylbutanamide

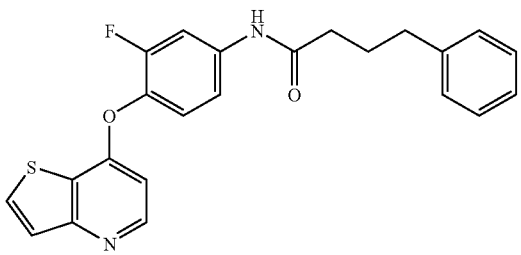

To a stirred solution of 4-phenylbutanoic acid (49 mg, 0.3 mmol) in 1 mL THF at −78° C. under nitrogen was added N-methyl morpholine (66 μL, 0.6 mmol) followed by isobutyl chloroformate (34 μL, 0.26 mmol). After 15 minutes, a solution of 3-fluoro-4-(thieno[3,2-b]pyridin-7-yloxy)aniline (Example 1, Step B) in 1 mL THF was added and the reaction mixture was warmed to reflux. After refluxing overnight, the reaction was cooled to room temperature and partitioned between CH$_2$Cl$_2$ (30 mL) and 10% citric acid (30 mL). The organics were isolated and washed 1×30 mL with 10% citric acid and 2×30 mL with saturated NaHCO$_3$. The organics were dried (MgSO$_4$), filtered, concentrated and loaded onto a Biotage 12S column with 2/3 EtOAc/hexanes and eluted. The fractions containing the product were pooled and concentrated to a white foam (63 mg, 77%). $^1$H NMR (400 MHz, CDCl$_3$) δ 8.48 (d, 1H), 7.75 (d, 1H), 7.73 (m, 1H), 7.69 (br s, 1H), 7.55 (d, 1H), 7.29 (m, 2H), 7.20 (m, 5H), 6.50 (d, 1H), 2.72 (m, 2H), 2.38 (m, 2H), 2.09 (m, 2H). LRMS (ESI pos) m/e 407.0 (M+1).

Example 84

Preparation of 2-(4-chlorobenzyloxy)-N-(3-fluoro-4-(thieno[3,2-b]pyridin-7-yloxy)phenyl)acetamide

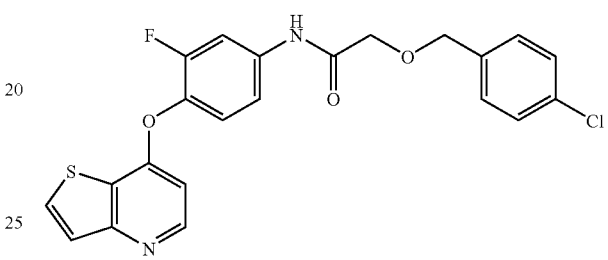

Prepared according to the method of Example 83, substituting 2-(4-chlorobenzyloxy)acetic acid for 4-phenylbutanoic acid. The product was isolated as a clear oil (90 mg, 100%). $^1$H NMR (400 MHz, CDCl$_3$) δ 8.51 (d, 1H), 8.39 (br s, 1H), 7.77 (m, 1H), 7.75 (d, 1H), 7.57 (d, 1H), 7.39 (m, 2H), 7.32 (m, 2H), 7.25 (m, 2H), 6.50 (d, 1H), 4.65 (d, 2H), 4.12 (s, 2H). LRMS (ESI pos) m/e 443.0 (M+1).

Example 85

Preparation of 2-(3-chlorobenzyloxy)-N-(3-fluoro-4-(thieno[3,2-b]pyridin-7-yloxy)phenyl)acetamide

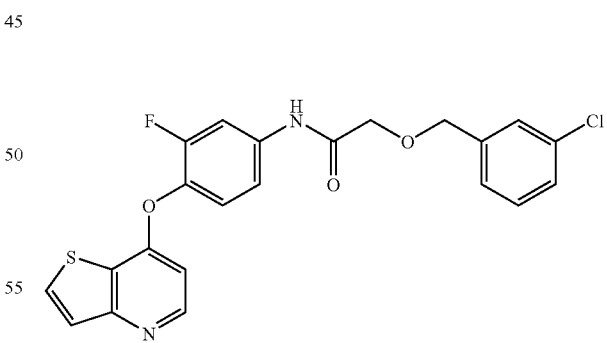

Prepared according to the method of Example 83, substituting 2-(3-chlorobenzyloxy)acetic acid for 4-phenylbutanoic acid. The product was isolated as a yellow solid (71 mg, 80%). $^1$H NMR (400 MHz, CDCl$_3$) δ 8.51 (d, 1H), 8.40 (br s, 1H), 7.78 (m, 1H), 7.75 (d, 1H), 7.57 (d, 1H), 7.39 (m, 2H), 7.25 (m, 4H), 6.50 (d, 1H), 4.65 (d, 2H), 4.13 (s, 2H). LRMS (ESI pos) m/e 442.9 (M+1).

Example 86

Preparation of 2-(2-chlorobenzyloxy)-N-(3-fluoro-4-(thieno[3,2-b]pyridin-7-yloxy)phenyl)acetamide

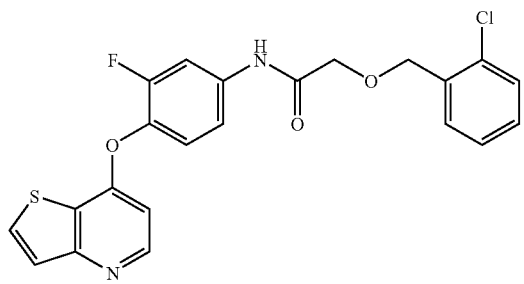

Prepared according to the method of Example 83, substituting 2-(2-chlorobenzyloxy)acetic acid for 4-phenylbutanoic acid. The product was isolated as a clear oil (74 mg, 84%). $^1$H NMR (400 MHz, CDCl$_3$) δ 8.53 (br s, 1H), 8.51 (d, 1H), 7.78 (m, 1H), 7.75 (d, 1H), 7.57 (d, 1H), 7.45 (m, 2H), 7.33 (m, 2H), 7.25 (m, 2H), 6.50 (d, 1H), 4.78 (d, 2H), 4.19 (s, 2H). LRMS (ESI pos) m/e 442.9 (M+1).

Example 87

Preparation of 2-(benzyloxy)-N-(3-fluoro-4-(thieno[3,2-b]pyridin -7-yloxy)phenyl)propanamide

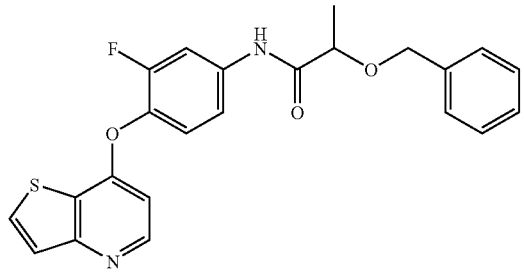

Prepared according to the method of Example 83, substituting 2-(benzyloxy)propanoic acid for 4-phenylbutanoic acid. 2-(benzyloxy)propanoic acid was prepared according to the method of Kato, D.; et al., *J. Org. Chem.* 2003 68(19), 7234. The product was isolated as a yellow oil (100 mg, 94%). $^1$H NMR (400 MHz, CDCl$_3$) δ 8.56 (br s, 1H), 8.50 (d, 1H), 7.76 (m, 1H), 7.75 (d, 1H), 7.57 (d, 1H), 7.39 (m, 4H), 7.23 (m, 2H), 7.25 (m, 2H), 6.49 (d, 1H), 4.67 (dd, 2H), 4.12 (m, 1H), 1.53 (d, 3H). LRMS (APCI pos) m/e 423.2 (M+1).

Example 88

Preparation of N-(3-fluoro-4-(thieno[3,2-b]pyridin-7-yloxy)phenyl)-2-oxo-1-phenylpyrrolidine-3-carboxamide

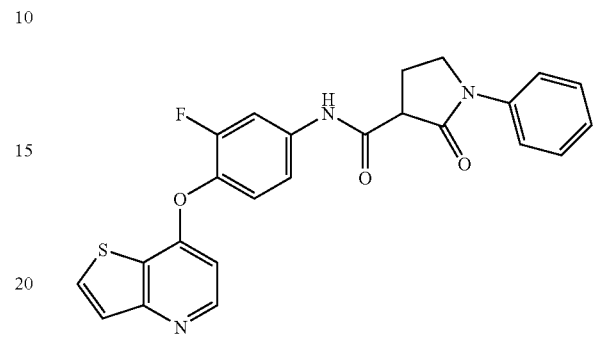

Prepared according to the method of Example 83, substituting 2-oxo-1-phenylpyrrolidine-3-carboxylic acid for 4-phenylbutanoic acid. The product was isolated as a yellow oil (70 mg, 78%). $^1$H NMR (400 MHz, CDCl$_3$) δ 9.95 (br s, 1H), 8.51 (d, 1H), 7.82 (dd, 1H), 7.75 (d, 1H), 7.59 (m, 2H), 7.57 (d, 1H), 7.43 (m, 2H), 7.26 (m, 3H), 6.50 (d, 1H), 3.93 (m, 2H), 3.70 (dd, 1H), 2.70 (m, 1H), 2.59 (m, 1H). LRMS (ESI pos) m/e 448.0 (M+1).

Example 89

Preparation of N-(3-fluoro-4-(thieno[3,2-b]pyridin-7-yloxy)phenyl)-1-(4-fluorophenyl)-2-oxopyrrolidine-3-carboxamide

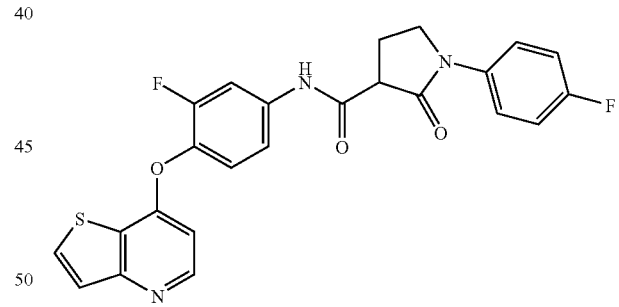

A solution of 1-(4-fluorophenyl)-2-oxopyrrolidine-3-carboxylic acid (38 mg, 0.169 mmol), EDCI (88 mg, 0.461 mmol), and HOBt (62 mg, 0.461 mmol) in DMF (3 ml) was stirred at room temperature for 1 hour. 3-Fluoro-4-(thieno[3,2-b]pyridin-7-yloxy)aniline (Example 1, Step B; 40 mg, 0.154 mmol) was added followed by Et$_3$N (0.064 mL, 0.461 mmol). After stirring for 2 hours, the reaction mixture was diluted with EtOAc and washed with saturated aqueous NH$_4$Cl, saturated aqueous NaHCO$_3$, and brine. The organic layer was dried over MgSO$_4$ and concentrated under reduced pressure to give the crude material that was purified by silica gel flash column chromatography (3:1=Et$_2$O:EtOAc to 1:3=Et$_2$O:EtOAc) to afford 38 mg (53%) of the desired product. $^1$H NMR (400 MHz, CD$_3$OD/CDCl$_3$) δ 8.45 (d, 1H), 7.92 (d, 1H), 7.85 (dd, 1H), 7.61 (m, 2H), 7.54 (d, 1H), 7.44 (m, 1H), 7.30 (t, 1H), 7.12 (m, 2H), 6.59 (d, 1H), 3.99 (m, 2H), 3.80 (dd, 1H), 2.67 (m, 1H), 2.52 (m, 1H); $^{19}$F NMR (376 MHz, CD$_3$OD/CDCl$_3$) δ −117.6, −128.3. LRMS (ESI pos) m/e 466.1 (M+1).

Example 90

Preparation of 1-(4-chlorophenyl)-N-(3-fluoro-4-(thieno[3,2-b]pyridin-7-yloxy)phenyl)-2-oxopyrrolidine-3-carboxamide

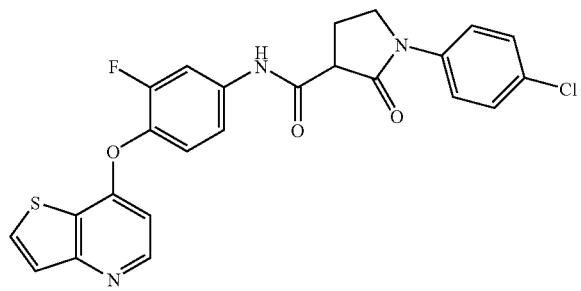

Prepared according to the procedure for Example 89, substituting 1-(4-chlorophenyl)-2-oxopyrrolidine-3-carboxylic acid for 1-(4-fluorophenyl) -2-oxopyrrolidine-3-carboxylic acid. The crude was purified by silica gel flash column chromatography (4:1=Et$_2$O:EtOAc to 1:3=Et$_2$O:EtOAc) to afford 15 mg (20%) of the desired product. $^1$H NMR (400 MHz, CD$_3$OD/CDCl$_3$) δ 8.45 (d, 1H), 7.92 (d, if H), 7.85 (dd, 1H), 7.62 (m, 2H), 7.54 (d, 1H), 7.43 (m, 1H), 7.38 (m, 2H), 7.30 (t, 1H), 6.59 (d, 1H), 4.03 (m, 1H), 3.95 (m, 1H), 2.67 (m, 1H), 2.50 (m, 1H); $^{19}$F NMR (376 MHz, CD$_3$OD/CDCl$_3$) δ −128.2. LRMS (ESI pos) m/e 482.0, 484.0 (M+1, Cl pattern) detected.

Example 91

Preparation of 1-(3-chloro-4-fluorophenyl)-N-(3-fluoro-4-(thieno[3,2-b]pyridin-7-yloxy)phenyl)-2-oxopyrrolidine-3-carboxamide

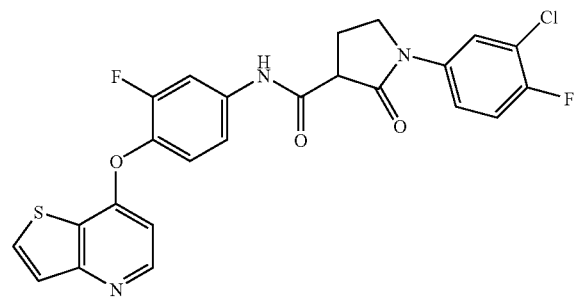

Prepared according to the procedure for Example 89, substituting 1-(3-chloro-4-fluorophenyl)-2-oxopyrrolidine-3-carboxylic acid for 1-(4-fluorophenyl) -2-oxopyrrolidine-3-carboxylic acid. The crude was purified by silica gel flash column chromatography (3:1=Et2O:EtOAc to 1:3=Et2O:EtOAc) to afford 21.1 mg (28%) of the desired product. 1H NMR (400 MHz, CD3OD/CDCl3) δ 8.45 (d, 1H), 7.91 (d, 1H), 7.87 (m, 1H), 7.84 (dd, 1H), 7.54 (d, 1H), 7.51 (m, 1H), 7.43 (m, 1H), 7.30 (t, 1H), 7.22 (t, 1H), 6.59 (d, 1H), 4.02 (m, 1H), 3.96 (m, 1H), 2.67 (m, 1H), 2.50 (m, 1H); $^{19}$F NMR (376 MHz, CD3OD/CDCl3) δ −120.4, −128.1. LRMS (ESI pos) m/e 500.0, 502.0 (M+1, Cl pattern) detected.

Example 92

Preparation of N-(4-(2-(3-(diethylamino)prop-1-ynyl)thieno[3,2-b]pyridin-7-yloxy)-3-fluorophenyl)-1-(4-fluorophenyl)-2-oxopyrrolidine-3-carboxamide

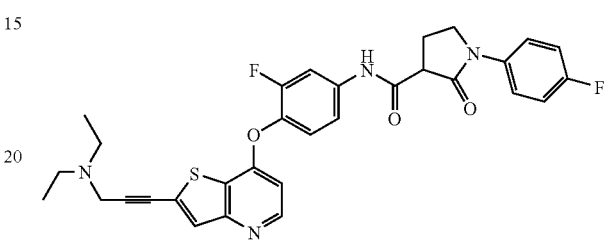

Prepared according to the procedure for Example 89, substituting 4-(2-(3-(diethylamino)prop-1-ynyl)thieno[3,2-b]pyridin-7-yloxy)-3-fluoroaniline (Example 6, Step B) for 1-(4-fluorophenyl)-2-oxopyrrolidine-3-carboxylic acid. The crude was purified by silica gel flash column chromatography (3% MeOH in CH$_2$Cl$_2$) to afford 4.5 mg (58%) of the desired product. $^1$H NMR (400 MHz, CD$_3$OD) δ 8.49 (d, 1H), 7.88 (dd, 1H), 7.65 (m, 2H), 7.57 (s, 1H), 7.45 (m, 1H), 7.37 (t, 1H), 7.14 (t, 2H), 6.74 (d, 1H), 3.98 (m, 2H), 3.77 (s, 2H), 2.68 (q, 4H), 2.59 (m, 1H), 2.47 (m, 1H), 1.15 (t, 6H); $^{19}$F NMR (376 MHz, CD$_3$OD/CDCl$_3$) δ −119.2, −129.9. LRMS (ESI pos) m/e 575.1 (M+1).

Example 93

Preparation of N-(4-(2-(3-(diethylamino)prop-1-ynyl)thieno[3,2-b]pyridin-7-yloxy)-3-fluorophenyl)-2-(piperidin-4-yl)acetamide bis(2,2,2-trifluoroacetate)

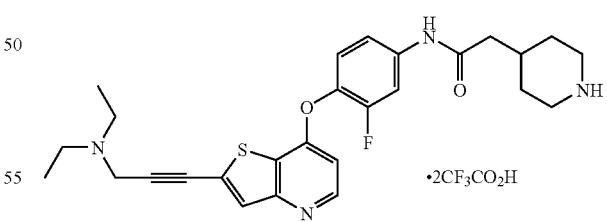

To a stirred solution of tert-butyl 4-(2-(4-(2-(3-(diethylamino)prop-1-ynyl)thieno[3,2-b]pyridin-7-yloxy)-3-fluorophenylamino)-2-oxoethyl)piperidine-1-carboxylate (Example 35; 2 mg, 0.00336 mmol) in methylene chloride (3 mL) was added 2,2,2-trifluoroacetic acid (3.83 mg, 0.0336 mmol). The reaction was stirred for 4 hours at room temperature. The reaction mixture was concentrated to dryness to give the product as a clear oil. Yield: 1.2 mg (47%). LRMS (esi pos) m/e 495 (M+1).

Example 94

Preparation of N-(3-fluoro-4-(4-methylpiperidinylmethyl)phenylthieno[3,2-b]pyridin-7-yloxy)phenyl)-N-(4-fluorophenyl)cyclopropane-1,1-dicarboxamide

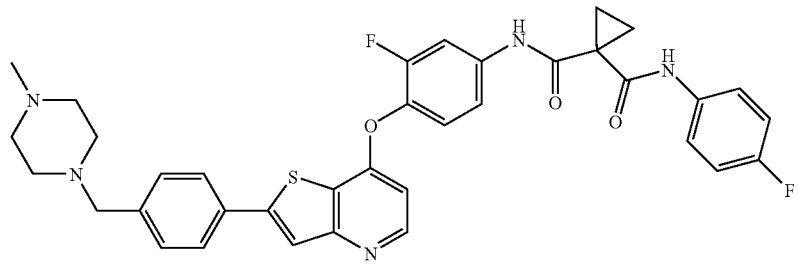

Step A: Preparation of 4-(7-(4-amino-2-fluorophenoxy)thieno[3,2-b]pyridin-2-yl)benzaldehyde: A sealable tube was charged with cesium carbonate (0.380 g, 1.17 mmol), 3-fluoro-4-(2-iodothieno[3,2-b]pyridin-7-yloxy)benzenamine (Example 6, Step A; 0.300 g, 0.777 mmol) obtained from 4-formylphenylboronic acid (0.146 g, 0.971 mmol), toluene (4 mL) and EtOH (1 mL). The reaction mixture was degassed under nitrogen for 10 minutes and Pd(PPh$_3$)$_4$ (0.0449 g, 0.0388 mmol) was added. The reaction mixture was to 80° C. for 18 hours, then cooled to room temperature and diluted with water (20 mL). The reaction mixture was extracted with EtOAc, and the combined organic layers were dried organic over sodium sulfate, filter and concentrated. The crude residue was purified by Biotage 40S eluting with 2:1 EtOAc/Hexane to provide 350 mg (98%) of the desired product as a yellow solid. LRMS (APCI pos) m/e 365 (M+1).

Step B: Preparation of 3-fluoro-4-(2-(4-((4-methylpiperazin-1-yl)methyl)phenyl)thieno[3,2-b]pyridin-7-yloxy)aniline: A 20 mL vial was charged with 1-methylpiperazine (0.0457 mL, 0.412 mmol), 4-(7-(4-amino-2-fluorophenoxy)thieno[3,2-b]pyridin-2-yl)benzaldehyde (Example 94, Step A; 0.150 g, 0.329 mmol) and CH$_2$Cl$_2$ (5 mL). The reaction mixture was stirred for 30 minutes and sodium triacetoxyborohydride (0.0977 g, 0.461 mmol) was added slowly over five minutes, and then the reaction mixture was stirred at room temperature for 4 hours. The reaction mixture was poured into Na$_2$CO$_3$ (100 mL) and extracted with CH$_2$Cl$_2$ (2×100 mL). The organic layers were over sodium sulfate, filtered and concentrated to provide the product (103 mg, 64%) as a brown solid. LRMS (APCI+) 449 (M+1H).

Step C: Preparation of N-(3-fluoro-4-(4-methylpiperidinyl)methyl)phenylthieno[3,2-b]pyridin-7-yloxy)phenyl)-N-(4-fluorophenyl)cyclopropane-1,1-dicarboxamide: Prepared from 1-((4-fluorophenyl)carbamoyl)cyclopropanecarboxylic acid (37.32 mg, 0.1672 mmol) and 3-fluoro-4-(2-(4-((4-methylpiperazin-1-yl)methyl)phenyl)thieno[3,2-b]pyridin-7-yloxy)benzenamine (50 mg, 0.1115 mmol) using the procedure described for Example 72, Step B. The product was purified by Biotage 40S column eluting with 2:1 EtOAc/Hexane. Obtained the product (1.1 mg, 1.5%) as a white solid. $^1$H NMR (CDCl$_3$, 400 MHz) δ 9.97 (s, 1H), 8.47 (d, J=5.5 Hz, 1H), 8.12 (s, 1H), 7.73 (m, 4H), 7.45 (m, 5H), 7.07 (t, J=8.8 Hz, 2H), 6.48 (d, J=5.5 Hz, 1H), 3.56 (s, 2H), 2.52 (br s, 4H), 2.31 (s, 3H), 1.82 (m, 2H), 1.62 (m, 6H). LRMS (esi pos) m/e 654 (M+1).

Example 95

Preparation of 1-(3-fluoro-4-(2-(4-N-methylbenzamido)thieno[3,2-b]pyridin-7-yloxy)phenyl)-3-(2-phenylacetyl)thiourea

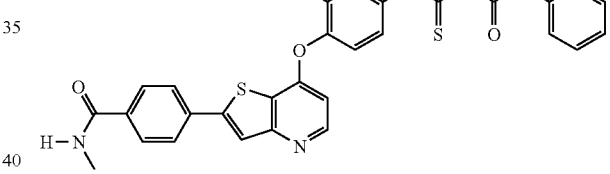

Step A: Preparation of 4-(7-(4-amino-2-fluorophenoxy)thieno[3,2-b]pyridin-2-yl)-N-methylbenzamide: Prepared from 3-fluoro-4-(2-iodothieno[3,2-b]pyridin-7-yloxy)benzenamine (Example 6, Step A; 0.300 g, 0.777 mmol) and 4-(methylcarbamoyl)phenylboronic acid (0.174 g, 0.971 mmol) according to the procedure described for Example 94, Step A. Purified by trituration from hot MeOH to obtain the product (210 mg, 96%) as a brown solid. LRMS (APCI pos) m/e 394 (M+1).

Step B: Preparation of 1-(3-fluoro-4-(2-(4-N-methylbenzamido)thieno[3,2-b]pyridin-7-yloxy)phenyl)-3-(2-phenylacetyl)thiourea: A round bottom flask was charged with 4-(7-(4-amino-2-fluorophenoxy)thieno[3,2-b]pyridin-2-yl)-N-methylbenzamide (100 mg, 0.254 mmol) and 1:1 toluene/ethanol (1 mL), and 2-phenylethanoyl isothiocyanate (90.1 mg, 0.508 mmol; prepared according to the procedure described by J. Org. Chem. 1964, 29, 1115-1119) was added as a solution in toluene (0.5 mL). The crude reaction mixture was concentrated in vacuo, and redissolved in MeOH, and the product (26 mg, 17%) was collected as a white precipitate by filtration as a white waxy solid. LRMS (APCI+) 96% 571 m/z (M+1) detected; $^1$H NMR (CDCl$_3$, 400 MHz) δ 12.54 (s, 1H), 8.55 (s, 1H), 8.48 (d, J=5.9 Hz, 3H), 8.01 (m, 1H), 7.93 (s, 1H), 7.86 (m, 5H), 7.43 (m, 3H), 7.33 (m, 3H), 6.64 (d, J=5.9 Hz, 1H), 6.25 (br s, 1H), 3.77 (s, 2H), 3.06 (d, J=4.7 Hz, 3H).

Example 96

Preparation of N-(3-fluoro-4-(2-(5-((4-methylpiperazin-1-yl)methyl)furan-2-yl)thieno[3,2-b]pyridin-7-yloxy)phenylcarbamothioyl)-2-phenylacetamide

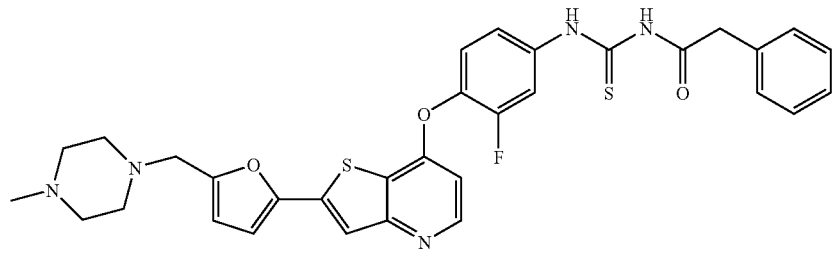

Step A: Preparation of 1-((5-bromofuran-2-yl)methyl)-4-methylpiperazine: A round-bottomed flask was charged with 1-methylpiperazine (2.02 mL, 18.2 mmol), 5-bromofuran-2-carbaldehyde (3.03 g, 17.3 mmol), and $CH_2Cl_2$ (30 mL). The reaction mixture was stirred for 30 minutes, and then sodium triacetoxy borohydride (4.77 g, 22.5 mmol) was added slowly over five minutes. The reaction mixture was stirred at room temperature for 4 hours, then poured into $Na_2CO_3$ (100 mL) and extracted with $CH_2Cl_2$ (2×100 mL). The combined organic layers were dried over sodium sulfate, filtered and concentrated to provide the product (2.35 g, 50%) as an orange solid. LRMS (esi pos) m/e 260 (M+1).

Step B: Preparation of 1-methyl-4-((5-(tributylstannyl)furan-2-yl)methyl)piperazine: A round-bottomed flask was charged with 1-((5-bromofuran-2-yl)methyl)-4-methylpiperazine (1.29 g, 4.88 mmol), and THF (20 mL). The solution was cooled to −78° C. in a dry ice/acetone bath. tert-Butyllithium (6.56 mL, 10.5 mmol; 1.6 M in pentane) was added, and the reaction mixture was stirred for 30 minutes. Tributylchlorostannane (1.12 mL, 4.15 mmol) was added the reaction mixture was stirred for 30 minutes. The reaction mixture was quenched by adding pH 7 phosphate buffer (20 mL) and warming to room temperature. The reaction mixture was extracted with EtOAc (50 mL), washed with brine (2×50 mL), dried over sodium sulfate, filter and concentrate. Purify by Biotage 40S (EtOAc). Isolated product (1.20 g, 52%) as a green oil. $^1$H NMR ($CDCl_3$, 400 MHz) δ 6.47 (d, J=3.1 Hz, 1H), 6.21 (d, J=2.3 Hz, 1H), 3.62 (s, 2H), 2.50 (br s, 8H), 2.27 (s, 3H), 1.53 (m, 6H), 1.33 (m, 6H), 1.06 (m, 6H), 0.88 (m, 9H).

Step C: Preparation of 3-fluoro-4-(2-(5-((4-methylpiperazin-1-yl)methyl)furan-2-yl)thieno[3,2-b]pyridin-7-yloxy)benzenamine: A round-bottomed flask was charged with 3-fluoro-4-(2-iodothieno[3,2-b]pyridin-7-yloxy)benzenamine (Example 6, Step A; 0.600 g, 1.55 mmol), 1-methyl-4-((5-(tributylstannyl)furan-2-yl)methyl)piperazine (0.802 g, 1.71 mmol), $PdCl_2(PPh_3)_2$ (0.050 g, 0.075 mmol), and dioxane (8 mL). The reaction mixture was heated to 90° C. for 18 hours under nitrogen and then cooled to room temperature. The reaction mixture was diluted with brine (100 mL) and extracted with EtOAc (100 mL). The combined organic layers were dried over sodium sulfate, filter and concentrated. The residue was purified by Biotage 40S eluting with $CHCl_3$/ MeOH saturated $NH_3$. (95:5) to provide 430 mg (60%) of the product as a light green solid. $^1$H NMR ($CDCl_3$, 400 MHz). δ 8.43 (d, J=5.5 Hz, 1H), 7.62 (s, 1H), 7.03 (t, J=8.6 Hz, 1H), 6.69 (d, J=3.5 Hz, 1H), 6.48 (m, 3H), 6.34 (d, J=3.1 Hz, 1H), 3.88 (s, 2H), 3.66 (s, 2H), 2.61 (m, 8H), 2.29 (s, 3H).

Step D: Preparation of N-(3-fluoro-4-(2-(5-((4-methylpiperazin -yl)methyl)furan-yl)thieno[3,2-b]pyridin-7-yloxy) phenylcarbamothioyl)-2-phenylacetamide: To a 5 mL round bottom flask was added 3-fluoro-4-(2-(5-((4-methylpiperazin-1-yl)methyl)furan-2-yl)thieno[3,2-b]pyridin-7-yloxy) benzenamine (32 mg, 0.0713 mmol) and 1:1 toluene/ethanol (1 mL). 2-Phenylethanoyl isothiocyanate (25.3 mg, 0.143 mmol; prepared according to the procedure described by J. Org. Chem. 1964, 29, 1115-1119) was added as a solution in toluene (0.5 mL). After stirring for 30 minutes at room temperature, the crude was concentrated in vacuo. The crude was dissolved in MeOH and purified by preparative TLC, eluting with 9:1 $CH_2Cl_2$/MeOH. The product was collected at Rf 0.4 just above the unreacted starting material at Rf 0.3 to provide the product (5 mg, 10%) as a white solid. LRMS (APCI+) m/e 626 (M+1) detected; $^1$H NMR ($CDCl_3$, 400 MHz) δ 9.98 (s, 1H), 8.45 (d, J=5.5 Hz, 1H), 8.22 (s, 1H), 7.75 (d, J=13.7 Hz, 1H), 7.62 (s, 1H), 7.45 (m, 2H), 7.24 (m, 2H), 7.07 (t, J=8.6 Hz, 2H), 6.71 (s, 1H), 6.35 (s, 1H), 3.66 (s, 2H), 2.58 (m, 8H), 2.29 (s, 3H), 1.79 (m, 4H).

Example 97

Preparation of 1-(3-fluoro-4-(2-(4-(1-(4-methylpiperidinyl)methyl)phenylthieno[3,2-b]pyridin-7-yloxy)phenyl)-3-(2-phenylacetyl)thiourea

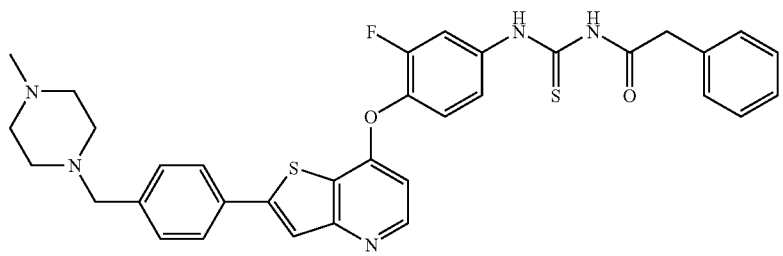

Step A: Preparation of 1-(3-fluoro-4-(2-(4-(1-(4-methylpiperidinyl)methyl)phenylthieno[3,2-b]pyridin-7-yloxy)phenyl)-3-(2-phenylacetyl)thiourea: Prepared from 3-fluoro-4-(2-(4-((4-methylpiperazin-1-yl)methyl)phenyl)thieno[3,2-b]

pyridin-7-yloxy)benzenamine (Example 94, Step B; 32 mg, 0.0713 mmol) and 2-phenylethanoyl isothiocyanate (85.1 mg, 0.480 mmol; prepared according to the procedure described by J. Org. Chem. 1964, 29, 1115-1119) using the procedure described for Example 96, Step D. The crude product was purified by preparative TLC 9:1 CH$_2$Cl$_2$/MeOH). The product was obtained as a white solid (4.8 mg, 11%). $^1$H NMR (CDCl$_3$, 400 MHz) δ 12.50 (bs, 1H), 8.50 (m, 2H), 7.95 (d, J=8.6 Hz, 1H), 7.75 (m, 3H), 7.40 (m, 5H), 7.28 (m, 4H), 6.50 (d, J=8.6 Hz, 1H), 3.70 (s, 2H), 3.5 (s, 2H), 2.50 (bs, 8H), 2.30 (s, 3H). LRMS (esi+) m/e 626 (M+1) detected.

Example 98

Preparation of 1-(3-fluoro-4-(2-(4-(1-pyrazolo)methyl)phenylthieno[32-b]pyridin-7-yloxy)phenyl)-3-(2-phenylacetyl)thiourea

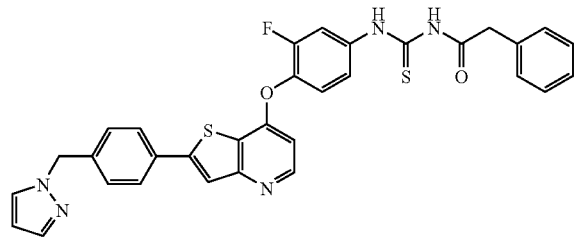

Step A: Preparation of 4-(2-(4-((1H-pyrazol-1-yl)methyl)phenyl)thieno[3,2-b]pyridin-7-yloxy)-3-fluorobenzenamine (100 mg, 0.240 mmol): Prepared from 3-fluoro-4-(2-iodothieno[3,2-b]pyridin-7-yloxy)benzenamine (Example 6, Step A; 0.300 g, 0.777 mmol) and 4-((1H-pyrazol-1-yl)methyl)phenylboronic acid (0.196 g, 0.971 mmol) using the procedure described for Example 94, Step A, to provide the product (210 mg, 36%) as a brown solid. LRMS (esi+) m/e 417 (M+1) detected.

Step B: Preparation of 1-(3-fluoro-4-(2-(4-(1-pyrazolo)methyl)phenylthieno[3,2-b]pyridin-7-yloxy)phenyl)-3-(2-phenylacetyl)thiourea: Prepared from 4-(2-(4-((1H-pyrazol-1-yl)methyl)phenyl)thieno[3,2-b]pyridin-7-yloxy)-3-fluorobenzenamine (100 mg, 0.240 mmol) and 2-phenylethanoyl isothiocyanate (85.1 mg, 0.480 mmol; prepared according to the procedure described by J. Org. Chem. 1964, 29, 1115-1119) using the procedure described for Example 96, Step D, to provide the product (55 mg, 38%) as a white solid. $^1$H NMR (CDCl$_3$, 400 MHz) δ 12.59 (s, 1H), 8.57 (s, 1H), 8.32 (d, J=6.2 Hz, 1H), 8.03 (q, 2.3, 11.7, 1H), 7.98 (d, J=4.3 Hz, 1H), 7.76 (s, 1H), 7.40 (m, 12H), 6.71 (d, J=7.8 Hz, 2H), 5.37 (s, 2H), 3.78 (s, 2H). LRMS (APCI+) m/e 594 (M+1) detected.

Example 99 (Representative Example)

Preparation of N-(4-fluorophenyl)-N-(4-(2-phenylthieno[3,2-b]pyridin-7-yloxy)phenyl)cyclopropane-1,1-dicarboxamide

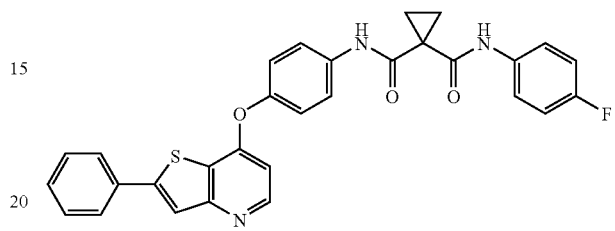

Step A: Preparation of 4-(2-phenylthieno[3,2-b]pyridin-7-yloxy)benzenamine: This compound can be prepared from 4-(2-iodothieno[3,2-b]pyridin-7-yloxy)benzenamine (Example 72, Step A) and phenylboronic acid using the procedure described for Example 94, Step A.

Step B: Preparation of N-(4-(2-phenylthieno[3,2-b]pyridin-7-yloxy)phenyl)-N-(4-fluorophenyl)cyclopropane-1,1-dicarboxamide: The title compound can be prepared from 4-(2-phenylthieno[3,2-b]pyridin-7-yloxy)benzenamine and 1-((4-fluorophenyl)carbamoyl)cyclopropane carboxylic acid (prepared from cyclopropane-1,1-dicarboxylic acid and 4-fluoroaniline using the methods described in WO 2005/030140 and by Shih and Rankin, Synth. Comm. 1996, 26(4), 833-836) using the procedure described for Example 73.

Example 100

Preparation of 1-(3-fluoro-4-(2-(2-furyl)thieno[3,2-b]pyridin-7-yloxy)phenyl)-3-(2-phenylacetyl)thiourea

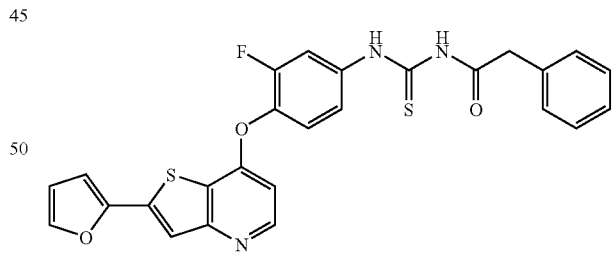

Step A: 3-fluoro-4-(2-(furan-2-yl)thieno[3,2-b]pyridin-7-yloxy)benzenamine: A 100 mL, single-neck, round-bottomed flask was charged with 3-fluoro-4-(2-iodothieno[3,2-b]pyridin-7-yloxy)benzenamine (0.300 g, 0.7768 mmol) from Example 6, Step A, PdCl$_2$(PPh$_3$)$_2$ (0.02726 g, 0.03884 mmol), tributyl(furan-2-yl)stannane (0.2931 ml, 0.9322 mmol), and dioxane (8 mL). Heat to 90° C. for 6 hours under nitrogen and cool to room temperature. The reaction mixture was diluted with brine (100 mL) and extracted with EtOAc (100 mL). The reaction mixture was purified by triturating with hot MeOH. The product (170 mg, 57%) was isolated as a brown solid. LRMS (APCI+) m/e 327 (M+1) detected.

Step B: Preparation of 1-(3-fluoro-4-(2-(2-furyl)thieno[3,2-b]pyridin-7-yloxy)phenyl)-3-(2-phenylacetyl)thiourea:

Prepared from 3-fluoro-4-(2-(furan-2-yl)thieno[3,2-b]pyridin-7-yloxy)benzenamine (100 mg, 0.306 mmol) obtained in Step A and 2-phenylethanoyl isothiocyanate (109 mg, 0.613 mmol; prepared according to the procedure described by *J. Org. Chem.* 1964, 29, 1115-1119) using the procedure described for Example 96, Step D. Collected the product (6 mg, 4%) as a white solid. $^1$H NMR (CDCl$_3$, 400 MHz) δ 12.6 (s, 1H), 8.53 (s, 1H), 8.39 (d, J=6.6 Hz, 1H), 8.07 (d, J=13.2 Hz, 1H), 7.90 (s, 1H), 7.61 (d, J=6.2 Hz, 1H), 7.44 (m, 7H), 7.04 (s, 1H), 6.73 (d, J=6.2 Hz, 1H), 6.62 (s, 1H), 3.78 (s, 2H). LRMS (APCI+) m/e 504 (M+1) detected.

Example 101

Preparation of 1-(3-fluoro-4-(2-(4-carboethoxy)phenylthieno[3,2-b]pyridin-7-yloxy)phenyl)-3-(2-phenylacetyl)thiourea

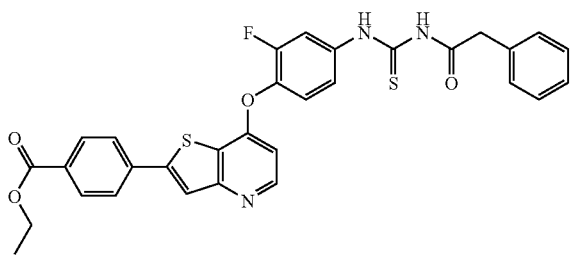

Step A: Ethyl 4-(7-(4-amino-2-fluorophenoxy)thieno[3,2-b]pyridin-2-yl)benzoate: Prepared from 3-fluoro-4-(2-iodothieno[3,2-b]pyridin-7-yloxy)benzenamine (Example 6, Step A; 0.300 g, 0.777 mmol) and 4-(methoxycarbonyl)phenylboronic acid (0.175 g, 0.971 mmol), using the procedure described for Example 94, Step A. The product (178 mg, 47%) was isolated as a brown solid. LRMS (APCI+) m/e 409 (M+1) detected.

Step B: Preparation of 1-(3-fluoro-4-(2-(2-furyl)thieno[3,2-b]pyridin-7-yloxy)phenyl)-3-(2-phenylacetyl)thiourea:

Prepared from ethyl 4-(7-(4-amino-2-fluorophenoxy)thieno[3,2-b]pyridin-2-yl)benzoate (20 mg, 0.049 mmol) and 2-phenylethanoyl isothiocyanate (17 mg, 0.098 mmol; prepared according to the procedure described by *J. Org. Chem.* 1964, 29, 1115-1119) using the procedure described for Example 96, Step D. The product (2 mg, 6%) was collected as an orange solid. $^1$H NMR (CDCl$_3$, 400 MHz) δ 12.59 (s, 1H), 8.46 (m, 2H), 8.18 (d, J=6.6 Hz, 2H), 8.06 (m, 2H), 7.89 (d, J=6.6 Hz, 2H), 7.87 (m, 3H), 7.46 (m, 4H), 7.34 (m, 1H), 6.75 (s, 1H), 4.45 (q, J=7.4, 14.4 Hz, 2H), 2.32 (s, 1H), 1.44 (t, J=7.4, Hz, 3H). LRMS (APCI+) m/e 586 (M+1) detected.

Example 102

Preparation of N-(3-fluoro-4-(2-(3-(4-methylpiperazin-1-yl)prop-1-ynyl)thieno[3,2-b]pyridin-7-yloxy)phenyl)-1-(4-fluorophenyl)-2-oxopyrrolidine-3-carboxamide

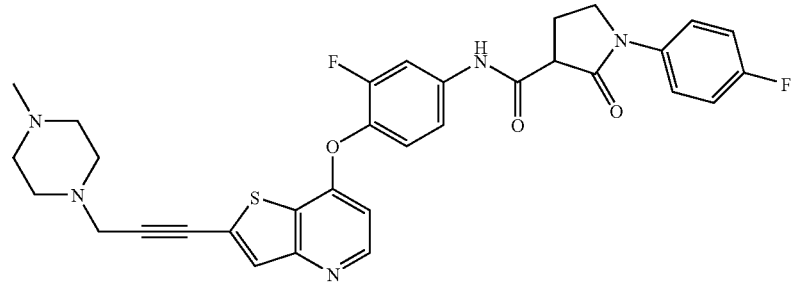

Step A: Preparation of N-(3-fluoro-4-(2-(3-(4-methylpiperazin-1-yl)prop-1-ynyl)thieno[3,2-b]pyridin-7-yloxy)phenyl)-1-(4-fluorophenyl)-2-oxopyrrolidine-3-carboxamide:

The title compound was prepared from 3-fluoro-4-(2-(3-(4-methylpiperazin-1-yl)prop-1-ynyl)thieno[3,2-b]pyridin-7-yloxy)aniline (Example 17, Step B) and 1-(4-fluorophenyl)-2-oxopyrrolidine-3-carboxylic acid according to the procedure described for Example 89. The crude was purified by silica gel flash column chromatography (5% MeOH in CH$_2$Cl$_2$) to afford 4.7 mg (31%) of the desired product. $^1$H NMR (400 MHz, CD$_3$OD) δ 8.49 (d, 1H), 7.89 (dd, 1H), 7.63 (m, 2H), 7.60 (s, 1H), 7.45 (m, 1H), 7.37 (t, 1H), 7.14 (t, 2H), 6.69 (d, 1H), 3.97 (m, 2H), 3.68 (s, 2H), 2.75 (m, 4H), 2.58 (m, 3H), 2.47 (m, 3H), 2.30 (s, 3H); $^{19}$F NMR (376 MHz, CD$_3$OD) δ −119.2, −129.9. LRMS (ESI pos) m/e 602.3 (M+1).

Example 103

Preparation of N-(3-fluoro-4-(2-(3-(4-methylpiperazin-1-yl)prop-1-ynyl)thieno[3,2-b]pyridin-7-yloxy)phenyl)-1-(4-fluorophenyl)-2-oxo-1,2-dihydropyridine-3-carboxamide

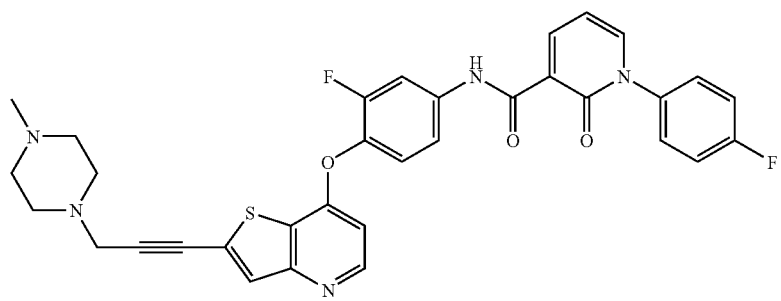

Step A: Preparation of N-(3-fluoro-4-(2-(3-(4-methylpiperazin-1-yl)prop-1-ynyl)thieno[3,2-b]pyridin-7-yloxy)phenyl)-1-(4-fluorophenyl)-2-oxo-1,2-dihydropyridine-3-carboxamide: The title compound was prepared from 3-fluoro-4-(2-(3-(4-methylpiperazin-1-yl)prop-1-ynyl)thieno[3,2-b]pyridin-7-yloxy)aniline (Example 17, Step B) and 1-(4-fluorophenyl)-2-oxo-1,2-dihydropyridine-3-carboxylic acid (prepared from methyl 2-oxo-2H-pyran-3-carboxylate with 4-fluoroaniline and followed by hydrolysis using the methods described in US 2005/0239820) according to the procedure for Example 89. The crude was purified by silica gel flash column chromatography (5% MeOH in $CH_2Cl_2$) to afford 3 mg (19%) of the desired product. $^1$H NMR (400 MHz, $CD_3OD/CDCl_3$) δ 8.73 (dd, 1H), 8.45 (d, 1H), 7.98 (dd, 1H), 7.84 (dd, 1H), 7.58 (s, 1H), 7.48 (m, 2H), 7.40 (d, 1H), 7.31 (t, 2H), 6.74 (t, 1H), 6.63 (d, 1H), 3.64 (s, 2H), 2.60-2.76 (m, 8H), 2.33 (s, 3H); $^{19}$F NMR (376 MHz, $CD_3OD/CDCl_3$) δ −112.1, −127.6. LRMS (ESI pos) m/e 612.1 (M+1).

Example 104

Preparation of N-(3-fluoro-4-(2-(3-(4-methylpiperazin-1-yl)prop-1-ynyl)thieno[3,2-b]pyridin-7-yloxy)phenyl)-2-(4-fluorophenyl)-3-oxo-2,3-dihydropyridazine-4-carboxamide Step A: Preparation of (E)-2-(2-(4-fluorophenyl)hydrazono) acetaldehyde: A mixture of 1-(4-fluorophenyl)hydrazine hydrochloride (5.0 g, 30.75 mmol), water (20 mL), and acetic acid (20 mL) was added with stirring to a 40% aqueous solution of glyoxal (17.6 mL, 153.8 mmol) over 20 minutes. Stirring was continued for 2 hours and then the mixture was filtered. The precipitate was washed with water and dried to afford 5.0 g (98%) of the desired product. $^1$H NMR (400 MHz, $CDCl_3$) δ 9.56 (d, 1H), 8.63 (br s, 1H), 7.24 (m, 1H), 7.16 (m, 2H), 7.06 (m, 2H); $^{19}$F NMR (376 MHz, $CDCl_3$) δ −120.3. LRMS (ESI pos) m/e 151.1 (M−16).

Step B: Preparation of (E)-5-(2-(2-(4-fluorophenyl)hydrazono)ethylidene)-2,2-dimethyl-1,3-dioxane-4,6-dione: A suspension of the dioxan-dione (1.44 g, 10.0 mmol) and (E)-2-(2-(4-fluorophenyl)hydrazono)acetaldehyde (1.66 g, 10.0 mmol) in toluene (15 mL) was treated with acetic acid (5 drops) and with piperidine (5 drops). The reaction mixture was then stirred at room temp for 17 hours. The precipitated condensation product was filtered and thoroughly washed with light petroleum to afford 2.87 g (98%) of the desired product. $^1$H NMR (400 MHz, $CD_3OD/CDCl_3$) δ 8.72 (d, 1H), 8.24 (d, 1H), 7.32 (m, 2H), 7.08 (t, 2H), 1.76 (s, 6H); $^{19}$F NMR (376 MHz, $CDCl_3$) δ −119.1.

Step C: Preparation of 2-(4-fluorophenyl)-3-oxo-2,3-dihydropyridazine-4-carboxylic acid: A mixture of (E)-5-(2-(2-(4-fluorophenyl)hydrazono)ethylidene)-2,2-dimethyl-1,3-dioxane-4,6-dione (0.60 g, 2.05 mmol) and NaOMe (0.133 g, 2.46 mmol) in MeOH (10 mL) was heated under reflux for 15 hours. The salt was treated with cold 1 N HCl solution, extrated with $CH_2Cl_2$, dried over $MgSO_4$, and concentrated to afford 0.42 g (87%) of the desired product. $^1$H NMR (400 MHz, $CDCl_3$) δ 13.57 (br s, 1H), 8.29 (m, 2H), 7.63 (m, 2H), 7.24 (m, 2H); $^{19}$F NMR (376 MHz, $CDCl_3$) δ −110.7. LRMS (ESI pos) m/e 235.1 (M+1).

Step D: Preparation of N-(3-fluoro-4-(2-(3-(4-methylpiperazin-1-yl)prop-1-ynyl)benzo[b]thiophen-7-yloxy)phenyl)-2-(4-fluorophenyl)-3-oxo-2,3-dihydropyridazine-4-carboxamide: The title compound was prepared from 3-fluoro-4-(2-(3-(4-methylpiperazin-1-yl)prop-1-ynyl)thieno[3,2-b]pyridin-7-yloxy)aniline, obtained from

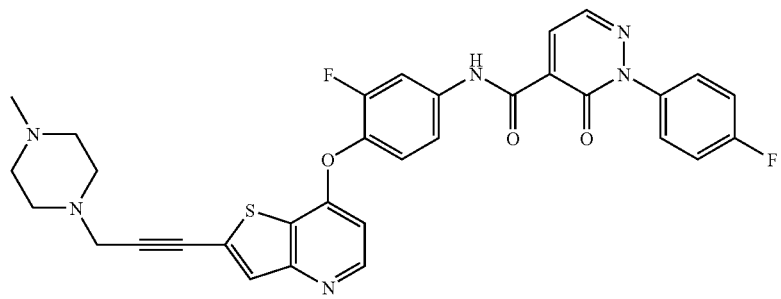

Example 17, Step B and 2-(4-fluorophenyl)-3-oxo-2,3-dihydropyridazine-4-carboxylic acid according to the procedure for Example 89. The crude was purified by silica gel flash column chromatography (5% MeOH in CH$_2$Cl$_2$) to afford 6.1 mg (18%) of the desired product. $^1$H NMR (400 MHz, CD$_3$OD) δ 8.49 (d, 1H), 8.35 (d, 1H), 8.30 (d, 1H), 8.04 (dd, 1H), 7.67 (m, 2H), 7.60 (s, 1H), 7.49 (m, 1H), 7.41 (t, 1H), 7.29 (t, 2H), 6.71 (d, 1H), 3.68 (s, 2H), 2.57-2.74 (m, 8H), 2.30 (s, 3H); $^{19}$F NMR (376 MHz, CD$_3$OD) δ −114.8, −129.5.

Example 105

Preparation of 2-benzyl-5-(3-fluoro-4-(2-(3-(4-methylpiperazin-1-yl)prop-1-ynyl)thieno[3,2-b]pyridin-7-yloxy)phenyl)pyrimidin-4(3H)-one

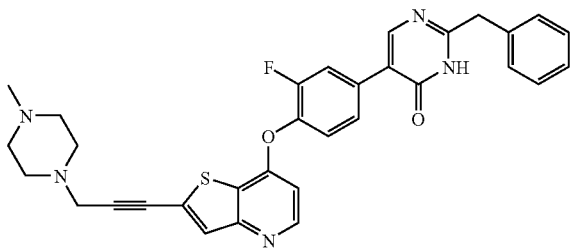

Step A: Preparation of 2-benzyl-4-methoxypyrimidine: A solution of 2-chloro-4-methoxypyrimidine (0.500 g, 3.46 mmol) and PdCl$_2$(PPh$_3$)$_2$ (0.121 g, 0.173 mmol) in THF (10 mL) was sparged with N$_2$. Benzylzinc(II) bromide (8.30 mL, 4.15 mmol; 0.5 M solution in THF) was added and the reaction mixture was at reflux for 1 hour. The reaction mixture was cooled to room temperature and then partitioned between EtOAc and H$_2$O. The phases were separated, and the aqueous phase was re-extracted with EtOAc (1×). The combined organic layers were dried (Na$_2$SO$_4$), filtered and concentrated to yield a crude dark brown oil. The crude product was purified by flash column chromatography, eluting with 20:1 dichloromethane/EtOAc. The desired product (0.676 g, 98%) was obtained as a dark yellow oil. $^1$H NMR (400 MHz, CDCl$_3$) δ 8.34 (d, J=5.9 Hz, 1H), 7.41-7.25 (m, 4H), 7.21 (m, 1H), 6.53 (d, J=5.5 Hz, 1H), 4.16 (s, 2H), 3.95 (s, 3H). LRMS (ESI pos) m/e 201 (M+1).

Step B: Preparation of 2-benzylpyrimidin-4(3H)-one: To a solution of 2-benzyl-4-methoxypyrimidine (0.675 g, 3.37 mmol) in AcOH (15 mL) was added HBr (2.28 mL, 20.2 mmol; 48 wt % in H$_2$O). The reaction mixture was stirred at 95° C. for 2 hours. The reaction mixture was cooled to room temperature and diluted with H$_2$O. The pH of the reaction mixture was adjusted to 5-6 with 6 M aqueous NaOH and then partitioned between EtOAc and H$_2$O. The phases were separated, and the aqueous phase was re-extracted with EtOAc (1×). The combined organic layers were dried (Na$_2$SO$_4$), filtered and concentrated to yield a crude yellow solid. Purification of the crude product was achieved by trituration with dichloromethane and diethyl ether. The resulting solid was filtered, washed with diethyl ether, collected and dried under vacuum to yield the desired product (0.531 g, 85%) as an off-white solid. $^1$H NMR (400 MHz, DMSO-d$_6$) δ 7.79 (d, J=6.6 Hz, 1H), 7.31 (m, 4H), 7.23 (m, 1H), 6.10 (d, J=6.6 Hz, 1H), 3.83 (s, 2H). LRMS (ESI pos) m/e 187 (M+1).

Step C: Preparation of 2-benzyl-5-bromopyrimidin-4(3H)-one: To a solution of 2-benzylpyrimidin-4(3H)-one (0.531 g, 2.85 mmol) in CHCl$_3$ (15 mL) and methanol (3 mL) was added bromine (0.146 mL, 2.85 mmol). The reaction mixture was stirred at room temperature for 3 hours and then quenched with 10% sodium bisulfite solution. The reaction mixture was partitioned between EtOAc and H$_2$O. The phases were separated, and the aqueous phase was re-extracted with EtOAc (1×). The combined organic layers were dried (Na$_2$SO$_4$), filtered and concentrated to yield a crude yellow solid. Purification of the crude product was achieved by trituration with dichloromethane. The resulting solid was filtered, washed with dichloromethane, collected and dried under vacuum to yield the desired product (0.302 g, 40%) as an off-white solid. $^1$H NMR (400 MHz, DMSO-d$_6$) δ 13.23 (br s, 1H), 8.25 (s, 1H), 7.35-7.28 (m, 4H), 7.27-7.22 (m, 1H), 3.87 (s, 2H). LRMS (ESI pos) m/e 265, 267 (M+1, Br pattern).

Step D: Preparation of 2-benzyl-5-(4-(benzyloxy)-3-fluorophenyl)pyrimidin-4(3H)-one: A solution of 2-benzyl-5-bromopyrimidin-4(3H)-one (0.300 g, 1.13 mmol), 4-(benzyloxy)-3-fluorophenylboronic acid (0.334 g, 1.36 mmol), Pd(PPh$_3$)$_4$ (0.065 g, 0.057 mmol) and lithium chloride (0.240 g, 5.66 mmol) in dioxane (3 mL) and 2 M aq Na$_2$CO$_3$ (0.3 mL) was stirred at 100° C. for 18 hours. The reaction mixture was partitioned between EtOAc and H$_2$O. The phases were separated, and the aqueous phase was re-extracted with EtOAc (3×). The combined organic layers were dried (Na$_2$SO$_4$), filtered and concentrated to yield a crude dark yellow solid. Purification of the crude product was achieved by trituration with dichloromethane. The resulting solid was filtered, washed with dichloromethane, collected and dried under vacuum. The filtrate was concentrated and the trituration procedure was repeated (2×) with EtOAc. The solids were combined to yield the desired product (0.284 g, 65%) as a pale yellow solid. $^1$H NMR (400 MHz, DMSO-d$_6$) δ 12.93 (br s, 1H), 8.13 (s, 1H), 7.66 (dd, J=2.3, 13.3 Hz, 1H), 7.53-7.22 (s, 12H), 5.21 (s, 2H), 3.90 (s, 2H). LRMS (APCI pos) m/e 387 (M+1).

Step E: Preparation of 2-benzyl-5-(3-fluoro-4-hydroxyphenyl)pyrimidin-4(3H)-one: A suspension of 2-benzyl-5-(4-(benzyloxy)-3-fluorophenyl)pyrimidin-4(3H)-one (0.284 g, 0.735 mmol) in trifluoroacetic acid (3 mL) was stirred at 40° C. for 2 hours and then at room temperature for 16 hours. The reaction mixture was concentrated to dryness and then purified by flash column chromatography, eluting with 20:1 dichloromethane/MeOH. The desired product (0.177 g, 81%) was obtained as a white solid. $^1$H NMR (400 MHz, DMSO-d$_6$) δ 12.89 (br s, 1H), 9.98 (s, 1H), 8.08 (s, 1H), 7.58 (dd, J=2.3, 13.3 Hz, 1H), 7.39-7.30 (m, 5H), 7.28-7.22 (m, 1H), 6.96 (dd, J=8.2, 9.4 Hz, 1H), 3.89 (s, 2H). LRMS (ESI pos) m/e 297 (M+1).

Step F: Preparation of 2-benzyl-5-(3-fluoro-4-(2-iodothieno[3,2-b]pyridin-7-yloxy)phenyl)pyrimidin-4(3H)-one: To a mixture of 7-chloro-2-iodothieno[3,2-b]pyridine (0.030 g, 0.10 mmol; prepared according to the procedure described by Ragan, J. A. Org. Proc. Res. Dev. 2003, 7, 676) and 2-benzyl-5-(3-fluoro-4-hydroxyphenyl)pyrimidin-4(3H)-one (0.025 g, 0.084 mmol) in DMF (1 mL) was added Cs$_2$CO$_3$ (0.033 g, 0.10 mmol). The reaction mixture was stirred at 130° C. for 18 hours. The reaction mixture was partitioned between EtOAc and saturated aqueous NaCl. The phases were separated, and the aqueous phase was re-extracted with EtOAc (2×). The combined organic layers were dried (Na$_2$SO$_4$), filtered and concentrated to yield a crude dark yellow solid. Purification of the crude product was achieved by flash column chromatography (25:1 dichloromethane/methanol) and then by trituration with dichloromethane. The resulting solid was filtered, washed with dichloromethane, collected and dried under vacuum to yield the desired product (0.008 g, 17%) as a pale yellow solid. LRMS (ESI pos) m/e 556 (M+1).

Step G: Preparation of 2-benzyl-5-(3-fluoro-4-(2-(3-(4-methylpiperazin-1-yl)prop-1-ynyl)thieno[3,2-b]pyridin-7-yloxy)phenyl)pyrimidin-4(3H)-one: A mixture of 2-benzyl-5-(3-fluoro-4-(2-iodothieno[3,2-b]pyridin-7-yloxy)phenyl)pyrimidin-4(3H)-one (8.0 mg, 0.014 mmol), 1-methyl-4-(prop-2-ynyl)piperazine (Example 17, Step A; 5.0 mg, 0.036 mmol), copper(I) iodide (0.1 mg, 0.0007 mmol), and triethylamine (0.020 ml, 0.14 mmol) in THF (0.5 mL) was sparged with $N_2$ for 5 minutes, and then $Pd(PPh_3)_4$ (1.0 mg, 0.0007 mmol) was added. The sealed reaction was stirred at 50° C. for 3 hours. The reaction mixture was purified directly by silica gel chromatography, eluting with 10:1 dichloromethane/methanol. The desired product (6.6 mg, 81%) was obtained as a pale yellow solid. $^1$H NMR (400 MHz, d6-DMSO) δ 8.58 (d, J=5.5 Hz, 1H), 8.29 (s, 1H), 7.93 (dd, J=1.9, 12.5 Hz, 1H), 7.81 (s, 1H), 7.74 (m, 1H), 7.54 (t, J=8.6 Hz, 1H), 7.39-7.32 (m, 4H), 7.29-7.24 (m, 1H), 6.76 (d, J=5.1 Hz, 1H), 3.94 (s, 2H), 3.68 (s, 2H), 2.55-2.46 (m, 8H), 1.23 (s, 3H). LRMS (ESI pos) m/e 566 (M+1).

Example 106 c-Met Enzyme Assay

The assay for the determination of cMet kinase activity is based on an enzyme linked immunosorbant assay (ELISA). A compound of Formula I, 50 pM cMet (His-tagged recombinant human Met (amino acids 974-end), expressed by baculovirus), and 5 μM ATP in assay buffer (25 mM MOPS, pH 7.4, 5 mM $MgCl_2$, 0.5 mM $MnCl_2$, 100 μM Sodium Orthovanadate, 0.01% Triton X-100, 1 mM DTT, final DMSO concentration 1% (v/v)) are incubated on a 0.25 mg/mL PGT coated plates for 20 minutes at room temperature. The reaction mixture is removed by washing and the phosphorylated polymer substrate is detected with 0.2 μg/mL phosphotyrosine specific monoclonal antibody (PY20) conjugated to horseradish peroxidase (HRP). After the addition of 1M phosphoric acid to stop the development, the chromogenic substrate (TMB) color is quantitiated by spectrophotometry at 450 nm.

Example 107

The cellular activity of the compounds of the present invention may be determined by the following procedure. MKN45 cells were plated in Costar 3904 96-well plates in growth media (RPMI, 10% FBS) at a density of 15000 cells/well and incubated at 37° C., 5% $CO_2$ overnight. The following day, one-tenth volume of a 10× concentration of compounds was added to the wells in a 11-point dilution series. The dilutions series was composed of an initial 1:3 dilution in DMSO, followed by a 1:20 dilution in HBSS, for a final DMSO concentration on cells of 0.5%. Control wells were treated with 0.5% DMSO. The typical range of dilution was 5 μM to 0.3 nM, which was expanded to 25 μM depending on the potency of the compound. Once compound was added to the cells, plates were incubated for one hour at 37° C., 5% $CO_2$. Plates were then washed in PBS, fixed in 4% formaldehyde and rehydrated with a 10% methanol solution. The plates were then blocked with Licor blocking buffer. The total phosphorylated cMet levels were measured by incubating with a rabbit polyclonal antibody against phosphorylated cMet followed by an anti-rabbit antibody conjugated to Alexa Fluor 680. Signal was normalized for differences in cell number by reference to the levels of the housekeeping protein GAPDH. Cells were incubated with a mouse monoclonal antibody against GAPDH followed by an anti-mouse antibody labeled with IRdye 800. Signal was measured on the Licor. The overall fluorescent signal from the Alexa Fluor 680 is normalized by dividing the value by the fluorescent value of the IRdye 800 signal. The fluorescent signal of the control wells was defined as 100% and the percent of inhibition of phosphorylated cMet was expressed as percent of control. $IC_{50}$ values were determined from the percent of control data using a standard 4-parameter logistical model.

Example 108

N-(3-fluoro-4-(2-(5-((4-methylpiperazin-1-yl)methyl)furan-2-yl)thieno[3,2-b]pyridin-7-yloxy)phenyl)-N-(4-fluorophenyl)cyclopropane-1,1-dicarboxamide

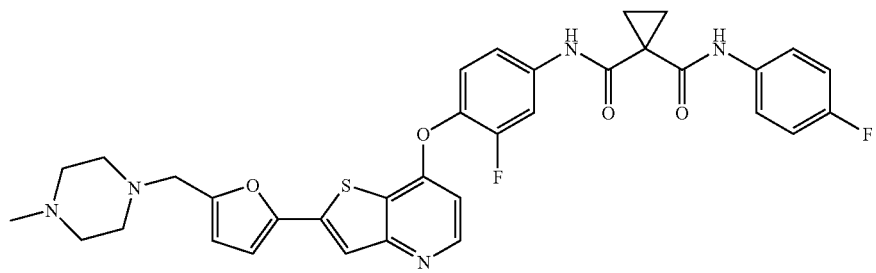

Prepared from 1-((4-fluorophenyl)carbamoyl)cyclopropane carboxylic acid (0.07635 g, 0.3421 mmol) and 3-fluoro-4-(2-(5-((4-methylpiperazin-1-yl)methyl)furan-2-yl)thieno[3,2-b]pyridin-7-yloxy)benzenamine (Example 96, Step C, 0.100 g, 0.2280 mmol) using the procedure described for Example 72, Step B. The product was purified by Biotage 40S column eluting with 2:1 EtOAc/Hexane. Obtained the product (3 mg, 2%) as a white solid. LRMS (APCI−) 642 m/z (M−1) detected. $^1$H NMR (CDCl3, 400 MHz) 9.98 (s, 1H), 8.45 (d, J=5.5 Hz, 1H), 8.22 (s, 1H), 7.75 (d, J=13.7 Hz, 1H), 7.62 (s, 1H), 7.45 (m, 2H), 7.24 (m, 2H), 7.07 (t, J=8.6 Hz, 2H), 6.71 (s, 1H), 6.35 (s, 1H), 3.66 (s, 2H), 2.58 (m, 8H), 2.29 (s, 3H), 1.79 (m, 4H).

Example 109

Preparation of N-(3-fluoro-4-(2-(3-(4-methylpiperazin-1-yl)prop-1-ynyl)thieno[3,2-b]pyridin-7-yloxy)phenyl)-N-(4-fluorophenyl)cyclopropane-1,1-dicarboxamide

Example 110

Preparation of N-(4-(2-(3-(4-ethylpiperazin-1-yl)prop-1-ynyl)thieno[3,2-b]pyridin-7-yloxy)-3-fluorophenyl)-N-(4-fluorophenyl)cyclopropane-1,1-dicarboxamide

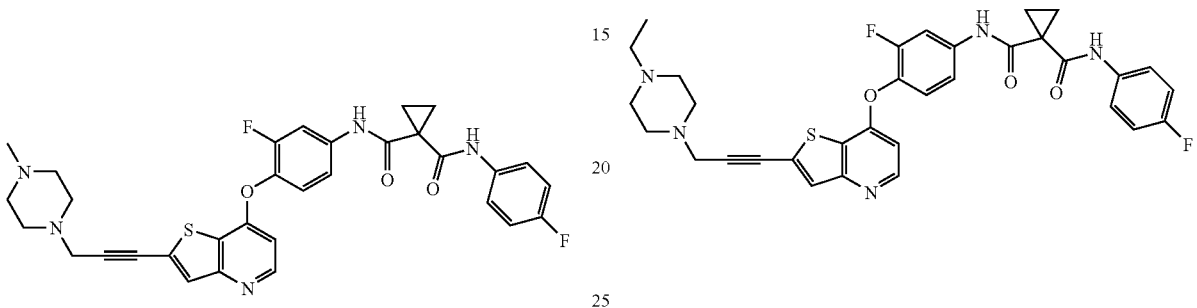

Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 50 mg, 0.0845 mmol) and 1-methyl-4-(prop-2-ynyl)piperazine (Example 17, Step A, 29.2 mg, 0.211 mmol) using the procedure described for Example 6, Step B. The crude was purified by preparative TLC (1 mm thickness, Rf=0.56), eluting with 10% MeOH (containing 7N NH$_3$) in CHCl$_3$. The product was obtained as a waxy solid (36 mg, 69%). HPLC: 100% purity (220 nm); LRMS (APCI+): 100% purity, 220 nm, m/z 602 (M+1) detected; $^1$H NMR (CDCl$_3$, 400 MHz) δ 10.18 (s, 1H), 8.64 (s, 1H), 8.47 (d, J=5 Hz, 1H), 7.77 (m, 1H), 7.56 (s, 1H), 7.44 (m, 2H), 7.26 (m, 2H), 7.04 (m, 2H), 6.51 (d, J=5 Hz, 1H), 3.60 (s, 2H), 2.4-2.8 (m, 8H), 2.32 (s, 3H), 1.77 (m, 2H), 1.63 (m, 2H).

Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 50 mg, 0.0845 mmol) and 1-ethyl-4-(prop-2-ynyl)piperazine (Example 18, Step A, 32.2 mg, 0.211 mmol) using the procedure described for Example 6, Step B. The crude was purified by preparative TLC (1 mm thickness, Rf=0.67), eluting with 10% MeOH (containing 7N NH$_3$) in CHCl$_3$. The product was obtained as a waxy solid (5 mg, 10%). HPLC: 100% purity (220 nm); LRMS (APCI−): 100% purity, 220 nm, m/z 614 (M−1) detected; $^1$H NMR (400 MHz, CDCl$_3$) δ 10.04 (s, 1H), 8.49 (d, J=5 Hz, 1H), 8.31 (br s, 1H), 7.75 (m, 1H), 7.58 (s, 1H), 7.43 (m, 2H), 7.24 (m, 2H), 7.06 (m, 2H), 6.52 (d, J=5 Hz, 1H), 3.64 (m, 2H), 3.61 (s, 2H), 2.4-2.8 (m, 8H), 1.80 (m, 2H), 1.62 (m, 2H), 1.12 (m, 3H).

Example 111

Preparation of N-(4-(2-(3-(4-(dimethylamino)piperidin-1-yl)prop-1-ynyl)thieno[3,2-b]pyridin-7-yloxy)-3-fluorophenyl)-N-(4-fluorophenyl)cyclopropane-1,1-dicarboxamide

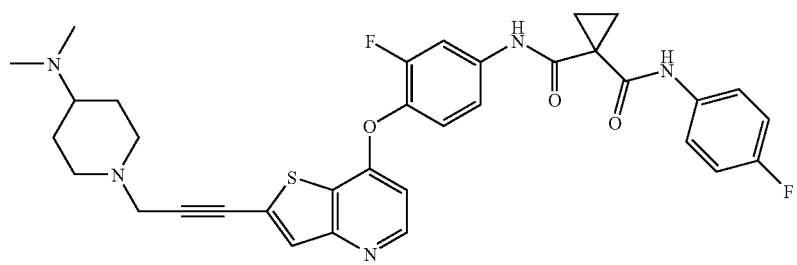

Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 50 mg, 0.0845 mmol) and N,N-dimethyl-1-(prop-2-ynyl)piperidin-4-amine (Example 20, Step A, 35.1 mg, 0.211 mmol) using the procedure described for Example 6, Step B. The crude was purified by preparative TLC (1 mm thickness, Rf=0.32), eluting with 10% MeOH (containing 7N NH$_3$) in CHCl$_3$. The product was further purified by trituration with 3:1 pentane/DCM (5 mL) and filtered. The product was obtained as a waxy solid (4 mg, 7%). HPLC: 100% purity (220 nm); LCMS (APCI+): 100% purity, 220 nm, m/z 630 (M+1) detected; $^1$H NMR (400 MHz, CDCl$_3$) δ 10.06 (s, 1H), 8.49 (m, 1H), 8.17 (br s, 1H), 7.77 (m, 1H), 7.59 (s, 1H), 7.45 (m, 2H), 7.26 (m, 2H, overlaps chloroform), 7.07 (m, 2H), 6.51 (m, 1H), 3.59 (s, 2H), 3.02 (m, 2H), 2.30 (m, 9H), 1.82 (m, 4H), 1.62 (m, 4H).

Example 112

N-(3-fluoro-4-(2-(4-(methylcarbamoyl)phenyl)thieno[3,2-b]pyridin-7-yloxy)phenyl)-N-(4-fluorophenyl)cyclopropane-1,1-dicarboxamide was diluted with water (50 mL) and the organic layer was isolated and dried over sodium sulfate. The organics were filtered and concentrated to get the acid fluoride as a white solid (1.8 g, 80%). $^1$H NMR (CDCl$_3$, 400 MHz) δ 10.44 (s, 1H), 7.61 (m, 2H), 7.17 (m, 2H), 1.69 (m, 4H).

Step B: Preparation of N-(3-fluoro-4-(2-(4-(methylcarbamoyl)phenyl)thieno[3,2-b]pyridin-7-yloxy)phenyl)-N-(4-fluorophenyl)cyclopropane-1,1-dicarboxamide: A 20 mL sealable tube was charged with 4-(7-(4-amino-2-fluorophenoxy)thieno[3,2-b]pyridin-2-yl)-N-methylbenzamide (Example 95, Step A, 0.240 g, 0.610 mmol), 1-((4-fluorophenyl)carbamoyl)cyclopropanecarbonyl fluoride (0.172 g, 0.763 mmol), and acetonitrile (5 mL). The mixture was heated under nitrogen to 50° C. for 12 hours. The reaction was then cooled to room temperature and concentrated to dryness. The crude residue was purified by 3 triturations with hot acetonitrile to obtain product (202 mg, 64%) and as a white solid. LRMS (esi+) 599 m/z (M+1) detected. $^1$H NMR (d$_6$-DMSO,

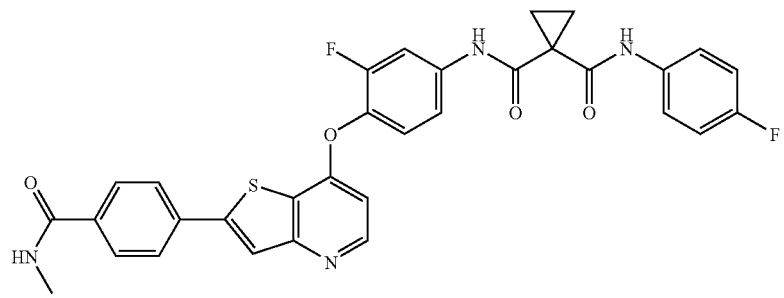

Step A: Preparation of 1-(4-fluorophenylcarbamoyl)cyclopropanecarbonyl fluoride: A round-bottomed flask was charged with 2,4,6-trifluoro-1,3,5-triazine (2.66 ml, 19.7 mmol) and CH$_2$Cl$_2$ (25 mL). Next, 1-((4-fluorophenyl)carbamoyl)cyclopropanecarboxylic acid (2.20 g, 9.86 mmol) and pyridine (0.797 ml, 9.86 mmol) in CH$_2$Cl$_2$ (20 mL) (Prepared following a procedure from Ryan, K.; et. al. *Tetrahedron* 56 (2000) 3309-3318) were added under nitrogen. After stirring for 2 hours, a white precipitate formed. The mixture 400 MHz) δ 10.41 (s, 1H), 10 (s, 1H), 8.55 (m, 2H), 8.20 (s, 1H), 8.00 (m, 5H), 7.64 (m, 2H), 7.52 (m, 2H), 7.16 (m, 2H), 6.65 (m, 1H), 2.82 (d, J=4 Hz, 3H), 1.48 (br s, 4H).

Example 113

N-(4-(2-(4-carbamoylphenyl)thieno[3,2-b]pyridin-7-yloxy)-3-fluorophenyl)-N-(4-fluorophenyl)cyclopropane-1,1-dicarboxamide

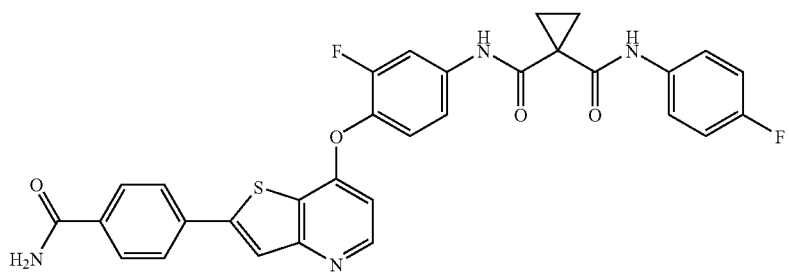

A sealable vial, was charged with 4-carbamoylphenylboronic acid (0.0312 g, 0.189 mmol), N-(3-fluoro-4-(2-iodothieno[3,2-b]pyridin-7-yloxy)phenyl)-N-(4-fluorophenyl)cyclopropane-1,1-dicarboxamide (Example 12, Step A, 0.100 g, 0.0947 mmol), Cs$_2$CO$_3$ (0.0309 g, 0.0947 mmol), toluene (2 mL) and EtOH (1 mL). Under nitrogen Pd(PPh$_3$)$_4$ (0.00547 g, 0.00473 mmol) was added and the reaction heated to 80° C. for 18 hours. The mixture was then cooled to room temperature, diluted with water (20 mL), and extracted with ethyl acetate (30 mL) and MeOH (2 mL). The organics were dried over sodium sulfate, filtered and concentrated to get crude product. The crude product was purified by reverse phase C-18 column chromatography to get product (6.9 mg, 13%) as a white solid. LRMS (esi+) 585 m/z (M+1) detected. $^1$H NMR (d$_6$-DMSO, 400 MHz) δ 8.48 (d, J=6 Hz, 1H), 7.96 (m, 5H), 7.87 (m, 1H), 7.57 (m, 2H), 7.37 (m, 2H), 7.07 (t, J=9.0 Hz, 2H), 6.65 (d, J=6 Hz, 1H), 1.64 (s, 4H).

Example 114

N-(4-(2-(4-(cyclopropylcarbamoyl)phenyl)thieno[3,2-b]pyridin-7-yloxy)-3-fluorophenyl)-N-(4-fluorophenyl)cyclopropane-1,1-dicarboxamide

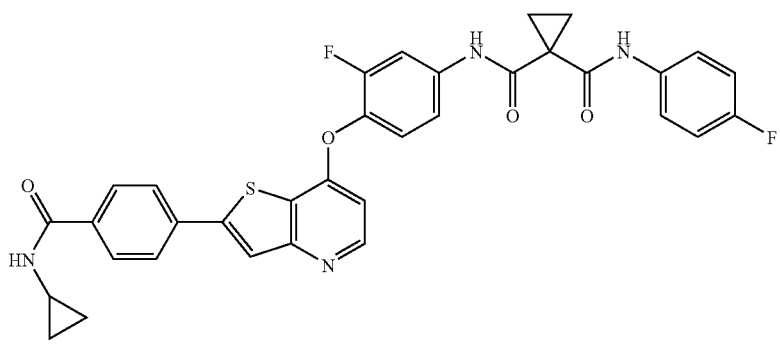

Prepared according to the procedure for Example 113, substituting 4-(cyclopropylcarbamoyl)phenylboronic acid (0.0388 g, 0.189 mmol) for 4-carbamoylphenylboronic acid. Product was purified by reverse phase C-18 column chromatography to get product (13.5 mg, 23%) as a white solid. LRMS (esi+) 625 m/z (M+1) detected. $^1$H NMR (d$_6$-DMSO, 400 MHz) δ 8.47 (d, J=6 Hz, 1H), 7.90 (m, 5H), 7.85 (d, J=14 Hz, 1H), 7.57 (m, 2H), 7.43 (m, 2H), 7.07 (t, J=9.0 Hz, 2H), 6.65 (d, J=6 Hz, 1H), 1.64 (s, 4H), 0.84 (m, 2H), 0.67 (m, 2H).

Example 115

N-(3-fluoro-4-(2-(3-(methylcarbamoyl)phenyl)thieno[3,2-b]pyridin-7-yloxy)phenyl)-N-(4-fluorophenyl)cyclopropane-1,1-dicarboxamide

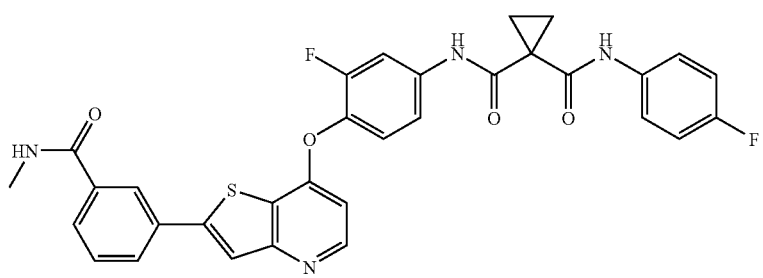

Prepared according to the procedure for Example 113, substituting 3-(methylcarbamoyl)phenylboronic acid (0.0339 g, 0.189 mmol) for 4-carbamoylphenylboronic acid. Product was purified by reverse phase C-18 column chromatography. Product containing fractions were pooled and concentrated to get product (7.3 mg, 13%) as a white solid. LRMS (esi+) 625 m/z (M+1) detected. $^1$H NMR (d$_6$-DMSO, 400 MHz) δ 8.48 (d, J=6 Hz, 1H), 8.28 (s, 1H), 8.00 (d, J=9

Hz, 1H), 7.88 (m, 3H), 7.61 (m, 3H), 7.43 (m, 3H), 7.07 (t, J=9 Hz, 2H), 6.65 (d, J=6 Hz, 1H), 1.64 (s, 4H).

Example 116

1-(3-Fluoro-4-(2-(3-(4-methylpiperazin-1-yl)prop-1-ynyl)thieno[3,2-b]pyridin-7-yloxy)phenyl)-3-(pyridin-2-yl)urea

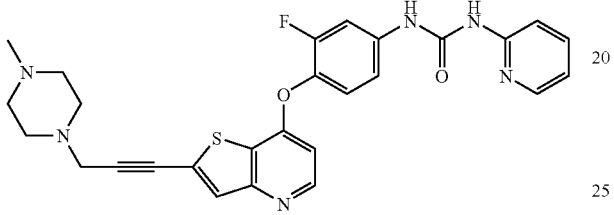

Step A: 3-Fluoro-4-(2-(3-(4-methylpiperazin-1-yl)prop-1-ynyl)thieno[3,2-b]pyridin-7-yloxy)aniline: A round-bottomed flask was charged with 3-fluoro-4-(2-iodothieno[3,2-b]pyridin-7-yloxy)aniline (Example 6, Step A, 200 mg, 0.477 mmol), 1-methyl-4-(prop-2-ynyl)piperazine (Example 17, Step A, 205.8 mg, 1.19 mmol), tetrakis(triphenylphosphine)palladium (0) (55.1 mg, 0.0477 mmol), copper(I) iodide (9.074 mg, 0.0477 mmol), N-ethyl-N-isopropylpropan-2-amine (2.49 ml, 14.3 mmol) and THF (25 mL). The reaction mixture was stirred at 60° C. until the starting material had been consumed (4 hours). Then the reaction mixture was cooled to room temperature and partitioned between EtOAc (100 mL) and H$_2$O (100 mL). The phases were separated, and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (0.159 g, 84.2%). LRMS (APCI pos): m/e 397 (M+1). $^1$H NMR (400 MHz, CDCl$_3$) δ 8.44 (d, 1H), 7.58 (s, 1H), 7.01 (t, 1H), 6.43-6.58 (m, 3H), 3.90 (br s, 2H), 3.61 (s, 2H), 2.48-2.83 (m, 8H), 2.38 (s, 3H).

Step B: Preparation of 1-(3-fluoro-4-(2-(3-(4-methylpiperazin-1-yl)prop-1-ynyl)thieno[3,2-b]pyridin-7-yloxy)phenyl)-3-(pyridin-2-yl)urea: A round-bottomed flask was charged with azido(pyridin-2-yl)methanone (18.7 mg, 0.13 mmol, see J. Med. Chem. 2001, 44, 4615 for prep. and use) and THF (10 mL). The reaction mixture was stirred at 80° C. until the starting material had been consumed (4 hours). 3-fluoro-4-(2-(3-(4-methylpiperazin-1-yl)prop-1-ynyl)thieno[3,2-b]pyridin-7-yloxy)aniline (10.0 mg, 0.025 mmol) was then added. The reaction mixture was stirred at 80° C. until the starting material had been consumed (4 hour). The reaction mixture was then partitioned between EtOAc (50 mL) and H$_2$O (50 mL). The phases were separated and the aqueous phase was re-extracted with EtOAc (3×50 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (10.2 mg, 78.3%). LRMS (APCI pos): >99% purity, 254 nm, m/e 517 (M+1). $^1$H NMR (400 MHz, CD$_3$OD) δ 8.43 (d, 1H), 8.28 (m, 1H), 7.80 (d, 1H), 7.71 (m, 1H), 7.58 (s, 1H), 7.31 (m, 2H), 7.16 (d, 1H), 7.00 (t, 1H), 6.64 (d, 1H), 3.62 (s, 2H), 2.14-2.78 (m, 8H), 2.22 (s, 3H).

Example 117

Preparation of N-(3-fluoro-4-(2-(3-(4-(hydroxymethyl)piperidin-1-yl)prop-1-ynyl)thieno[3,2-b]pyridin-7-yloxy)phenyl)-N-(4-fluorophenyl)cyclopropane-1,1-dicarboxamide

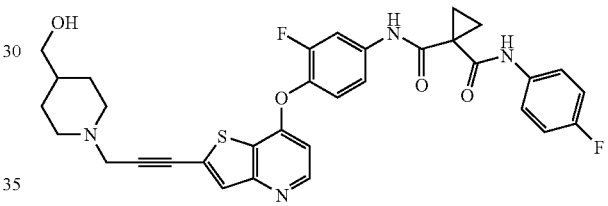

Step A: Preparation of (1-(prop-2-ynyl)piperidin-4-yl)methanol: Prepared from piperidin-4-yl methanol (1.15 g, 10.00 mmol) using the procedure described for Example 16, Step A. The product was obtained as an oil (1.51 g, 86%). $^1$H NMR (400 MHz, CDCl$_3$) δ 3.49 (d, J=7 Hz, 2H), 3.30 (d, J=2 Hz, 2H), 2.92 (m, 2H), 2.24 (t, J=2 Hz, 1H), 2.21 (m, 1H), 2.18 (m, 1H), 1.87 (br s, 1H), 1.77 (m, 2H), 1.49 (m, 1H), 1.32 (m, 2H).

Step B: Preparation of N-(3-fluoro-4-(2-(3-(4-(hydroxymethyl)piperidin-1-yl)prop-1-ynyl)thieno[3,2-b]pyridin-7-yloxy)phenyl)-N-(4-fluorophenyl)cyclopropane-1,1-dicarboxamide: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 20 mg, 0.0338 mmol) and (1-(prop-2-ynyl)piperidin-4-yl)methanol (10.4 mg, 0.0676 mmol) using the procedure described for Example 6, Step B. The crude was purified by preparative TLC (1 mm thickness, Rf=0.72) eluting with 20% MeOH/DCM. The product was obtained as a beige powder (6.7 mg, 32%). HPLC: 100% purity (220 nm); LRMS (APCI+): 100% purity, 220 nm, m/z 617 (M+1) detected; $^1$H NMR (400 MHz, CDCl$_3$) δ 10.14 (s, 1H), 8.48 (d, J=5 Hz, 1H), 8.42 (s, 1H), 7.75 (m, 1H), 7.59 (s, 1H), 7.47 (m, 2H), 7.28 (m, 1H), 7.21 (m, 1H), 7.05 (t, J=9 Hz, 2H), 6.52 (d, J=5

Hz, 1H), 3.65 (s, 2H), 3.53 (d, J=6 Hz, 2H), 3.09 (m, 2H), 2.38 (m, 2H), 1.86 (m, 2H), 1.81 (m, 2H), 1.64 (m, 2H), 1.55 (m, 1H), 1.45 (m, 2H).

Example 118

Preparation of N-(3-fluoro-4-(2-(3-methyl-3-(piperidin-1-yl)but-1-ynyl)thieno[3,2-b]pyridin-7-yloxy)phenyl)-N-(4-fluorophenyl)cyclopropane-1,1-dicarboxamide

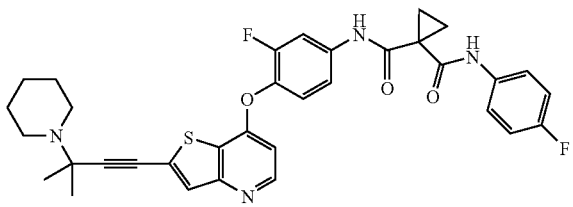

Step A: Preparation of 1-(2-methylbut-3-yn-2-yl)piperidine: Prepared from piperidine (0.426 g, 5.00 mmol) according to the procedure described for Example 13, Step A. $^1$H NMR (400 MHz, CDCl$_3$) δ 2.58 (m, 4H), 2.27 (s, 1H), 1.61 (m, 4H), 1.43 (m, 2H), 1.40 (s, 6H). Yield: 580 mg (71%).

Step B: Preparation of N-(3-fluoro-4-(2-(3-methyl-3-(piperidin-1-yl)but-1-ynyl)thieno[3,2-b]pyridin-7-yloxy)phenyl)-N-(4-fluorophenyl)cyclopropane-1,1-dicarboxamide: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 20 mg, 0.0338 mmol) and 1-(2-methylbut-3-yn-2-yl)piperidine (10.2 mg, 0.0676 mmol) using the procedure described for Example 6, Step B. The crude was purified by preparative TLC (1 mm thickness, Rf=0.34) eluting with 10% MeOH/DCM. A second purification by preparative TLC was conducted (0.5 mm thickness, Rf=0.49), eluting with 15% MeOH in EtOAc, in order to obtain product of adequate purity. The product was obtained as a beige powder (8 mg, 38%). HPLC: 98% purity (254 nm); LCMS (APCI-): 100% purity, 220 nm, m/z 613 (M-1) detected; $^1$H NMR (400 MHz, CDCl$_3$) δ 10.04 (s, 1H), 8.48 (d, J=6 Hz, 1H), 8.15 (s, 1H), 7.74 (m, 1H), 7.55 (s, 1H), 7.45 (m, 2H), 7.24 (m, 2H), 7.07 (t, J=9 Hz, 2H), 6.50 (d, J=6 Hz, 1H), 2.66 (br s, 4H), 1.81 (m, 2H), 1.64 (m, 6H), 1.51 (m, 8H).

Example 119

Preparation of N-(3-fluoro-4-(2-(3-(4-(hydroxymethyl)piperidin-1-yl)-3-methylbut-1-ynyl)thieno[3,2-b]pyridin-7-yloxy)phenyl)-N-(4-fluorophenyl)cyclopropane-1,1-dicarboxamide

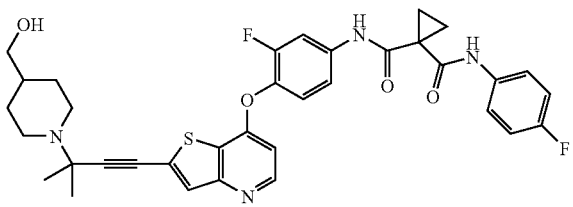

Step A: Preparation of (1-(2-methylbut-3-yn-2-yl)piperidin-4-yl)methanol: Prepared from piperidin-4-yl methanol (0.576 g, 5.00 mmol) according to the procedure described for Example 13, Step A. The product was obtained as a beige solid (640 mg, 47%). $^1$H NMR (400 MHz, CDCl$_3$) δ 4.75 (br s, 1H), 3.50 (d, J=6 Hz, 2H), 2.29 (s, 1H), 2.18 (m, 2H), 1.81 (m 2H), 1.69 (s, 4H), 1.54 (m, 1H), 1.41 (s, 6H).

Step B: Preparation of N-(3-fluoro-4-(2-(3-(4-(hydroxymethyl)piperidin-1-yl)-3-methylbut-1-ynyl)thieno[3,2-b]pyridin-7-yloxy)phenyl)-N-(4-fluorophenyl)cyclopropane-1,1-dicarboxamide: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 20 mg, 0.0338 mmol) and (1-(2-methylbut-3-yn-2-yl)piperidin-4-yl)methanol (12.3 mg, 0.0676 mmol) using the procedure described for Example 6, Step B. The crude was purified by preparative TLC (1 mm thickness, Rf=0.63) eluting with 20% MeOH/DCM. The compound required a second purification by preparative TLC (0.5 mm thickness, Rf=0.11), eluting with 15% MeOH in EtOAc, to obtain product of adequate purity. The product was obtained as a beige powder (5 mg, 23%). HPLC: 99% purity (254 nm); LCMS (APCI-): 100% purity, 220 nm, m/z 643 (M-1) detected; $^1$H NMR (400 MHz, CDCl$_3$) δ 10.08 (s, 1H), 8.49 (d, J=5 Hz, 1H), 8.23 (s, 1H), 7.78 (m, 1H), 7.56 (s, 1H), 7.45 (m, 2H), 7.27 (m, 2H), 7.07 (t, J=9 Hz, 2H), 6.53 (d, J=5 Hz, 1H), 3.53 (d, J=6 Hz, 2H), 3.22 (br s, 2H), 2.31 (br s, 2H), 1.82 (m, 4H), 1.62 (m, 10H), 1.36 (m, 2H).

Example 120

Preparation of N-(4-(2-(3-(1H-imidazol-1-yl)-3-methylbut-1-ynyl)thieno[3,2-b]pyridin-7-yloxy)-3-fluorophenyl)-N-(4-fluorophenyl)cyclopropane-1,1-dicarboxamide

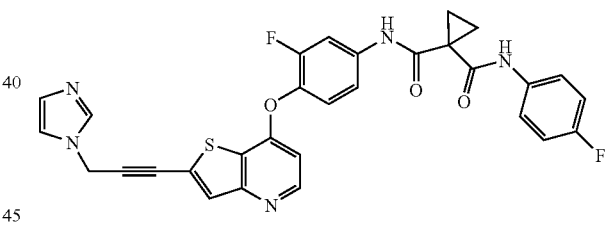

Step A: Preparation of 1-(prop-2-ynyl)-1H-imidazole: Prepared from 1H-imidazole (0.681 g, 10.00 mmol) according to the procedure described for Example 16, Step A. The resulting crude was resuspended in diethyl ether (30 mL) and refiltered to remove an oily impurity. The filtrate was concentrated to an oil (904 mg, 78%). $^1$H NMR (400 MHz, CDCl$_3$) δ 7.59 (s, 1H), 7.09 (m, 1H), 7.04 (m, 1H), 4.74 (d, J=3 Hz, 2H), 2.51 (t, J=3 Hz, 1H).

Step B: Preparation of N-(4-(2-(3-(1H-imidazol-1-yl)-3-methylbut-1-ynyl)thieno[3,2-b]pyridin-7-yloxy)-3-fluorophenyl)-N-(4-fluorophenyl)cyclopropane-1,1-dicarboxamide: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 20 mg, 0.0338 mmol) and 1-(prop-2-ynyl)-1H-imidazole (7.18 mg, 0.0676 mmol) using the procedure described for Example 6, Step B. The crude was purified by preparative TLC (1 mm thickness, Rf=0.65) eluting with 20% MeOH/DCM. The product was re-purified by preparative TLC (0.5 mm thickness, Rf=0.06), eluting with 15% MeOH in EtOAc, to obtain product of adequate purity. The product was obtained as a beige powder (4 mg, 18%). HPLC: 88% purity (220 nm); LRMS (APCI−): 100% purity, 220 nm, m/z 568 (M−1) detected; $^1$H NMR (400 MHz, CDCl$_3$) δ 10.22 (s, 1H), 8.52 (d, J=6 Hz, 1H), 8.32 (s, 1H), 7.75 (m, 1H), 7.70 (br s, 1H), 7.67 (s, 1H), 7.44 (m, 2H), 7.24 (m, 2H), 7.15 (br s, 2H), 7.06 (t, J=8 Hz, 2H), 6.55 (d, J=6 Hz, 1H), 5.05 (s, 2H), 1.82 (m, 2H), 1.62 (m, 2H).

Example 121

Preparation of N-(3-fluoro-4-(2-(3-methyl-3-(4-methylpiperazin-1-yl)but-1-ynyl)thieno[3,2-b]pyridin-7-yloxy)phenyl)-N-(4-fluorophenyl)cyclopropane-1,1-dicarboxamide

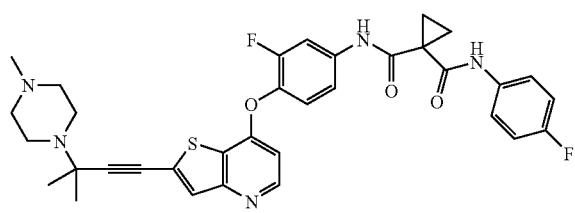

Step A: Preparation of 1-methyl-4-(2-methylbut-3-yn-2-yl)piperazine: Prepared from 1-methylpiperazine (2.00 g, 20.0 mmol) according to the procedure described for Example 13, Step A. The product was obtained as a beige solid (2.3 g, 69%). $^1$H NMR (400 MHz, CDCl$_3$) δ 2.70 (br s, 4H), 2.49 (br s, 4H), 2.29 (s, 3H), 2.28 (s, 1H), 1.40 (s, 6H).

Step B: Preparation of N-(3-fluoro-4-(2-(3-methyl-3-(4-methylpiperazin-1-yl)but-1-ynyl)thieno[3,2-b]pyridin-7-yloxy)phenyl)-N-(4-fluorophenyl)cyclopropane-1,1-dicarboxamide: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 20 mg, 0.0338 mmol) and 1-methyl-4-(2-methylbut-3-yn-2-yl)piperazine (11.2 mg, 0.0676 mmol) using the procedure described for Example 6, Step B. The crude was purified by preparative TLC (1 mm thickness, Rf=0.16) eluting with 10% MeOH/DCM. The compound was re-purified by preparative TLC (0.5 mm thickness, Rf=0.84) eluting with 15% MeOH (containing 7N NH$_3$) in CHCl$_3$, to obtain product of adequate purity. The product was obtained as a beige powder (4 mg, 18%). HPLC: 95% purity (220 nm); LCMS (APCI−): 100% purity, 220 nm, m/z 629 (M−1) detected; $_1$H NMR (400 MHz, CDCl$_3$) δ 9.95 (s, 1H), 8.49 (d, J=5 Hz, 1H), 8.40 (br s, 1H), 7.73 (m, 1H), 7.54 (s, 1H), 7.44 (m, 2H), 7.21 (m, 2H), 7.06 (t, J=9 Hz, 2H), 6.54 (d, J=5 Hz, 1H), 2.84 (m, 4H), 2.65 (m, 4H), 2.39 (s, 3H), 1.82 (m, 2H), 1.64 (m, 2H), 1.51 (s, 6H).

Example 122

1-benzyl-5-chloro-N-(3-fluoro-4-(2-(3-(4-methylpiperazin-1-yl)prop-1-ynyl)thieno[3,2-b]pyridin-7-yloxy)phenyl)-2-oxo-1,2-dihydropyridine-3-carboxamide

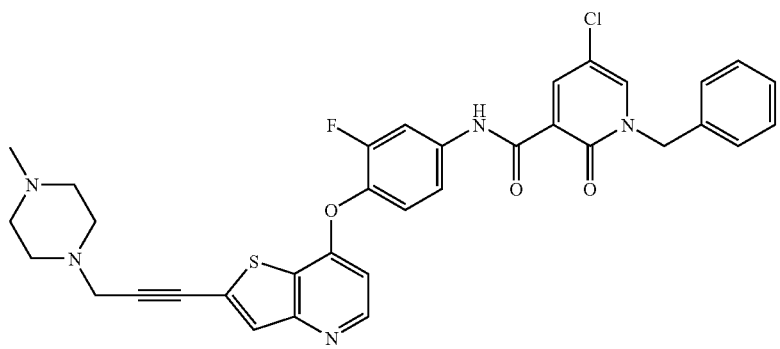

Prepared from 3-fluoro-4-(2-(3-(4-methylpiperazin-1-yl)prop-1-ynyl)thieno[3,2-b]pyridin-7-yloxy)aniline (Example 17, Step B) and 1-benzyl-5-chloro 2-oxo-1,2-dihydropyridine-3-carboxylic acid according to the procedure of Example 89. The crude was purified by silica gel flash column chromatography (5% MeOH in CH$_2$Cl$_2$) to afford 16.7 mg (52%) of the desired product. LRMS (APCI pos) m/e 642.1, 644.1 (M+1, Cl pattern). $^1$H-NMR (400 MHz, CD$_3$OD) δ 8.50 (t, 2H), 8.29 (d, 1H), 8.02 (dd, 1H), 7.59 (s, 1H), 7.33-7.48 (m, 7H), 6.71 (d, 1H), 5.32 (s, 2H), 3.67 (s, 2H), 2.56-2.74 (m, 8H), 2.30 (s, 3H); $^{19}$F NMR (376 MHz, CD$_3$OD) δ −129.7.

Example 123

N-(3-fluoro-4-(2-(3-(4-methylpiperazin-1-yl)prop-1-ynyl)thieno[3,2-b]pyridin-7-yloxy)phenyl)-2-(4-fluorophenyl)-6-methyl-3-oxo-2,3-dihydropyridazine-4-carboxamide

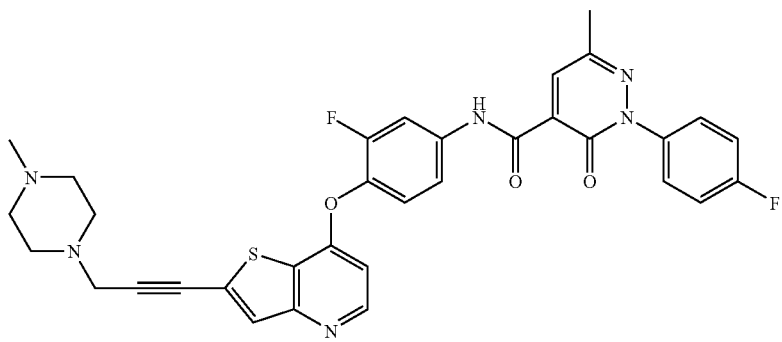

Step A: Preparation of (E)-2-(2-(4-fluorophenyl)hydrazono)propanal: A mixture of (4-fluorophenyl)hydrazine HCl salt (2.0 g, 12.30 mmol), water (10 mL), and acetic acid (10 mL) was added with stirring to a 40% aqueous solution of 2-oxopropanal (9.41 mL, 61.5 mmol) for 20 minutes. Stirring was continued for 4 hours and the mixture was then filtered. The precipitate was washed with water and dried to afford the desired products. The crude was purified by silica gel flash column chromatography (1:50 to 1:10=EtOAc:CH$_2$Cl$_2$) to afford 2.05 g (93%) along with byproduct. $^1$H-NMR (400 MHz, CDCl$_3$) δ 9.47 (s, 1H), 8.09 (br. s, 1H), 7.24 (m, 2H), 7.06 (t, 2H), 1.98 (s, 3H); $^{19}$F NMR (376 MHz, CDCl$_3$) δ -121.0.

Step B: Preparation of 2-(4-fluorophenyl)-6-methyl-3-oxo-2,3-dihydropyridazine-4-carboxylic acid: A suspension of 2,2-dimethyl-1,3-dioxane-4,6-dione (0.71 g, 4.93 mmol) and (E)-2-(2-(4-fluorophenyl)hydrazono)propanal (0.889 g, 4.934 mmol) in toluene (20 mL) was treated with acetic acid (5 drops) and with piperidine (5 drops). The reaction mixture was then stirred at room temp for 17 hours. The precipitated condensation/cyclization product was filtered off and thoroughly washed with light petroleum to afford 0.709 g (58%) of the desired product. LRMS (ESI pos) m/e 249.1 (M+1). $^1$H-NMR (400 MHz, CD$_3$OD) δ 7.96 (s, 1H), 7.61 (m, 2H), 7.24 (t, 2H), 2.45 (s, 3H); $^{19}$F NMR (376 MHz, CD$_3$OD) δ -115.1.

Step C: Preparation of N-(3-fluoro-4-(2-(3-(4-methylpiperazin-1-yl)prop-1-ynyl)thieno[3,2-b]pyridin-7-yloxy)phenyl)-2-(4-fluorophenyl)-6-methyl-3-oxo-2,3-dihydropyridazine-4-carboxamide: Prepared from 3-fluoro-4-(2-(3-(4-methylpiperazin-1-yl)prop-1-ynyl)thieno[3,2-b]pyridin-7-yloxy)aniline (Example 17, Step B) and 2-(4-fluorophenyl)-6-methyl-3-oxo-2,3-dihydropyridazine-4-carboxylic acid according to the procedure of Example 89. The crude was purified by silica gel flash column chromatography (5% MeOH in CH$_2$Cl$_2$) to afford 4.5 mg (14%) of the desired product. LRMS (ESI pos) m/e 627.3 (M+1). $^1$H-NMR (400 MHz, CDCl$_3$/CD$_3$OD) δ 8.47 (d, 1H), 8.32 (s, 1H), 8.0 (dd, 1H), 7.62 (m, 3H), 7.45 (d, 1H), 7.34 (t, 1H), 7.27 (t, 2H), 6.65 (d, 1H), 3.66 (s, 2H), 2.77 (m, 8H), 2.56 (s, 3H), 2.34 (s, 3H); $^{19}$F NMR (376 MHz, CDCl$_3$/CD$_3$OD) δ -113.2, -127.6.

Example 124

Preparation of tert-butyl 4-(2-(7-(4-(1-(carbamoyl)cyclopropanecarboxamido)-2-fluorophenoxy)thieno[3,2-b]pyridin-2-yl)ethynyl)piperidine-1-carboxylate

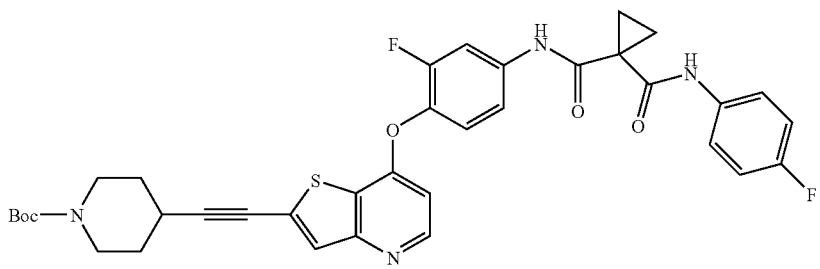

Step A: Preparation of tert-butyl 4-ethynylpiperidine-1-carboxylate: To a stirred suspension of tert-butyl 4-formylpiperidine-1-carboxylate (0.427 g, 2.00 mmol), K$_2$CO$_3$ (0.553 g, 4.00 mmol), and MeOH (25 mL) was added all at once the Bestman-Ohira reagent, dimethyl 2-oxo-1-diazo-propylphosphonate (0.461 g, 2.40 mmol, see *Synthesis* 2004, 1, 59-62). Stirring was continued for 20 hours under nitrogen. The reaction was diluted with Et$_2$O (50 mL), washed with a 2:1 mixture of water and aqueous saturated NaHCO$_3$ (20 mL), dried (Na$_2$SO$_4$), filtered, and concentrated in vacuo. Yield: 253 mg (55%). $^1$H NMR (400 MHz, CDCl$_3$) δ 3.72 (m, 2H), 3.19 (m, 2H), 2.58 (m, 1H), 2.10 (d, J=2 Hz, 1H), 1.77 (m, 2H), 1.61 (m, 2H), 1.46 (s, 9H).

Step B: Preparation of tert-butyl 4-(2-(7-(4-(1-(carbamoyl)cyclopropane-carboxamido)-2-fluorophenoxy)thieno[3,2-b]pyridin-2-yl)ethynyl)piperidine-1-carboxylate: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 350 mg, 0.592 mmol) and tert-butyl 4-ethynylpiperidine-1-carboxylate (186 mg, 0.888 mmol) using the procedure described for Example 6, Step B. The crude was purified by Biotage Flash 40M eluting with 20% EtOAc/hexanes (500 mL), 1:1 EtOAc/hexanes (1 L), followed by 2:1 EtOAc/hexanes (1.5 L). The product was isolated as a wax (293 mg, 68%). HPLC: 92% purity (254 nm); LRMS (APCI+): m/z 673, 573 (loss of BOC) (M+1) detected; $^1$H NMR (400 MHz, CDCl$_3$) δ 10.12 (s, 1H), 8.47 (d, J=6 Hz, 1H), 8.33 (s, 1H), 7.77 (m, 1H), 7.44 (m, 2H), 7.25 (m, 3H), 7.06 (t, J=9 Hz, 2H), 6.50 (d, J=6 Hz, 1H), 3.77 (m, 2H), 3.23 (m, 2H), 2.87 (m, 1H), 1.89 (m, 2H), 1.80 (m, 2H), 1.70 (m, 2H), 1.62 (m, 2H), 1.47 (s, 9H).

Example 125

Preparation of N-(3-fluoro-4-(2-(2-(piperidin-4-yl)ethynyl)thieno[3,2-b]pyridin-7-yloxy)phenyl)-N-(4-fluorophenyl)cyclopropane-1,1-dicarboxamide

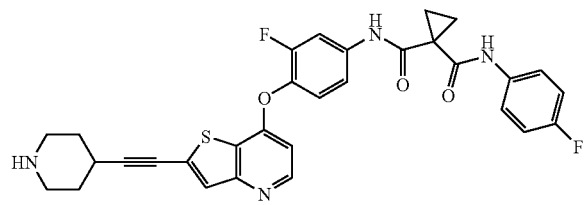

A mixture of tert-butyl 4-(2-(7-(4-(1-(carbamoyl)cyclopropanecarboxamido)-2-fluorophenoxy)thieno[3,2-b]pyridin-2-yl)ethynyl)piperidine-1-carboxylate (Example 124, Step B, 20 mg, 0.0297 mmol) and 2,2,2-trifluoroacetic acid (339 mg, 2.97 mmol) were stirred at room temperature for 30 minutes. The reaction was concentrated in vacuo, using toluene to azeotrope (3×5 mL). The residue was partioned between EtOAc (5 mL) and 1:1 water/saturated aqueous NaHCO$_3$ (5 mL). The phases were separated and the aqueous phase was re-extracted with EtOAc (2×5 mL). The combined organic phases were washed with brine (5 mL), dried (Na$_2$SO$_4$), filtered, and concentrated in vacuo. The product was purified by preparative TLC (0.5 mm thickness, Rf=0.22), eluting with 10% MeOH (containing 7N NH$_3$) in CHCl$_3$. The product was obtained as a beige powder (10 mg, 55%). HPLC: 93% purity (220 nm); LRMS (APCI+): 94% purity, 220 nm, m/z 573 (M+1) detected; $^1$H NMR (400 MHz, CDCl$_3$) δ 10.07 (s, 1H), 8.47 (d, J=6 Hz, 1H), 8.30 (s, 1H), 7.76 (m, 1H), 7.52 (s, 1H), 7.44 (m, 2H), 7.24 (m, 2H), 7.06 (t, J=9 Hz, 2H), 6.51 (d, J=6 Hz, 1H), 3.12 (m, 3H), 2.79 (m, 3H), 2.00 (m, 2H), 1.80 (m, 4H), 1.62 (m, 2H).

Example 126

Preparation of N-(3-fluoro-4-(2-(3-(piperidin-4-yl)prop-1-ynyl)thieno[3,2-b]pyridin-7-yloxy)phenyl)-N-(4-fluorophenyl)cyclopropane-1,1-dicarboxamide

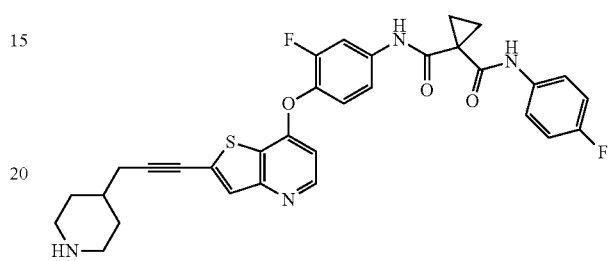

Step A: Preparation of tert-butyl 4-(prop-2-ynyl)piperidine-1-carboxylate: Prepared from tert-butyl 4-(2-oxoethyl)piperidine-1-carboxylate (0.455 g, 2.00 mmol) according to the procedure described for Example 124, Step A. The product was obtained as an oil (223 mg, 45%). $^1$H NMR (400 MHz, CDCl$_3$) δ 4.11 (m, 2H), 2.69 (m, 2H), 2.14 (m, 2H), 1.99 (t, J=3 Hz, 1H), 1.75 (m, 2H), 1.61 (m, 1H), 1.46 (s, 9H), 1.18 (m, 2H).

Step B: Preparation of tert-butyl 4-(3-(7-(4-(1-(carbamoyl)cyclopropane-carboxamido)-2-fluorophenoxy)thieno[3,2-b]pyridin-2-yl)prop-2-ynyl)piperidine-1-carboxylate: Prepared from N-(3-fluoro-4-(2-iodothieno[3,2-b]pyridin-7-yloxy)phenyl)-N-(4-fluorophenyl)cyclopropane-1,1-dicarboxamide (Example 12, Step A, 50 mg, 0.0845 mmol) and tert-butyl 4-(prop-2-ynyl)piperidine-1-carboxylate (37.8 mg, 0.169 mmol) using the procedure described for Example 6, Step B. The reaction was purified by preparative TLC (1 mm thickness, Rf=0.52), eluting with 10% MeOH/DCM. The product was subject to a second preparative TLC purification (0.5 mm thickness, Rf=0.09), eluting with 1:1 EtOA/hexanes. The product was obtained as a beige powder (25 mg, 31%). LRMS (APCI–): m/z 685 (M–1) detected.

Step C: Preparation of N-(3-fluoro-4-(2-(3-(piperidin-4-yl)prop-1-ynyl)thieno[3,2-b]pyridin-7-yloxy)phenyl)-N-(4-fluorophenyl)cyclopropane-1,1-dicarboxamide: Prepared from tert-butyl 4-(3-(7-(4-(1-(carbamoyl)cyclopropanecarboxamido)-2-fluorophenoxy)thieno[3,2-b]pyridin-2-yl)prop-2-ynyl)piperidine-1-carboxylate (25 mg, 0.0364 mmol) according to the procedure described for Example 124, Step C. The product was purified by preparative TLC (0.5 mm thickness, Rf=0.19), eluting with 10% MeOH (containing 7N NH$_3$) in CHCl$_3$. The product was obtained as a beige powder (11 mg, 44%). HPLC: 86% purity (220 nm); LRMS (APCI+): 100% purity, 220 nm, m/z 587 (M+1) detected; $^1$H NMR (400 MHz, CDCl$_3$) δ 10.09 (s, 1H), 8.47 (d, J=6 Hz, 1H), 8.34 (s, 1H), 7.73 (m, 1H), 7.51 (s, 1H), 7.44 (m, 2H), 7.24 (m, 2H), 7.06 (t, J=9 Hz, 2H), 6.49 (d, J=6 Hz, 1H), 3.10 (m, 2H), 2.64 (m, 2H), 2.44 (m, 2H), 1.79 (m, 6H), 1.62 (m, 2H), 1.26 (m, 2H).

Example 127

N-(3-fluoro-4-(2-(3-(4-methylpiperazin-1-yl)prop-1-ynyl)thieno[3,2-b]pyridin-7-yloxy)phenyl)-1-(4-fluorophenyl)-3-methyl-2-oxopyrrolidine-3-carboxamide

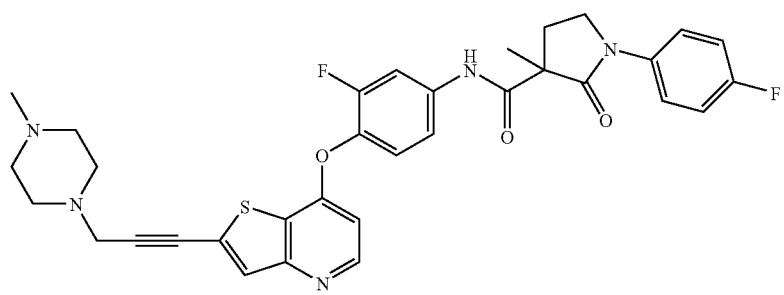

Step A: Preparation of methyl 1-(4-fluorophenyl)-2-oxopyrrolidine-3-carboxylate: To a solution of 1-(4-fluorophenyl)-2-oxopyrrolidine-3-carboxylic acid (0.20 g, 0.90 mmol) in a mixture of Et$_2$O (6 mL), MeOH (2 mL), and THF (2 mL) was added (diazomethyl)trimethylsilane (1.1 mL, 2.0 M) at 0° C. The resulting mixture was stirred for 30 minutes at room temperature, quenched with AcOH, and diluted with EtOAc. The organic layer was washed with water, NaHCO$_3$ solution (2×), and brine, dried over MgSO$_4$, and concentrated under reduced pressure to give the desired product (0.206 g, 98%). LRMS (ESI pos) m/e 238.0 (M+1).

Step B: Preparation of methyl 1-(4-fluorophenyl)-3-methyl-2-oxopyrrolidine-3-carboxylate: LiH (13.8 mg, 1.737 mmol) was added to the solution of methyl 1-(4-fluorophenyl)-2-oxopyrrolidine-3-carboxylate (0.206 g, 0.868 mmol) in DMF (5 mL) at 0° C. After 30 minutes stirring, iodomethane (0.16 mL, 2.61 mmol) was added to the reaction mixture at 0° C., and then the reaction was warmed to room temperature. The reaction mixture was stirred for 17 hours and heated at 40° C. for 3 hours. After cooling to room temperature, the mixture was treated with EtOAc, quenched with ice water, extracted with EtOAc, washed with brine, dried over MgSO$_4$, and concentrated to give the crude material that was purified by silica gel flash column chromatography (19:1=CH$_2$Cl$_2$:EtOAc) to afford 0.149 g (68%) of the desired product. LRMS (ESI pos) m/e 252.1 (M+1). $^1$H-NMR (400 MHz, CDCl$_3$) δ 7.61 (m, 2H), 7.07 (m, 2H), 3.94 (m, 1H), 3.78 (m, 1H), 3.75 (s, 3H), 2.68 (m, 1H), 2.06 (m, 1H), 1.55 (s, 3H); $^{19}$F NMR (376 MHz, CDCl$_3$) δ −117.6.

Step C: Preparation of 1-(4-fluorophenyl)-3-methyl-2-oxopyrrolidine-3-carboxylic acid: LiOH (1.2 mL, 1.19 mmol, 1.0 M in H$_2$O) was added to a solution of methyl 1-(4-fluorophenyl)-3-methyl-2-oxopyrrolidine-3-carboxylate (0.149 g, 0.593 mmol) in a mixture of THF (4.5 mL) and MeOH (1.5 mL) at room temperature for 1 hour. The reaction mixture was acidified with aq. 1 N HCl solution (1.4 mL), extracted with EtOAc, washed with brine, dried over MgSO$_4$, and concentrated to afford the desired product (0.13 g, 92%). $^1$H-NMR (400 MHz, CD$_3$OD) δ 7.62 (m, 2H), 7.13 (t, 2H), 3.97 (m, 1H), 3.86 (m, 1H), 2.63 (m, 1H), 2.13 (m, 1H), 1.47 (s, 3H); $^{19}$F NMR (376 MHz, CD$_3$OD) δ −119.3.

Step D: Preparation of N-(3-fluoro-4-(2-(3-(4-methylpiperazin-1-yl)prop-1-ynyl)thieno[3,2-b]pyridin-7-yloxy)phenyl)-1-(4-fluorophenyl)-3-methyl-2-oxopyrrolidine-3-carboxamide: Prepared from 3-fluoro-4-(2-(3-(4-methylpiperazin-1-yl)prop-1-ynyl)thieno[3,2-b]pyridin-7-yloxy)aniline (Example 17, Step B) and 1-(4-fluorophenyl)-3-methyl-2-oxopyrrolidine-3-carboxylic acid according to the procedure of Example 89. The crude was purified by silica gel flash column chromatography (5% MeOH in CH$_2$Cl$_2$) to afford 26 mg (84%) of the desired product. The crude was purified by silica gel flash column chromatography (5% MeOH in CH$_2$Cl$_2$) to afford 66 mg (62%) of the desired product. LRMS (APCI pos) m/e 616.1 (M+1). $^1$H-NMR (400 MHz, CD$_3$OD) δ 8.49 (d, 1H), 7.87 (dd, 1H), 7.68 (m, 2H), 7.59 (s, 1H), 7.45 (m, 1H), 7.36 (t, 1H), 7.15 (t, 2H), 6.69 (d, 1H), 4.25 (t, 2H), 3.91 (m, 2H), 3.68 (s, 2H), 2.79 (m, 2H), 2.56 (m, 2H), 2.30 (s, 3H), 2.18 (m, 2H), 1.66 (s, 3H); $^{19}$F NMR (376 MHz, CD$_3$OD) δ −119.0, −130.0.

Example 128

N-(3-fluoro-4-(2-(4-(methylcarbamoyl)phenyl)thieno[3,2-b]pyridin-7-yloxy)phenyl)-2-(4-fluorophenyl)-3-oxo-2,3-dihydropyridazine-4-carboxamide

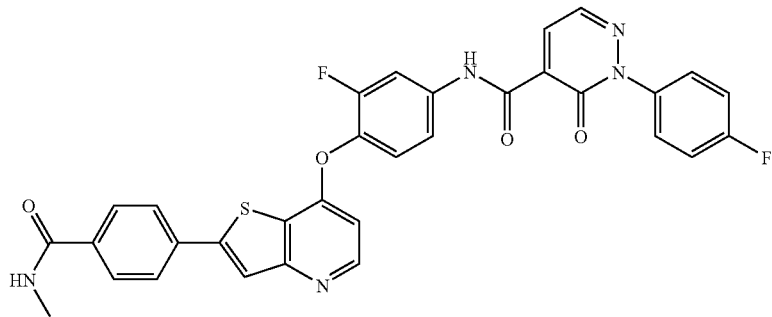

Prepared from 4-(7-(4-amino-2-fluorophenoxy)thieno[3,2-b]pyridin-2-yl)-N-methylbenzamide (Example 95, Step A) and 2-(4-fluorophenyl)-3-oxo-2,3-dihydropyridazine-4-carboxylic acid (Example 104, Step C) according to the procedure of Example 89. The crude was purified by silica gel flash column chromatography (3% MeOH in CH$_2$Cl$_2$) to afford 12.5 mg (40%) of the desired product. LRMS (APCI pos) m/e 610.2 (M+1). $^1$H-NMR (400 MHz, CDCl$_3$/CD$_3$OD) δ 8.46 (d, 1H), 8.41 (d, 1H), 8.33 (d, 1H), 8.01 (dd, 1H), 7.94 (m, 2H), 7.87 (m, 3H), 7.65 (m, 2H), 7.47 (m, 1H), 7.37 (t, 1H), 7.28 (t, 2H), 6.63 (d, 1H), 2.98 (s, 3H); $^{19}$F NMR (376 MHz, CDCl$_3$/CD$_3$OD) δ −112.8, −127.6.

Example 129

N-(3-fluoro-4-(2-(4-(morpholine-4-carbonyl)phenyl)thieno[3,2-b]pyridin-7-yloxy)phenyl)-2-(4-fluorophenyl)-3-oxo-2,3-dihydropydidazine-4-carboxamide Prepared from (4-(7-(4-amino-2-fluorophenoxy)thieno[3,2-b]pyridin-2-yl)phenyl)(morpholino)methanone (Example 129, Step A) and 2-(4-fluorophenyl)-3-oxo-2,3-dihydropyridazine-4-carboxylic acid (Example 104, Step C) according to the procedure of Example 89. The crude was purified by silica gel flash column chromatography (3% MeOH in CH$_2$Cl$_2$) to afford 5.4 mg (24%) of the desired product. LRMS (ESI pos) m/e 666.3 (M+1). $^1$H-NMR (400 MHz, CDCl$_3$/CD$_3$OD) δ 8.47 (d, 1H), 8.38 (d, 1H), 8.31 (d, 1H), 8.03 (dd, 1H), 7.93 (dd, 2H), 7.87 (s, 1H), 7.67 (m, 2H), 7.57 (d, 2H), 7.48 (m, 1H), 7.40 (t, 1H), 7.28 (t, 2H), 6.66 (d, 1H), 3.68-3.78 (m, 6H), 3.53 (m, 2H); $^{19}$F NMR (376 MHz, CDCl$_3$/CD$_3$OD) δ −114.0, −128.6.

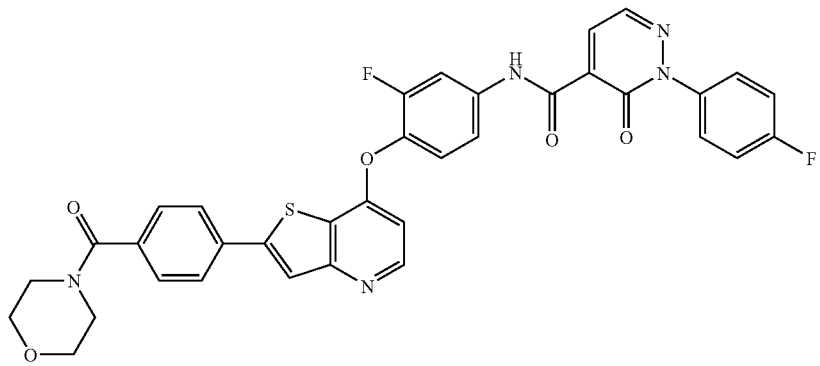

Example 130

N-(3-fluoro-4-(2-(4-(morpholine-4-carbonyl)phenyl)thieno[3,2-b]pyridin-7-yloxy)phenyl)-N-(4-fluorophenyl)cyclopropane-1,1-dicarboxamide

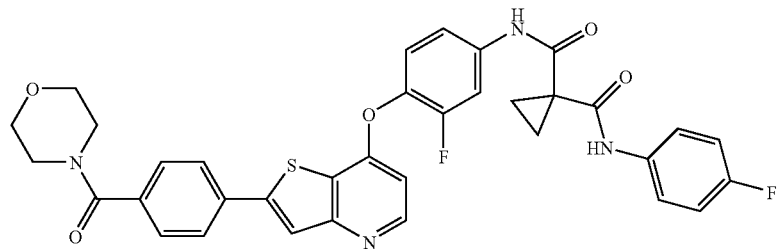

Step A: Preparation of (4-(7-(4-amino-2-fluorophenoxy)thieno[3,2-b]pyridin-2-yl)phenyl)(morpholino)methanone:
A sealable tube was charged with 3-fluoro-4-(2-iodothieno[3,2-b]pyridin-7-yloxy)aniline (Example 6, Step A, 0.200 g, 0.518 mmol), cesium carbonate (0.253 g, 0.777 mmol), 4-(morpholine-4-carbonyl)phenylboronic acid (0.183 g, 0.777 mmol) and DME (2 mL). The mixture was degassed under nitrogen for 10 minutes and Pd(PPh$_3$)$_4$ (0.0299 g, 0.0259 mmol) was added as a solid. The mixture was heated to 85° C. for 18 hours. The crude was diluted with water (300 mL), extracted with EtOAc/MeOH (4:1, 2×300 mL), dried organic over sodium sulfate, filtered and concentrated. The crude product was purified by preparative TLC (2.0 mm thickness) eluting with EtOAc/MeOH (9:1) to give product (31 mg, 12%) as a white solid. LRMS (APCI+) 450 m/z (M+1) detected.

Step B: Preparation of N-(3-fluoro-4-(2-(4-(morpholine-4-carbonyl)phenyl)then[3,2-b]pyridin-7-yloxy)phenyl)-N-(4-fluorophenyl)cyclopropane-1,1-dicarboxamide: Made according to the procedure for Example 112, Step B substituting (4-(7-(4-amino-2-fluorophenoxy)then[3,2-b]pyridin-2-yl)phenyl)(morpholino)methanone (15 mg, 0.030 mmol) for 4-(7-(4-amino-2-fluorophenoxy)thieno[3,2-b]pyridin-2-yl)-N-methylbenzamide. The product was purified by preparative TLC (1.0 mm thickness) eluting with EtOAc and was isolated (4.4 mg, 21%) at Rf 0.8 as a off white solid. LRMS (esi+) 655 m/z (M+1) detected. $^1$H NMR (CDCl$_3$, 400 MHz) δ 10.14 (s, 1H), 8.49 (d, J=6 Hz, 1H), 8.30 (s, 1H), 7.79 (m, 3H), 7.49 (m, 2H), 7.25 (m, 2H), 7.06 (t, J=9 Hz, 1H), 6.51 (d, J=6 Hz, 1H), 3.69 (br s, 8H), 1.81 (m, 2H), 1.61 (m, 2H).

Example 131

Preparation of 4-(7-(6-chloropyridin-3-yloxy)thieno[3,2-b]pyridin-2-yl)-N-methylbenzamide

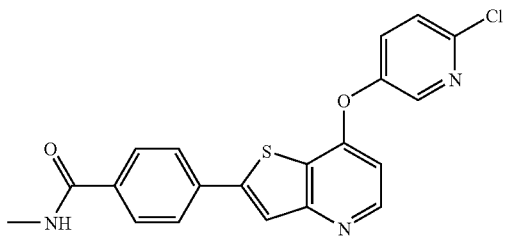

Step A: Preparation of 7-(6-chloropyridin-3-yloxy)-2-iodothieno[3,2-b]pyridine: Related methodology was described in WO 2005/121125. A stirred mixture of 7-chloro-2-iodothieno[3,2-b]pyridine (1.48 g, 5.00 mmol, prepared according to Ragan, J. A. Org. Proc. Res. 2003, 7, 676), cesium carbonate (2.44 g, 7.50 mmol), and DMF (50 mL) was heated to 135° C. under nitrogen with an attached reflux condenser. Next a solution of 6-chloropyridin-3-ol (0.972 g, 7.50 mmol) in DMF (20 mL) was added dropwise by syringe (2 mL approx every 5 min over a period of 50 minutes). The reaction was heated for 4 hours more after addition was complete. The reaction was left stirring at room temperature for 18 hours for convenience. The dark mixture was partitioned between EtOAc (100 mL) and water (100 mL). The phases were separated, and the aqueous phase was re-extracted with EtOAc (50 mL). The combined organic phases were washed with water (3×200 mL), brine (200 mL), dried (Na₂SO₄), filtered, and concentrated in vacuo. The crude was purified by Biotage Flash 40M, eluting with 20% EtOAc/hexanes (1 L) followed by 1:1 EtOAc/hexanes (1 L). The product was obtained as a beige solid (628 mg, 32%). ¹H NMR (400 MHz, CDCl₃) δ 8.49 (d, J=6 Hz, 1H), 8.33 (d, J=2 Hz, 1H), 7.80 (s, 1H), 7.48 (m, 1H), 7.43 (d, J=9 Hz, 1H), 6.54 (d, J=6 Hz, 1H).

Step B: Preparation of 4-(7-(6-chloropyridin-3-yloxy)thieno[3,2-b]pyridin-2-yl)-N-methylbenzamide: A stirred mixture of 4-(methylcarbamoyl)phenylboronic acid (0.112 g, 0.625 mmol), 7-(6-chloropyridin-3-yloxy)-2-iodothieno[3,2-b]pyridine (0.194 g, 0.50 mmol), cesium carbonate (0.244 g, 0.750 mmol), toluene (4 mL) and EtOH (1 mL) was sparged with nitrogen for 5 minutes and then Pd(PPh₃)₄ (0.0347 g, 0.0300 mmol) was added. The reaction was heated to 85° C. for 5 hours in a sealed vessel. The mixture was diluted with DCM (20 mL) and water (20 mL). The phases were separated, and the organic was dried (Na₂SO₄), filtered, and concentrated in vacuo. The crude was purified by preparative TLC (2 mm thickness, Rf=0.36) eluting with 10% MeOH/CHCl₃. The product was obtained as a solid (129 mg, 59%). HPLC: 98% purity (220 nm); LRMS (ESI+): 97% purity, 220 nm, m/z 396 (M+1) detected; ¹H NMR (400 MHz, CDCl₃) δ 8.55 (d, J=6 Hz, 1H), 8.36 (d, J=3 Hz, 1H), 7.85 (m, 2H), 7.79 (m, 3H), 7.53 (d, J=9 Hz, 1H), 7.44 (d, J=9 Hz, 1H), 6.59 (d, J=6 Hz, 1H), 6.41 (br d, J=5 Hz, 1H), 3.05 (d, J=5 Hz, 3H).

Example 132

Preparation of 4-(7-(6-(4-(N-methylaminocarbonyl)phenyl)pyridin-3-yloxy)thieno[3,2-b]pyridin-2-yl)-N-methylbenzamide

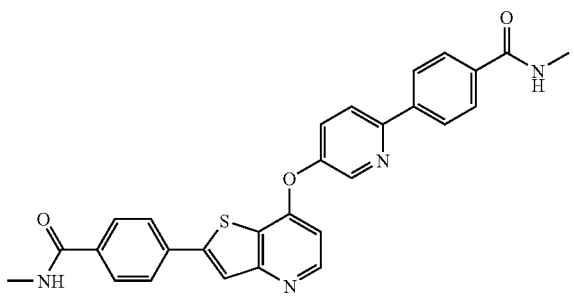

This compound was prepared in Example 130, Step B, from 7-(6-chloropyridin-3-yloxy)-2-iodothieno[3,2-b]pyridine (Example 130, Step A, 0.194 g, 0.50 mmol) and separated during the below purifications. The crude was partially purified by preparative TLC (2 mm thickness, Rf=0.32) eluting with 10% MeOH/CHCl₃. The product was subjected to a second purification by preparative TLC (0.5 mm thickness, Rf=0.13), eluting with 10% MeOH/CHCl₃. The product was obtained as a solid (5 mg, 2%). HPLC: 96% purity (254 nm); LCMS (ESI+): 90% purity, 220 nm, m/z 495 (M+1) detected; ¹H NMR (400 MHz, CDCl₃+MeOD-d3) δ 8.65 (m, 1H), 8.53 (m, 1H), 8.07 (m, 2H), 7.85 (m, 8H), 7.70 (m, 1H), 7.58 (m, 2H), 6.72 (m, 1H), 3.01 (s, 6H).

Example 133

2-methoxyethyl 4-(7-(2-fluoro-4-(1-(4-fluorophenylcarbamoyl)cyclopropanecarboxamido)phenoxy)thieno[3,2-b]pyridin-2-yl)benzoate

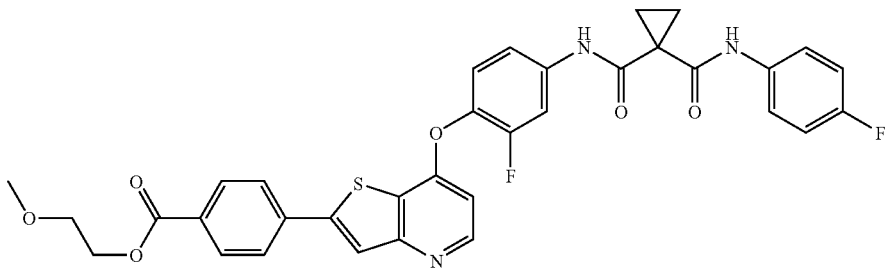

Step A: Preparation of 2-methoxyethyl 4-(7-(4-amino-2-fluorophenoxy)thieno[3,2-b]pyridin-2-yl)benzoate: A round-bottomed flask was charged with 4-(methoxycarbonyl)phenylboronic acid (0.472 g, 2.62 mmol), 3-fluoro-4-(2-iodothieno[3,2-b]pyridin-7-yloxy)aniline (Example 6, Step A, 0.750 g, 1.94 mmol), cesium carbonate (0.949 g, 2.91 mmol), and 2-methoxyethanol (10 mL). The mixture was purged with nitrogen for 10 minutes and then Pd(PPh₃)₄ (0.135 g, 0.117 mmol) was added. The mixture was heated under nitrogen to 85° C. for 18 hours and then cooled to room temperature. The mixture was diluted with water (30 mL) and the resulting precipitate collected by filtration. After drying under high vacuum, the product was isolated (0.26 mg, 25%) as an off-white solid. LRMS (esi+) 439 m/z (M+1) detected.

Step B: Preparation of 2-methoxyethyl 4-(7-(2-fluoro-4-(1-(4-fluorophenylcarbamoyl)cyclopropanecarboxamido)phenoxy)thieno[3,2b]pyridin-2-yl)benzoate: Prepared according to the procedure for Example 112, Step B substituting 2-methoxyethyl 4-(7-(4-amino-2-fluorophenoxy)thieno[3,2-b]pyridin-2-yl)benzoate (0.257 g, 0.586 mmol) for 4-(7-(4-amino-2-fluorophenoxy)thieno[3,2-b]pyridin-2-yl)-N-methylbenzamide. The crude product was purified by preparative TLC (2.0 mm thickness) eluting with EtOAc. The product was isolated (350 mg, 87%) at Rf 0.8 as an off-white solid. LRMS (esi+) 644 m/z (M+1) detected. ¹H NMR (CDCl₃, 400 MHz) δ 10.14 (s, 1H), 8.49 (d, J=5.5 Hz, 1H), 8.38 (s, 1H), 8.14 (d, J=8.6 Hz, 2H), 7.80 (m, 4H), 7.45 (m, 2H), 7.38 (m, 1H), 7.24 (m, 1H), 7.05 (t, J=8.6 Hz, 2H), 6.51 (d, J=5.5 Hz, 1H), 4.51 (m, 2H), 3.75 (m, 2H), 3.45 (s, 3H), 1.80 (m, 2H), 1.62 (m, 2H)

Example 134

4-(7-(2-fluoro-4-(1-(4-fluorophenylcarbamoyl)cyclopropanecarboxamido) phenoxy)thieno[3,2-b]pyridin-2-yl)benzoic acid

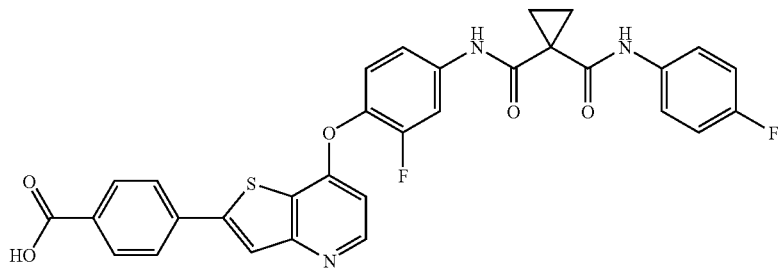

A flask was charged with 2-methoxyethyl 4-(7-(2-fluoro-4-(1-(4-fluorophenylcarbamoyl)cyclopropanecarboxamido) phenoxy)thieno[3,2b]pyridin-2-yl)benzoate (Example 132, Step B, 0.350 g, 0.5438 mmol), lithium hydroxide (0.1302 g, 5.438 mmol), water (3 mL) and T14F (2 mL). After stirring at room temperature for 18 hours, the mixture was acidified to pH 1 with HCl (aq. 1N). Filtration of the precipitate and drying the product under vacuum gave a light gray solid (200 mg, 60%). LRMS (esi+) 586 m/z (M+1) detected. $^1$H NMR (CDCl$_3$, 400 MHz) δ 10.52 (s, 1H), 10.07 (s, 1H), 8.65 (d, J=5.5 Hz, 1H), 8.25 (s, 1H), 8.07 (s, 4H), 7.97 (m, 1H), 7.66 (m, 2H), 7.54 (m, 2H), 7.15 (t, J=9.0 Hz, 2H), 6.81 (d, J=5.9 Hz, 1H), 1.50 (m, 4H).

Example 135

Preparation of N-(4-fluorophenyl)-N-(5-(2-(4-(methylcarbamoyl)phenyl)thieno[3,2-b]pyridin-7-yloxy) pyridin-2-yl)cyclopropane-1,1-dicarboxamide

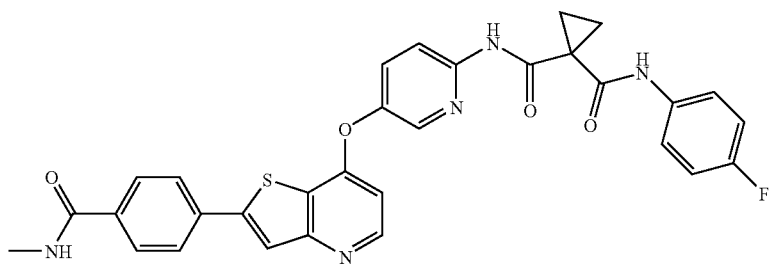

Step A: Preparation of 4-(7-(6-aminopyridin-3-yloxy) thieno[3,2-b]pyridin-2-yl)-N-methylbenzamide: To a stirred mixture of 4-(7-(6-chloropyridin-3-yloxy)thieno[3,2-b]pyridin-2-yl)-N-methylbenzamide (Example 130, Step B, 78 mg, 0.197 mmol), lithium bis(trimethylsilyl)amide (LHMDS, 0.433 mL, 0.433 mmol, 1M in hexanes), and Pd$_2$(dba$_3$) (9.02 mg, 0.00985 mmol), was added P,P-dicyclohexyl(3-(2-N, N-dimethylaminophenyl)-phenyl)phosphine (7.75 mg, 0.0197 mmol). The mixture was sparged with nitrogen for 2 minutes, and then heated to 80° C. for 18 hours. After cooling to room temperature, 2N aqueous HCl (0.5 mL) was added and stirring was continued for 1 hour at room temperature. The mixture was partitioned between dichloromethane (5 mL) and 1:1 saturated aqueous NaHCO$_3$/water (5 mL). The phases were separated, and the aqueous phase was re-extracted with dichloromethane (2×2 mL). The combined organic phases were dried (Na$_2$SO$_4$), filtered, and concentrated. The crude was purified by preparative TLC plate (1 mm thickness, Rf=0.45) eluting with 15% MeOH/CHCl$_3$. The product was obtained as a beige, waxy solid (11 mg, 12%). $^1$H NMR (400 MHz, 1:1 CDCl$_3$/CD$_3$OD) δ 8.44 (d, J=5 Hz, 1H), 7.84-7.95 (m, 6H), 7.41 (m, 1H), 6.71 (d, J=9 Hz, 1H), 6.63 (d, J=5 Hz, 1H), 2.97 (s, 3H).

Step B: Preparation of 1-((4-fluorophenyl)carbamoyl)cyclopropanecarbonyl fluoride: Based on a procedure from Ryan, K., et. al. *Tetrahedron* 2000, 56, 3309-3318. A round-bottomed flask was charged with 2,4,6-trifluoro-1,3,5-triazine (2.66 mL, 19.7 mmol) and DCM (25 mL). Next, under nitrogen 1-((4-fluorophenyl)carbamoyl)cyclopropanecarboxylic acid (2.20 g, 9.86 mmol) and pyridine (0.797 ml, 9.86 mmol) in DCM (20 mL) were added. The mixture was stirred for 2 hours and a white precipitate formed. The reaction was diluted with water (50 mL) and the organics separated. The organics were then dried over sodium sulfate, filtered, and concentrated to obtain the acid fluoride as a white solid. $^1$H NMR (400 MHz, CDCl$_3$) δ 10.44 (s, 1H), 7.61 (m, 2H), 7.17 (m, 2H), 1.69 (m, 4H).

Step C: Preparation of N-(4-fluorophenyl)-N-(5-(2-(4-(methylcarbamoyl)phenyl)thieno[3,2-b]pyridin-7-yloxy)pyridin-2-yl)cyclopropane-1,1-dicarboxamide: A stirred mixture of 4-(7-(6-aminopyridin-3-yloxy)thieno[3,2-b]pyridin-2-yl)-N-methyl-benzamide (11 mg, 0.029 mmol) and 1-((4-fluorophenyl)carbamoyl)cyclopropanecarbonyl fluoride (9.9 mg, 0.044 mmol), in CH$_3$CN (0.5 mL) was heated at 100° C. for 3 hours. After cooling to room temperature, the mixture was partitioned between EtOAc (5 mL) and 1:1 saturated aqueous NaHCO$_3$/water (5 mL). The phases were separated, and the aqueous phase was re-extracted with EtOAc (2×5 mL). The combined organic phases were washed with brine (5 mL), dried (Na$_2$SO$_4$), filtered, and concentrated. The crude was purified by preparative TLC (0.5 mm thickness, Rf=0.30), eluting with 10% MeOH/CHCl$_3$. The product was obtained as a beige solid (2 mg, 11%). HPLC: 100% purity (220 nm); LRMS (ESI+): 94% purity, 220 nm, m/z 582 (M+1) detected; $^1$H NMR (400 MHz, CDCl$_3$) δ 9.59 (s, 1H), 9.01 (s, 1H), 8.53 (d, J=5 Hz, 1H), 8.29 (m, 2H), 7.85 (m, 5H), 7.55 (m, 3H), 7.04 (t, J=9 Hz, 2H), 6.56 (d, J=5 Hz, 1H), 6.19 (m, 1H), 3.06 (d, J=5 Hz, 3H), 1.82 (m, 2H), 1.68 (m, 2H).

Example 136

N-(3-fluoro-4-(2-(4-(methoxy(methyl)carbamoyl)phenyl)thieno[3,2-b]pyridin-7-yloxy)phenyl)-N-(4-fluorophenyl)cyclopropane-1,1-dicarboxamide A screw capped vial was charged with 4-(7-(2-fluoro-4-(1-(4-fluorophenylcarbamoyl)cyclopropanecarboxamido)phenoxy)thieno[3,2-b]pyridin-2-yl)benzoic acid (Example 133, 11 mg, 0.019 mmol), HOBT-H$_2$O (5.8 mg, 0.038 mmol), N-methoxymethanamine hydrochloride (3.7 mg, 0.038 mmol), N$^1$-((ethylimino)methylene)-N$^3$,N$^3$-dimethylpropane-1,3-diamine hydrochloride (7.2 mg, 0.038 mmol) and DMF (2 mL). The mixture was heated to 40° C. for 48 hours. After cooling to room temperature, the mixture was diluted with water (15 mL) and extracted with EtOAc (10 mL). The organics were dried over sodium sulfate, filtered and concentrated. The crude product was purified by preparative TLC (0.5 mm thickness) eluting with EtOAc/MeOH 9:1 to give product (5.0 mg, 40%) at Rf=0.4. LRMS (APCI+) 629 m/z (M+1) detected. $^1$H NMR (CDCl$_3$, 400 MHz) δ 10.11 (s, 1H), 8.49 (d, J=6 Hz, 1H), 8.36 (s, 1H), 7.78 (m, 6H), 7.46 (m, 2H), 7.23 (m, 2H), 7.06 (t, J=9 Hz, 2H), 6.50 (d, J=6 Hz, 1H), 3.60 (s, 3H), 3.40 (s, 3H), 1.80 (m, 2H), 1.62 (m, 2H).

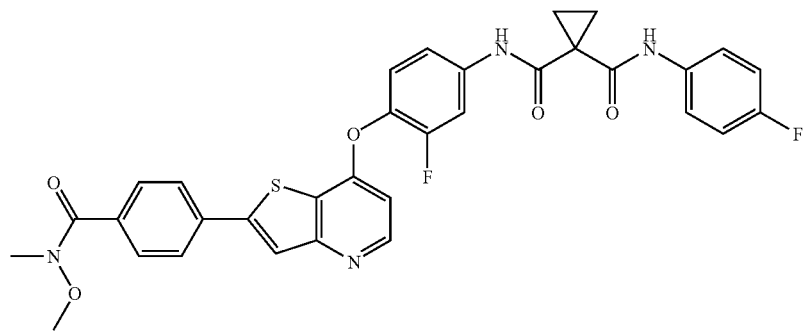

Example 137

N-(3-fluoro-4-(2-(4-(quinuclidin-3-ylcarbamoyl)phenyl)thieno[3,2-b]pyridin-7-yloxy)phenyl)-N-(4-fluorophenyl)cyclopropane-1,1-dicarboxamide

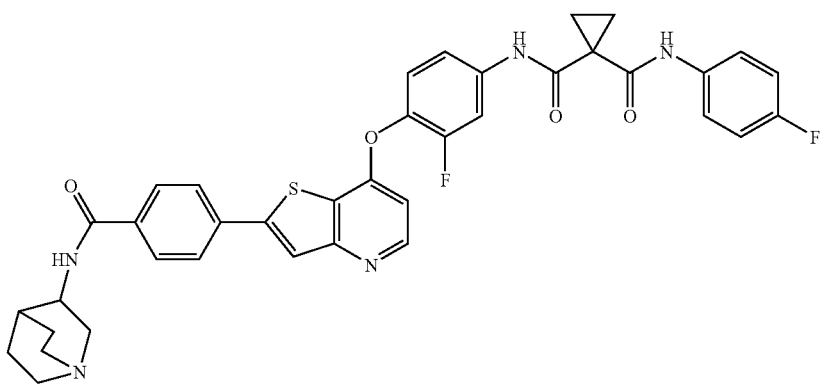

Made according to the procedure for Example 135 substituting quinuclidin-3-amine (4.7 mg, 0.038 mmol) for N-methoxymethanamine hydrochloride. The crude product was purified by preparative TLC (0.5 mm thickness) eluting with EtOAc/MeOH 9:1. Isolated product (4.3 mg, 32%) at Rf 0.4. LRMS (esi+) 694 m/z (M+1) detected $^1$H NMR (CDCl$_3$, 400 MHz) δ 10.13 (s, 1H), 8.50 (d, J=6 Hz, 1H), 8.20 (s, 1H), 7.83 (m, 6H), 7.46 (m, 2H), 7.25 (m, 2H), 7.07 (t, J=9 Hz, 2H), 6.51 (d, J=6 Hz, 1H), 6.26 (d, J=7 Hz, 1H) 3.2-1.8 (m, 16H).

Example 138

N-(3-fluoro-4-(2-(4-(methylcarbamoyl)phenyl) thieno[3,2-b]pyridin-7-yloxy)phenyl)-1-methyl-2-oxo-1,2-dihydropyridine-3-carboxamide

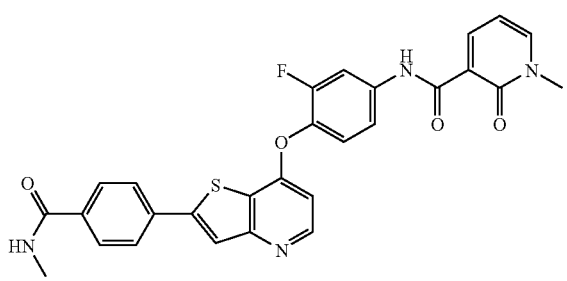

Step A: Preparation of methyl 1-methyl-2-oxo-1,2-dihydropyridine-3-carboxylate: LiH (10 mg, 1.3 mmol) was added to the solution of methyl 2-oxo-1,2-dihydropyridine-3-carboxylate (0.10 g, 0.65 mmol) in DMF (3 mL) at 0° C. After stirring for 30 minutes, iodomethane (0.08 mL, 1.30 mmol) was added to the reaction mixture at the temperature, and the reaction was warmed to room temperature. After stirring for 3 days, the reaction mixture was diluted with EtOAc, quenched with ice water, extracted with EtOAc, dried over MgSO$_4$, and concentrated to give the desired product. $^1$H NMR (400 MHz, CDCl$_3$) δ 8.17 (dd, 1H), 7.58 (dd, 1H), 6.27 (t, 1H), 3.91 (s, 3H), 3.61 (s, 3H).

Step B: Preparation of 1-methyl-2-oxo-1,2-dihydropyridine-3-carboxylic acid: LiOH (1.3 mL, 1.3 mmol, 1.0 M) was added to a solution of methyl 1-methyl-2-oxo-1,2-dihydropyridine-3-carboxylate (0.11 g, 0.65 mmol) in a mixture of THF-MeOH (3:1 ratio, 8 mL) at room temperature. After stirring for 2 hours, 1 N HCl (1.3 mL) was added. The reaction mixture was extracted with EtOAc, dried over MgSO$_4$, and concentrated to give the desired product (0.044 g, 44% for 2 step process). $^1$H NMR (400 MHz, CD$_3$OD) δ 8.45 (dd, 1H), 8.06 (dd, 1H), 6.66 (t, 1H), 3.71 (s, 3H).

Step C: Preparation of N-(3-fluoro-4-(2-(4-(methylcarbamoyl)phenyl)thieno[3,2-b]pyridin-7-yloxy)phenyl)-1-methyl-2-oxo-1,2-dihydropyridine-3-carboxamide: Prepared from 4-(7-(4-amino-2-fluorophenoxy)thieno[3,2-b]pyridin-2-yl)-N-methylbenzamide (Example 95, Step A) and 1-methyl-2-oxo-1,2-dihydropyridine-3-carboxylic acid according to the procedure of Example 89. The crude was purified by silica gel flash column chromatography (3% MeOH in CH$_2$Cl$_2$) to afford 11.1 mg (30%) of the desired product. LRMS (ESI pos) m/e 529.2 (M+1). $^1$H NMR (400 MHz, CDCl$_3$/CD$_3$OD) δ 8.59 (dd, 1H), 8.46 (d, 1H), 8.01 (dd, 1H), 7.94 (m, 2H), 7.88 (m, 3H), 7.67 (s, 1H), 7.47 (m, 1H), 7.36 (t, 1H), 6.64 (m, 2H), 3.75 (s, 3H), 2.98 (s, 3H); $^{19}$F NMR (376 MHz, CDCl$_3$/CD$_3$OD) 6-128.2.

Example 139

N-(3-fluoro-4-(2-(4-(4-methylpiperazine-1-carbonyl) phenyl)thieno[3,2-b]pyridin-7-yloxy)phenyl)-N-(4-fluorophenyl)cyclopropane-1,1-dicarboxamide

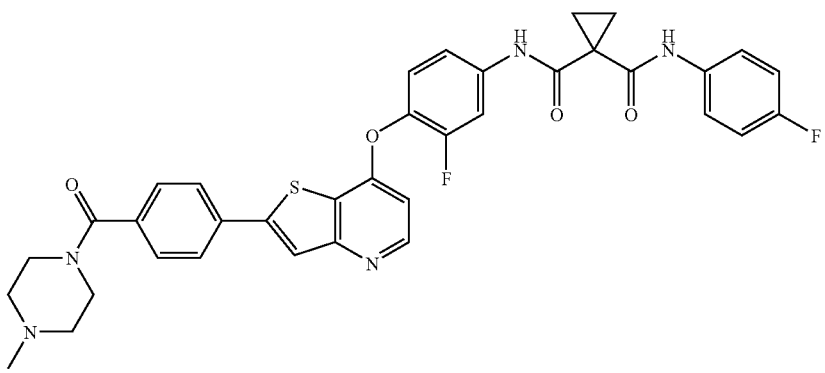

Prepared according to the procedure for Example 135 substituting 1-methylpiperazine (1.9 mg, 0.019 mmol) for N-methoxymethanamine hydrochloride. The crude product was purified using reverse phase chromatography. Isolated product (1.0 mg, 7%). LRMS (APCI+) 668 m/z (M+1) detected.

Example 140

N-(4-(2-(4-(1,3-dihydroxypropan-2-ylcarbamoyl)
phenyl)thieno[3,2-b]pyridin-7-yloxy)-3-fluorophe-
nyl)-N-(4-fluorophenyl)cyclopropane-1,1-dicarboxa-
mide

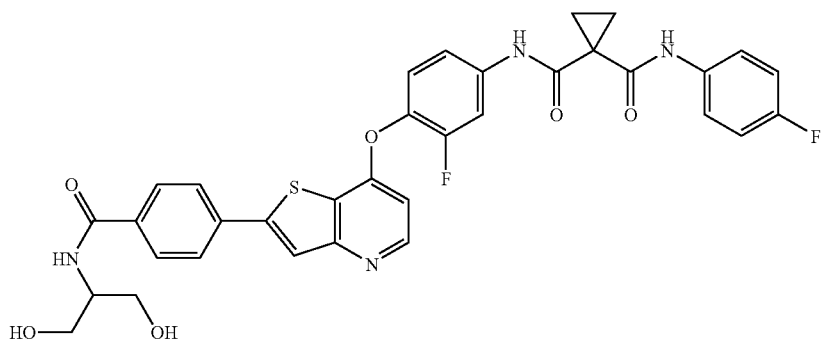

Made according to the procedure for Example 135 substituting 2-aminopropane-1,3-diol (3.4 mg, 0.038 mmol) for N-methoxymethanamine hydrochloride. Purified by preparative TLC (0.5 mm thickness) eluting with EtOAc/MeOH 9:1. Isolated product (0.8 mg, 6%) at Rf 0.3. LRMS (esi+) 659 m/z (M+1) detected.

Example 141

N-(3-fluoro-4-(2-(4-(2-(piperidin-1-yl)ethylcarbam-
oyl)phenyl)thieno[3,2-b]pyridin-7-yloxy)phenyl)-N-
(4-fluorophenyl)cyclopropane-1,1-dicarboxamide

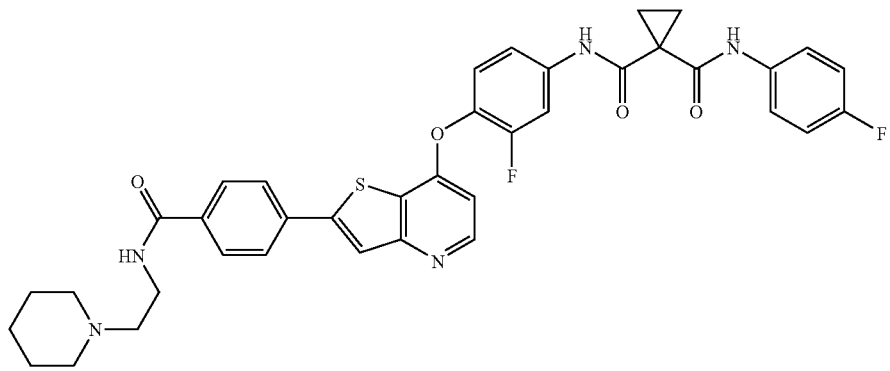

Prepared according to the procedure for Example 135 substituting 2-(piperidin-1-yl)ethanamine (4.8 mg, 0.038 mmol) for N-methoxymethanamine hydrochloride. Purified using reverse phase chromatography. Isolated product (0.6 mg, 4%). LRMS (APCI+) 696 m/z (M+1) detected.

Example 142

(R)—N-(4-(2-(4-(2,3-dihydroxypropylcarbamoyl)phenyl)thieno[3,2-b]pyridin-7-yloxy)-3-fluorophenyl)-N-(4-fluorophenyl)cyclopropane-1,1-dicarboxamide

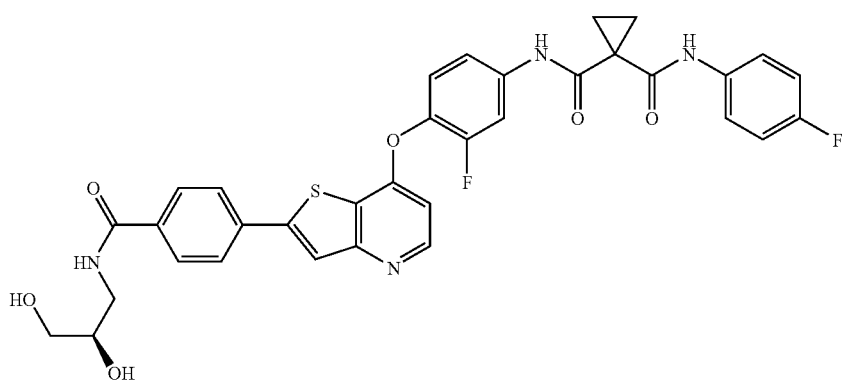

Prepared according to the procedure for Example 135 substituting (R)-3-aminopropane-1,2-diol (3.4 mg, 0.038 mmol) for N-methoxymethanamine hydrochloride. Purified using reverse phase chromatography. Isolated product (0.7 mg, 5%). LRMS (APCI+) 685 m/z (M+1) detected.

Example 143

4-(7-(2-fluoro-4-(1-methyl-6-oxo-2-(phenylamino)-1,6-dihydropyrimidin-5-yl)phenoxy)thieno[3,2-b]pyridin-2-yl)-N-methylbenzamide

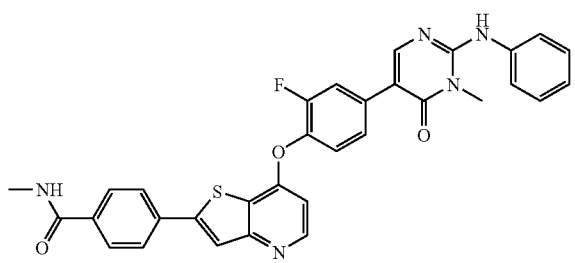

Step A: Preparation of 5-bromo-2-chloropyrimidin-4(3H)-one: Prepared from 5-bromo-2,4-dichloropyrimidine (10.00 g, 43.88 mmol) as described in EP 1506967. Final Product (4.59 g, 50%).

Step B: Preparation of 5-bromo-2-chloro-3-methylpyrimidin-4(3H)-one: To a solution of 5-bromo-2-chloropyrimidin-4(3H)-one (1.00 g, 4.78 mmol) in DME (12 mL)/DMF (3 mL) under nitrogen at 0° C., LiH (0.044 g, 5.25 mmol) was added, and the reaction mixture was stirred for 15 minutes at room temperature. Iodomethane (0.589 mL, 9.45 mmol) was then added and the reaction mixture was stirred at room temperature for 30 minutes and then at 60° C. for 1.5 hours. The reaction mixture was quenched with H$_2$O and then partitioned between EtOAc and saturated aqueous NaCl. The phases were separated, and the aqueous phase was re-extracted with EtOAc (1×). The combined organic layers were dried (Na$_2$SO$_4$), filtered and concentrated to yield a crude yellow oil. The crude product was purified by flash column chromatography, eluting with 25:1 dichloromethane/EtOAc. The desired product (0.764 g, 72%) was obtained as a yellow crystalline solid. $^1$H NMR (400 MHz, DMSO-d$_6$) δ 8.26 (s, 1H), 3.59 (s, 3H). LRMS (ESI pos) m/e 223, 225 (M+, Br pattern).

Step C: Preparation of 5-bromo-3-methyl-2-(phenylamino)pyrimidin-4(3H)-one: A mixture of 5-bromo-2-chloro-3-methylpyrimidin-4(3H)-one (0.510 g, 2.282 mmol), aniline (0.271 ml, 2.967 mmol) and NaHCO$_3$ (0.767 g, 9.129 mmol) in n-BuOH (15 mL) was stirred at 60° C. for 16 hours. The reaction mixture was cooled to room temperature and then diluted with EtOAc. The EtOAc layer was washed with H$_2$O and saturated aqueous NaCl. The aqueous phase was re-extracted with EtOAc (1×). The combined EtOAc layers were dried (Na$_2$SO$_4$), filtered and concentrated to yield the desired product (0.636 g, 99%) as a pale yellow solid that was used without further purification. $^1$H NMR (400 MHz, DMSO-d$_6$) δ 8.95 (br s, 1H), 7.94 (s, 1H), 7.47 (m, 2H), 7.35 (m, 2H), 7.14 (m, 1H), 3.53 (s, 3H). LRMS (ESI pos) m/e 280, 281 (M+, Br pattern).

Step D: Preparation of 5-(4-(benzyloxy)-3-fluorophenyl)-3-methyl-2-(phenylamino)pyrimidin-4(3H)-one: A suspension of 5-bromo-3-methyl-2-(phenylamino)pyrimidin-4(3H)-one (0.145 g, 0.518 mmol), 4-(benzyloxy)-3-fluorophenylboronic acid (0.153 g, 0.621 mmol), Pd(PPh$_3$)$_4$ (0.030 g, 0.026 mmol) and lithium chloride (0.110 g, 2.59 mmol) in dioxane (1.5 mL) and 2M aqueous Na$_2$CO$_3$ (1.5 mL) was stirred at 100° C. for 20 minutes. The reaction mixture was cooled to room temperature and then partitioned between EtOAc and H$_2$O. The phases were separated, and the aqueous phase was re-extracted with EtOAc (1×). The combined organic layers were dried (Na$_2$SO$_4$), filtered and concentrated to yield a crude black solid. The crude product was purified by flash column chromatography, eluting with 10:1 dichloromethane/EtOAc. The desired product (0.133 g, 64%) was obtained as an off-white waxy solid. $^1$H NMR (400 MHz, DMSO-d$_6$) δ 8.90 (br s, 1H), 7.93 (s, 1H), 7.59 (dd, J=1.95, 13.7 Hz, 1H), 7.55-7.31 (m, 10H), 7.22 (t, J=9.0 Hz, 1H), 7.14 (t, J=7.4 Hz, 1H), 5.20 (s, 2H), 3.55 (s, 3H). LRMS (ESI pos) m/e 402 (M+1).

Step E: Preparation of 5-(3-fluoro-4-hydroxyphenyl)-3-methyl-2-(phenylamino)pyrimidin-4(3H)-one: A solution of 5-(4-(benzyloxy)-3-fluorophenyl)-3-methyl-2-(phenylamino)pyrimidin-4(3H)-one (0.133 g, 0.331 mmol) in TFA (1.5 mL) was stirred at 40° C. for 3.5 hours. The reaction mixture was concentrated to dryness and then purified by flash column chromatography, eluting with 20:1 dichloromethane/MeOH. The desired product (0.103 g, 100%) was obtained as a foamy white solid. $^1$H NMR (400 MHz, DMSO-$d_6$) δ 9.81 (br s, 1H), 8.96 (br s, 1H), 7.86 (s, 1H), 7.56-7.45 (m, 3H), 7.37 (t, J=7.4 Hz, 2H), 7.27 (m, 1H), 7.15 (t, J=7.2 Hz, 1H), 6.92 (t, J=9.0 Hz, 1H), 3.54 (s, 3H). LRMS (APCI pos) m/e 312 (M+1).

Step F: Preparation of 5-(3-fluoro-4-(2-iodothieno[3,2-b]pyridin-7-yloxy)phenyl)-3-methyl-2-(phenylamino)pyrimidin-4(3H)-one: A suspension of 5-(3-fluoro-4-hydroxyphenyl)-3-methyl-2-(phenylamino)pyrimidin-4(3H)-one (0.113 g, 0.266 mmol), 7-chloro-2-iodothieno[3,2-b]pyridine (0.075 g, 0.254 mmol; prepared according to the procedure of Ragan, J. A. *Org. Proc. Res.* 2003, 7, 676) and DMAP (0.003 g, 0.025 mmol) in bromobenzene (3 mL) was stirred under nitrogen. The reaction mixture was allowed to stir for 7 days at 150° C. and then for 2 days at room temperature. The reaction was concentrated in vacuo to remove as much bromobenzene as possible. The resulting gummy brown residue was dissolved in CH$_2$Cl$_2$ and then EtOAc was added to yield a dark brown solid precipitate that was filtered and washed with EtOAc. The filtrate, which contained the desired product, was concentrated and purified by flash column chromatography, eluting with 10:1 CH$_2$Cl$_2$/MeOH. Product containing fractions were pooled and concentrated to yield (0.020 mg) of the desired product. Impure fractions were pooled, concentrated and repurified by flash column chromatography, eluting with 20:1 CH$_2$Cl$_2$/MeOH. The product isolated from the two purifications were combined to yield the desired product (39 mg; 27%) as a yellow solid. LRMS (APCI pos) m/e 571 (M+1).

Step G: Preparation of 4-(7-(2-fluoro-4-(1-methyl-6-oxo-2-(phenylamino)-1,6-dihydropyrimidin-5-yl)phenoxy)thieno[3,2-b]pyridin-2-yl)-N-methylbenzamide: A suspension of 5-(3-fluoro-4-(2-iodothieno[3,2-b]pyridin-7-yloxy)phenyl)-3-methyl-2-(phenylamino)pyrimidin-4(3H)-one (0.018 g, 0.032 mmol), 4-(methylcarbamoyl)phenylboronic acid (0.007 g, 0.038 mmol), Pd(PPh$_3$)$_4$ (0.002 g, 0.002 mmol) and LiCl (0.005 g, 0.126 mmol) in dioxane (1 mL) and 2M aqueous Na$_2$CO$_3$ (1 mL) was stirred at 100° C. for 30 minutes. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 10:1 CH$_2$Cl$_2$/MeOH. The product was obtained (9.5 mg; 52%) as a pale yellow solid. $^1$H NMR (400 MHz, DMSO-$d_6$) δ 9.04 (br s, 1H), 8.60-8.53 (m, 2H), 8.20 (s, 1H), 8.11 (s, 1H), 8.04-7.94 (m, 4H), 7.89 (dd, 1H), 7.69 (m, 1H), 7.57-7.48 (m, 3H), 7.38 (m, 2H), 7.17 (m, 1H), 6.70 (dd, 1H), 3.59 (s, 3H), 2.82 (d, 3H). LRMS (APCI pos) m/e 578 (M+1).

Example 144

5-(3-fluoro-4-(2-(4-(morpholine-4-carbonyl)phenyl)thieno[3,2-b]pyridin-7-yloxy)phenyl)-3-methyl-2-(phenylamino)pyrimidin-4(3H)-one A suspension of 5-(3-fluoro-4-(2-iodothieno[3,2-b]pyridin-7-yloxy)phenyl)-3-methyl-2-(phenylamino)pyrimidin-4(3H)-one (Example 143, Step F, 0.018 g, 0.0316 mmol), 4-(morpholine-4-carbonyl)phenylboronic acid (0.009 g, 0.038 mmol), Pd(PPh$_3$)$_4$ (0.002 g, 0.002 mmol) and lithium chloride (0.005 g, 0.126 mmol) in dioxane (1 mL) and 2 M aqueous Na$_2$CO$_3$ (1 mL) was stirred at 100° C. for 30 minutes. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 10:1 CH$_2$Cl$_2$/MeOH. The product was obtained (12.9 mg; 65%) as a pale yellow solid. $^1$H NMR (400 MHz, DMSO-$d_6$) δ 9.04 (br s, 1H), 8.55 (d, 1H), 8.17 (s, 1H), 8.12 (s, 1H), 7.99 (m, 2H), 7.89 (dd, 1H), 7.69 (m, 1H), 7.58-7.49 (m, 5H), 7.38 (m, 2H), 7.17 (m, 1H), 6.70 (dd, 1H), 3.63 (m, 8H), 3.59 (s, 3H). LRMS (APCI pos) m/e 634 (M+1).

Example 145

N-(3-fluoro-4-(2-(3-(4-methylpiperazin-1-yl)prop-1-ynyl)thieno[3,2-b]pyridin-7-yloxy)phenyl)-2-phenoxybenzamide Prepared from 3-fluoro-4-(2-(3-(4-methylpiperazin-1-yl)prop-1-ynyl)thieno[3,2-b]pyridin-7-yloxy)aniline (Example 17, Step B) and 2-phenoxybenzoic acid according to the procedure of Example 89. The crude was purified by silica gel flash column chromatography (10% MeOH in CH$_2$Cl$_2$) to afford 25 mg (67%) of the desired product. LRMS (ESI pos) m/e 593.3 (M+1). $^1$H-NMR (400 MHz, CDCl$_3$) δ 8.92 (s, 1H), 8.48 (d, 1H), 8.36 (d, 1H), 7.87 (dd, 1H), 7.58 (s, 1H), 7.46 (t, 3H), 7.29 (m, 3H), 7.21 (d, 1H), 7.17 (m, 2H), 6.91 (d, 1H), 6.51 (dd, 1H), 3.60 (s, 2H), 2.52-2.71 (m, 8H), 2.32 (s, 3H); $^{19}$F NMR (376 MHz, CDCl$_3$) δ −126.7.

Example 146

4-(cyclopropylmethyl)-N-(3-fluoro-4-(2-(4-(methylcarbamoyl)phenyl)thieno[3,2-b]pyridin-7-yloxy)phenyl)-3-oxo-3,4-dihydropyrazine-2-carboxamide

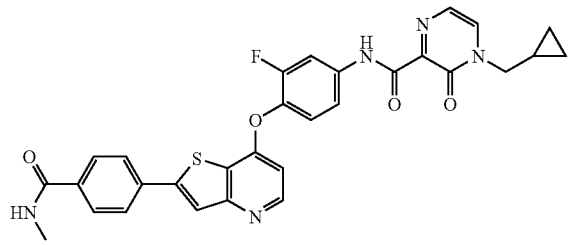

Step A: Preparation of methyl 4-(cyclopropylmethyl)-3-oxo-3,4-dihydropyrazine-2-carboxylate: LiH (7.7 mg, 0.97 mmol) was added to the solution of methyl 2-oxo-1,2-dihydropyridine-3-carboxylate (0.10 g, 0.65 mmol) in DMF (3 mL) at 0° C. After stirring for 30 minutes, (bromomethyl)cyclopropane (0.18 g, 1.30 mmol) was added to the reaction mixture at the temperature, and the reaction was warmed to 50° C. After stirring for 3 days at 50° C., the reaction mixture was diluted with EtOAc, quenched with ice water, extracted with EtOAc, dried over MgSO$_4$, and concentrated. The crude was purified by silica gel flash column chromatography (2% MeOH in CH$_2$Cl$_2$) to afford 87 mg (64%) of the desired product.

Step B: Preparation of 4-(cyclopropylmethyl)-3-oxo-3,4-dihydropyrazine-2-carboxylic acid: LiOH (0.84 mL, 0.84 mmol, 1.0 M) was added to a solution of methyl 4-(cyclopropylmethyl)-3-oxo-3,4-dihydropyrazine-2-carboxylate (87 mg, 0.42 mmol) in a mixture of THF-MeOH (3:1 ratio, 2 mL) at room temperature. After stirring for 2 hours, the reaction mixture was acidified to pH 1 with aq. 1N HCl solution (0.14 mL) and then concentrated to afford the desired product salt. $^1$H NMR (400 MHz, CD$_3$OD) δ 7.67 (d, 1H), 7.37 (m, 1H), 3.86 (d, 2H), 1.32 (m, 1H), 0.61 (m, 2H), 0.45 (m, 2H).

Step C: Preparation of 4-(cyclopropylmethyl)-N-(3-fluoro-4-(2-(4-(methylcarbamoyl)phenyl)thieno[3,2-b]pyridin-7-yloxy)phenyl)-3-oxo-3,4-dihydropyrazine-2-carboxamide: Prepared from 4-(7-(4-amino-2-fluorophenoxy)thieno[3,2-b]pyridin-2-yl)-N-methylbenzamide (Example 95, Step A) and 4-(cyclopropylmethyl)-3-oxo-3,4-dihydropyrazine-2-carboxylic acid according to the procedure of Example 89. The crude was purified by silica gel flash column chromatography (5% MeOH in CH$_2$Cl$_2$) to afford 8 mg (22%) of the desired product. LRMS (ESI pos) m/e 570.2 (M+1). $^1$H NMR (400 MHz, CDCl$_3$/CD$_3$OD) δ 8.47 (d, 1H), 8.08 (dd, 1H), 8.03 (d, 1H), 7.93 (q, 4H), 7.79 (d, 1H), 7.76 (s, 1H), 7.55 (m, 1H), 7.40 (t, 1H), 6.67 (d, 1H), 4.02 (d, 2H), 2.97 (s, 3H), 1.41 (m, 1H), 0.69 (m, 2H), 0.52 (m, 2H); $^{19}$F NMR (376 MHz, CDCl$_3$/CD$_3$OD) δ −128.6.

Example 147

N-(3-Fluoro-4-(2-(4-(methylcarbamoyl)phenyl)thieno[3,2-b]pyridin-7-yloxy)phenyl)-1-methyl-2-oxopyrrolidine-3-carboxamide

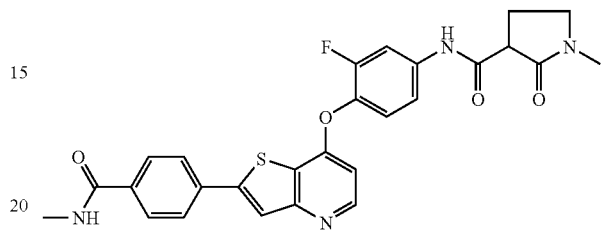

Step A: Preparation of N-(3-fluoro-4-(2-iodothieno[3,2-b]pyridin-7-yloxy)phenyl)-1-methyl-2-oxopyrrolidine-3-carboxamide: A round-bottomed flask was charged with 3-fluoro-4-(2-iodothieno[3,2-b]pyridin-7-yloxy)aniline (Example 6, Step A, 200.0 mg, 0.5179 mmol), 1-methyl-2-oxopyrrolidine-3-carboxylic acid (148.3 mg, 1.04 mmol), N$^1$-((ethylimino)methylene)-N$^3$,N$^3$-dimethylpropane-1,3-diamine hydrochloride (297.8 mg, 1.55 mmol), 1H-benzo[d][1,2,3]triazol-1-ol (209.9 mg, 1.55 mmol), N-ethyl-N-isopropylpropan-2-amine (334.7 mg, 2.59 mmol) and THF (25 mL). The reaction mixture was stirred at room temperature until the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (dichloromethane/7 M NH$_3$ in MeOH from 100/1 to 10/1, v/v) to afford product (213 mg, 80.4%). LRMS (APCI pos) m/e 512 (M+1). $^1$H NMR (400 MHz, CDCl$_3$) δ 10.06 (s, 1H), 8.42 (d, 1H), 7.79 (dd, 1H), 7.76 (s, 1H), 7.29 (m, 1H), 7.19 (t, 1H), 6.45 (dd, 1H), 3.43-3.49 (m, 3H), 2.94 (s, 3H), 2.36-2.61 (m, 2H).

Step B: Preparation of N-(3-fluoro-4-(2-(4-(methylcarbamoyl)phenyl)thieno[3,2-b]pyridin-7-yloxy)phenyl)-1-methyl-2-oxopyrrolidine-3-carboxamide: A round-bottomed flask was charged with N-(3-fluoro-4-(2-iodothieno[3,2-b]pyridin-7-yloxy)phenyl)-1-methyl-2-oxopyrrolidine-3-carboxamide (20.0 mg, 0.039 mmol), 4-(methylcarbamoyl)phenylboronic acid (21.0 mg, 0.117 mmol), tetrakis(triphenylphosphine)palladium (9.04 mg, 0.0078 mmol), Na$_2$CO$_3$ (0.098 ml, 0.20 mmol) and DME (10 mL). The reaction mixture was stirred at 60° C. until the starting material had been consumed (overnight). Then the reaction mixture was cooled to room temperature and partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 50/1 to 10/1, v/v) to give product (5.3 mg, the yield is 26.1%). LRMS (APCI neg): >99% purity, 254 nm, m/e 517 (M−1). $^1$H NMR (400 MHz, DMSO-d$_6$) δ 10.05 (s, 1H), 8.50 (m, 1H), 7.79-7.87 (m, 5H), 7.21-7.33 (m, 2H), 6.51 (d, 1H), 6.17 (d, 1H), 3.38-3.49 (m, 3H), 3.05 (d, 3H), 2.95 (s, 3H), 2.38-2.70 (m, 2H).

Example 148

N-(3-Fluoro-4-(2-(4-(methylcarbamoylphenyl)thieno[3,2-b]pyridin-7-yloxy)phenyl)-2-oxopyrrolidine-3-carboxamide

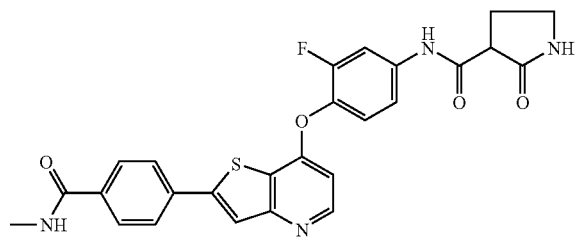

Step A: Preparation of 2-oxopyrrolidine-3-carboxylic acid: A flask was charged with methyl 2-oxopyrrolidine-3-carboxylate (500 mg, 3.49 mmol), potassium trimethylsilanolate (1344 mg, 10.48 mmol) and THF (10 mL). The reaction mixture was stirred at room temperature until the starting material had been consumed (overnight). Then HCl (20 mL, 2.0M in $Et_2O$) was added and the mixture was stirred for 30 minutes. Then the mixture was filtered to remove the solid and the solvent was removed under reduced pressure to give the crude product (188.7 mg, 41.84%), which was used for next step without further purification.

Step B: Preparation of N-(3-fluoro-4-(2-iodothieno[3,2-b]pyridin-7-yloxy)phenyl)-2-oxopyrrolidine-3-carboxamide: A flask was charged with 3-fluoro-4-(2-iodothieno[3,2-b]pyridin-7-yloxy)aniline (Example 6, Step A, 150.0 mg, 0.388 mmol), 2-oxopyrrolidine-3-carboxylic acid (100.3 mg, 0.777 mmol), $N^1$-((ethylimino)methylene)-$N^3$,$N^3$-dimethylpropane-1,3-diamine hydrochloride (223.4 mg, 1.17 mmol), 1H-benzo[d][1,2,3]triazol-1-ol (157.5 mg, 1.17 mmol), N-ethyl-N-isopropylpropan-2-amine (0.347 ml, 1.94 mmol) and THF (100 mL). The reaction mixture was stirred at room temperature until the starting material had been consumed (overnight). Then the reaction mixture was partitioned between EtOAc (100 mL) and $H_2O$ (100 mL). The phases were separated and the aqueous phase was re-extracted with EtOAc (3×100 mL). The combined organic layers were dried ($Na_2SO_4$), filtered and concentrated to yield a crude product. The crude product was purified by silica gel chromatography (EtOAc/Hexane from 1/4 to 4/1, v/v) to afford product (85.0 mg, 44%). LRMS (APCI pos): >97% purity, 254 nm, m/e 498 (M+1).

Step C: Preparation of N-(3-fluoro-4-(2-(4-(methylcarbamoyl)phenyl)thieno[3,2-b]pyridin-7-yloxy)phenyl)-2-oxopyrrolidine-3-carboxamide: A round-bottomed flask was charged with N-(3-fluoro-4-(2-iodothieno[3,2-b]pyridin-7-yloxy)phenyl)-2-oxopyrrolidine-3-carboxamide (15.0 mg, 0.030 mmol), 4-(methyl carbamoyl)phenylboronic acid (16.2 mg, 0.091 mmol), tetrakis(triphenylphosphine)palladium (6.97 mg, 0.0060 mmol), $Na_2CO_3$ (0.0754 ml, 0.15 mmol) and DME (10 mL). The reaction mixture was stirred at 100° C. until the starting material had been consumed (4 hours). Then the reaction mixture was cooled to room temperature and partitioned between EtOAc (100 mL) and $H_2O$ (100 mL). The phases were separated and the aqueous phase was re-extracted with EtOAc (3×100 mL). The combined organic layers were dried ($Na_2SO_4$), filtered and concentrated to yield a crude product. The crude product was purified by silica gel chromatography (DCM/7 M $NH_3$ in MeOH from 50/1 to 10/1, v/v) to give product (3.6 mg, 23.7%). LRMS (APCI pos): >99% purity, 254 nm, m/e 505 (M+1). $^1$H NMR (400 MHz, $CD_3OD$) δ 8.47 (d, 1H), 7.84-8.00 (m, 6H), 7.32-7.46 (m, 2H), 6.65 (d, 1H), 3.38-3.56 (m, 3H), 2.95 (s, 3H), 2.34-2.62 (m, 2H).

Example 149

N-(3-Fluoro-4-(2-(1,2,3,6-tetrahydropyridin-4-yl)thieno[3,2-b]pyridin-7-yloxy)phenyl)-2-(4-fluorophenyl)-3-oxo-2,3-dihydropyridazine-4-carboxamide

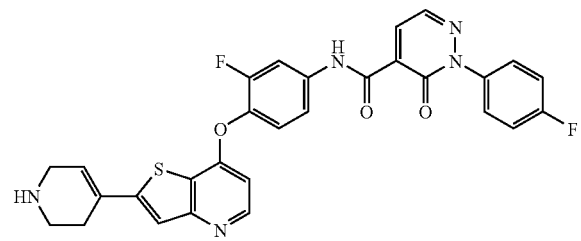

Step A: Preparation of tert-butyl 4-(7-(4-amino-2-fluorophenoxy)thieno[3,2-b]pyridin-2-yl)-5,6-dihydropyridine-1(2H)-carboxylate: A round-bottomed flask was charged with 3-fluoro-4-(2-iodothieno[3,2-b]pyridin-7-yloxy)aniline (Example 6, Step A, 200.0 mg, 0.518), tert-butyl 4-(4,4,5,5-tetramethyl-1,3,2-dioxaborolan-2-yl) -5,6-dihydropyridine-1(2H)-carboxylate (160.1 mg, 0.518 mmol), tetrakis(triphenylphosphine)palladium (119.7 mg, 0.104 mmol), $Na_2CO_3$ (1.30 ml, 2.59 mmol) and DME (50 mL). The reaction mixture was stirred under nitrogen at 100° C. until the starting material had been consumed (4 hours). Then the reaction mixture was cooled to room temperature and partitioned between EtOAc (100 mL) and $H_2O$ (100 mL). The phases were separated and the aqueous phase was re-extracted with EtOAc (3×100 mL). The combined organic layers were dried ($Na_2SO_4$), filtered and concentrated to yield a crude product. The crude product was purified by silica gel chromatography (DCM/7 M $NH_3$ in MeOH from 50/1 to 10/1, v/v) to give product (183.4 mg, 80%). LRMS (APCI pos): m/e 442 (M+1). $^1$H NMR (400 MHz, $CD_3OD$) δ 8.41 (d, 1H), 7.36 (s, 1H), 7.03 (t, 1H), 6.54 (dd, 1H), 6.47 (m, 2H), 6.30 (m, 1H), 4.13 (m, 2H), 3.83 (br s, 2H), 3.68 (m, 2H), 2.64 (m, 2H), 1.50 (s, 9H).

Step B: Preparation of tert-butyl 4-(7-(2-fluoro-4-(2-(4-fluorophenyl)-3-oxo-2,3-dihydropyridazine-4-carboxamido)phenoxy)thieno[3,2-b]pyridin-2-yl)-5,6-dihydropyridine-1(2H)-carboxylate: A round-bottomed flask was charged with tert-butyl 4-(7-(4-amino-2-fluorophenoxy)thieno[3,2-b]pyridin-2-yl)-5,6-dihydropyridine-1(2H)-carboxylate (30.0 mg, 0.068 mmol), 2-(4-fluorophenyl)-3-oxo-2,3-dihydropyridazine-4-carboxylic acid (Example 104, Step C, 31.8 mg, 0.136 mmol), $N^1$-((ethylimino)methylene)-$N^3$,$N^3$-dimethylpropane-1,3-diamine hydrochloride (39.1 mg, 0.204 mmol), 1H-benzo[d][1,2,3]triazol-1-ol (27.5 mg, 0.204 mmol), N-ethyl-N-isopropylpropan-2-amine (0.061 ml, 0.340 mmol) and DMF (5 mL). The reaction mixture was stirred at room temperature for 48 hours. Then the reaction was partitioned between EtOAc (50 mL) and $H_2O$ (50 mL).

The phases were separated and the aqueous phase was re-extracted with EtOAc (3×100 mL). The combined organic layers were dried (Na₂SO₄), filtered and concentrated to yield a crude product. The crude product was purified by silica gel chromatography (DCM/7 M NH₃ in MeOH from 100/1 to 10/1, v/v) to afford product (27.3 mg, 61.1%). LRMS (APCI pos) m/e 658 (M+1). ¹H NMR (400 MHz, CDCl₃) δ 11.82 (s, 1H), 8.42 (m, 2H), 8.24 (d, 1H), 7.98 (dd, 1H), 7.21-7.66 (m, 7H), 6.58 (s, 1H), 6.30 (m, 1H), 4.18 (m, 2H), 3.68 (m, 2H), 2.62 (m, 2H), 1.52 (s, 9H).

Step C: Preparation of N-(3-fluoro-4-(2-(1,2,3,6-tetrahydropyridin-4-yl)thieno[3,2-b]pyridin-7-yloxy)phenyl)-2-(4-fluorophenyl)-3-oxo-2,3-dihydropyridazine-4-carboxamide: A single-neck, round-bottomed flask was charged with tert-butyl 4-(7-(2-fluoro-4-(2-(4-fluorophenyl)-3-oxo-2,3-dihydropyridazine-4-carboxamido)phenoxy)thieno[3,2-b]pyridin-2-yl)-5,6-dihydropyridine-1(2H)-carboxylate (27.3 mg, 0.0415 mmol) and CF₃CO₂H (5 mL). The reaction mixture was stirred at room temperature until the starting material had been consumed (four hours). Then the solvent was removed and the residue was purified by silica gel chromatography (DCM/7 M NH₃ in MeOH from 50/1 to 10/1, v/v) to afford product (16.7 mg, 72.2%). LRMS (APCI pos): >99% purity, 254 nm, m/e 558 (M+1). ¹H NMR (400 MHz, CDCl₃) δ 11.83 (s, 1H), 8.42 (m, 2H), 8.24 (d, 1H), 7.95 (dd, 1H), 7.60 (m, 2H), 7.38 (m, 2H), 7.24 (m, 3H), 6.48 (d, 1H), 6.40 (s, 1H), 3.59 (m, 2H), 3.15 (m, 2H), 2.58 (m, 2H).

Example 150

N-(3-fluoro-4-(2-(4-(morpholine-4-carbonyl)phenyl)thieno[3,2-b]pyridin-7-yloxy)phenyl)-3-(4-fluorophenyl)-2-oxo-3-azabicyclo[3.1.0]hexane-1-carboxamide fluorobenzenamine (12 g, 79 mmol), DIEA (15 ml, 87 mmol) and DMAP (0.97 mg, 7.9 mmol) in CH₂Cl₂ (200 mL) at 0° C. under nitrogen. The reaction was stirred at 0° C. for 1 hour. The reaction mixture was poured into ice and water, extracted with CH₂Cl₂, washed with saturated aqueous NaHCO₃ and brine. The organic layer was dried with Na₂SO₄, filtered and concentrated. The residue was purified by flash column chromatography (50% EtOAc in hexane) to afford the product (18.3 g, 92% yield) as brown oil. ¹H NMR (400 MHz, CDCl₃): δ 7.16-7.22 (m, 2H), 7.08-7.12 (m, 2H), 5.80-5.90 (m, 1H), 5.07-5.17 (m, 2H), 4.27-4.32 (m, 2H), 3.67 (s, 3H), 3.20 (s, 2H).

Step C: Preparation of methyl 3-(4-fluorophenyl)-2-oxo-3-aza-bicyclo[3.1.0]hexane-1-carboxylate: A solution of methyl 3-(allyl(4-fluorophenyl)amino)-3-oxopropanoate (10 g, 39.7 mmol) in acetic acid (50 mL) was added into a suspension of manganese (III) acetate dihydrate (21 g, 79.7 mmol) and copper (II) acetate monohydrate (7.9 g, 39.7 mmol) in acetic acid (200 mL). The reaction was allowed to stir for 3 days at room temperature. The reaction was quenched with 10% aqueous sodium bisulfite solution (100 mL). The reaction mixture was diluted with EtOAc, washed with saturated aqueous NaHCO₃, brine, dried with Na₂SO₄, filtered and concentrated. The residue was purified by flash column chromatography (50% EtOAc in hexane) to afford the product (1.2 g, 12% yield) as a brown power. LRMS (APCI pos) m/e 250.1 (M+1). ¹H NMR: (CDCl₃, 400 MHz) δ 7.49-7.54 (m, 2H), 7.02-7.07 (m, 2H), 4.02-4.07 (m, 1H), 3.83 (s, 3H), 3.70 (d, 1H), 2.45-2.53 (m, 1H), 2.02-2.09 (m, 1H), 1.29-1.33 (m, 1H).

Step D: Preparation of 3-(4-fluorophenyl)-2-oxo-3-aza-bicyclo[3.1.0]hexane-1-carboxylic acid: LiOH (0.2 g, 8.4 mmol) was added into a suspension of methyl 3-(4-fluorophenyl)-2-oxo-3-aza-bicyclo[3.1.0]hexane-1-carboxylate

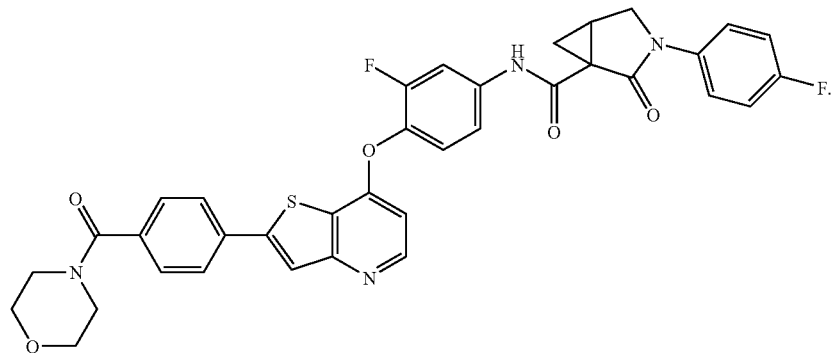

Step A: Preparation of N-allyl-4-fluorobenzenamine: A suspension of 4-fluorobenzenamine (25 g, 225 mmol), 3-bromoprop-1-ene (19.0 ml, 225 mmol) and K₂CO₃ (31.1 g, 225 mmol) was stirred in THF (1 L) for 2 days. Water (20 mL) and EtOAc (1 L) were added into the reaction mixture. The organics was separated and washed with brine, dried with Na₂SO₄, filtered and concentrated. The residue was purified by flash column chromatography (20% EtOAc in hexane) to afford the product (16 g, 47.0% yield) as orange brown oil. ¹H NMR (400 MHz, CDCl₃): δ 6.85-6.90 (m, 2H), 6.53-6.60 (m, 2H), 5.89-6.01 (m, 1H), 5.25-5.32 (m, 1H), 5.15-5.20 (m, 1H), 3.71-3.77 (m, 2H), 3.66 (br s, 1H).

Step B: Preparation of methyl 3-(allyl(4-fluorophenyl)amino)-3-oxopropanoate: Methyl 3-chloro-3-oxopropanoate (9.4 ml, 87 mmol) was added into a solution of N-allyl-4-

(1.2 g, 4.8 mmol) in THF (20 mL) and water (1 mL). The reaction was allowed to stir for 1 hour. The reaction mixture was poured into water and neutralized with 1M HCl. The mixture was extracted with EtOAc, washed with brine, dried with Na₂SO₄, filtered and concentrated to afford the title compound (1 g, 79% yield) as a light brown solid. LRMS (APCI pos) m/e 235.9 (M+1). ¹H NMR: (DMSO-d₆, 400 MHz): δ 12.70 (br s, 1H), 7.57-7.62 (m, 2H), 7.17-7.23 (m, 2H), 4.06 (dd, 1H), 3.70 (dd, 1H), 2.50-2.56 (m, 1H), 1.76-1.81 (m, 1H), 1.29-1.33 (dd, 1H).

Step E: Preparation of N-(3-fluoro-4-(2-(4-(morpholine-4-carbonyl)phenyl)thieno[3,2-b]pyridin-7-yloxy)phenyl)-3-(4-fluorophenyl)-2-oxo-3-azabicyclo[3.1.0]hexane-1-carboxamide: To a stirred solution of 3-(4-fluorophenyl)-2-oxo-3-aza-bicyclo[3.1.0]hexane-1-carboxylic acid (20 mg, 0.085 mmol) in 500 uL of dichloromethane at room temperature under nitrogen was added HOBt (19.5 mg, 0.128 mmol), EDCI (24.5 mg, 0.128 mmol) and DIEA (45 uL, 0.225 mmol). After 15 minutes a solution of (4-(7-(4-amino-2-fluorophenoxy)thieno[3,2-b]pyridin-2-yl)phenyl)(morpholino)methanone (Example 129, Step A, 34 mg, 0.077 mmol) in 500 uL dichloromethane was added by pipet. After stirring overnight, the reaction was diluted to 30 mL with CH$_2$Cl$_2$ and washed 1×30 mL with 10% sodium carbonate solution. The organics were dried (MgSO$_4$), filtered and concentrated. The crude product was loaded onto Biotage 12S column and eluted initially with dichloromethane and then after about 100 mL of elution, switched to 2/98 MeOH/dichloromethane. Pure product containing fractions were pooled and concentrated to a white glass (12 mg, 21% yield). LRMS (APCI pos) m/e 667.4 (M+1). $^1$H NMR: (CDCl$_3$, 400 MHz): δ 10.52 (s, 1H), 8.50 (d, 1H), 7.83 (m, 1H), 7.82 (s, 1H), 7.80 (s, 2H), 7.54-7.46 (m, 4H), 7.31 (m, 2H), 7.24 (m, 1H), 7.11 (m, 2H), 6.52 (d, 1H), 4.12 (m, 1H), 3.90-3.60 (br m, 8H), 3.78 (d, 1H), 2.81 (m, 1H), 2.05 (m, 1H), 1.39 (m, 1H).

Example 151

4-benzyl-N-(3-fluoro-4-(2-(4-(morpholine-4-carbonyl)phenyl)thieno[3,2-b]pyridin-7-yloxy)phenyl)-3-oxo-3,4-dihydropyrazine-2-carboxamide Step A: Preparation of methyl 4-benzyl-3-oxo-3,4-dihydropyrazine-2-carboxylate: LiH (7.8 mg, 0.980 mmol) was added to the solution of methyl 3-oxo-3,4-dihydropyrazine-2-carboxylate (100 mg, 0.65 mmol) in DMF (3 mL) at 0° C. After 30 minutes stirring, (chloromethyl)benzene (0.15 mL, 1.30 mmol) was added to the reaction mixture at 0° C., and then the reaction was warmed to room temperature. After 4 hours stirring, the reaction mixture was quenched with ice water, extracted with EtOAc, washed with brine, dried over MgSO$_4$, and concentrated to give the crude material that was purified by silica gel flash column chromatography (2% MeOH in CH$_2$Cl$_2$) to afford 0.102 g (64%) of the desired product. $^1$H-NMR (400 MHz, CDCl$_3$) δ 7.38 (m, 6H), 7.29 (d, 1H), 5.14 (s, 2H), 3.98 (s, 3H).

Step B: Preparation of 4-benzyl-3-oxo-3,4-dihydropyrazine-2-carboxylic acid: LiOH (0.82 mL, 0.82 mmol, 1.0 M in H$_2$O) was added to a solution of methyl 4-benzyl-3-oxo-3,4-dihydropyrazine-2-carboxylate (100 mg, 0.41 mmol) in a mixture of THF (4.5 mL) and MeOH (1.5 mL) at room temperature for 4 hours. The reaction mixture was acidified to pH 1 with aq. 1N HCl solution and treated with water (5 mL), extracted with EtOAc, washed with brine, dried over MgSO$_4$, and concentrated to afford 77 mg (82%) of the desired product. 1H-NMR (400 MHz, CD$_3$OD) δ 8.0 (d, 1H), 7.68 (d, 1H), 7.36-7.42 (m, 5H), 5.29 (s, 2H).

Step C: Preparation of 4-benzyl-N-(3-fluoro-4-(2-(4-(morpholine-4-carbonyl)phenyl)thieno[3,2-b]pyridin-7-yloxy)phenyl)-3-oxo-3,4-dihydropyrazine-2-carboxamide: Prepared from (4-(7-(4-amino-2-fluorophenoxy)thieno[3,2-b]pyridin-2-yl)phenyl)(morpholino)methanone (Example 129, Step A) and 4-benzyl-3-oxo-3,4-dihydropyrazine-2-carboxylic acid according to the procedure of Example 89. The crude was purified by silica gel flash column chromatography (2% MeOH in CH$_2$Cl$_2$) to afford 12 mg (45%) of the desired product. LRMS (APCI pos) m/e 662.2 (M+1). $^1$H-NMR (400 MHz, CDCl$_3$/CD$_3$OD) δ 8.03 (dd, 1H), 7.96 (d, 1H), 7.92 (d, 2H), 7.85 (s, 1H), 7.77 (d, 1H), 7.56 (m, 3H), 7.36-7.46 (m,

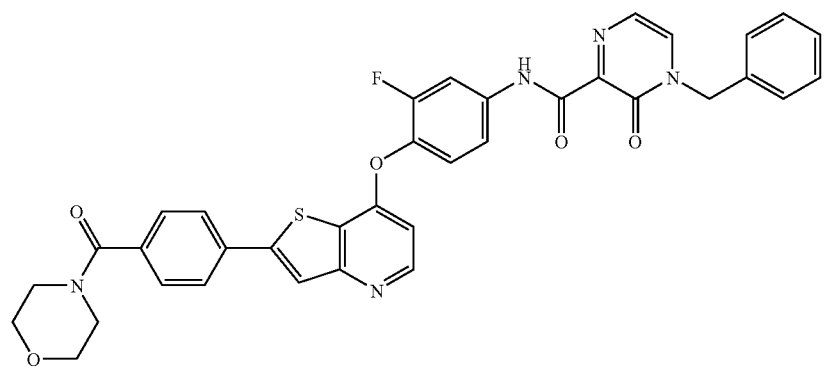

7H), 6.66 (d, 1H), 5.33 (s, 2H), 3.68-3.81 (m, 8H); $^{19}$F NMR (376 MHz, CDCl$_3$/CD$_3$OD) δ −128.2.

Example 152

N-(3-fluoro-4-(2-(4-(morpholine-4-carbonyl)phenyl) thieno[3,2-b]pyridin-7-yloxy)phenyl)-4-methyl-3-oxo-3,4-dihydropyrazine-2-carboxamide

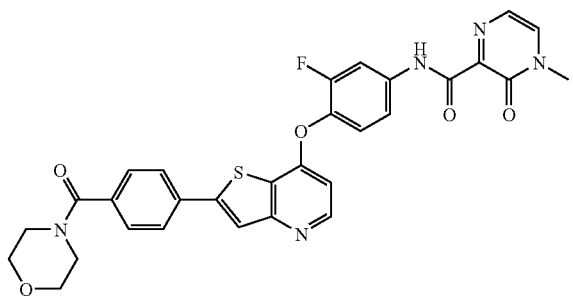

Prepared from (4-(7-(4-amino-2-fluorophenoxy)thieno[3,2-b]pyridin-2-yl)phenyl)(morpholino)methanone (prepared as in Example 129, Step A) and 4-methyl-3-oxo-3,4-dihydropyrazine-2-carboxylic acid (prepared from methyl 3-oxo-3,4-dihydropyrazine-2-carboxylate with iodomethane and followed by hydrolysis using the methods described in Example 149, Steps A and B) according to the procedure of Example 89. The crude was purified by silica gel flash column chromatography (5% MeOH in CH$_2$Cl$_2$) to afford 6.6 mg (25%) of the desired product. LRMS (APCI pos) m/e 586.2 (M+1). $^1$H-NMR (400 MHz, CDCl$_3$/CD$_3$OD) δ 8.47 (d, 1H), 8.07 (dd, 1H), 7.92 (m, 3H), 7.86 (s, 1H), 7.76 (d, 1H), 7.55 (m, 3H), 7.39 (t, 1H), 6.67 (d, 1H), 3.75 (s, 3H), 3.55-3.80 (m, 8H); $^{19}$F NMR (376 MHz, CDCl$_3$/CD$_3$OD) δ −128.3.

Example 153

N-(3-fluoro-4-(2-(4-methylpiperazin-1-yl)thieno[3,2-b]pyridin-7-yloxy)phenyl)-2-(4-fluorophenyl)-3-oxo-2,3-dihydropyridazine-4-carboxamide

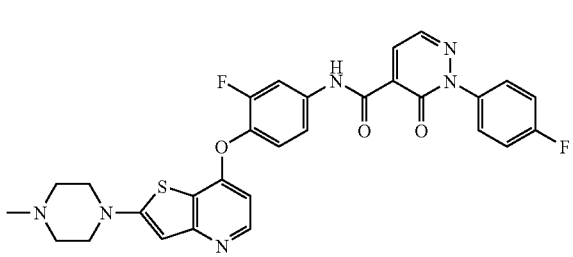

Step A: Preparation of 3-fluoro-4-(2-(4-methylpiperazin-1-yl)thieno[3,2-b]pyridin-7-yloxy)aniline: A round-bottomed flask was charged with 3-fluoro-4-(2-iodothieno[3,2-b]pyridin-7-yloxy)aniline (Example 6, Step A, 200.0 mg, 0.518 mmol), 1-methyl piperazine (0.172 ml, 1.55 mmol), copper(I) iodide (29.59 mg, 0.155 mmol), (S)-pyrrolidine-2-carboxylic acid (17.89 mg, 0.155 mmol), K$_2$CO$_3$ (357.9 mg, 2.59 mmol) and DMSO (25 mL). The reaction mixture was stirred at 100° C. until the starting material had been consumed (overnight). Then the reaction was cooled to room temperature and partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (158.5 mg, 85%). LRMS (APCI pos): >95% purity, 254 nm, m/e 359.3 (M+1). $^1$H NMR (400 MHz, CD$_3$OD) δ 8.11 (d, 1H), 6.96 (t, 1H), 6.53 (dd, 1H), 6.49 (m, 1H), 6.29 (m, 2H), 3.36 (m, 4H), 2.60 (m, 4H), 2.33 (s, 3H).

Step B: Preparation of N-(3-fluoro-4-(2-(4-methylpiperazin-1-yl)thieno[3,2-b]pyridin-7-yloxy)phenyl)-2-(4-fluorophenyl)-3-oxo-2,3-dihydropyridazine-4-carboxamide: A round-bottomed flask was charged with 3-fluoro-4-(2-(4-methylpiperazin-1-yl)thieno[3,2-b]pyridin-7-yloxy)aniline (40.0 mg, 0.112 mmol), 2-(4-fluorophenyl)-3-oxo-2,3-dihydropyridazine-4-carboxylic acid (39.2 mg, 0.167 mmol), N$^1$-((ethylimino)methylene)-N$^3$,N$^3$-dimethylpropane-1,3-diamine hydrochloride (64.2 mg, 0.335 mmol), 1H-benzo[d][1,2,3]triazol-1-ol (45.2 mg, 0.335 mmol), N-ethyl-N-isopropylpropan-2-amine (0.0996 ml, 0.558 mmol) and DMF (10 mL). The reaction mixture was stirred at room temperature until the starting material had been consumed (overnight). Then the reaction was partitioned between EtOAc (50 mL) and H$_2$O (50 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (48.3 mg, 75.3%). LRMS (APCI pos): >99% purity, 254 nm, m/e 575 (M+1). $^1$H NMR (400 MHz, CDCl$_3$) δ 11.80 (s, 1H), 8.40 (d, 1H), 8.28 (d, 1H), 8.23 (d, 1H), 7.92 (dd, 1H), 7.61 (m, 2H), 7.36 (m, 1H), 7.17-7.24 (m, 3H), 6.36 (s, 1H), 6.29 (d, 1H), 3.37 (m, 4H), 2.58 (m, 4H), 2.36 (s, 3H).

Example 154

N-(3-Fluoro-4-(2-(piperidin-4-yl)thieno[3,2-b]pyridin-7-yloxy)phenyl)-2-(4-fluorophenyl)-3-oxo-2,3-dihydropyridazine-4-carboxamide

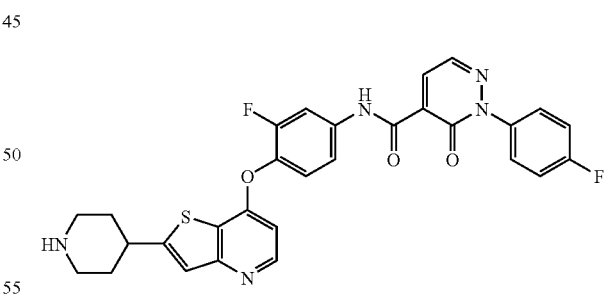

Step A: Preparation of tert-butyl 4-(7-(4-amino-2-fluorophenoxy)thieno[3,2-b]pyridin-2-yl)piperidine-1-carboxylate: A round-bottomed flask was charged with tert-butyl 4-(7-(4-amino-2-fluorophenoxy)thieno[3,2-b]pyridin-2-yl)-5,6-dihydropyridine-1(2H)-carboxylate (Example 149, Step A, 146.3 mg, 0.3314 mmol), palladium on carbon (117.7 mg, 0.099 mmol, 10%) and MeOH (10 mL). The air was exchanged with nitrogen three times and then was exchanged with hydrogen another three times. Then the reaction was stirred under hydrogen at room temperature until the starting material had been consumed (2 hours). The mixture was filtered to remove the palladium on carbon and then the solvent was removed under reduced pressure to afford crude product. The crude product was purified by silica gel chromatography (dichloromethane/7 M NH$_3$ in MeOH from 100/1 to 10/1, v/v) to afford product (144.5 mg, 98.3%). LRMS (APCI pos): >95% purity, 254 nm, m/e 444 (M+1). $^1$H NMR (400 MHz, CD$_3$Cl) δ 8.41 (d, 1H), 7.27 (m, 1H), 7.02 (t, 1H), 6.54 (dd, 1H), 6.46 (m, 2H), 4.24 (m, 2H), 3.84 (br s, 2H), 3.07 (m, 1H), 2.88 (m, 2H), 2.09 (m, 2H), 1.74 (m, 2H), 1.49 (s, 9H).

Step B: Preparation of tert-butyl 4-(7-(2-fluoro-4-(2-(4-fluorophenyl)-3-oxo-2,3-dihydropyridazine-4-carboxamido)phenoxy)thieno[3,2-b]pyridin-2-yl)piperidine-1-carboxylate: A round-bottomed flask was charged with tert-butyl 4-(7-(4-amino-2-fluorophenoxy)thieno[3,2-b]pyridin-2-yl)piperidine-1-carboxylate (144.5 mg, 0.326 mmol), 2-(4-fluorophenyl)-3-oxo-2,3-dihydropyridazine-4-carboxylic acid (228.9 mg, 0.977 mmol), N$^1$-((ethylimino)methylene)-N$^3$,N$^3$-dimethylpropane-1,3-diamine hydrochloride (312.3 mg, 1.63 mmol), 1H-benzo[d][1,2,3]triazol-1-ol (220.1 mg, 1.63 mmol), N-ethyl-N-isopropylpropan-2-amine (421.1 mg, 3.26 mmol) and DMF (10 mL). The reaction mixture was stirred at room temperature until the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (87.3 mg, 40.62%). LRMS (APCI pos): >95% purity, 254 nm, m/e 660 (M+1). $^1$H NMR (400 MHz, CD$_3$Cl) δ 11.83 (s, 1H), 8.45 (d, 1H), 8.42 (d, 1H), 8.24 (d, 1H), 7.95 (dd, 1H), 7.37-7.68 (m, 5H), 7.21-7.28 (m, 2H), 6.48 (d, 1H), 4.24 (m, 2H), 3.08 (m, 1H), 2.89 (m, 2H), 2.07 (m, 2H), 1.75 (m, 2H), 1.49 (s, 9H).

Step C: Preparation of N-(3-fluoro-4-(2-(piperidin-4-yl)thieno[3,2-b]pyridin-7-yloxy)phenyl)-2-(4-fluorophenyl)-3-oxo-2,3-dihydropyridazine-4-carboxamide: A round-bottomed flask was charged with tert-butyl 4-(7-(2-fluoro-4-(1-(4-fluorophenyl)-6-oxo-1,6-dihydropyridazine-5-carboxamido)phenoxy)thieno[3,2-b]pyridin-2-yl)piperidine-1-carboxylate (87.3 mg, 0.132 mmol) and CF$_3$COOH (5 mL). The reaction mixture was stirred at room temperature until the starting material had been consumed (one hour). Then the solvent was removed and the residue was purified by silica gel chromatography (dichloromethane/7 M NH$_3$ in MeOH from 50/1 to 10/1, v/v) to afford product (38.5 mg, 52%). LRMS (APCI pos): >99% purity, 254 nm, m/e 560 (M+1). $^1$H NMR (400 MHz, CDCl$_3$) δ 11.83 (s, 1H), 8.44 (d, 1H), 8.41 (d, 1H), 8.24 (d, 1H), 7.95 (dd, 1H), 7.61 (m, 2H), 7.38 (m, 1H), 7.21-7.28 (m, 4H), 6.46 (d, 1H), 3.23 (m, 2H), 3.06 (m, 1H), 2.79 (m, 2H), 2.11 (m, 2H), 1.77 (m, 2H), Example 155

N-(3-Fluoro-4-(2-(1-methylpiperidin-4-yl)thieno[3,2-b]pyridin-7-yloxy)phenyl)-2-(4-fluorophenyl)-3-oxo-2,3-dihydropyridazine-4-carboxamide

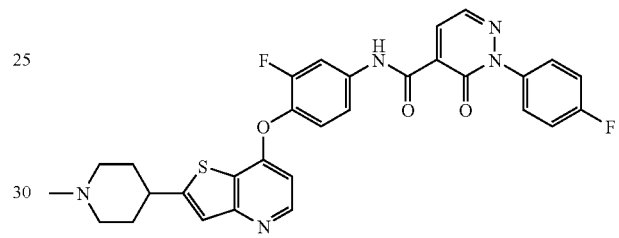

A round-bottomed flask was charged with N-(3-fluoro-4-(2-(piperidin-4-yl)thieno[3,2-b]pyridin-7-yloxy)phenyl)-2-(4-fluorophenyl)-3-oxo-2,3-dihydropyridazine-4-carboxamide (Example 154, Step C, 20.0 mg, 0.0357 mmol), formaldehyde (8.68 mg, 0.107 mmol, 37%), NaBH(OAc)$_3$ (37.9 mg, 0.179 mmol) and THF (10 mL). The reaction mixture was stirred at room temperature until the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (dichloromethane/7 M NH$_3$ in MeOH from 100/1 to 10/1, v/v) to afford product (19.1 mg, 93.2%). LRMS (APCI pos): >99% purity, 254 nm, m/e 573 (M). $^1$H NMR (400 MHz, CDCl$_3$) δ 11.83 (s, 1H), 8.44 (d, 1H), 8.41 (d, 1H), 8.24 (d, 1H), 7.94 (dd, 1H), 7.61 (m, 2H), 7.38 (m, 1H), 7.21-7.28 (m, 4H), 6.46 (d, 1H), 2.99 (m, 2H), 2.91 (m, 1H), 2.34 (s, 3H), 2.06-2.17 (m, 4H), 1.94 (m, 2H).

Example 156

(R)—N-(3-fluoro-4-(2-(4-(3-hydroxypyrrolidine-1-carbonyl)phenyl)thieno[3,2-b]pyridin-7-yloxy)phenyl)-2-(4-fluorophenyl)-3-oxo-2,3-dihydropyridazine-4-carboxamide

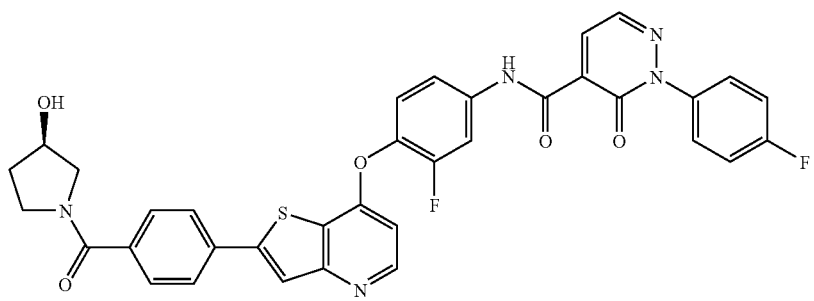

Step A: Preparation of 2-(4-fluorophenyl)-3-oxo-2,3-dihydropyridazine-4-carbonyl fluoride: Prepared according to the procedure for Example 112, Step A substituting 2-(4-fluorophenyl)-3-oxo-2,3-dihydropyridazine-4-carboxylic acid (2.00 g, 8.54 mmol) for 1-((4-fluorophenyl)carbamoyl)cyclopropanecarboxylic acid. Obtained the product (1.76 g, 70%) as a yellow solid. $^{19}$F NMR (CDCl$_3$, 376 MHz) δ 31.5 (s), −111.8 (m).

Step B: Preparation of 4-(7-(4-amino-2-fluorophenoxy)thieno[3,2-b]pyridin-2-yl)benzoic acid: A round-bottomed flask was charged with 4-(methoxycarbonyl)phenylboronic acid (4.95 g, 27.5 mmol), 3-fluoro-4-(2-iodothieno[3,2-b]pyridin-7-yloxy)aniline (Example 6, Step A, 7.08 g, 18.3 mmol), cesium carbonate (8.96 g, 27.5 mmol) and 2-methoxyethanol (1.40 g, 18.3 mmol) (100 mL). The mixture was purged with nitrogen for 10 minutes and then Pd(PPh$_3$)$_4$ (1.27 g, 1.10 mmol) was added as a solid. The mixture was heated under nitrogen to 90° C. for 48 hours and then cooled to room temperature. NaOH (10 mL, 5N) was added and the mixture was stirred for 2 hours. The mixture was extracted with EtOAc (2×300 mL). The aqueous phase was acidified with HCl (2N) to pH 7. The formed precipitate was collected by filtration and washed with water to get the product (7.6 g, 109%, contains residual water) as a beige solid. LRMS (esi+) 381 m/z (M+1) detected.

Step C: Preparation of 4-(7-(2-fluoro-4-(2-(4-fluorophenyl)-3-oxo-2,3-dihydropyridazine-4-carboxamido)phenoxy)thieno[3,2-b]pyridin-2-yl)benzoic acid: Prepared according to the procedure for Example 112, Step B substituting 4-(7-(4-amino-2-fluorophenoxy)thieno[3,2-b]pyridin-2-yl)benzoic acid (1.25 g, 3.29 mmol) for 4-(7-(4-amino-2-fluorophenoxy)thieno[3,2-b]pyridin-2-yl)-N-methylbenzamide and 2-(4-fluorophenyl)-3-oxo-2,3-dihydropyridazine-4-carbonyl fluoride (1.70 g, 5.75 mmol) for 1-((4-fluorophenyl)carbamoyl)cyclopropanecarbonyl fluoride. When the reaction was complete, water (20 mL) was added and the product (1.59 g, 80%) was collected by filtration to get a brown solid. LRMS (esi+) 597 m/z (M+1) detected.

Step D: Preparation of (R)—N-(3-fluoro-4-(2-(4-(3-hydroxypyrrolidine-1-carbonyl)phenyl)thieno[3,2-b]pyridin-7-yloxy)phenyl)-2-(4-fluorophenyl)-3-oxo-2,3-dihydropyridazine-4-carboxamide: A capped vial was charged with 4-(7-(2-fluoro-4-(1-(4-fluorophenyl)-6-oxo-1,6-dihydropyridazine-5-carboxamido)phenoxy)thieno[3,2-b]pyridin-2-yl)benzoic acid (0.100 g, 0.168 mmol), HOBT-H$_2$O (0.103 g, 0.671 mmol), EDCI (0.129 g, 0.671 mmol), and DMF (2 mL). After stirring for 45 minutes, (R)-pyrrolidin-3-ol (0.0584 g, 0.671 mmol) and Hunig's base (0.175 ml, 1.01 mmol) were added. After stirring for 18 hours, water (20 mL) was added. The formed precipitate was isolated by filtration. After drying, (62 mg, 55%) of product was isolated as orange solid. LRMS (esi+) 666 m/z (M+1) detected. $^1$H NMR (CDCl$_3$, 400 MHz) δ 11.84 (s, 1H), 8.47 (s, 1H), 8.39 (d, J=4 Hz, 1H), 8.22 (d, J=4 Hz, 1H), 7.97 (m, 1H), 7.76 (m, 3H), 7.62 (m, 4H), 7.39 (d, J=9 Hz, 1H), 7.26 (m, 3H), 6.52 (d, J=6 Hz, 1H), 4.50 (br s, 1H), 3.72 (m, 5H), 2.07 (m, 2H).

Example 157

N-(4-(2-(4-(1,3-dihydroxypropan-2-ylcarbamoyl)phenyl)thieno[3,2-b]pyridin-7-yloxy)-3-fluorophenyl)-2-(4-fluorophenyl)-3-oxo-2,3-dihydropyridazine-4-carboxamide

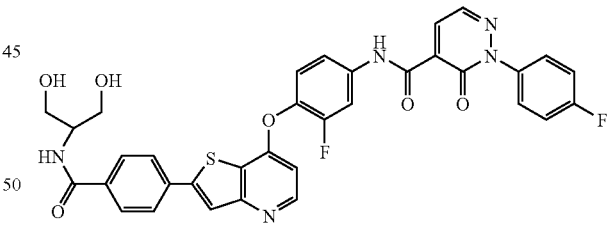

Prepared according to the procedure for Example 156, Step D substituting 2-aminopropane-1,3-diol (0.0611 g, 0.671 mmol) for (R)-pyrrolidin-3-ol. The reaction was stirred for 18 hours and water (20 mL) was added at the end of the reaction to result in formation of a precipitate. Filtration of the precipitate followed by drying under high vacuum gave the product (16 mg, 13%) as orange solid. LRMS (esi+) 670 m/z (M+1) detected. $^1$H NMR (CDCl$_3$, 400 MHz) δ 11.71 (s, 1H), 8.55 (d, J=6 Hz, 1H), 8.38 (d, J=4 Hz, 1H), 8.27 (d, J=4 Hz, 1H), 8.20 (s, 1H), 8.09 (m, 1H), 8.01 (m, 3H), 7.69 (m, 2H), 7.58 (m, 2H), 7.42 (t, J=9 Hz, 2H), 6.71 (d, J=5 Hz, 1H), 4.68 (br s, 1H), 4.01 (m, 1H), 3.54 (m, 6H).

Example 158

N-(3-fluoro-4-(2-(4-(1-methylpiperidin-4-ylcarbamoyl)phenyl)thieno[3,2-b]pyridin-7-yloxy)phenyl)-2-(4-fluorophenyl)-3-oxo-2,3-dihydropyridazine-4-carboxamide

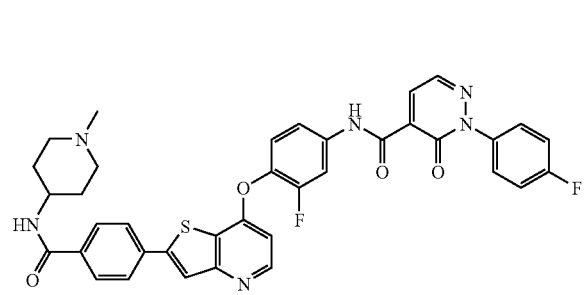

Prepared according to the procedure for Example 156, Step D substituting 1-methylpiperidin-4-amine (0.076 g, 0.671 mmol) for (R)-pyrrolidin-3-ol. The product was isolated by filtration (156 mg, 48%) as orange solid. LRMS (esi+) 693 m/z (M+1) detected. $^1$H NMR (CDCl$_3$, 400 MHz) δ 11.85 (s, 1H), 8.50 (d, J=6 Hz, 1H), 8.41 (d, J=4 Hz, 1H), 8.24 (d, J=4 Hz, 1H), 7.99 (m, 1H), 7.82 (m, 4H), 7.61 (m, 2H), 7.41 (d, J=10 Hz, 1H), 7.27 (m, 3H), 6.53 (d, J=6 Hz, 1H), 6.11 (d, J=7 Hz, 1H), 4.03 (m, 1H), 2.86 (m, 2H), 2.33 (s, 3H), 2.20 (m, 2H), 2.09 (m, 2H), 1.66 (m, 2H).

Example 159

4-benzyl-N-(3-fluoro-4-(2-(4-(methylcarbamoyl)phenyl)thieno[3,2-b]pyridin-7-yloxy)phenyl)-3-oxo-3,4-dihydropyrazine-2-carboxamide

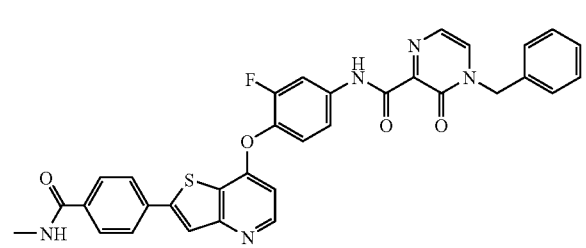

Prepared from 4-(7-(4-amino-2-fluorophenoxy)thieno[3,2-b]pyridin-2-yl)-N-methylbenzamide (Example 95, Step A) and 4-benzyl-3-oxo-3,4-dihydropyrazine-2-carboxylic acid (Example 149, Step B) according to the procedure of Example 89. The crude was purified by silica gel flash column chromatography (5% MeOH in CH$_2$Cl$_2$) to afford 7.3 mg (32%) of the desired product. LRMS (APCI pos) m/e 606.2 (M+1). $^1$H-NMR (400 MHz, CDCl$_3$/CD$_3$OD) δ 8.47 (d, 1H), 8.06 (dd, 1H), 7.91 (m, 6H), 7.79 (m, 1H), 7.54 (m, 1H), 7.39 (m, 6H), 6.64 (d, 1H), 5.33 (s, 2H), 2.98 (s, 3H); $^{19}$F NMR (376 MHz, CDCl$_3$/CD$_3$OD) δ −128.3.

Example 160

N-(3-Fluoro-4-(2-(1-isopropylpiperidin-4-yl)thieno[3,2-b]pyridin-7-yloxy)phenyl)-2-(4-fluorophenyl)-3-oxo-2,3-dihydropyridazine-4-carboxamide

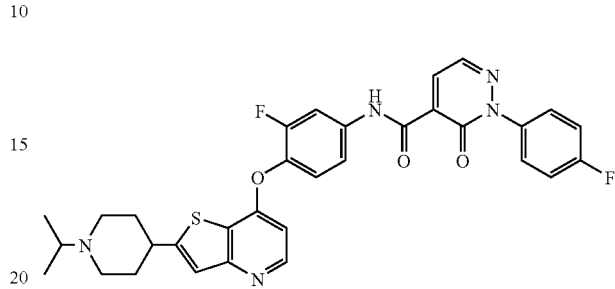

A round-bottomed flask was charged with N-(3-fluoro-4-(2-(piperidin-4-yl)thieno[3,2-b]pyridin-7-yloxy)phenyl)-2-(4-fluorophenyl)-3-oxo-2,3-dihydropyridazine-4-carboxamide (Example 154, Step C, 35.0 mg, 0.0625 mmol), propan-2-one (36.3 mg, 0.625 mmol), NaBH(OAc)$_3$ (66.3 mg, 0.313 mmol) and THF (10 mL). The reaction mixture was stirred at room temperature until the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford crude product. The crude product was further purified by preparative reverse phase HPLC to afford product (5.8 mg, 15.4%). LRMS (APCI pos): >99% purity, 254 nm, m/e 602 (M+1). $^1$H NMR (400 MHz, DMSO-d$_6$) δ 11.71 (s, 1H), 8.52 (d, 1H), 8.39 (d, 1H), 8.26 (d, 1H), 8.05 (m, 1H), 7.69 (m, 2H), 7.61 (m, 1H), 7.52 (m, 1H), 7.34-7.46 (m, 3H), 6.70 (d, 1H), 3.12-3.41 (m, 6H), 2.33 (m, 2H), 1.97 (m, 2H), 1.28 (d, 6H).

Example 161

N-(3-Fluoro-4-(2-(4-oxocyclohex-1-enyl)thieno[3,2-b]pyridin-7-yloxy)phenyl)-2-(4-fluorophenyl)-3-oxo-2,3-dihydropyridazine-4-carboxamide

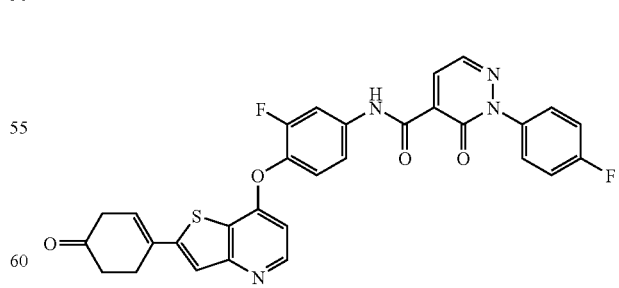

Step A: Preparation of 4-(2-(1,4-dioxaspiro[4.5]dec-7-en-8-yl)thieno[3,2-b]pyridin-7-yloxy)-3-fluoroaniline: A round-bottomed flask was charged with 3-fluoro-4-(2-iodothieno[3,2-b]pyridin-7-yloxy)aniline (Example 6, Step A, 0.461 g, 1.19 mmol), 1,4-dioxaspiro[4.5]dec-7-en-8-ylboronic acid (0.659 g, 3.58 mmol), tetrakis(triphenylphosphine) palladium (0.276 g, 0.239 mmol), Na$_2$CO$_3$ (2.98 ml, 5.97 mmol) and dioxane (50 mL). The reaction mixture was stirred at 100° C. until the starting material had been consumed (overnight). Then the reaction was cooled to room temperature and partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 50/1 to 10/1, v/v) to afford product (0.418 g, 87.9%). LRMS (APCI pos): >97% purity, 254 nm, m/e 399 (M+1). $^1$H NMR (400 MHz, CDCl$_3$) δ 8.40 (d, 1H), 7.34 (s, 1H), 7.01 (t, 1H), 6.42-6.56 (m, 3H), 6.28 (s, 1H), 4.04 (s, 4H), 3.82 (br s, 2H), 2.80 (m, 2H), 2.52 (m, 2H), 1.98 (m, 2H).

Step B: Preparation of N-(4-(2-(1,4-dioxaspiro[4.5]dec-7-en-8-yl)thieno[3,2-b]pyridin-7-yloxy)-3-fluorophenyl)-2-(4-fluorophenyl)-3-oxo-2,3-dihydropyridazine-4-carboxamide: A round-bottomed flask was charged with 4-(2-(1,4-dioxaspiro[4.5]dec-7-en-8-yl)thieno[3,2-b]pyridin-7-yloxy)-3-fluoroaniline (100.0 mg, 0.256 mmol), 2-(4-fluorophenyl)-3-oxo-2,3-dihydropyridazine-4-carboxylic acid (Example 104, Step C, 70.53 mg, 0.301 mmol), N$^1$-((ethylimino)methylene)-N$^3$,N$^3$-dimethylpropane-1,3-diamine hydrochloride (144.3 mg, 0.753 mmol), 1H-benzo[d][1,2,3]triazol-1-ol (101.7 mg, 0.753 mmol), N-ethyl-N-isopropylpropan-2-amine (162.2 mg, 1.255 mmol) and DMF (10 mL). The reaction mixture was stirred at room temperature until LC-MS showed that the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 50/1 to 10/1, v/v) to afford product (103 mg, 66.8%). LRMS (APCI pos): >99% purity, 254 nm, m/e 615 (M+1). $^1$H NMR (400 MHz, CDCl$_3$) δ 11.82 (s, 1H), 8.41 (m, 2H), 8.23 (d, 1H), 7.98 (d, 1H), 7.60 (m, 2H), 7.39 (m, 2H), 7.24 (m, 3H), 6.46 (d, 1H), 6.28 (m, 1H), 4.04 (s, 4H), 2.78 (m, 2H), 2.52 (m, 2H), 1.98 (m, 2H).

Step C: Preparation of N-(3-fluoro-4-(2-(4-oxocyclohex-1-enyl)thieno[3,2-b]pyridin-7-yloxy)phenyl)-2-(4-fluorophenyl)-3-oxo-2,3-dihydropyridazine-4-carboxamide: A round-bottomed flask was charged with N-(4-(2-(1,4-dioxaspiro[4.5]dec-7-en-8-yl)thieno[3,2-b]pyridin-7-yloxy)-3-fluorophenyl)-2-(4-fluorophenyl)-3-oxo-2,3-dihydropyridazine-4-carboxamide (153 mg, 0.249-mmol) and CF$_3$COOH (10 mL). The reaction mixture was stirred at room temperature until the starting material had been consumed (overnight). Then the solvent was removed and the residue was purified by silica gel chromatography (dichloromethane/7 M NH$_3$ in MeOH from 50/1 to 10/1, v/v) to give product (40.8 mg, 28.7%). LRMS (APCI pos): >99% purity, 254 nm, m/e 571 (M+1). $^1$H NMR (400 MHz, CDCl$_3$) δ 11.84 (s, 1H), 8.45 (d, 1H), 8.41 (d, 1H), 8.24 (d, 1H), 7.96 (d, 1H), 7.58-7.62 (m, 2H), 7.40 (m, 1H), 7.20-7.28 (m, 4H), 6.51 (d, 1H), 6.42 (m, 1H), 3.14 (m, 2H), 3.02 (m, 2H), 2.71 (m, 2H).

Example 162

N-(3-Fluoro-4-(2-(4-oxocyclohexyl)thieno[3,2-b]pyridin-7-yloxy)phenyl)-2-(4-fluorophenyl)-3-oxo-2,3-dihydropyridazine-4-carboxamide

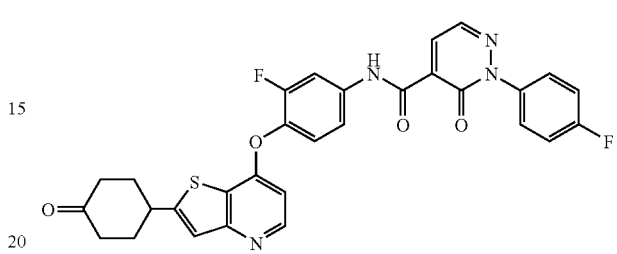

Step A: Preparation of 4-(2-(1,4-dioxaspiro[4.5]decan-8-yl)thieno[3,2-b]pyridin-7-yloxy)-3-fluoroaniline: A round-bottomed flask was charged with 4-(2-(1,4-dioxaspiro[4.5]dec-7-en-8-yl)thieno[3,2-b]pyridin-7-yloxy)-3-fluoroaniline (Example 161, Step A, 50.0 mg, 0.125 mmol), palladium on carbon (44.6 mg, 0.0376 mmol, 10%) and MeOH (10 mL). The air was exchanged with nitrogen three times and then was exchanged with hydrogen another three times. Then the reaction mixture was stirred under hydrogen at room temperature until the starting material had been consumed (overnight). The mixture was filtrated to remove the palladium on carbon and then the solvent was removed under reduced pressure to afford crude product. The crude product was purified by silica gel chromatography (DCM/7 M NH$_3$ in MeOH from 100/1 to 10/1, v/v) to afford product (12.8 mg, 25.5%). LRMS (APCI pos): m/e 401 (M+1). $^1$H NMR (400 MHz, CDCl$_3$) δ 8.40 (m, 1H), 7.25 (s, 1H), 7.02 (t, 1H), 6.42-6.60 (m, 3H), 4.00 (s, 4H), 3.81 (br s, 2H), 2.89 (m, 1H), 2.14 (m, 2H), 1.90 (m, 4H), 1.72 (m, 2H).

Step B: Preparation of N-(4-(2-(1,4-dioxaspiro[4.5]decan-8-yl)thieno[3,2-b]pyridin-7-yloxy)-3-fluorophenyl)-2-(4-fluorophenyl)-3-oxo-2,3-dihydropyridazine-4-carboxamide: A 100 mL, single-neck, round-bottomed flask was charged with 4-(2-(1,4-dioxaspiro[4.5]decan-8-yl)thieno[3,2-b]pyridin-7-yloxy)-3-fluoroaniline (12.8 mg, 0.032 mmol), 2-(4-fluorophenyl)-3-oxo-2,3-dihydropyridazine-4-carboxylic acid (Example 104, Step C, 22.5 mg, 0.096 mmol), N$^1$-((ethylimino)methylene)-N$^3$,N$^3$-dimethylpropane-1,3-diamine hydrochloride (30.6 mg, 0.160 mmol), 1H-benzo[d][1,2,3]triazol-1-ol (21.6 mg, 0.160 mmol), N-ethyl-N-isopropylpropan-2-amine (41.3 mg, 0.320 mmol) and DMF (10 mL). The reaction mixture was stirred at room temperature until LC-MS showed that the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 50/1 to 10/1, v/v) to afford product (13.3 mg, 67.5%). LRMS (APCI pos): m/e 617 (M+1).

Step C: Preparation of N-(3-Fluoro-4-(2-(4-oxocyclohexyl)thieno[3,2-b]pyridin-7-yloxy)phenyl)-2-(4-fluorophenyl)-3-oxo-2,3-dihydropyridazine-4-carboxamide: A round-bottomed flask was charged with N-(4-(2-(1,4-dioxaspiro[4.5]decan-8-yl)thieno[3,2-b]pyridin-7-yloxy)-3-fluorophenyl)-2-(4-fluorophenyl)-3-oxo-2,3-dihydropyridazine-4-carboxamide (13.3 mg, 0.0216 mmol) and CF₃COOH (5 mL). The reaction mixture was stirred at room temperature the starting material had been consumed (1 hour). Then the solvent was removed and the residue was purified by silica gel chromatography (DCM/7 M NH₃ in MeOH from 50/1 to 10/1, v/v) to give product (5.3 mg, 42.9%). LRMS (APCI pos): >99% purity, 254 nm, m/e 573 (M+1). ¹H NMR (400 MHz, CD₃OD) δ 11.84 (s, 1H), 8.46 (d, 1H), 8.41 (d, 1H), 8.24 (d, 1H), 7.95 (dd, 1H), 7.57-7.65 (m, 2H), 7.39 (m, 1H), 7.34 (s, 1H), 7.21-7.30 (m, 3H), 6.49 (d, 1H), 3.45 (m, 1H), 2.34-2.61 (m, 6H), 2.09 (m, 2H).

Example 163

N-(4-(2-(4-(Dimethylamino)cyclohexyl)thieno[3,2-b]pyridin-7-yloxy)-3-fluorophenyl)-2-(4-fluorophenyl)-3-oxo-2,3-dihydropyridazine-4-carboxamide

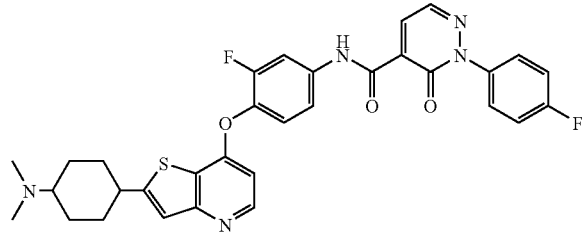

A round-bottomed flask was charged with N-(3-fluoro-4-(2-(4-oxocyclohexyl)thieno[3,2-b]pyridin-7-yloxy)phenyl)-2-(4-fluorophenyl)-3-oxo-2,3-dihydropyridazine-4-carboxamide (Example 162, Step C, 3.2 mg, 0.0056 mmol), dimethylamine (1.3 mg, 0.028 mmol), NaBH(OAc)₃ (3.6 mg, 0.017 mmol) and CH₂Cl₂ (2 mL). The reaction mixture was stirred at room temperature until the starting material had been consumed (overnight). Then the reaction was partitioned between EtOAc (30 mL) and H₂O (30 mL). The phases were separated and the aqueous phase was re-extracted with EtOAc (3×30 mL). The combined organic layers were dried (Na₂SO₄), filtered and concentrated to yield a crude product. The crude product was purified by silica gel chromatography (DCM/7 M NH₃ in MeOH from 50/1 to 10/1, v/v) to afford product (2.1 mg, 62%). LRMS (APCI pos): m/e 602 (M+1). ¹H NMR (400 MHz, CDCl₃) δ 11.82 (s, 1H), 8.43 (d, 1H), 8.41 (d, 1H), 8.24 (d, 1H), 7.95 (dd, 1H), 7.60 (m, 2H), 7.38 (m, 1H), 7.21-7.32 (m, 4H), 6.45 (d, 1H), 3.22 (m, 1H), 2.30 (s, 6H), 2.22 (m, 1H), 1.55-1.94 (m, 8H).

Example 164

5-(2,5-difluoro-4-(2-(4-(morpholine-4-carbonyl)phenyl)thieno[3,2-b]pyridin-7-yloxy)phenyl)-3-methyl-2-(phenylamino)pyrimidin-4(3H)-one

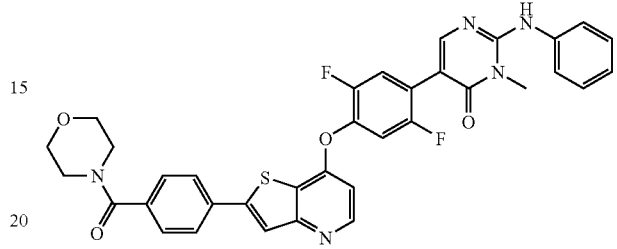

Step A: Preparation of 5-(2,5-difluoro-4-methoxyphenyl)-3-methyl-2-(phenylamino)pyrimidin-4(3H)-one: A suspension of 5-bromo-3-methyl-2-(phenylamino)pyrimidin-4(3H)-one (Example 143, Step C, 0.100 g, 0.357 mmol), 2,5-difluoro-4-methoxyphenylboronic acid (0.081 g, 0.428 mmol), Pd(PPh₃)₄ (0.021 g, 0.018 mmol) and lithium chloride (0.076 g, 1.78 mmol) in dioxane (2 mL) and 2M aqueous Na₂CO₃ (2 mL) was stirred at 100° C. for 15 minutes. The reaction mixture was cooled to room temperature and then partitioned between EtOAc and H₂O. The layers were separated and the aqueous layer was re-extracted with EtOAc (1×). The combined organic layers were dried over Na₂SO₄, filtered and concentrated. The crude product was purified by flash column chromatography, eluting with 5:1 CH₂Cl₂/EtOAc. The product was obtained (77 mg; 63%) as a grey-white solid. ¹H NMR (400 MHz, DMSO-d₆) δ 8.95 (br s, 1H), 7.74 (s, 1H), 7.55-7.49 (m, 2H), 7.39-7.28 (m, 3H), 7.18-7.13 (m, 2H), 3.86 (s, 3H), 3.54 (s, 3H). LRMS (ESI pos) m/e 344 (M+1).

Step B: Preparation of 5-(2,5-difluoro-4-hydroxyphenyl)-3-methyl-2-(phenylamino)pyrimidin-4(3H)-one: 5-(2,5-difluoro-4-methoxyphenyl)-3-methyl-2-(phenylamino)pyrimidin-4(3H)-one (0.066 g, 0.192 mmol) was dissolved in AcOH (2 mL) and HBr (1.087 ml, 9.612 mmol; 48 wt % in H₂O) was added. The mixture was stirred at 125° C. for 3 days. The reaction mixture was cooled to room temperature and then diluted with H₂O. The pH of the reaction mixture was adjusted to a pH of about 5 with 6M aqueous NaOH, which resulted in the formation of an off-white precipitate that was filtered and washed with H₂O. The solid was dried directly in the fritted funnel under vacuum overnight and then dissolved through with MeOH/THF and concentrated. The product was obtained (58 mg; 92%) as an off-white solid. ¹H NMR (400 MHz, DMSO-d₆) δ 10.33 (br s, 1H), 8.91 (br s, 1H), 7.70 (s, 1H), 7.55-7.48 (m, 2H), 7.36 (t, 2H), 7.23 (m, 1H), 7.14 (m, 1H), 6.77 (m, 1H), 3.53 (s, 3H). LRMS (ESI pos) m/e 330 (M+1).

Step C: Preparation of 5-(2,5-difluoro-4-(2-iodothieno[3,2-b]pyridin-7-yloxy)phenyl)-3-methyl-2-(phenylamino)pyrimidin-4(3H)-one: A mixture of 5-(2,5-difluoro-4-hydroxyphenyl)-3-methyl-2-(phenylamino)pyrimidin-4(3H)-one (0.031 g, 0.093 mmol), 7-chloro-2-iodothieno[3,2-b]pyridine (0.025 g, 0.085 mmol; prepared according to the procedure of Ragan, J. A. Org. Proc. Res. 2003, 7, 676) and DMAP (0.010 g, 0.085 mmol) in bromobenzene (1.5 mL) under nitrogen was stirred at 150° C. for 6 days. The reaction was concentrated in vacuo to remove as much bromobenzene as possible and then purified directly by flash column chromatography, eluting with 20:1 CH$_2$Cl$_2$/MeOH. The product was obtained (10.5 mg; 21%) as a yellow solid. LRMS (APCI pos) m/e 589 (M+1).

Step D: Preparation of 5-(2,5-difluoro-4-(2-(4-(morpholine-4-carbonyl)phenyl)thieno[3,2-b]pyridin-7-yloxy)phenyl)-3-methyl-2-(phenylamino)pyrimidin-4(3H)-one: A suspension of 5-(2,5-difluoro-4-(2-iodothieno[3,2-b]pyridin-7-yloxy)phenyl)-3-methyl-2-(phenylamino)pyrimidin-4(3H)-one (0.0105 g, 0.0178 mmol), 4-(morpholine-4-carbonyl)phenylboronic acid (0.005 g, 0.021 mmol), Pd(PPh$_3$)$_4$ (0.001 g, 0.001 mmol) and lithium chloride (0.003 g, 0.071 mmol) in dioxane (0.5 mL) and 2M aqueous Na$_2$CO$_3$ (0.5 mL) was stirred at 100° C. for 30 minutes. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 20:1 CH$_2$Cl$_2$/MeOH. The product was obtained (4.5 mg; 39%) as a pale yellow solid. $^1$H NMR (400 MHz, CDCl$_3$) δ 8.54 (br s, 1H), 7.96 (s, 1H), 7.84-7.77 (m, 3H), 7.57-7.46 (m, 5H), 7.42 (t, 2H), 7.24 (m, 1H), 7.08 (m, 1H), 6.71-6.62 (m, 2H), 3.99-3.40 (m, 8H), 3.68 (s, 3H). LRMS (APCI pos) m/e 652 (M+1).

Example 165

2-(benzylamino)-5-(3-fluoro-4-(2-(4-(morpholine-4-carbonyl)phenyl)thieno[3,2-b]pyridin-7-yloxy)phenyl)-3-methylpyrimidin-4(3H)-one Step B: Preparation of 2-(benzylamino)-5-(4-(benzyloxy)-3-fluorophenyl)-3-methylpyrimidin-4(3H)-one: A suspension of 2-(benzylamino)-5-bromo-3-methylpyrimidin-4(3H)-one (0.130 g, 0.442 mmol), 4-(benzyloxy)-3-fluorophenylboronic acid (0.130 g, 0.530 mmol), Pd(PPh$_3$)$_4$ (0.026 g, 0.022 mmol) and lithium chloride (0.075 g, 1.77 mmol) in dioxane (2 mL) and 2M aqueous Na$_2$CO$_3$ (2 mL) was stirred at 100° C. for 1 hour. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 10:1 CH$_2$Cl$_2$/EtOAc. The product was obtained (146 mg; 80%) as an off-white foam solid. $^1$H NMR (400 MHz, DMSO-d$_6$) δ 7.89 (s, 1H), 7.55 (dd, 1H), 7.48-7.43 (m, 2H), 7.43-7.29 (m, 8H), 7.26-7.15 (m, 2H), 5.18 (s, 2H), 4.62 (d, 2H), 3.42 (s, 3H). LRMS (APCI pos) m/e 416 (M+1).

Step C: Preparation of 2-(benzylamino)-5-(3-fluoro-4-hydroxyphenyl)-3-methylpyrimidin-4(3H)-one: A solution of 2-(benzylamino)-5-(4-(benzyloxy)-3-fluorophenyl)-3-methylpyrimidin-4(3H)-one (0.145 g, 0.349 mmol) in TFA (4 mL) was stirred at 40° C. for 5 hours. The reaction was concentrated to dryness and then dried under vacuum to yield a crude residue that was purified by flash column chromatography, eluting with 20:1 CH$_2$Cl$_2$/MeOH. The product was obtained (105 mg; 93%) as a white foam solid. $^1$H NMR (400 MHz, DMSO-d$_6$) δ 9.74 (br s, 1H), 7.93 (br s, 1H), 7.84 (s, 1H), 7.45 (m, 1H), 7.38-7.29 (m, 4H), 7.27-7.20 (m, 2H), 6.89 (t, 1H), 4.62 (d, 2H), 3.41 (s, 3H). LRMS (APCI pos) m/e 326 (M+1).

Step D: Preparation of 2-(benzylamino)-5-(3-fluoro-4-(2-iodothieno[3,2-b]pyridin-7-yloxy)phenyl)-3-methylpyrimi-

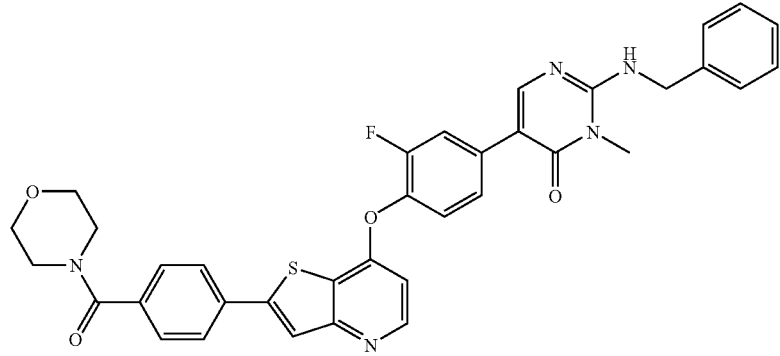

Step A: Preparation of 2-(benzylamino)-5-bromo-3-methylpyrimidin-4(3H)-one: A mixture of 5-bromo-2-chloro-3-methylpyrimidin-4(3H)-one (Example 143, Step B, 0.100 g, 0.448 mmol), phenylmethanamine (0.064 ml, 0.582 mmol) and NaHCO$_3$ (0.150 g, 1.79 mmol) in n-BuOH (3 mL) was stirred at 60° C. for 4 hours. The reaction mixture was cooled to room temperature and then diluted with EtOAc. The EtOAc layer was washed with H$_2$O and saturated aqueous NaCl. The aqueous phase was re-extracted with EtOAc (1×). The combined EtOAc layers were dried (Na$_2$SO$_4$), filtered and concentrated to yield the desired product (0.130 g, 99%) as a pale yellow solid that was used without further purification. $^1$H NMR (400 MHz, DMSO-d$_6$) δ 7.96 (t, 1H), 7.90 (s, 1H), 7.32 (s, 2H), 7.31 (m, 2H), 7.23 (m, 1H), 4.57 (d, 2H), 3.39 (s, 3H). LRMS (ESI pos) m/e 294, 296 (M+, Br pattern).

din-4(3H)-one: A mixture of 2-(benzylamino)-5-(3-fluoro-4-hydroxyphenyl)-3-methylpyrimidin-4(3H)-one (0.036 g, 0.112 mmol), 7-chloro-2-iodothieno[3,2-b]pyridine (0.030 g, 0.102 mmol; prepared according to the procedure of Ragan, J. A. Org. Proc. Res. 2003, 7, 676) and DMAP (0.025 g, 0.20 mmol) in bromobenzene (1.5 mL) under nitrogen was stirred at 150° C. for 3 days. The reaction was concentrated in vacuo to remove as much bromobenzene as possible. MeOH was added to the residue and a brown solid precipitate was filtered and discarded. The filtrate was concentrated and then purified by flash column chromatography, eluting with 20:1 CH$_2$Cl$_2$/MeOH. The product was obtained (15.7 mg; 27%) as a yellow solid. LRMS (APCI pos) m/e 585 (M+1).

Step E: Preparation of 2-(benzylamino)-5-(3-fluoro-4-(2-(4-(morpholine-4-carbonyl)phenyl)thieno[3,2-b]pyridin-7-yloxy)phenyl)-3-methylpyrimidin-4(3H)-one: A suspension of 2-(benzylamino)-5-(3-fluoro-4-(2-iodothieno[3,2-b]pyridin-7-yloxy)phenyl)-3-methylpyrimidin-4(3H)-one (0.0157 g, 0.0269 mmol), 4-(morpholine-4-carbonyl)phenylboronic acid (0.008 g, 0.032 mmol), Pd(PPh$_3$)$_4$ (0.002 g, 0.002 mmol) and lithium chloride (0.005 g, 0.107 mmol) in dioxane (0.5 mL) and 2M aqueous Na$_2$CO$_3$ (0.5 mL) was stirred at 100° C. for 30 minutes. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 20:1 CH$_2$Cl$_2$/MeOH. The product was obtained (11.4 mg; 66%) as a pale yellow solid. $^1$H NMR (400 MHz, CDCl$_3$) δ 8.50 (d, 1H), 7.99 (s, 1H), 7.84-7.78 (m, 3H), 7.66 (dd, 1H), 7.55-7.45 (m 3H), 7.43-7.32 (m, 5H), 7.32-7.24 (m, 2H), 658 (d, 1H), 4.72 (d, 2H), 3.96-3.60 (m, 8H), 3.50 (s, 3H). LRMS (APCI pos) m/e 648 (M+1).

Example 166

6-(3-fluoro-4-(2-(4-(morpholine-4-carbonyl)phenyl)thieno[3,2-b]pyridin-7-yloxy)phenyl)-1-phenyl-2,3-dihydroimidazo[1,2-a]pyrimidin-5(1H)-one

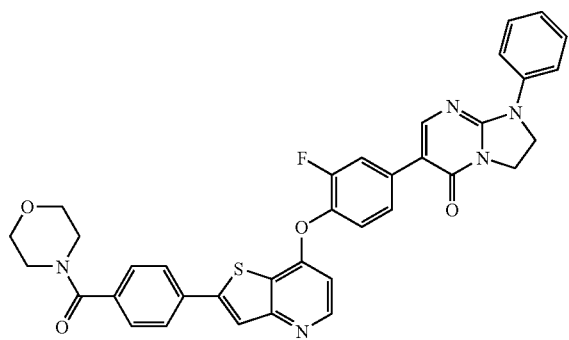

Step A: Preparation of 4-methoxy-N-phenylpyrimidin-2-amine: A sealed tube was charged with 2-chloro-4-methoxypyrimidine (1.00 g, 6.92 mmol) in 2-propanol (5 mL). Aniline (0.757 ml, 8.30 mmol) and DIEA (1.45 ml, 8.30 mmol) were added and the reaction mixture was heated at 100° C. until the reaction was complete by HPLC. The reaction mixture was cooled to room temperature. The resulting thick suspension was filtered, washed with ethanol, collected and dried under vacuum to yield the desired product (0.164 g) as a white solid. The filtrate was concentrated and then partitioned between EtOAc and saturated aqueous NaCl. The phases were separated, and the aqueous phase was re-extracted with EtOAc (1×). The combined organic layers were dried (Na$_2$SO$_4$), filtered and concentrated to yield a yellow solid. The crude product was purified by flash column chromatography, eluting with 25:1 dichloromethane/EtOAc. The desired product (0.548 g) was obtained as a white solid which was combined with the filtered product to yield 0.712 g (51%) total desired product. $^1$H-NMR (400 MHz, DMSO-d$_6$) δ 9.51 (s, 1H), 8.20 (d, 1H), 7.77 (d, 2H), 7.27 (t, 2H), 6.94 (t, 1H), 6.28 (d, 1H), 3.91 (s, 3H). LRMS (ESI pos) m/e 202 (M+1).

Step B: Preparation of 2-(phenylamino)pyrimidin-4(3H)-one: To a solution of 4-methoxy-N-phenylpyrimidin-2-amine (0.632 g, 3.14 mmol) in acetic acid (20 mL) was added HBr (2.132 ml, 18.84 mmol; 48 wt % in H$_2$O). The reaction mixture was heated at a temperature ranging from about 90° C. to about 95° C. for 3 hours. The reaction mixture was cooled to room temperature and diluted with H$_2$O. The pH of the reaction mixture was adjusted to about 5 to about 6 with 6M aqueous NaOH which resulted in the formation of a solid precipitate. The solid was filtered, washed with H$_2$O, collected and dried under vacuum to yield the desired product (0.553 g, 94%) as a white solid. $^1$H-NMR (400 MHz, DMSO-d$_6$) δ 10.74 (br s, 1H), 8.81 (br s, 1H), 7.76 (s, 1H), 7.60 (d, 2H), 7.31 (t, 2H), 7.02 (t, 1H), 5.81 (s, 1H). LRMS (ESI pos) m/e 188 (M+1).

Step C: Preparation of 5-bromo-2-(phenylamino)pyrimidin-4(3H)-one: To a suspension of 2-(phenylamino)pyrimidin-4(3H)-one (0.200 g, 1.07 mmol) in CHCl$_3$ (5 mL) and a small amount of MeOH at 0° C. was added bromine (0.0547 ml, 1.07 mmol). The reaction was stirred for 40 minutes, diluted with H$_2$O, and then quenched with 10% sodium bisulfite solution. The reaction mixture was diluted with EtOAc, the layers were separated and the aqueous layer was re-extracted with EtOAc (1×). The combined organic layers were dried over Na$_2$SO$_4$, filtered and concentrated. The product was obtained (0.284 g; 100%) as a white solid. $^1$H-NMR (400 MHz, DMSO-d$_6$) δ 11.32 (br s, 1H), 8.89 (br s, 1H), 8.04 (s, 1H), 7.55 (d, 2H), 7.33 (m, 2H), 7.06 (t, 1H). LRMS (ESI pos) m/e 266, 268 (M+, Br pattern).

Step D: Preparation of 6-bromo-1-phenyl-2,3-dihydroimidazo[1,2-a]pyrimidin-5(1H)-one: To a solution of 5-bromo-2-(phenylamino)pyrimidin-4(3H)-one (0.082 g, 0.308 mmol) in DMF (8 mL) was added K$_2$CO$_3$ (0.043 g, 0.308 mmol) and 1,2-dibromoethane (0.029 ml, 0.339 mmol). The reaction was stirred at 60° C. overnight, cooled to room temperature and then partitioned between EtOAc and saturated NaCl. The layers were separated and the aqueous layer was re-extracted with EtOAc (1×). The combined organic layers were dried over Na$_2$SO$_4$, filtered and concentrated. The crude product was purified by trituration with Et$_2$O/CH$_2$Cl$_2$. The resulting solid was washed with Et$_2$O, and the filtrate discarded. The solid was then dissolved with CH$_2$Cl$_2$/MeOH, concentrated and dried under vacuum. The product was obtained (75 mg; 83%) as a white solid. $^1$H-NMR (400 MHz, DMSO-d$_6$) δ 8.05 (s, 1H), 7.75 (m, 2H), 7.42 (m, 2H), 7.15 (m, 1H), 4.18 (m, 4H). LRMS (ESI pos) m/e 292, 294 (M+, Br pattern).

Step E: Preparation of 6-(4-(benzyloxy)-3-fluorophenyl)-1-phenyl-2,3-dihydroimidazo[1,2-a]pyrimidin-5(1H)-one: A suspension of 6-bromo-1-phenyl-2,3-dihydroimidazo[1,2-a]pyrimidin-5(1H)-one (0.075 g, 0.257 mmol), 4-(benzyloxy)-3-fluorophenylboronic acid (0.076 g, 0.308 mmol), Pd(PPh$_3$)$_4$ (0.015 g, 0.013 mmol) and lithium chloride (0.044 g, 1.03 mmol) in dioxane (2 mL) and 2M aqueous Na$_2$CO$_3$ was stirred at 100° C. for 30 minutes. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 10:1 CH$_2$Cl$_2$/EtOAc. The product was obtained (84 mg; 79%) as a pale tan solid. $^1$H-NMR (400 MHz, DMSO-d$_6$) δ 8.04 (s, 1H), 7.82 (m, 2H), 7.61 (dd, 1H), 7.50-7.31 (m, 8H), 7.25 (t, 1H), 7.14 (t, 1H), 5.21 (s, 2H), 4.20 (m, 4H). LRMS (APCI pos) m/e 414 (M+1).

Step F: Preparation of 6-(3-fluoro-4-hydroxyphenyl)-1-phenyl-2,3-dihydroimidazo[1,2-a]pyrimidin-5(1H)-one: A solution of 6-(4-(benzyloxy)-3-fluorophenyl)-1-phenyl-2,3-dihydroimidazo[1,2-a]pyrimidin-5(1H)-one (0.084 g, 0.20 mmol) in TFA (2 mL) was stirred at 40° C. for 3 hours. The reaction was concentrated to dryness and then dried under vacuum to yield a crude residue that was purified by flash column chromatography, eluting with 25:1 CH$_2$Cl$_2$/MeOH.

The product was obtained (80 mg; 94%) as a white solid as a TFA salt. $^1$H-NMR (400 MHz, DMSO-d$_6$) δ 9.89 (br s, 1H), 7.98 (s, 1H), 7.82 (m, 2H), 7.52 (dd, 1H), 7.42 (m, 2H), 7.32 (m, 1H), 7.14 (m, 1H), 6.95 (m, 1H), 4.19 (m, 4H). LRMS (APCI pos) m/e 324 (M+1).

Step G: Preparation of 6-(3-fluoro-4-(2-iodothieno[3,2-b]pyridin-7-yloxy)phenyl)-1-phenyl-2,3-dihydroimidazo[1,2-a]pyrimidin-5(1H)-one: A mixture of 6-(3-fluoro-4-hydroxyphenyl)-1-phenyl-2,3-dihydroimidazo[1,2-a]pyrimidin-5(1H)-one (0.078 g, 0.186 mmol), 7-chloro-2-iodothieno[3,2-b]pyridine (0.050 g, 0.169 mmol; prepared according to the procedure of Ragan, J. A. *Org. Proc. Res.* 2003, 7, 676) and DMAP (0.021 g, 0.169 mmol) in bromobenzene (1.5 mL) under nitrogen was stirred at 150° C. for two days. The reaction was concentrated in vacuo to remove as much bromobenzene as possible and then purified directly by flash column chromatography, eluting with 30:1 CH$_2$Cl$_2$/MeOH. The product was obtained (35 mg; 36%) as a yellow solid. LRMS (APCI pos) m/e 583 (M+1).

Step H: Preparation of 6-(3-fluoro-4-(2-(4-(morpholine-4-carbonyl)phenyl)thieno[3,2-b]pyridin-7-yloxy)phenyl)-1-phenyl-2,3-dihydroimidazo[1,2-a]pyrimidin-5(1H)-one: A suspension of 6-(3-fluoro-4-(2-iodothieno[3,2-b]pyridin-7-yloxy)phenyl)-1-phenyl-2,3-dihydroimidazo[1,2-a]pyrimidin-5(1H)-one (0.035 g, 0.060 mmol), 4-(morpholine-4-carbonyl)phenylboronic acid (0.017 g, 0.0721 mmol), Pd(PPh$_3$)$_4$ (0.003 g, 0.003 mmol) and lithium chloride (0.010 g, 0.240 mmol) in dioxane (1 mL) and 2M aqueous Na$_2$CO$_3$ (1 mL) was stirred at 100° C. for 50 minutes. The reaction mixture was cooled to room temperature and then partitioned between EtOAc and H$_2$O. The layers were separated and the aqueous layer was re-extracted with EtOAc (1×). The combined organic layers were dried over Na$_2$SO$_4$, filtered and concentrated. The crude product was purified by flash column chromatography, eluting with 20:1 CH$_2$Cl$_2$/MeOH. The product was obtained (23 mg; 59%) as a pale yellow solid. $^1$H-NMR (400 MHz, CDCl$_3$) δ 8.51 (d, 1H), 8.01 (s, 1H), 7.85-7.79 (m, 3H), 7.73-7.65 (m, 3H), 7.55-7.49 (m, 3H), 7.46 (m, 2H), 7.30 (m, 1H), 7.22, (m, 1H), 6.59 (dd, 1H), 4.33 (m, 4H), 3.95-3.36 (m, 8H). LRMS (APCI pos) m/e 646 (M+1).

Example 167

2-(1H-benzo[d]imidazol-2-yl)-N-(3-fluoro-4-(2-(4-(morpholine-4-carbonyl)phenyl)thieno[3,2-b]pyridin-7-yloxy)phenyl)acetamide

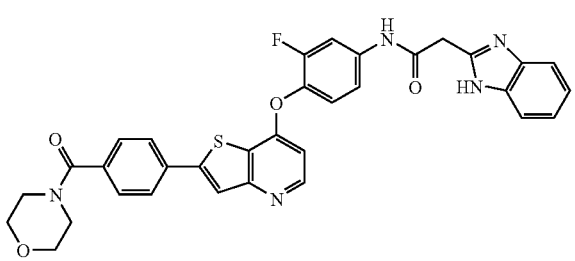

Prepared from (4-(7-(4-amino-2-fluorophenoxy)thieno[3,2-b]pyridin-2-yl)phenyl)(morpholino)methanone (Example 129, Step A) and 2-(1H-benzo[d]imidazol-2-yl)acetic acid according to the procedure of Example 89. The crude was purified by preparative HPLC to afford the desired product (1.9 mg, 6%). LRMS (ESI pos) m/e 607.9 (M+1). $^1$H-NMR (400 MHz, CD$_3$OD) δ 8.53 (d, 1H), 7.94 (m, 4H), 7.81 (m, 2H), 7.61 (m, 4H), 7.47 (m, 2H), 6.74 (d, 1H), 3.73 (m, 8H), 3.50 (m, 2H); $^{19}$F NMR (376 MHz, CD$_3$OD) δ −129.6.

Example 168

N-(3-fluoro-4-(2-(1-(piperidin-4-yl)-1H-pyrazol-4-yl)thieno[3,2-b]pyridin-7-yloxy)phenyl)-2-(4-fluorophenyl)-3-oxo-2,3-dihydropyridazine-4-carboxamide

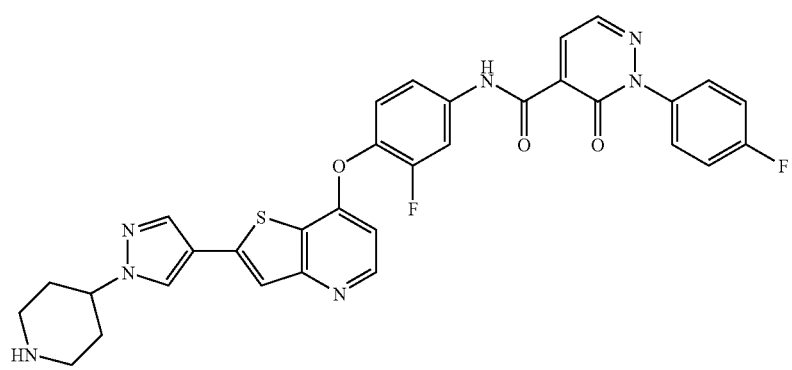

Step A: Preparation of tert-butyl 4-(4-(7-(4-amino-2-fluorophenoxy)thieno[3,2-b]pyridin-2-yl)-1H-pyrazol-1-yl)piperidine-1-carboxylate: A round-bottomed flask was charged with tert-butyl 4-(4-(4,4,5,5-tetramethyl-1,3,2-dioxaborolan-2-yl)-1H-pyrazol-1-yl)piperidine-1-carboxylate (0.0366 g, 0.0971 mmol, prepared according to WO 2006/021886), 3-fluoro-4-(2-iodothieno[3,2-b]pyridin-1-yloxy)aniline (Example 6, Step A, 0.025 g, 0.0647 mmol), potassium carbonate (0.0134 g, 0.0971 mmol), DMF (2 mL) and water (0.5 mL). The reaction was degassed by bubbling nitrogen through the mixture and then Pd(PPh$_3$)$_4$ (0.00374 g, 0.00324 mmol) was added as a solid. The mixture was heated to 100° C. using a CEM microwave for 30 minutes. The mixture was cooled to room temperature and extracted with EtOAc. Concentration and purification by preparative TLC (0.5 mm thickness) eluting with 3:1 EtOAc/hexane gave the product (14 mg, 42%) at Rf 0.2 as a clear oil. LRMS (esi+) 510 m/z (M+1) detected.

Step B: Preparation of N-(3-fluoro-4-(2-(1-(piperidin-4-yl)-1H-pyrazol-4-yl)thieno[3,2-b]pyridin-7-yloxy)phenyl)-2-(4-fluorophenyl)-3-oxo-2,3-dihydropyridazine-4-carboxamide: A round-bottomed flask was charged with 2-(4-fluorophenyl)-3-oxo-2,3-dihydropyridazine-4-carboxylic acid (Example 104, Step C, 12.9 mg, 0.0549 mmol), EDCI (10.5 mg, 0.0549 mmol), HOBT-H$_2$O (8.41 mg, 0.0549 mmol), tert-butyl 4-(4-(7-(4-amino-2-fluorophenoxy)thieno[3,2-b]pyridin-2-yl)-1H-pyrazol-1-yl)piperidine-1-carboxylate (14.0 mg, 0.0275 mmol), Hunig's base (7.10 mg, 0.0549 mmol) and DMF (4 mL). After stirring for 18 hours, the reaction was diluted with water and extracted with EtOAc. The organics were dried over sodium sulfate, filtered and concentrated. Purification by preparative TLC (0.5 mm thickness) 9:1 EtOAc/MeOH gave a band at Rf 0.7 that was isolated, washed from silica with 9:1 EtOAc/MeOH and concentrated to get an oil. HCl (4 mL, 4N dioxane) was added and stirred for 18 hours. The mixture was concentrated to get an orange oil. MeOH (4 mL) was added and the formed precipitate filtered to give (4.2 mg, 23%) as an off white solid. LRMS (esi+) 626 m/z (M+1) detected.

Example 169

N-(3-fluoro-4-(2-(4-(morpholine-4-carbonyl)phenyl)thieno[3,2-b]pyridin-7-yloxy)phenyl)-4-(4-fluorophenyl)-3-oxo-3,4-dihydropyrazine-2-carboxamide

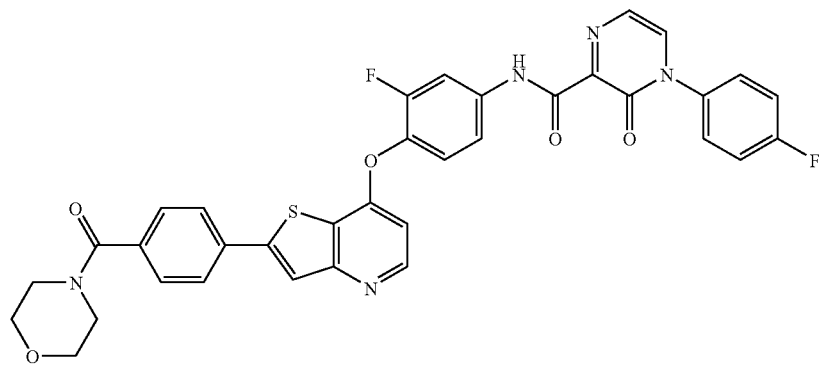

Step A: Preparation of 5-chloro-1-(4-fluorophenyl)-3-methoxypyrazin-2(1H)-one: 3,5-dichloro-1-(4-fluorophenyl)pyrazin-2(1H)-one (13.0 g, 50.2 mmol; prepared according to the general methods described by M. Tutonda, et al., *Tetrahedron,* 1990, 46, 5715) dissolved in absolute methanol (100 mL) was treated with NaOMe (6.78 g, 125 mmol). The reaction mixture was stirred at room temp for 1 hour, neutralized with 2N HCl (Et$_2$O solution), and evaporated the solvent under reduced pressure. The residue was treated with EtOAc, washed with 0.5N HCl solution, dried over MgSO$_4$, and concentrated under reduced pressure to give the desired product (12.8 g, 100%). LRMS (ESI pos) m/e 254.9, 256.9 (M+1, Cl pattern). $^1$H-NMR (400 MHz, CDCl$_3$) δ 7.39 (m, 2H), 7.20 (t, 2H), 6.95 (s, 1H), 4.05 (s, 3H); $^{19}$F-NMR (376 MHz, CDCl$_3$) δ −111.5.

Step B: Preparation of 1-(4-fluorophenyl)-3-methoxypyrazin-2(1H)-one: K$_2$CO$_3$ (1.09 g, 7.85 mmol) and 10% Pd/C (0.42 g, 0.39 mmol) were added to 5-chloro-1-(4-fluorophenyl)-3-methoxypyrazin-2(1H)-one (2.0 g, 7.85 mmol) in MeOH (100 mL) at room temperature. Hydrogen gas was treated with balloon to the reaction mixture. After 6 hours stirring, the reaction mixture was filtered with MeOH and concentrated under reduced pressure. The crude was treated with CH$_2$Cl$_2$, washed with water, dried over MgSO$_4$, and concentrated to give the desired product (1.55 g, 90%). LRMS (ESI pos) m/e 221.0 (M+1). $^1$H-NMR (400 MHz, CDCl$_3$) δ 7.49 (m, 2H), 7.27 (t, 2H), 7.10 (d, 1H), 6.98 (d, 1H), 3.98 (s, 3H); $^{19}$F-NMR (376 MHz, CDCl$_3$) δ −114.7.

Step C: Preparation of 3-chloro-1-(4-fluorophenyl)pyrazin-2(1H)-one: POCl$_3$ (5.6 mL, 61.3 mmol) was added dropwise to a solution of 1-(4-fluorophenyl)-3-methoxypyrazin-2(1H)-one in DMF (30 mL) with stirring at 0° C. followed by heating at 90° C. for 1.5 hours. The residue was cooled to 0° C., quenched by adding saturated sodium acetate solution, extracted with CH$_2$Cl$_2$, washed with water, dried over MgSO$_4$, and concentrated. The crude was purified by silica gel flash column chromatography (0.7% MeOH in CH$_2$Cl$_2$) to afford 3.52 g (64%) of the desired product. LRMS (ESI pos) m/e 224.9, 227.0 (M+1, Cl pattern). $^1$H-NMR (400 MHz, CDCl$_3$) δ 7.41 (m, 2H), 7.21 (m, 4H); $^{19}$F-NMR (376 MHz, CDCl$_3$) δ −110.9.

Step D: Preparation of 4-(4-fluorophenyl)-3-oxo-3,4-dihydropyrazine-2-carbonitrile: A mixture of 3-chloro-1-(4-fluorophenyl)pyrazin-2(1H)-one (1.0 g, 4.5 mmol), dppf (0.25 g, 0.45 mmol), Pd$_2$(dba)$_3$ (0.20 g, 0.22 mmol) and Zn(CN)$_2$ (0.31 g, 2.7 mmol) in N-methylpyrrolidone (20 mL) was heated at 120° C. for 15 hours in a sealed vial. The residue was cooled to room temperature, treated with EtOAc (300 mL), washed with a solution of saturated aq. NH$_4$Cl, conc. NOH, water (72 mL, a ratio of 4:1:4) and brine, dried over MgSO$_4$, and concentrated. The crude was purified by silica gel flash column chromatography (100% CH$_2$Cl$_2$) to afford 0.77 g (80%) of the desired product. LRMS (ESI pos) m/e 216.0 (M+1). ¹H-NMR (400 MHz, CDCl₃) δ 7.58 (d, 1H), 7.46 (d, 1H), 7.42 (m, 2H), 7.26 (m, 2H); ¹⁹F-NMR (376 MHz, CDCl₃) δ −109.6.

Step E: Preparation of 4-(4-fluorophenyl)-3-oxo-3,4-dihydropyrazine-2-carboxylic acid: A mixture of 4-(4-fluorophenyl)-3-oxo-3,4-dihydropyrazine-2-carbonitrile (0.42 g, 1.95 mmol) and H₂SO₄ (4.16 mL, 78.1 mmol) was stirred at room temperature for 17 hours. Then the reaction mixture (amide intermediate) was added to MeOH (50 mL), and then the reaction was heated to 70° C. for 2.5 hours. The reaction mixture (methyl ester compound) was quenched with ice-water and treated with aq. 2N NaOH solution (for hydrolysis) at 0° C. The mixture was acidified with aq. 1N HCl, extracted with EtOAc, dried over MgSO₄, and concentrated to afford 0.315 g (69% for 3-step process in one pot reaction) of the desired product which was rinsed with Et₂O. ¹H-NMR (400 MHz, DMSO-d₆) δ 7.90 (d, 1H), 7.60 (m, 2H), 7.52 (d, 1H), 7.42 (t, 2H).

Step F: Preparation of N-(3-fluoro-4-(2-(4-(morpholine-4-carbonyl)phenyl)thieno[3,2-b]pyridin-7-yloxy)phenyl)-4-(4-fluorophenyl)-3-oxo-3,4-dihydropyrazine-2-carboxamide: Prepared from (4-(7-(4-amino-2-fluorophenoxy)thieno[3,2-b]pyridin-2-yl)phenyl)(morpholino)methanone (Example 129, Step A) and 4-(4-fluorophenyl)-3-oxo-3,4-dihydropyrazine-2-carboxylic acid according to the procedure of Example 89. The crude was purified by silica gel flash column chromatography (3 to 5% MeOH in CH₂Cl₂) to afford 47 mg (72%) of the desired product. LRMS (APCI pos) m/e 666.2 (M+1). ¹H-NMR (400 MHz, CDCl₃/CD₃OD) δ 8.47 (d, 1H), 8.06 (dd, 1H), 7.93 (d, 2H), 7.90 (d, 1H), 7.87 (s, 1H), 7.82 (d, 1H), 7.59 (m, 4H), 7.52 (d, 1H), 7.40 (t, 1H), 7.34 (m, 3H), 6.67 (d, 1H), 3.69-3.79 (m, 8H); ¹⁹F NMR (376 MHz, CDCl₃/CD₃OD) δ −112.7, −128.7.

Example 170

N-(3-fluoro-4-(2-(4-(methylcarbamoylphenylthieno[3,2-b]pyridin-7-yloxy)phenyl)-4-(4-fluorophenyl)-3-oxo-3,4-dihydropyrazine-2-carboxamide

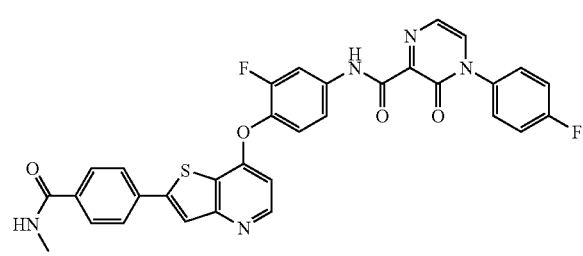

Prepared from 4-(7-(4-amino-2-fluorophenoxy)thieno[3,2-b]pyridin-2-yl)-N-methylbenzamide (prepared as in Example 95, Step A) and 4-(4-fluorophenyl)-3-oxo-3,4-dihydropyrazine-2-carboxylic acid (prepared as in Example 169, Step E) according to the procedure of Example 89. The crude was purified by silica gel flash column chromatography (3% MeOH in CH₂Cl₂) to afford 12 mg (26%) of the desired product. LRMS (APCI pos) m/e 610.1 (M+1). ¹H-NMR (400 MHz, CDCl₃/CD₃OD) δ 8.46 (d, 1H), 8.05 (d, 1H), 7.85-7.95 (m, 7H), 7.57 (m, 2H), 7.49 (m, 1H), 7.35 (m, 3H), 6.64 (d, 1H), 2.98 (s, 3H); ¹⁹F NMR (376 MHz, CDCl₃/CD₃OD) δ −111.4, −127.7.

Example 171

N-(3-fluoro-4-(2-(piperidin-4-yl)thieno[3,2-b]pyridin-7-yloxy)phenyl)-4-(4-fluorophenyl)-3-oxo-3,4-dihydropyrazine-2-carboxamide

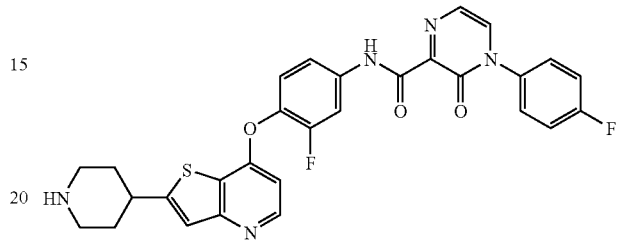

Step A: Preparation of tert-butyl 4-(7-(2-fluoro-4-(4-(4-fluorophenyl)-3-oxo-3,4-dihydropyrazine-2-carboxamido)phenoxy)thieno[3,2-b]pyridin-2-yl)piperidine-1-carboxylate: Prepared according to the procedure of Example 154, Step B, substituting 4-(4-fluorophenyl)-3-oxo-3,4-dihydropyrazine-2-carboxylic acid (49.7 mg, 0.212 mmol) for 2-(4-fluorophenyl)-3-oxo-2,3-dihydropyridazine-4-carboxylic acid. Purified by Si column chromatography (Biotage 12M) eluting with 3% MeOH/DCM to afford the desired product as yellow solid. Yield: 15.6 mg, 22.3%. LRMS (APCI pos) m/e 660.1 (M+H).

Step B: Preparation of N-(3-fluoro-4-(2-(piperidin-4-yl)thieno[3,2-b]pyridin-7-yloxy)phenyl)-4-(4-fluorophenyl)-3-oxo-3,4-dihydropyrazine-2-carboxamide: Prepared according to the procedure of Example 154, Step C, substituting tert-butyl 4-(7-(2-fluoro-4-(4-(4-fluorophenyl)-3-oxo-3,4-dihydropyrazine-2-carboxamido)phenoxy)thieno[3,2-b]pyridin-2-yl)piperidine-1-carboxylate (15 mg, 0.0227 mmol) for tert-butyl 4-(7-(2-fluoro-4-(1-(4-fluorophenyl)-6-oxo-1,6-dihydropyridazine-5-carboxamido)phenoxy)thieno[3,2-b]pyridin-2-yl)piperidine-1-carboxylate. Yield: 11.4 mg, 90%. LRMS (APCI pos) m/e 560.2 (M+H).

Example 172

N-(3-fluoro-4-(2-(1-methylpiperidin-4-yl)thieno[3,2-b]pyridin-7-yloxy)phenyl)-4-(4-fluorophenyl)-3-oxo-3,4-dihydropyrazine-2-carboxamide

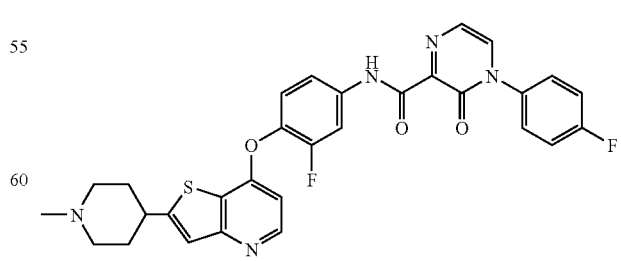

Prepared according to the procedure of Example 155, substituting N-(3-fluoro-4-(2-(piperidin-4-yl)thieno[3,2-b]pyridin-7-yloxy)phenyl)-4-(4-fluorophenyl)-3-oxo-3,4-dihydro-

Example 173

N-(3-fluoro-4-(2-(4-methylpiperazine-1-carbonyl)
thieno[3,2-b]pyridin-7-yloxy)phenyl)-2-(4-fluo-
rophenyl)-3-oxo-2,3-dihydropyridazine-4-carboxam-
ide

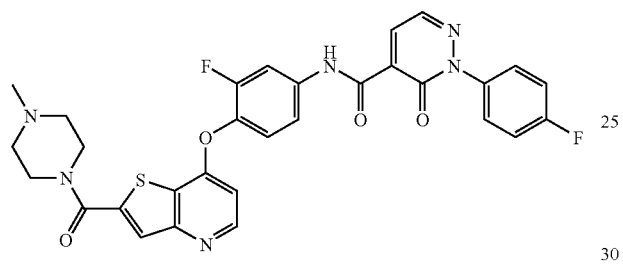

Step A: Preparation of 7-(4-amino-2-fluorophenoxy)
thieno[3,2-b]pyridine-2-carbonitrile: A mixture of 3-fluoro-
4-(2-iodothieno[3,2-b]pyridin-7-yloxy)aniline (Example 6, Step A; 0.50 g, 1.3 mmol) and CuCN (0.14 g, 1.6 mmol) was refluxed for 90 minutes in DMF (5 mL). The residue was poured into 25% aq. NaCN (30 mL), extracted with CHCl$_3$, dried over MgSO$_4$, and concentrated. The crude was purified by silica gel flash column chromatography (0.5% MeOH in CH$_2$Cl$_2$) to afford 0.179 g (49%) of the desired product. LRMS (APCI pos) m/e 286.2 (M+1). $^1$H-NMR (400 MHz, CDCl$_3$) δ 8.62 (d, 1H), 8.08 (s, 1H), 7.05 (t, 1H), 6.67 (d, 1H), 6.53 (m, 2H), 3.87 (s, 2H); $^{19}$F-NMR (376 MHz, CDCl$_3$) δ −128.4.

Step B: Preparation of N-(4-(2-cyanothieno[3,2-b]pyridin-7-yloxy)-3-fluorophenyl)-2-(4-fluorophenyl)-3-oxo-2,3-dihydropyridazine-4-carboxamide: Prepared from 7-(4-amino-2-fluorophenoxy)thieno[3,2-b]pyridine-2-carbonitrile and 2-(4-fluorophenyl)-3-oxo-2,3-dihydropyridazine-4-carboxylic acid (Example 104, Step C) according to the procedure of Example 89. The crude was purified by silica gel flash column chromatography (5% MeOH in CH$_2$Cl$_2$) to afford 73 mg (83%) of the desired product. LRMS (APCI pos) m/e 502.2 (M+1). $^1$H-NMR (400 MHz, CDCl$_3$) δ 11.89 (s, 1H), 8.64 (d, 1H), 8.42 (d, 1H), 8.25 (d, 1H), 8.11 (s, 1H), 7.99 (dd, 1H), 7.60 (m, 2H), 7.43 (d, 1H), 7.27 (m, 3H), 7.67 (d, 1H); $^{19}$F NMR (376 MHz, CDCl$_3$/CD$_3$OD) δ −111.3, −126.0.

Step C: Preparation of 7-(2-fluoro-4-(2-(4-fluorophenyl)-3-oxo-2,3-dihydropyridazine-4-carboxamido)phenoxy)thieno[3,2-b]pyridine-2-carboxylic acid: Prepared from N-(4-(2-cyanothieno[3,2-b]pyridin-7-yloxy)-3-fluorophenyl)-2-(4-fluorophenyl)-3-oxo-2,3-dihydropyridazine-4-carboxamide according to the procedure of Example 169, Step E. The crude was rinsed with Et$_2$O to afford 12 mg (23%) of the desired product. LRMS (APCI pos) m/e 521.2 (M+1).

Step D: Preparation of N-(3-fluoro-4-(2-(4-methylpiperazine-1-carbonyl)thieno[3,2-b]pyridin-7-yloxy)phenyl)-2-(4-fluorophenyl)-3-oxo-2,3-dihydropyridazine-4-carboxamide: A mixture of 7-(2-fluoro-4-(2-(4-fluorophenyl)-3-oxo-2,3-dihydropyridazine-4-carboxamido)phenoxy)thieno[3,2-b]pyridine-2-carboxylic acid (12 mg, 0.023 mmol), EDCI (13.3 mg, 0.069 mmol), and HOBt (9.4 mg, 0.069 mmol) in DMF (1 mL) was stirred at room temperature for 30 minutes. 1-Methylpiperazine (6.9 mg, 0.069 mmol) was added followed by Et$_3$N (7 mg, 0.069 mmol). After stirring for 2 hours, the reaction mixture was diluted with EtOAc and washed with saturated aqueous NH$_4$Cl, saturated aqueous NaHCO$_3$, and brine. The organic layer was dried over MgSO$_4$ and concentrated under reduced pressure to give the crude material that was purified by silica gel flash column chromatography (5% MeOH in CH$_2$Cl$_2$) to afford 11 mg (79%) of the desired product. LRMS (APCI pos) m/e 603.3 (M+1). $^1$H-NMR (400 MHz, CD$_3$OD) δ 8.87 (d, 1H), 8.37 (d, 1H), 8.32 (d, 1H), 8.14 (d, 1H), 8.03 (s, 1H), 7.68 (m, 2H), 7.57 (m, 2H), 7.24-7.32 (m, 3H), 3.61 (m, 4H), 2.98 (s, 3H); $^{19}$F-NMR (376 MHz, CD$_3$OD) δ −114.7, −129.3.

Example 174

7-(2-fluoro-4-(2-(4-fluorophenyl)-3-oxo-2,3-dihy-
dropyridazine-4-carboxamido)phenoxy)thieno[3,2-b]
pyridine-2-carboxamide

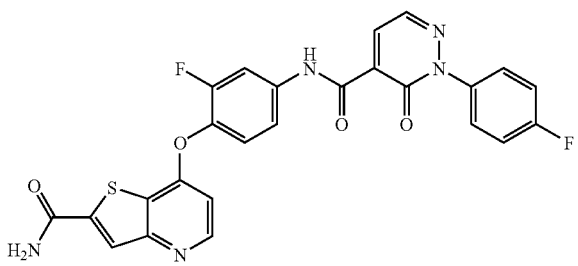

A mixture of N-(4-(2-cyanothieno[3,2-b]pyridin-7-yloxy)-3-fluorophenyl)-2-(4-fluorophenyl)-3-oxo-2,3-dihydropyridazine-4-carboxamide (Example 173, Step B, 10 mg, 0.02 mmol) and H$_2$SO$_4$ (0.53 mL, 9.97 mmol) was stirred at room temperature for 17 hours. The reaction mixture was quenched with ice. The mixture was treated with 2N NaOH, extracted with CH$_2$Cl$_2$ (500 mL) and DMF (40 mL), dried over MgSO$_4$, and concentrated to afford the desired product which was rinsed with Et$_2$O. LRMS (APCI pos) m/e 520.3 (M+1). $^1$H-NMR (400 MHz, DMSO-d$_6$) δ 11.72 (s, 1H), 8.59 (d, 1H), 8.38 (d, 1H), 8.27 (m, 2H), 8.06 (d, 1H), 7.69 (m, 2H), 7.57 (m, 2H), 7.42 (t, 2H), 6.79 (d, 1H); $^{19}$F NMR (376 MHz, CDCl$_3$/CD$_3$OD) δ −112.9, −128.3.

Example 175

N-(4-(2-(1-Ethylpiperidin-4-yl)thieno[3,2-b]pyridin-7-yloxy)-3-fluorophenyl)-2-(4-fluorophenyl)-3-oxo-2,3-dihydropyridazine-4-carboxamide

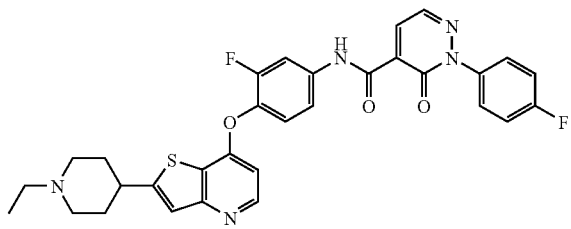

A round-bottomed flask was charged with N-(3-fluoro-4-(2-(piperidin-4-yl)thieno[3,2-b]pyridin-7-yloxy)phenyl)-2-(4-fluorophenyl)-3-oxo-2,3-dihydropyridazine-4-carboxamide (Example 154, Step C, 43.4 mg, 0.0776 mmol), acetaldehyde (17.1 mg, 0.388 mmol), NaBH(OAc)$_3$ (82 mg, 0.388 mmol) and THF (10 mL). The reaction mixture was stirred at room temperature until the starting material had been consumed (overnight). Then the reaction was partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford crude product. The crude product was further purified with preparative HPLC to afford product (1.3 mg, 2.14%). LRMS (APCI neg): >97% purity, 254 nm, m/e 587 (M). $^1$H NMR (400 MHz, CD$_3$OD) δ 8.41 (d, 1H), 8.36 (d, 1H), 8.31 (d, 1H), 8.03 (dd, 1H), 7.67 (m, 2H), 7.49 (m, 1H), 7.39 (t, 1H), 7.29 (m, 3H), 6.62 (d, 1H), 2.60 (q, 2H), 2.32 (m, 2H), 2.19 (m, 2H), 1.94 (m, 1H), 1.18 (t, 3H), 0.90 (m, 4H).

Example 176

N-(3-Fluoro-4-(2-(1-methyl-1H-imidazol-2-yl)thieno[3,2-b]pyridin-7-yloxy)phenyl)-2-(4-fluorophenyl)-3-oxo-2,3-dihydropyridazine-4-carboxamide

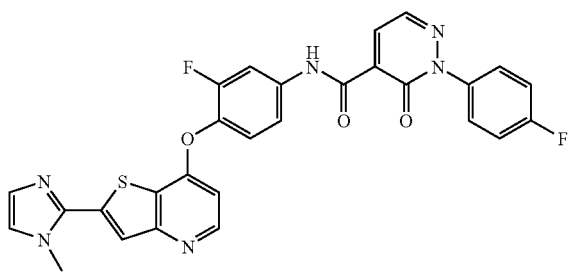

Step A: Preparation of N-(3-fluoro-4-(2-iodothieno[3,2-b]pyridin-7-yloxy)phenyl)-2-(4-fluorophenyl)-3-oxo-2,3-dihydropyridazine-4-carboxamide: A round-bottomed flask was charged with 3-fluoro-4-(2-iodothieno[3,2-b]pyridin-7-yloxy)benzenamine (Example 6, Step A, 1.00 g, 2.59 mmol), 2-(4-fluorophenyl)-3-oxo-2,3-dihydropyridazine-4-carboxylic acid (0.728 g, 3.11 mmol, example 104, step C), N$^1$-((ethylimino)methylene)-N$^3$,N$^3$-dimethylpropane-1,3-diamine hydrochloride (0.596 g, 3.11 mmol), 1H-benzo[d][1,2,3]triazol-1-ol (0.420 g, 3.11 mmol), N-ethyl-N-isopropylpropan-2-amine (0.669 g, 5.178 mmol) and DMF (50 mL). The reaction mixture was stirred at room temperature until the starting material had been consumed (overnight). Then the reaction was partitioned between EtOAc (200 mL) and H$_2$O (200 mL). The phases were separated and the aqueous phase was re-extracted with EtOAc (3×200 mL). The combined organic layers were dried (Na$_2$SO$_4$), filtered and concentrated to yield a crude product. The crude product was purified by silica gel chromatography (DCM/7 M NH$_3$ in MeOH from 100/1 to 10/1, v/v) to afford product (1.34 g, 85.8%). LRMS (APCI pos): >99% purity, 254 nm, m/e 603 (M+1). $^1$H NMR (400 MHz, CDCl$_3$) δ 11.85 (s, 1H), 8.43 (m, 2H), 8.24 (d, 1H), 7.96 (dd, 1H), 7.77 (s, 1H), 7.60 (m, 2H), 7.40 (m, 1H), 7.21-7.28 (m, 3H), 6.48 (m, 1H).

Step B: Preparation of N-(3-fluoro-4-(2-(1-methyl-1H-imidazol-2-yl)thieno[3,2-b]pyridin-7-yloxy)phenyl)-2-(4-fluorophenyl)-3-oxo-2,3-dihydropyridazine-4-carboxamide: A round-bottomed flask was charged with N-(3-fluoro-4-(2-iodothieno[3,2-b]pyridin-7-yloxy)phenyl)-2-(4-fluorophenyl)-3-oxo-2,3-dihydropyridazine-4-carboxamide (230 mg, 0.382 mmol), 1-methyl-2-(tributylstannyl)-1H-imidazole (850.3 mg, 2.29 mmol), tetrakis(triphenylphosphine)palladium (88.25 mg, 0.0764 mmol) and toluene (25 mL). The reaction mixture was stirred at 100° C. until LC-MS showed that the starting material had been consumed (4 hours). Then the reaction was cooled to room temperature and partitioned between EtOAc (100 mL) and H$_2$O (100 mL). The phases were separated and the aqueous phase was re-extracted with EtOAc (3×100 mL). The combined organic layers were dried (Na$_2$SO$_4$), filtered and concentrated to yield a crude product. The crude product was purified by silica gel chromatography (DCM/7 M NH$_3$ in MeOH from 50/1 to 10/1, v/v) to afford product (159.8 mg, 75.2%). LRMS (APCI pos): >99% purity, 254 nm, m/e 557 (M+1). $^1$H NMR (400 MHz, CDCl$_3$) δ 11.82 (s, 1H), 8.50 (m, 1H), 8.41 (m, 1H), 8.22 (m, 1H), 7.98 (m, 1H), 7.46-7.42 (m, 4H), 7.40 (m, 2H), 7.24 (m, 2H), 6.98 (d, 1H), 6.54 (m, 1H), 3.84 (s, 3H).

Example 177

N-(3-fluoro-4-(2-(1-(piperidin-4-yl)-1H-pyrazol-4-yl)thieno[3,2-b]pyridin-7-yloxy)phenyl)-2-(4-fluorophenyl)-3-oxo-2,3-dihydropyridazine-4-carboxamide

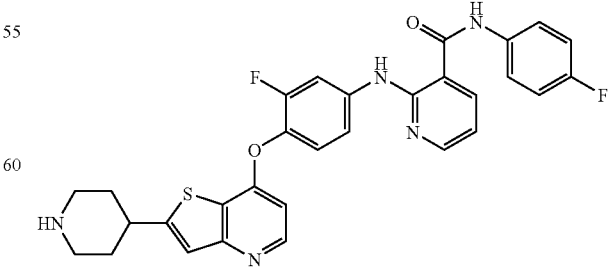

Step A: Preparation of ethyl 2-(4-(2-(1-(tert-butoxycarbonyl)piperidin-4-yl)thieno[3,2-b]pyridin-7-yloxy)-3-fluorophenylamino)nicotinate: A microwave vial was charged with ethyl 2-chloronicotinate (0.209 g, 1.13 mmol), Cs$_2$CO$_3$ (0.331 g, 1.01 mmol), tert-butyl 4-(7-(4-amino-2-fluorophenoxy)thieno[3,2-b]pyridin-2-yl)piperidine-1-carboxylate (Example 154, Step A, 0.200 g, 0.451 mmol), Palladium acetate (0.0101 g, 0.0451 mmol), PdCl$_2$(dppf)-dcm (0.0185 g, 0.0225 mmol), toluene (2 mL) and EtOH (1 mL). The mixture was heated to 110° C. for 3 hours. After cooling to room temperature, the mixture was diluted with water and extracted with EtOAc. The organics were isolated and dried (MgSO4). After filtration and concentration, the crude product was purified by preparative TLC (2.0 mm thickness, eluting with EtOAc. The product (175 mg, 59%) was isolated as a yellow solid. LRMS (esi+)593 m/z (M+1) detected.

Step B: Preparation of 2-(4-(2-(1-(tert-butoxycarbonyl)piperidin-4-yl)thieno[3,2-b]pyridin-7-yloxy)-3-fluorophenylamino)nicotinic acid: A round-bottomed flask was charged with ethyl 2-(4-(2-(1-(tert-butoxycarbonyl)piperidin-4-yl)thieno[3,2-b]pyridin-7-yloxy)-3-fluorophenylamino)nicotinate (0.100 g, 0.169 mmol) and THF (1 mL). NaOH (3.0 mL, 1N) was added and the mixture stirred for 1 hour. The mixture was then acidified to pH 6 with HCl aq. (1N) and extracted with EtOAc. The organics were dried (MgSO$_4$), filtered and concentrated to get product as a yellow solid. LRMS (esi+) 565 m/z (M+1) detected.

Step C: Preparation of tert-butyl 4-(7-(2-fluoro-4-(3-(4-fluorophenylcarbamoyl)pyridin-2-ylamino)phenoxy)thieno[3,2-b]pyridin-2-yl)piperidine-1-carboxylate: Prepared according to the procedure for Example 168, Step B substituting 2-(4-(2-(1-(tert-butoxycarbonyl)piperidin-4-yl)thieno[3,2-b]pyridin-7-yloxy)-3-fluorophenylamino)nicotinic acid (90 mg, 0.16 mmol) for 2-(4-fluorophenyl)-3-oxo-2,3-dihydropyridazine-4-carboxylic acid, and 4-fluorobenzenamine (89 mg, 0.80 mmol) for tert-butyl 4-(4-(7-(4-amino-2-fluorophenoxy)thieno[3,2-b]pyridin-2-yl)-1H-pyrazol-1-yl)piperidine-1-carboxylate. The crude product was purified by silica gel chromatography (EtOAc) to get the product (55 mg, 55%) as a light orange solid. LRMS (esi+) 658 m/z (M+1) detected.

Step D: Preparation of 2-(3-fluoro-4-(2-(piperidin-4-yl)thieno[3,2-b]pyridin-7-yloxy)phenylamino)-N-(4-fluorophenyl)nicotinamide: A round-bottomed flask was charged with tert-butyl 4-(7-(4-(3-((4-fluorophenyl)carbamoyl)pyridin-2-ylamino)-2-fluorophenoxy)thieno[3,2-b]pyridin-2-yl)piperidine-1-carboxylate (60 mg, 0.091 mmol) and TFA (3 mL). After stirring at room temperature for 4 hours, the mixture was concentrated under high vacuum and aqueous 1M Na$_2$CO$_3$ (5 mL) was added with stirring. The mixture was then extracted with EtOAc (10 mL) and the organics were isolated and dried over sodium sulfate, filtered and concentrated to get product (49 mg, 96%) as a yellow solid. LRMS (esi+) 558 m/z (M+1) detected.

Example 178

2-(3-fluoro-4-(2-(1-methylpiperidin-4-yl)thieno[3,2-b]pyridin-7-yloxy)phenylamino)-N-(4-fluorophenyl)nicotinamide

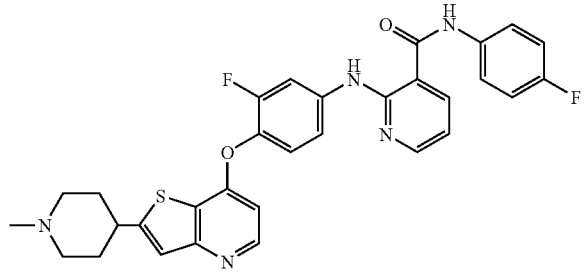

A round-bottomed flask was charged with 2-(3-fluoro-4-(2-(piperidin-4-yl)thieno[3,2-b]pyridin-7-yloxy)phenylamino)-N-(4-fluorophenyl)nicotinamide (Example 177, Step D, 47 mg, 0.084 mmol), formaldehyde (7.7 mg, 0.084 mmol) 33% in water and THF (5 mL). The mixture was stirred for 30 minutes and then NaBH(OAc)$_3$ (18 mg, 0.084 mmol) was added. The mixture was stirred for another 30 minutes and then HCl (1N, 1 mL) was added. The acid was neutralized with Na$_2$CO$_3$ and the mixture extracted with EtOAc. The organics were dried over sodium sulfate, filtered and concentrated to get product as a free base. The crude product was diluted in MeOH (2 mL) and HCl (0.1 mL, 4N Dioxane) added. The mixture was concentrated under high vacuum to get product (34 mg, 67%) as a yellow solid. LRMS (esi+) 572 m/z (M+1) detected. $^1$H NMR (CDCl$_3$, 400 MHz) δ 10.65 (s, 1H), 10.55 (br s, 2H). 9.14 (s, 1H), 8.39 (d, J=6 Hz, 2H), 8.34 (m, 1H), 8.18 (d, J=8 Hz, 1H), 8.03 (d, J=13 Hz, 1H), 7.65 (m, 2H), 7.12 (m, 4H), 6.78 (m, 1H), 6.50 (d, J=5.5 Hz, 1H), 3.36 (m, 2H), 3.13 (m, 1H), 2.81 (m, 2H), 2.26 (m, 4H), 2.05 (s, 3H).

Example 179

N-(4-(2-(4-ethylpiperazine-1-carbonyl)thieno[3,2-b]pyridin-7-yloxy)-3-fluorophenyl)-4-(4-fluorophenyl)-3-oxo-3,4-dihydropyrazine-2-carboxamide

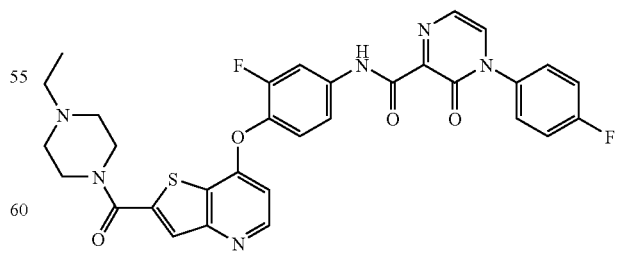

Step A: Preparation of 7-(4-amino-2-fluorophenoxy)thieno[3,2-b]pyridine-2-carboxylic acid: Prepared from 7-(4-amino-2-fluorophenoxy)thieno[3,2-b]pyridine-2-carbonitrile (Example 173, Step A) according to the procedure of Example 169, Step E. The crude was rinsed with Et$_2$O to afford the desired product. LRMS (APCI pos) m/e 305.2 (M+1).

Step B: Preparation of N-(4-(2-(4-ethylpiperazine-1-carbonyl)thieno[3,2-b]pyridin-7-yloxy)-3-fluorophenyl)-4-(4-fluorophenyl)-3-oxo-3,4-dihydropyrazine-2-carboxamide: Prepare from 7-(4-amino-2-fluorophenoxy)thieno[3,2-b]pyridine-2-carboxylic acid according to the procedure of Example 173, Step D. The crude was purified by silica gel flash column chromatography (5% MeOH in CH$_2$Cl$_2$) to afford 35 mg (35% in two step process) of the desired product. LRMS (APCI pos) m/e 617.3 (M+1). $^1$H-NMR (400 MHz, CD$_3$OD) δ 8.54 (d, 1H), 8.05 (dd, 1H), 7.92 (d, 1H), 7.78 (d, 1H), 7.73 (s, 1H), 7.61 (m, 2H), 7.53 (m, 1H), 7.42 (t, 1H), 7.34 (t, 2H), 6.75 (d, 1H), 3.82 (br s, 4H), 2.57 (br s, 4H), 2.50 (q, 2H), 1.13 (t, 3H); $^{19}$F-NMR (376 MHz, CD$_3$OD) δ −113.5, −129.5.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of Formula I:

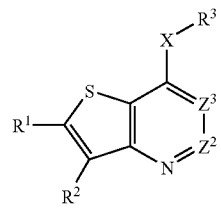

I or a pharmaceutically acceptable salt thereof, wherein:
X is O;
$Z^2$ and $Z^3$ are independently selected from CR$^4$;
R$^1$ is a monocyclic or bicyclic C$_3$-C$_{12}$ carbocyclyl, or C$_2$-C$_{20}$ heterocyclyl, wherein said carbocyclyl, and heterocyclyl, are optionally substituted with one or more groups independently selected from F, Cl, Br, I, CN, CF$_3$, oxo, OR$^{10}$, SR$^{10}$, —C(=Y)R$^{10}$, —C(=Y)OR$^{10}$, —C(=Y)NR$^{10}$R$^{11}$, —(CR$^{14}$R$^{15}$)$_n$—NR$^{10}$R$^{11}$, —NR$^{10}$C(=Y)R$^{13}$, —NR$^{10}$C(=Y)OR$^{11}$, —NR$^{12}$C(=Y)NR$^{10}$R$^{11}$, —NR$^{12}$SO$_2$R$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ cycloalkyl, C$_2$-C$_{20}$ heterocyclyl, C$_6$-C$_{20}$ aryl and C$_1$-C$_{20}$ heteroaryl, —(CR$^{14}$R$^{15}$)$_n$—NR$^{12}$C(=O)(CR$^{14}$R$^{15}$)$_m$NR$^{10}$R$^{11}$, and —C(=O)(CR$^{14}$R$^{15}$)$_n$NR$^{10}$R$^{11}$;
R$^2$ and R$^4$ are independently H, F, Cl, Br, I, CF$_3$, CN, —C(=Y)R$^{10}$, —C(=Y)OR$^{10}$, —C(=Y)NR$_{10}$R$^{11}$, —NR$^{10}$C(=Y)R$^{11}$, —NR$^{10}$C(=Y)R$^{11}$, —NR$^{12}$C(=Y)NR$^{10}$R$^{11}$, —NR$^{12}$SO$_2$NR$^{10}$R$^{11}$, —OR$^{10}$, —OC(=Y)R$^{10}$, —OC(=Y)OR$^{10}$, —OC(=Y)NR$^{10}$R$^{11}$, —C(=O)NR$^{12}$(CR$^{14}$R$^{15}$)$_r$NR$^{10}$R$^{11}$, —OP(=Y)(OR$^{10}$)(OR$^{11}$), —OP(OR$^{10}$)(OR$^{11}$), —SR$^{10}$, —S(O)R$^{10}$, —S(O)$_2$R$^{10}$, —S(O)$_2$NR$^{10}$R$^{11}$, —SC(=Y)R$^{10}$, —SC(=Y)R$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, OR$^{10}$, and NR$^{10}$R$^{11}$;
R$^3$ has the structure:

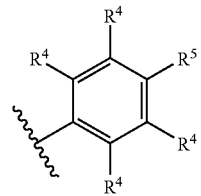

wherein the wavy line indicates the attachment to X, and each R$^4$ is independent of the other;
R$^5$ is:

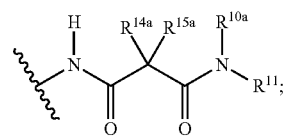

wherein R$^{14a}$ is null and R$^{10a}$ and R$^{15a}$ together with the atoms to which they are attached form an optionally substituted heteroaryl ring having a ring nitrogen atom and optionally having one or more additional heteroatoms selected from N, O and S;
R$^{10}$, R$^{11}$ and R$^{12}$ are independently H, OR$^a$, C$_1$-C$_{12}$ alkyl, C$_2$-C$_8$ alkenyl, or C$_2$-C$_8$ alkynyl, or monocyclic or bicyclic C$_3$-C$_{12}$ carbocyclyl, C$_2$-C$_{20}$ heterocyclyl, C$_6$-C$_{20}$ aryl, or C$_1$-C$_{20}$ heteroaryl, wherein said alkyl, alkenyl, alkynyl, carbocyclyl, heterocyclyl, aryl, and heteroaryl are optionally substituted with one or more groups independently selected from F, Cl, Br, I, SO$_2$R$^c$, CN, OR$^a$, NR$^a$R$^b$, C(=O)NR$^a$R$^b$, CR$^a$C(=O)R$^b$, C$_1$-C$_{12}$ alkyl, C$_2$-C$_8$ alkenyl, C$_2$-C$_8$ alkynyl, C$_3$-C$_{20}$ carbocyclyl, C$_6$-C$_{20}$ aryl, and C$_1$-C$_{20}$ heteroaryl;
R$^{13}$ is H, C$_1$-C$_{12}$ alkyl, C$_2$-C$_8$ alkenyl, C$_2$-C$_8$ alkynyl, (CR$^{14}$R$^{15}$)$_n$-cycloalkyl, (CR$^{14}$R$^{15}$)$_n$-heterocyclyl, (CR$^{14}$R$^{15}$)$_n$-aryl, (CR$^{14}$R$^{15}$)$_n$-heteroaryl, (CR$^{14}$R$^{15}$)$_n$—O—(CR$^{14}$R$^{15}$)$_m$-aryl, (CR$^{14}$R$^{15}$)$_n$—OR$^{10}$, (CR$^{14}$R$^{15}$)$_n$—NR$^{10}$R$^{11}$, (CR$^{14}$R$^{15}$)$_n$—NR$^{10}$C(=O)R$^{11}$, or (CR$^{14}$R$^{15}$)$_n$—NR$^{10}$(SO$_2$Me)—R$^{11}$, wherein said alkyl, alkenyl, alkynyl, cycloalkyl, heterocycloalkyl, and heteroaryl portions are optionally substituted with one or more groups independently selected from F, Cl, Br, I, oxo, SO$_2$R$^c$, CN, OR$^a$, C(=O)R$^a$, C(=O)OR$^a$, NR$^a$R$^b$, NR$^a$C(=O)R$^b$, C$_1$-C$_{12}$ alkyl, C$_2$-C$_8$ alkenyl, C$_2$-C$_8$ alkynyl, C$_3$-C$_{12}$ cycloalkyl, C$_2$-C$_{20}$ heterocyclyl, C$_6$-C$_{20}$ aryl, and C$_1$-C$_{20}$ heteroaryl;
R$^{14}$ and R$^{15}$ are independently H, C$_1$-C$_{12}$ alkyl, or (CR$^{14}$R$^{15}$)$_r$-aryl, or R[14] and R[15] together with the atoms to which they are attached form a saturated or partially unsaturated $C_3$-$C_{12}$ carbocyclic ring;

$R^a$ and $R^b$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, wherein said alkyl, alkenyl, alkynyl, carbocyclyl, heterocyclyl, aryl, and heteroaryl are optionally substituted with one or more alkyl or halogen groups;

$R^c$ is $C_1$-$C_{12}$ alkyl or $C_6$-$C_{20}$ aryl, wherein said alkyl and aryl are optionally substituted with one or more groups independently selected from F, Cl, Br, I, $OR^a$ and $C(=O)NR^aR^b$;

Y is independently O or S;

t is 1, 2, 3, 4, 5 or 6; and n and m are independently 0, 1, 2, 3, 4, 5 or 6.

2. The compound of claim 1, wherein Formula I is Formula Ib:

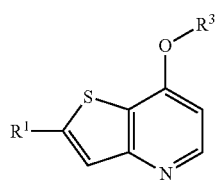

or a pharmaceutically acceptable salt thereof.

3. The compound of claim 1, wherein $R^1$ is selected from the structures:

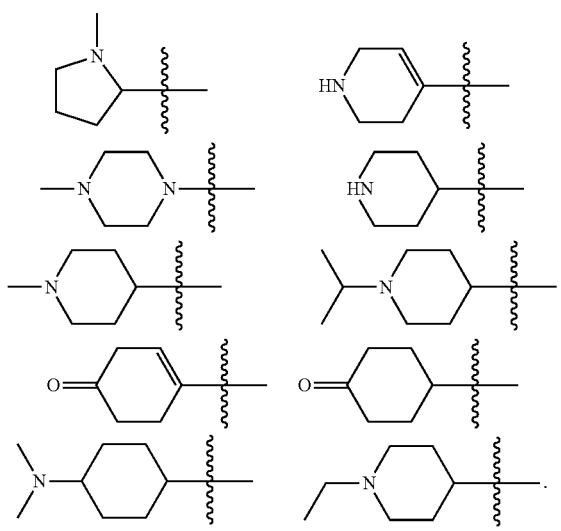

4. The compound of claim 1, wherein $R^3$ is selected from the structures:

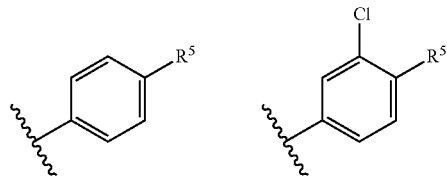

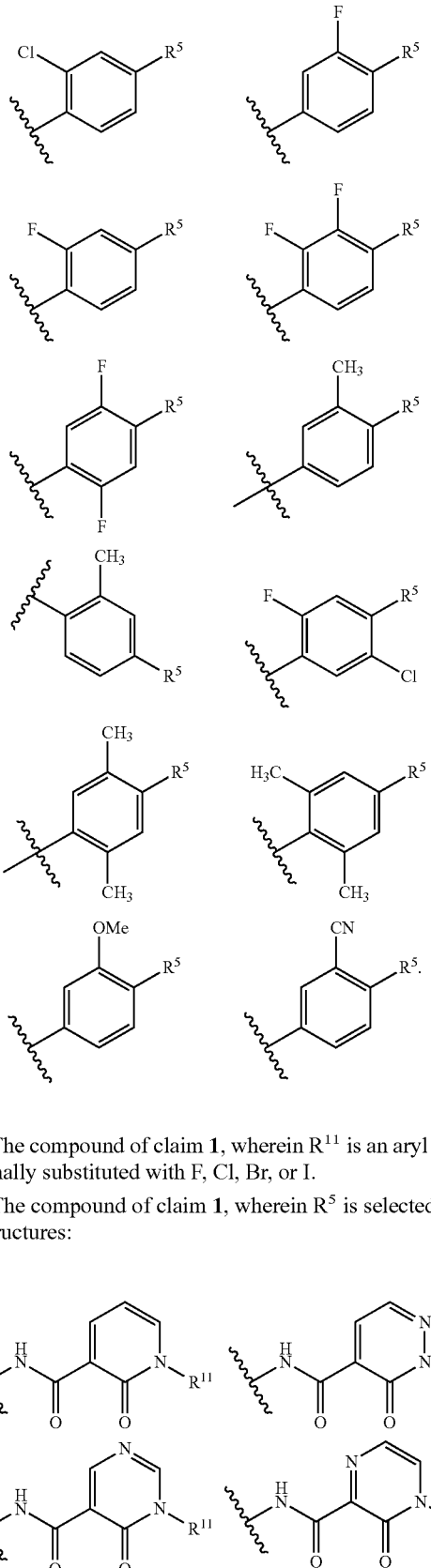

5. The compound of claim 1, wherein $R^{11}$ is an aryl group optionally substituted with F, Cl, Br, or I.

6. The compound of claim 1, wherein $R^5$ is selected from the structures:

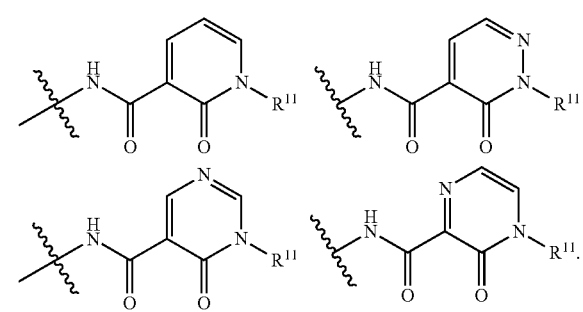

7. The compound of claim 1, wherein $R^5$ is selected from the structures:

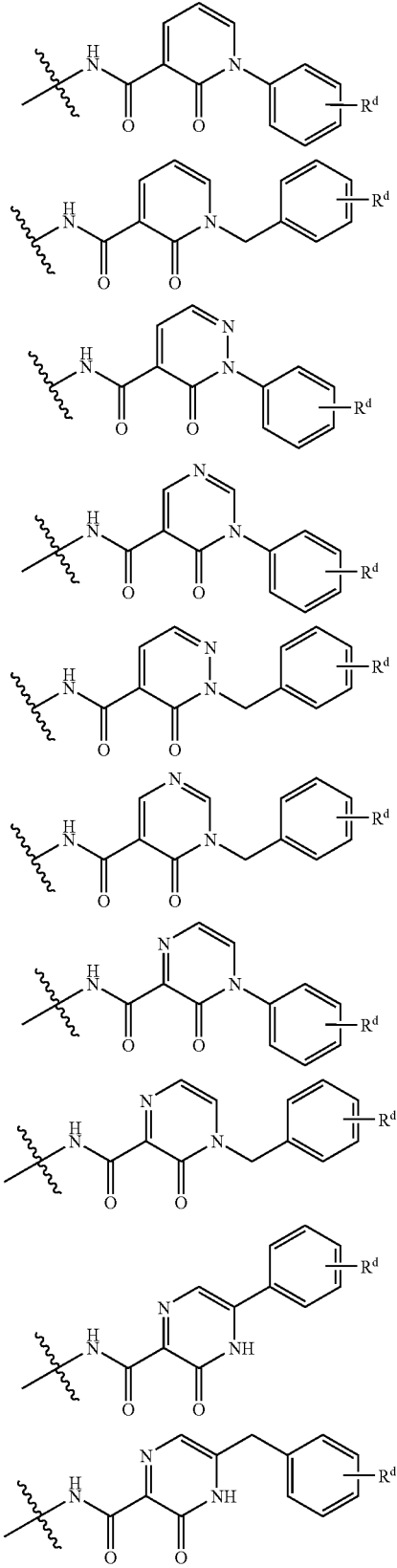

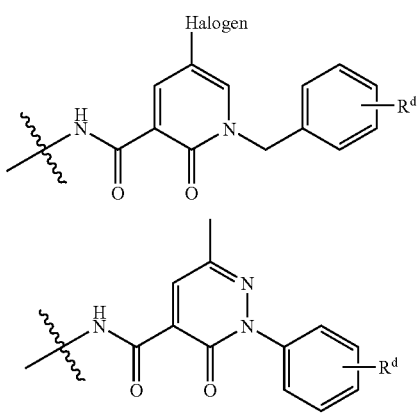

wherein the phenyl groups are optionally substituted with one or more $R^d$ groups independently selected from F, Cl, Br, I, $SO_2R^c$, CN, $OR^a$, $NR^aR^b$, C(=O) $NR^aR^b$, $CR^aC(=O)R^b$, $C_1$-$C_{12}$ alkyl, $C_2$-$C_8$ alkenyl, $C_2$-$C_8$ alkynyl, $C_6$-$C_{20}$ aryl, and $C_1$-$C_{20}$ heteroaryl.

8. A compound as defined in claim 1, which is:

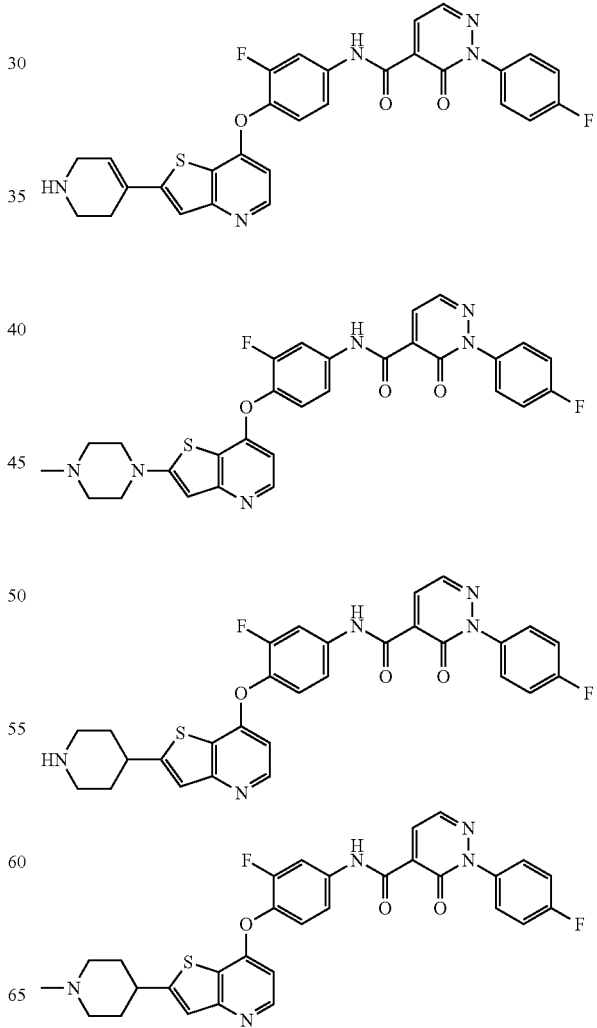

251
-continued
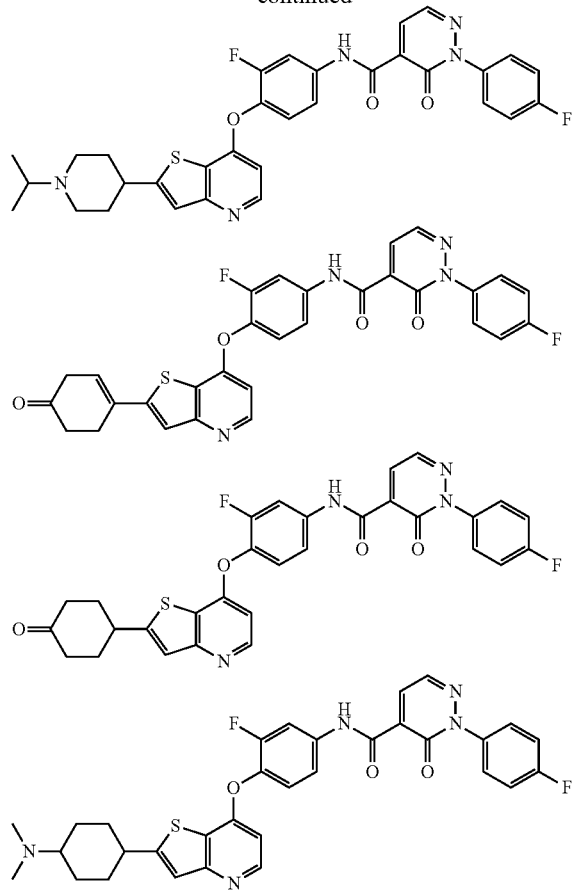
252
-continued
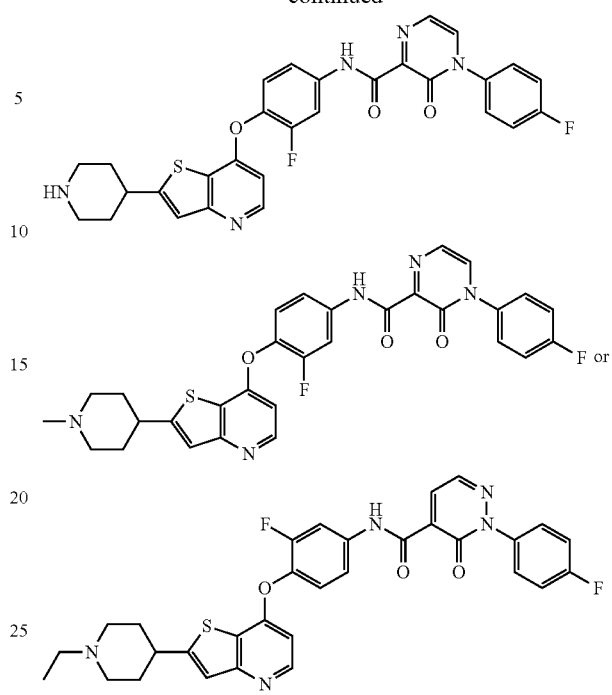
or a pharmaceutically acceptable salt thereof.
9. A pharmaceutical composition comprised of a compound of claim 1 and a pharmaceutically acceptable carrier.
* * * * *

UNITED STATES PATENT AND TRADEMARK OFFICE
CERTIFICATE OF CORRECTION

PATENT NO. : 8,003,662 B2
APPLICATION NO. : 11/699830
DATED : August 23, 2011
INVENTOR(S) : Blake et al.

It is certified that error appears in the above-identified patent and that said Letters Patent is hereby corrected as shown below:

On the Title Page, In Item (57) Abstract:

Replace:

in vitro, in situ, and in vivo

With:

*in vitro*, *in situ*, and *in vivo*

In the Claims

In Claim 1, Column 245, Line 60:

Replace:

-S(O)$_2$(OR$^{10}$

With:

-S(O)$_2$(OR$^{10}$)

In Claim 1, Column 245, Line 67:

Replace:

-C(=Y)NR$_{10}$R$^{11}$

With:

-C(=Y)NR$^{10}$R$^{11}$

Signed and Sealed this
Fifth Day of May, 2015

Michelle K. Lee
*Director of the United States Patent and Trademark Office*

In the Claims

In Claim 1, Column 246, Line 1, at the beginning of the line:

Add:

$-NR^{10}R^{11}$

In Claim 1, Column 246, Line 1:

Add:

$-NR^{10}C(=Y)OR^{11}$

In Claim 1, Column 246, Line 7:

Replace:

$-SC(=Y)R^{10}$

With:

$-SC(=Y)OR^{10}$

In Claim 7, Column 250, Line 23:

Replace:

$C_1$-$C_{12}$, alkyl,

With:

$C_1$-$C_{12}$ alkyl,